United States Patent
Bhargava et al.

(10) Patent No.: US 11,945,881 B2
(45) Date of Patent: Apr. 2, 2024

(54) NEOANTIGENS EXPRESSED IN OVARIAN CANCER AND THEIR USES

(71) Applicant: Janssen Biotech, Inc., Horsham, PA (US)

(72) Inventors: Vipul Bhargava, Warrington, PA (US); Vinod Krishna, Philadelphia, PA (US); David J. Pocalyko, Doylestown, PA (US); Pegah Safabakhsh, Jenkintown, PA (US); Manuel Alejandro Sepulveda, West Windsor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 227 days.

(21) Appl. No.: 17/174,505

(22) Filed: Feb. 12, 2021

(65) Prior Publication Data

US 2021/0261609 A1 Aug. 26, 2021

Related U.S. Application Data

(60) Provisional application No. 62/976,384, filed on Feb. 14, 2020.

(51) Int. Cl.
| | | |
|---|---|---|
| *A61K 38/00* | (2006.01) | |
| *A61K 45/06* | (2006.01) | |
| *C07K 1/107* | (2006.01) | |
| *C07K 2/00* | (2006.01) | |
| *C12N 15/86* | (2006.01) | |

(52) U.S. Cl.
CPC ............... *C07K 2/00* (2013.01); *A61K 45/06* (2013.01); *C07K 1/107* (2013.01); *C12N 15/86* (2013.01); *A61K 38/00* (2013.01); *C12N 2710/10041* (2013.01); *C12N 2710/24041* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,603,112 A | 7/1986 | Paoletti et al. |
| 4,769,330 A | 9/1988 | Paoletti et al. |
| 4,772,848 A | 9/1988 | Hummel |
| 4,837,028 A | 6/1989 | Allen |
| 4,897,445 A | 1/1990 | Coy et al. |
| 5,100,587 A | 3/1992 | Clough et al. |
| 5,179,993 A | 1/1993 | Bak et al. |
| 5,185,146 A | 2/1993 | Altenburger |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,545,807 A | 8/1996 | Surani et al. |
| 5,559,099 A | 9/1996 | Wickham et al. |
| 5,571,698 A | 11/1996 | Ladner et al. |
| 5,580,717 A | 12/1996 | Dower et al. |
| 5,635,363 A | 6/1997 | Altman et al. |
| 5,635,483 A | 6/1997 | Pettit et al. |
| 5,734,023 A | 3/1998 | Nag et al. |
| 5,747,323 A | 5/1998 | Darlix et al. |
| 5,780,588 A | 7/1998 | Pettit et al. |
| 5,820,866 A | 10/1998 | Kappler et al. |
| 5,821,337 A | 10/1998 | Carter et al. |
| 5,837,511 A | 11/1998 | Falck-Pedersen et al. |
| 5,846,782 A | 12/1998 | Wickham et al. |
| 5,851,806 A | 12/1998 | Kovesdi et al. |
| 5,885,793 A | 3/1999 | Griffiths et al. |
| 5,891,690 A | 4/1999 | Massie |
| 5,932,448 A | 8/1999 | Tso et al. |
| 5,965,541 A | 10/1999 | Wickham et al. |
| 5,969,108 A | 10/1999 | McCafferty et al. |
| 5,976,551 A | 11/1999 | Mottez et al. |
| 5,976,567 A | 11/1999 | Wheeler et al. |
| 5,981,225 A | 11/1999 | Kochanek et al. |
| 5,981,501 A | 11/1999 | Wheeler et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,150,584 A | 11/2000 | Kucherlapati et al. |
| 6,172,197 B1 | 1/2001 | McCafferty et al. |
| 6,197,302 B1 | 3/2001 | Hirsch et al. |
| 6,255,458 B1 | 7/2001 | Lonberg et al. |
| 6,268,411 B1 | 7/2001 | Schneck et al. |
| 6,270,772 B1 | 8/2001 | Burrows et al. |

(Continued)

FOREIGN PATENT DOCUMENTS

| | | |
|---|---|---|
| EP | 0451216 B1 | 1/1996 |
| EP | 0919627 A2 | 6/1999 |

(Continued)

OTHER PUBLICATIONS

Sequence alingnmet_7,2023.*
Sequence slignment_8, 2023.*
Ying et al., Nature Medicine, 1999, 5: 823-827.*
Christian L. Barrett et al: "Systematic transcriptome analysis reveals tumor-specific isoforms for ovarian cancer diagnosis and therapy" Proceedings of Thenational Academy of Sciences, vol. 112, No. 23 May 26, 2015 p. E3050-E3057.
Liu Song et al: "Efficient identification of neoantigen-specific T-cell responses in advanced human ovarian cancer", Journal for Immuunotherapy of Cancer, vol. 7, No. 1, Jun. 20, 2019 (Jun. 20, 2019).

(Continued)

*Primary Examiner* — Ileana Popa
(74) *Attorney, Agent, or Firm* — BakerHostetler

(57) ABSTRACT

The disclosure relates to ovarian cancer neoantigens, polynucleotides encoding them, vectors, host cells, recombinant virus particles, vaccines comprising the neoantigens, proteinaceous molecules binding the ovarian cancer neoantigens, and methods of making and using them.

21 Claims, 17 Drawing Sheets
Specification includes a Sequence Listing.

(56) References Cited

U.S. PATENT DOCUMENTS

| | | |
|---|---|---|
| 6,348,584 B1 | 2/2002 | Hodgson et al. |
| 6,440,442 B1 | 8/2002 | Ehrhard et al. |
| 6,521,404 B1 | 2/2003 | Griffiths et al. |
| 6,534,484 B1 | 3/2003 | Wheeler et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,586,410 B1 | 7/2003 | Wheeler et al. |
| 6,593,081 B1 | 7/2003 | Griffiths et al. |
| 6,673,901 B2 | 1/2004 | Koide |
| 6,815,432 B2 | 11/2004 | Wheeler et al. |
| 6,818,749 B1 | 11/2004 | Kashmiri et al. |
| 6,833,441 B2 | 12/2004 | Wang et al. |
| 7,074,904 B2 | 7/2006 | Wong et al. |
| 7,074,905 B2 | 7/2006 | Rhode et al. |
| 7,141,656 B2 | 11/2006 | Rhode et al. |
| 7,329,731 B2 | 2/2008 | Jakobsen et al. |
| 7,569,664 B2 | 8/2009 | Jakobsen et al. |
| 7,709,226 B2 | 5/2010 | Foote |
| 7,871,817 B2 | 1/2011 | Voss et al. |
| 8,377,447 B2 | 2/2013 | Burrows et al. |
| 8,748,356 B2 | 6/2014 | Raghunathan |
| 8,828,379 B2 | 9/2014 | Loset et al. |
| 9,079,941 B2 | 7/2015 | Ovaa et al. |
| 9,133,264 B2 | 9/2015 | Blankenstein et al. |
| 9,150,663 B2 | 10/2015 | Labrijn et al. |
| 9,624,292 B2 | 4/2017 | Voss et al. |
| 9,750,801 B2 | 9/2017 | Barouch et al. |
| 9,790,256 B2 | 10/2017 | Bunnik et al. |
| 9,884,075 B2 | 2/2018 | Bethune et al. |
| 10,035,832 B2 | 7/2018 | Schlom et al. |
| 11,446,398 B2 * | 9/2022 | Barrett .................. C12N 5/0647 |
| 2001/0049136 A1 | 12/2001 | Imler et al. |
| 2002/0155537 A1 | 10/2002 | Carter et al. |
| 2005/0074848 A1 | 4/2005 | Schwabe |
| 2009/0182127 A1 | 7/2009 | Naergaard et al. |
| 2010/0015133 A1 | 1/2010 | Igawa et al. |
| 2010/0028637 A1 | 2/2010 | Tavsanli et al. |
| 2010/0216708 A1 | 8/2010 | Jacobs et al. |
| 2010/0255056 A1 | 10/2010 | Jacobs et al. |
| 2010/0261620 A1 | 10/2010 | Almagro et al. |
| 2011/0123532 A1 | 5/2011 | Gurney et al. |
| 2012/0093934 A1 | 4/2012 | Santamaria |
| 2012/0149876 A1 | 6/2012 | Von et al. |
| 2012/0245332 A1 | 9/2012 | Schwabe et al. |
| 2012/0252742 A1 | 10/2012 | Kranz et al. |
| 2013/0195849 A1 | 8/2013 | Spreter et al. |
| 2013/0289253 A1 | 10/2013 | Luescher et al. |
| 2014/0303356 A1 | 10/2014 | Gramer et al. |
| 2015/0031566 A1 | 1/2015 | Napper et al. |
| 2015/0329617 A1 | 11/2015 | Winther et al. |
| 2016/0130319 A1 | 5/2016 | Li |
| 2017/0003288 A1 | 1/2017 | Heath et al. |
| 2017/0095544 A1 | 4/2017 | Santamaria |
| 2017/0121409 A1 | 5/2017 | Verona et al. |
| 2018/0064803 A1 | 3/2018 | Tomaka et al. |
| 2018/0104359 A1 | 4/2018 | Kamrud |
| 2018/0118849 A1 | 5/2018 | Klein et al. |
| 2018/0171340 A1 | 6/2018 | Kamrud et al. |
| 2018/0251513 A1 | 9/2018 | Stauss et al. |
| 2019/0030071 A1 | 1/2019 | De et al. |
| 2021/0145951 A1 | 5/2021 | Martin et al. |
| 2021/0154280 A1 | 5/2021 | Martin et al. |
| 2022/0362365 A1 | 11/2022 | Martin et al. |
| 2022/0378889 A1 | 12/2022 | Martin et al. |

FOREIGN PATENT DOCUMENTS

| | | |
|---|---|---|
| EP | 1230354 A2 | 8/2002 |
| EP | 1670823 A1 | 6/2006 |
| EP | 1882700 A1 | 1/2008 |
| EP | 2061807 A2 | 5/2009 |
| EP | 3215164 A1 | 9/2017 |
| EP | 3286210 A1 | 2/2018 |
| WO | 90/04036 A1 | 4/1990 |
| WO | 90/07861 A1 | 7/1990 |
| WO | 92/22653 A1 | 12/1992 |
| WO | 95/01447 A1 | 1/1995 |
| WO | 96/17070 A1 | 6/1996 |
| WO | 96/27011 A1 | 9/1996 |
| WO | 96/27677 A2 | 9/1996 |
| WO | 96/40964 A2 | 12/1996 |
| WO | 97/04119 A1 | 2/1997 |
| WO | 97/35996 A1 | 10/1997 |
| WO | 98/00524 A1 | 1/1998 |
| WO | 98/26048 A1 | 6/1998 |
| WO | 98/39411 A1 | 9/1998 |
| WO | 99/45962 A1 | 9/1999 |
| WO | 00/50573 A1 | 8/2000 |
| WO | 02/43478 A2 | 6/2002 |
| WO | 02/66630 A1 | 8/2002 |
| WO | 02/88172 A2 | 11/2002 |
| WO | 2005/048957 A2 | 6/2005 |
| WO | 2007/147901 A1 | 12/2007 |
| WO | 2009/085462 A1 | 7/2009 |
| WO | 2010/086189 A2 | 8/2010 |
| WO | 2011/143545 A1 | 11/2011 |
| WO | 2012/022811 A1 | 2/2012 |
| WO | 2012/177624 A2 | 12/2012 |
| WO | 2013/096291 A2 | 6/2013 |
| WO | 2013/157954 A1 | 10/2013 |
| WO | 2017/015064 A1 | 1/2017 |
| WO | 2017/091905 A1 | 6/2017 |
| WO | 2017/180770 A1 | 10/2017 |
| WO | 2017/220499 A1 | 12/2017 |
| WO | 2018/075235 A1 | 4/2018 |
| WO | 2018/106615 A2 | 6/2018 |
| WO | 2018/146205 A1 | 8/2018 |
| WO | 2019/008111 A1 | 1/2019 |
| WO | 2019/115816 A1 | 6/2019 |
| WO | 2019/135086 A1 | 7/2019 |
| WO | 2019/143949 A2 | 7/2019 |
| WO | 2019/191780 A1 | 10/2019 |
| WO | 2020/144615 A1 | 7/2020 |
| WO | 2022/189626 A2 | 9/2022 |
| WO | 2022/189639 A1 | 9/2022 |

OTHER PUBLICATIONS

Ross M.S et al: "An in vitro evaluation of neoantigens derived from gene fusion events in ovarian cancer patients", Gynecologic Oncology, vol. 149 supplement 1, Jun. 1, 2018 (Jun. 1, 2018), p. 8.

Ross Malcolm S. et al: "Neoepitope peptide vaccines and immune checkpoint blockade in a new preclinical ovarian cancer model Clinical CAncer Research", Clinical CAncer Research :s Abstract : AACR Special Conference: Addressing Critical Questions in Ovarian CAnceer Research and Treatment; Oct. 1-4, 2017; Pittsburgh, Aug. 1, 2018.

Ahl et al., "Enhancement of the in vivo circulation lifetime of L-a-distearoylphosphatidylcholine liposomes: importance of liposomal aggregation versus complement opsonization", Biochim. Biophys. Acta, 1997, vol. 1329, pp. 370-382.

Altschul et al., "Basic Local Alignment Search Tool", J. Mol. Biol., 1990, vol. 215, pp. 403-410.

Alving et al., "Liposomes as carriers of peptide antigens: induction of antibodies and cytotoxic T lymphocytes to conjugated and unconjugated peptides", Immunol. Rev., 1995, vol. 145, pp. 5-31.

Berger et al., "A Comprehensive Pan-Cancer Molecular Study of Gynecologic and Breast Cancers", Cancer Cell, 2018, vol. 33, No. 4, pp. 690-705.

Bruckdorfer et al., "From production of peptides in milligram amounts for research to multi-tons quantities for drugs of the future", Curr Pharm Biotechnol. 2004, vol. 5, No. 1, pp. 29-43.

Brüggemann et al., "Human antibody production in transgenic mice: expression from 100 kb of the human IgH locus", Eur. J. Immunol. 1991, vol. 21, pp. 1323-1326.

Brüggemann et al., "Production of human antibody repertoires in transgenic mice", Current Opinion in Biotechnology, 1997, vol. 8, Issue 4, pp. 455-458.

Fishwild et al., "High-avidity human IgG? monoclonal antibodies from a novel strain of minilocus transgenic mice", Nat Biotechnol., 1996, vol. 14, pp. 845-851.

(56) References Cited

OTHER PUBLICATIONS

Ge et al., "FusionMap: Detecting fusion genes from next-generation sequencing data at base-pair resolution", Bioinformatics. 2011, vol. 27, No. 14, pp. 1922-1928.
Gilboa, "Retroviral Gene Transfer: Applications to Human Therapy", Adv. Exp. Med. Biol. 1988, vol. 241, pp. 29-33.
Gorchakov et al., "A New Role for ns Polyprotein Cleavage in Sindbis Virus Replication", J Virol. 2008, vol. 82, No. 13, pp. 6218-6231.
Graham et al., "Characteristics of a human cell line transformed by DNA from human adenovirus Type 5", J. Gen. Virol., 1977, vol. 36, pp. 59-72.
Green et al., "Antibody engineering via genetic engineering of the mouse: XenoMouse strains are a vehicle for the facile generation of therapeutic human monoclonal antibodies", J Immunol Methods., 1999, vol. 231, pp. 11-23.
Green et al., "Antigen-specific human monoclonal antibodies from mice engineered with human Ig heavy and light chain YACs", Nature Genet., 1994, vol. 7, pp. 13-21.
Green et al., "Regulation of B cell development by variable gene complexity in mice reconstituted with human immunoglobulin yeast artificial chromosomes", Exp. Med., 1998, vol. 188, pp. 483-495.
Hoogenboom et al., "By-passing immunisation: Human antibodies from synthetic repertoires of germline VH gene segments rearranged in vitro", J Mol Biol, 1992, vol. 227, pp. 381-388.
Hosse et al., "A new generation of protein display scaffolds for molecular recognition", Protein Sci., 2006, vol. 15, pp. 14-27.
Juliano et al., "The effect of particle size and charge on the clearance rates of liposomes and liposome encapsulated drugs", Biochem. Biophys. Res. Commun., 1975, vol. 63, pp. 651-658.
Kim et al., "Enhancement of protein expression by alphavirus replicons by designing self-replicating subgenomic RNAs", PNAS, 2014, vol. 111, pp. 10708-10713.
Knappik et al., "Fully synthetic human combinatorial antibody libraries (HuCAL) based on modular consensus frameworks and CDRs randomized with trinucleotides", J Mol Biol., 2000, vol. 296, pp. 57-86.
Kohler et al., "Continuous cultures of fused cells secreting antibody of predefined specificity", Nature, 1975, vol. 256, pp. 495-497.
Krebs et al., "High-throughput generation and engineering of recombinant human antibodies", J Immunol Meth, 2001, vol. 254, pp. 67-84.
Krougliak et al., "Development of Cell Lines Capable of Complementing E1, E4, and Protein IX Defective Adenovirus Type 5 Mutants", Human Gene Therapy, 1995, vol. 6, No. 12, pp. 1575-1586.
Le et al., "PD-1 Blockade in Tumors with Mismatch-Repair Deficiency", N Engl J Med. 2015, vol. 372, No. 26, pp. 2509-2520.
Lonberg et al., "Antigen-specific human antibodies from mice comprising four distinct genetic modifications", Nature, 1994, vol. 368, pp. 856-859.
Lonberg et al., "Human Antibodies from Transgenic Mice", Int Rev Immunol 1995, vol. 13, pp. 65-93.
Lukas et al., "Solid-phase peptide synthesis under continuous-flow conditions", Proc. Nati. Acad. Sci. USA, 1981, vol. 78, No. 5, pp. 2791-2795.
Lusky et al., "Circular intermediates of recombinant adeno-associated virus have defined structural characteristics responsible for long-term episomal persistence in muscle tissue", J. Virol., 1998, vol. 72, pp. 8568-8577.
Markowitz et al., "Construction and use of a safe and efficient amphotropic packaging cell line", Virol., 1988, vol. 167, pp. 400-406.
Marks et al., "By-passing immunization: Human antibodies from V-gene libraries displayed on phage", J Mol Biol, 1991, vol. 222, pp. 581-597.

Meisinger-Henschel et al., "Genomic sequence of chorioallantois vaccinia virus Ankara the ancestor of modified vaccinia virus Ankara", J. Gen. Virol. 2007, vol. 88, pp. 3249-3259.
Mendez et al., "Functional transplant of megabase human immunoglobulin loci recapitulates human antibody response in mice", Nat Genet, 1997, vol. 15, pp. 146-156.
Meyer et al., "Mapping of deletions in the genome of the highly attenuated vaccinia virus MVA and their influence on virulence", J. Gen. Virol. 1991, vol. 72 pp. 1031-1038.
Meyers et al., "Optimal Alignments in Linear Space", Comput Appl Biosci., 1988, vol. 4, No. 1, pp. 11-17.
Meziere et al., "The comet-tail artifact. An ultrasound sign of alveolar-interstitial syndrome", Am J Respir Crit Care Med. 1997, vol. 156, No. 5, pp. 1640-1646.
Miller et al., "Improved retroviral vectors for gene transfer and expression", BioTechniques 1989, vol. 7, pp. 980-990.
Needleman et al., "A general method applicable to the search for similarities in the amino acid sequence of two proteins", J. Mol. Biol. 1970, vol. 48, pp. 444-453.
Nicaise et al., "Affinity Transfer by CDR Grafting on a Nonimmunoglobulin Scaffold," Protein Sci., 2004, vol. 13, pp. 1882-1891.
Nygren et al., "Scaffolds for Engineering Novel Binding Sites in Proteins", Curr. Opin. Struc. Biol., 1997, vol. 7, pp. 463-469.
Padlan, "A possible procedure for reducing the immunogenicity of antibody variable domains while preserving their ligand-binding properties", Mol Immunol 1991, vol. 28, pp. 489-498.
Piccini et al., "Vaccinia virus host range genes", Methods of Enzymology, 1987, vol. 153, pp. 545-563.
Rizvi et al., "Cancer immunology. Mutational landscape determines sensitivity to PD-1 blockade in non-small cell lung cancer", Science., 2015, vol. 348, No. 6230, pp. 124-128.
Rodenko et al., "Generation of peptide-MHC class I complexes through UV-mediated ligand exchange", Nature Protocols, 2006, vol. 1, pp. 1120-1132.
Romani et al., "Presentation of exogenous protein antigens by dendritic cells to T cell clones. Intact protein is presented best by immature, epidermal Langerhans cells", J. Exp. Med., 1989, vol. 169, pp. 1169-1178.
Sheets et al., "Efficient construction of a large nonimmune phage antibody library: the production of high-affinity human single-chain antibodies to protein antigens", PITAS USA, 1998, vol. 95, pp. 6157-6162.
Shi et al., "De novo selection of high-affinity antibodies from synthetic fab libraries displayed on phage as pIX fusion proteins", J Mol Biol, 2010, vol. 397, pp. 385-396.
Skerra, "Alternative non-antibody scaffolds for molecular recognition", Curr. Opin. Biotechnol., 2007, vol. 18, pp. 295-304.
Snyder et al. "Genetic basis for clinical response to CTLA-4 blockade in melanoma", N Engl J Med. 2014, vol. 371, No. 23, pp. 2189-2199.
Szoka, "Comparative properties and methods of preparation of lipid vesicles (liposomes)", Ann. Rev. Biophys. Bioeng., 1980, vol. 9, pp. 467-508.
Van Allen et al., "Genomic correlates of response to CTLA-4 blockade in metastatic melanoma", Science., 2015, vol. 350, No. 6257, pp. 207-211.
Vaughan et al., "Human Antibodies with Sub-nanomolar Affinities Isolated from a Large Non-immunized Phage Display Library", Nature Biotechnology, 1996, vol. 14, pp. 309-314.
Woyke et al., "Effect of Auristatin PHE on Microtubule Integrity and Nuclear Localization in Cryptococcus neoformans", Antimicrob Agents and Chemother. 2001, vol. 45, No. 12, pp. 3580-3584.
Yang et al., "Eradication of established tumors by a fully human monoclonal antibody to the epidermal growth factor receptor without concomitant chemotherapy", Cancer Res., 1999, vol. 59, pp. 1236-1243.
Yeh et al., "Efficient Dual Transcomplementation of Adenovirus E1 and E4 Regions from a 293-Derived Cell Line Expressing a Minimal E4 Functional Unit", J. Virol. 1996, vol. 70, pp. 559-565.

\* cited by examiner

SEQUENCE LISTING

<160> NUMBER OF SEQ ID NOS: 421

<210> SEQ ID NO 1
<211> LENGTH: 50
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 1

Met Ala Gly Gly Val Leu Arg Arg Leu Leu Cys Arg Glu Pro Asp Arg
1               5                   10                  15

Asp Gly Asp Lys Gly Ala Ser Arg Glu Glu Thr Val Val Pro Leu His
            20                  25                  30

Ile Gly Asp Pro Val Val Leu Pro Gly Ile Gly Gln Cys Tyr Ser Ala
        35                  40                  45

Leu Phe
    50

<210> SEQ ID NO 2
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggctggag gagtccttcg gcggctgttg tgtcgggagc ctgatcgcga tggggacaaa      60
ggcgcaagtc gagaggaaac tgttgtgcct cttcatattg gcgatcctgt tgtgctccct     120
ggcattgggc agtgttacag tgcactcttc                                      150

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Leu Asn Leu Ser Glu Thr Gln Phe Ala Gln Tyr Ala Glu Ile Val
1               5                   10                  15

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cagctgaacc tctccgagac ccagtttgcc cagtatgcgg agatcgtc                   48

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Pro Ile Leu Ala Ala Ile Gly Ile Gly Arg Leu Leu Cys Met Asp
1               5                   10                  15

Lys Ile Pro Ala Thr Ala Ser Leu Thr Pro
            20                  25

<210> SEQ ID NO 6

```
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcaccgatct tagcagctat tgggattggg aggctgctgt gtatggataa gatacctgct      60
acagccagct tgacacca                                                    78

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Val Gly Ala Met Thr Val Gly Gln Asp Gly Ser Arg
1               5                   10

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gttgtaggag caatgactgt tgggcaggat ggcagcaga                             39

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Thr Gly Asp Val Ala Val Glu Ile Ala Ser
1               5                   10

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aacactggag atgttgctgt tgagatcgct tct                                   33

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Thr Leu Asn Ile Thr Leu Ser Phe Asp Ser His His Gly His His
```

```
1               5                   10                  15
Pro Val Ser Val Ile
            20

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcaactttga atataacttt aagttttgat tcccaccatg gccatcaccc agtttcggtt    60
att                                                                 63

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Pro Glu Phe Glu Lys Cys Leu Phe Gln Lys Lys Val Val Ala
1               5                   10                  15

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgccggaat tgaaaagtg cctatttcag aagaaagtgg tagct                    45

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Glu Gln Ala Gly Cys Met Gln Cys Leu Ile
1               5                   10

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcggccgagc aggcgggctg catgcagtgc ctgatt                             36

<210> SEQ ID NO 17
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 17

Pro Gln Glu Glu Val Pro Phe Arg Met Asn Tyr Ser Ser Phe Leu Arg
1               5                   10                  15

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccacaggaag aagtgccatt caggatgaat tattcatcat tccttaga                 48

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gly Gly Arg Gly Ala Gln Glu Asn Ser Leu Asp
1               5                   10

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 cgaggggggca ggggtgctca ggagaattct ctggac                             36

<210> SEQ ID NO 21
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

His Phe Glu Cys Tyr His Cys Glu Ile Arg Ile Pro Arg Lys Ser Asn
1               5                   10                  15

Gly Ile Arg Gly Phe Leu Leu Thr Trp Arg Arg Asp Gly Asn Thr Ser
            20                  25                  30

Thr Ser Val Gln Gln Thr Thr Ser Ser Leu
        35                  40

<210> SEQ ID NO 22
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
```

```
cactttgagt gctaccactg tgagattaga atcccaagaa atcaaatggc catccgggga    60
tttctgctca cctggagaag ggatggaaat acttcaacaa gtgtgcagca aacaacttcc   120
tccttg                                                             126
```

<210> SEQ ID NO 23
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Tyr Glu Gly Phe Pro Val Pro Gly Leu Met Lys Trp Gln Leu Ser
1               5                   10                  15

Pro Val Gln Trp Pro Pro Val Ser Gln Gly Pro Glu Thr Arg Lys Gly
            20                  25                  30

Arg Lys Ala Ala Ser Leu Pro Leu
        35                  40
```

<210> SEQ ID NO 24
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gaatatgaag gcttccccgt cccgggactc atgaagtggc agctaagccc tgtccagtgg    60
ccacccgtca gccaagggcc agagaccagg aaaggaagaa aggcagcttc acttcctctt   120
```

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Tyr Gly Asn Asp Gln Trp Leu Gln Met Arg Lys Trp Arg His Arg Glu
1               5                   10                  15
```

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
tacggtaacg atcagtggct gcagatgagg aaatggaggc acagagag                 48
```

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Asn Lys Ser Cys Tyr Glu Asp Ala Gln Glu Lys Glu Asp Lys Val
1               5                   10                  15

Gly Glu Gly Ser Val Ser His Ser Val Leu Ser Ser Asn Thr Val Glu
            20                  25                  30

Met

<210> SEQ ID NO 28
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtaaacaaat cttgttatga agatgcacag gaaaagaag ataaagtagg agagggatca    60
gtttcacatt cagtcctaag cagcaacacg gttgagatg                          99

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Leu Phe Phe Val Ala Gly Glu Val Leu Arg His Glu Glu Phe Glu
1               5                   10                  15

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cttctgttct tcgtagccgg ggaggttctg cggcatgagg aatttgaa                48

<210> SEQ ID NO 31
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Leu Thr Leu Gly Ala Arg Asn Thr Leu Thr His Gly Ser Pro
1               5                   10                  15

Gly Pro Ser Gln Ala Thr Val Ala Val Ala Pro Leu Ser Gly Arg Ala
            20                  25                  30

Ala Val Ser Ala Ala Gly Gly Cys Val Phe Leu Leu Leu Pro Ala Cys
        35                  40                  45

Val Pro Arg Arg Cys His Trp Ile Pro
    50                  55

<210> SEQ ID NO 32
<211> LENGTH: 171
<212> TYPE: DNA
<213> ORGANISM: Artificial Sequence -continued
<220> FEATURE:
<223> OTHER INFORMATION: Description of Artificial Sequence: Synthetic
      polynucleotide

<400> SEQUENCE: 32
ggaggcctga ctctgggagc acgcaatact ctgacccatg gatcccctgg gcccagccaa    60
gccacagtgg ctgtggcgcc gctgtctggc cgggctgctg tttcagctgc tggtggctgt   120
gtgtttcttc tcctacctgc gtgtgtcccg agacgatgcc actggatccc c            171

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Cys Gly Ala Gln Lys Ala Cys Asp Val Asn Gln Leu Thr
1               5                   10                  15

Ser Ser

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgggcctcct gtggcgccca gaaggcatgt gatgtgaatc agctgacatc atct          54

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Tyr Leu Arg Met Gln Gly Leu Met Ala Gln Arg Leu Leu Leu Arg
1               5                   10                  15

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gggtacctga ggatgcaggg actcatggct cagcgacttc ttctgagg                 48

<210> SEQ ID NO 37
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Lys Val Ser His Met Thr Ser Val Leu Glu Ala Val Ala Phe Asp
1               5                   10                  15

Gln Ala Trp Asp Gln Glu Val Arg Pro Ala Leu Arg His Gln Pro Lys
            20                  25                  30

Asp Pro Leu Asn Leu Pro Ser Pro Pro Ala Asn Lys Gly Thr Ser Arg
        35                  40                  45

Cys

<210> SEQ ID NO 38
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gcaaaagtat ctcatatgac cagtgtgttg gaggctgtag cctttgacca ggcatgggac      60
caggaggtga ggccggctct caggcatcaa ccaaaggatc cactgaatct cccttctccc     120
cctgccaaca aggtacaag tagatgt                                          147

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Leu Ile Val Ala Glu Ile Val Thr Leu Leu Ile Ala Phe Ile
1               5                   10                  15

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttcctcatcg tggccgagat cgtcaccctg ctgattgcct tcatc                      45

<210> SEQ ID NO 41
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe His Leu Glu Ile Ala Lys Lys Pro Leu Leu Pro Leu Trp Glu Gly
1               5                   10                  15

Thr Ser Ser Val Lys His Pro Ser Leu
            20                  25

<210> SEQ ID NO 42
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ttccatctgg agatcgccaa gaaaccgctg ctgccctgt gggaagggac ctcgagtgtg    60
aagcatcctt ccctg    75

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Asn Phe Ile Thr Cys Phe Lys Gly Gly His Ala Ser Ala Ala Glu
1               5                   10                  15

Pro Arg Lys Gly Arg
            20

<210> SEQ ID NO 44
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aagaatttca tcacctgctt caaaggaggg cacgcgtctg cggctgaacc gcggaagggc    60
cgg    63

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Tyr Glu Glu Gln Phe Lys Gln Val Ala Asp Gly Leu Val Lys Val
1               5                   10                  15

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acctacgagg aacaattcaa gcaggtggct gacggcctgg tcaaggtg    48

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Ile Ala Ile Ser Leu Leu Gln Asn Pro Gln Arg Thr

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttcatcgcca tctcgctgtt gcagaacccc cagaggaca                                39

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Arg Ser Leu Ala Gly Thr Tyr Gly Arg Ser Pro Ser Pro Ala Thr
1               5                   10                  15

Arg Arg Lys Arg Ser Trp Ser Cys
            20

<210> SEQ ID NO 50
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctccgcagct tggctgggac ctatgggagg agccccagcc ccgcgacgag gaggaagcgg        60
agctggagct gc                                                           72

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Cys Gln Val Ser Asp His Leu Ala Thr Glu Tyr Val Phe Ser
1               5                   10                  15

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
acctgccagg tcagcgacca cctggccacg gagtacgtgt tctcg                        45

<210> SEQ ID NO 53
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 53

Ala Leu Thr Val Val Pro Pro Gly Leu Arg Leu Asp Arg Val Leu Leu
1               5                   10                  15

His Leu Trp

<210> SEQ ID NO 54
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gccctcacag tggtgccccc aggtcttcgc cttgatcgtg ttctcctgca tctatgg     57

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Gln Leu Leu Pro Gln His Gln Pro Arg Ala Val Leu Leu His Ile
1               5                   10                  15

Ala Trp Met Lys Gly
            20

<210> SEQ ID NO 56
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tgccagctgc tgccccagca ccagcccagg gcagtgttgc tgcatattgc atggatgaaa     60
ggc                                                                  63

<210> SEQ ID NO 57
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Leu Gln Glu Arg Met Glu Leu Leu Ala Cys Gly Ala Glu Arg Gly Ala
1               5                   10                  15

Gly Gly Trp Gly Gly Gly Gly Gly Gly Gly Gly Asp Arg Arg Gly
            20                  25                  30

Gly Gly Gly Ser Ala Pro Ala Leu Ala Asp Phe Ala Gly Gly Arg Gly
            35                  40                  45

<210> SEQ ID NO 58
<211> LENGTH: 144
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ttgcaggagc ggatggagtt gcttgcctgc ggagccgagc gcggggccgg cggctggggg    60
ggaggcggtg gcggcggcgg cggcgaccga agaggaggag gaggaagcgc gccagctctt   120
gcagactttg caggcggccg aggg                                          144

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Leu Arg Leu Arg Pro Asn Arg Arg Ala Ser Ser Ala Gln Thr Ala
1               5                   10                  15

Pro Thr Ser Ser Leu Ser Leu Trp Ser Gly Ala Ser Arg Arg Arg
                20                  25                  30

Pro Ala Gly Gly His Met Trp Cys Thr Ala Gly Arg Pro Ser Ser Arg
            35                  40                  45

Ser Gly Gln Asn Leu Thr Gly Thr Cys Thr Met Lys Pro Leu Ala Trp
        50                  55                  60

Glu Thr Phe Pro Thr Cys Trp Ala Trp Trp Gly Thr Ser Trp Ala Thr
65                  70                  75                  80

Gln Ser Gly Ser Gly Gly Met Pro Ser Gln Ala Ala Thr Ala Ser Arg
                85                  90                  95

Cys Cys Trp Trp Trp Thr Thr Arg Trp Phe Ala Ser Met Ala Arg Ser
            100                 105                 110

Met Cys Arg Thr Met Ser Ser Pro Ser
            115                 120

<210> SEQ ID NO 60
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
ttgcgcctgc ggcccaatcg gaggcgggcc tcatccgcac agacagcacc gacttcttca    60
ttgagcctct ggagcggggc cagcaggaga aggaggccag cgggaggaca catgtggtgt   120
accgccggga ggccgtccag caggagtggg cagaacctga cggggacctg cacaatgaag   180
cctttggcct gggagacctt cccaacctgc tgggcctggt gggggaccag ctgggcgaca   240
cagagcggaa gcggcggcat gccaagccag gcagctacag catcgaggtg ctgctggtgg   300
tggacgactc ggtggttcgc ttccatggca aggagcatgt gcagaactat gtcctcaccc   360
tca                                                                 363

<210> SEQ ID NO 61
<211> LENGTH: 41
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 61

Cys Ser Thr Phe Cys Gln Arg Lys Val Gly Leu Thr Tyr Thr Arg Leu
1               5                   10                  15

Ser Ala Pro Ala Ser Ser Leu Ala Thr Lys Thr Pro Gly Trp Pro Ser
            20                  25                  30

Leu Pro Leu Cys Ser Trp Cys His Thr
        35                  40

<210> SEQ ID NO 62
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
tgctccacct tctgccaacg caaggtaggt ctcacctaca ccaggctcag tgccccgcc       60 tcctccctcg ctacgaagac ccctgggtgg ccctccctcc ccttgtgctc ctggtgccac    120
acc                                                                  123

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Thr Asp Phe Ala Tyr Asp Ser Gly Lys Arg Leu Gly Trp Gly Arg
1               5                   10                  15

Val Ala Cys Asp Gln Val Phe Ser
            20

<210> SEQ ID NO 64
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cagacggact tcgcctacga ctcaggtaag agactggggt ggggcagggt ggcatgtgat     60
caagtgttca gt                                                         72

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Pro Ser Leu Ser Thr Arg Leu Thr Ser Lys Asp Pro Gln Pro Leu Gln
1               5                   10                  15

Ser His Tyr Trp Gly Leu Ile Gly Asn Asp Pro Phe Leu Arg Ser Lys

-continued

```
                20                  25                  30

Lys Arg Val Asn
        35

<210> SEQ ID NO 66
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
ccttcactct caacacggtt gacaagtaag gacccacagc ccctacaatc ccattattgg      60
gggctcatag gaaatgaccc cttcctaaga agcaaaaaaa gagttaac                 108

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Ile Pro Gly Asp Leu Ser Glu Ala His Gly Tyr Ser Phe Ser
1               5                  10                  15

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gtcattcctg gtgatttgtc agaagcacat ggctactcat tctcc                     45

<210> SEQ ID NO 69
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Glu Gly Pro Gly Gly Ser Gln Val Arg Arg Gly Phe Gly Gly Trp
1               5                  10                  15

Arg Gly Ala Gly Ser Asp Gln Leu Arg Ala Glu Leu Glu Ser Arg Ala
        20                  25                  30

Gln Ala Ala Arg Cys Ser Gly Arg Lys Glu Gly Arg Gly Ser Glu Ala
        35                  40                  45

Thr Arg
    50

<210> SEQ ID NO 70
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 70

```
gcggagggcc ccggggggcag ccaggtgagg aggggggtttg gtgggtggcg cggggccgga    60
agcgaccagt tgagggcgga gctggagagc cgagcacagg ccgccaggtg cagtgggcgg   120
aaggaaggga ggggctcgga ggcgaccaga                                    150
```

<210> SEQ ID NO 71
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Phe Gly Glu Arg Arg Asp Val Asp Gly Glu Arg Gly Trp Ile Gly Glu
1               5                   10                  15

Arg Gly Phe Leu Gly Arg Gly Ser Gln Gly Pro Arg Gly Thr Gly Ala
            20                  25                  30

Gly Arg Asp Pro Ala Gly Phe Glu Arg Arg Trp Leu Gly Val Phe Gly
        35                  40                  45

Gly Cys Leu Gly Ser Thr Gly Ser Arg Ser Leu Cys Pro Ala Leu Gly
    50                  55                  60

Gly Ser Gln Pro Gln Ala Leu Gly Val Ser Ala Pro Leu Ala Trp Gly
65                  70                  75                  80

Glu Gly Val Ser Ser Arg Gly Ala Cys Val Gln Ala Gly Thr Thr Leu
                85                  90                  95

Gly Ser Pro Phe Pro Ala His Gly Glu Asn Pro Pro Leu Leu Gln
            100                 105                 110

Trp Gly Arg Lys Gly Ala Glu Val Thr Ser Arg Leu Gly Ala Pro Ala
        115                 120                 125

Pro Phe Pro Ser Gly Ile Leu Thr Leu Gly Arg Glu Gly Pro Asp Arg
    130                 135                 140

Gln Thr Ala Gly Arg Thr Glu Leu Pro Pro Gly Val Gln Ala Gly Asn
145                 150                 155                 160

Gly Arg Ser Leu Leu Gly Arg Gly Arg Cys Arg Ala Gly
                165                 170
```

<210> SEQ ID NO 72
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
ttcggggagc gccgggatgt ggacggtgag cggggctgga ttggggagcg ggatttctc    60 gggcggggt ctcagggacc cagaggcacg gggcggggc gggacccggc gggcttcgag    120
cggcggtggc tgggggtatt cggcggatgt ctcggctcaa cggggtcccg tagcctttgt   180
cctgctttag ggggcagcca gcctcaggcc ttgggggtca gcgcgccctt ggcttggggt   240
gagggggtgt caagccgggg cgcctgtgtc caggctggca ctacgctcgg gtcacctttt   300
cctgcgcacg ggaaaaaccc tcccccgctt ttgcagtggg gccgaaaggg ggccgaggtc   360
acatcccgcc tcggtgcccc cgccccattt ccttctggaa tcctgacgtt ggggcggag   420 ggaccggacc gacagaccgc gggacggacg gaactccctc cgggagtgca ggcaggaaat   480
```
gggcggagcc tgcttggccg gggcaggtgc cgtgcgggc                     519

<210> SEQ ID NO 73
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Arg Val Leu Ile Thr Lys Thr Leu Val Ile Ser Val Ser Phe Met Cys
1               5                   10                  15

Pro Gly Phe Trp Ser Ala Ala Gln Cys Glu Val Arg Ser Ala Cys Leu
            20                  25                  30

Leu Leu Cys Glu Gly His Arg Trp Trp Gly Thr Cys Leu Thr Gly His
        35                  40                  45

Arg Leu Arg Arg Ser Pro Gly Thr Thr Gly Glu Lys
    50                  55                  60

<210> SEQ ID NO 74
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
agagtgctaa ttacaaaaac attggtaatt tctgtctctt tcatgtgtcc aggcttctgg      60
tcagcggcac agtgtgaagt gaggtcagct tgcttgctgc tctgtgaggg acacaggtgg     120
tggggcacct gccttactgg tcaccgcttg agaaggtcac ctgggaccac aggggaaaaa     180

<210> SEQ ID NO 75
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Lys Val Lys Thr Val Cys Ser Lys Val Gly Gly Ala Val Ile Leu Pro
1               5                   10                  15

Cys His Gly Glu Asn Met Pro Ser Thr Pro Ser Pro Gln Asp Met Pro
            20                  25                  30

Val Leu Phe Pro Ala Arg Pro Ala Pro Cys Thr Ile Ala Ala Ser Ala
        35                  40                  45

Phe Arg Arg Leu Gly Asp Pro Val Cys Val Ala Trp
    50                  55                  60

<210> SEQ ID NO 76
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
aaggtgaaga ctgtctgcag caaggtaggt ggcgctgtca ttcttccctg ccacggggag      60
aacatgccct ccacgccctc cccacaggac atgcccgtgc tgttccctgc ccgtcctgcc     120
ccatgcacca tcgctgcttc tgccttcaga aggctaggtg acccggtttg tgtggcctgg    180

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Asp Leu Pro Val Tyr Leu Lys Asp Pro Ala Tyr Phe Tyr Gly Tyr
1               5                   10                  15

<210> SEQ ID NO 78
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaagatttac cagtttactt aaaggatcct gcttattttt atggatat                 48

<210> SEQ ID NO 79
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Leu Lys Asp Glu Cys Asp Thr Val Lys Gly Trp Arg Leu Cys Asn
1               5                   10                  15

Gly Arg Ile Thr Gly Ala Glu Lys Lys Ala Lys Val Ile
            20                  25

<210> SEQ ID NO 80
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
agcctgaaag acgagtgtga tacggtgaaa ggatggaggc tgtgcaatgg gagaataact    60
ggggctgaga agaaagccaa ggtcatt                                        87

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Met Ala Lys Lys Gln Arg Pro Asp Thr Ala Phe Trp Val Gln His
1               5                   10                  15

<210> SEQ ID NO 82
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gccatggcaa agaaacagcg tccagacaca gctttctggg ttcaacat            48

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Thr Leu Gly Ser Lys Ser Gln Pro Pro Glu Asp Ile Lys Ala Leu
1               5                   10                  15

<210> SEQ ID NO 84
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
atgaccctgg gatccaagtc acagcctcca gaggacatca aggcactg            48

<210> SEQ ID NO 85
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ser Arg Arg Leu Lys Leu Ala Gln Gly Arg Leu Arg Gly Leu Glu Arg
1               5                   10                  15

Leu His Ser Pro Gln Pro Phe Leu Gln Pro Met Leu Pro Gln Gly Ala
                20                  25                  30

Gln Gly Pro Cys Lys Ala Pro Gly Gln Gly Gln Leu Leu Gly Gly Arg
            35                  40                  45

Arg Glu Pro Asp Pro Ser
        50

<210> SEQ ID NO 86
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
tcccgcagac tgaagctggc ccagggaaga ctacgagggc tggaaagact ccattcgcca     60
caacctttcc tccaaccgat gcttccgcaa ggtgcccaag accctgcaa agccccaggc    120 caagggcaac ttctgggcgg tcgacgtgag cctgatccca gc                      162

<210> SEQ ID NO 87
```

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Ala Thr Pro Ser Ser Ile Leu Cys Phe Arg Leu Ala Cys Leu Trp
1               5                   10                  15

Leu Leu Arg Lys Gly Leu Leu Asp Leu Thr Trp
            20                  25

<210> SEQ ID NO 88
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
caggcaacgc cgtcatctat tctgtgcttc agactggctt gcctgtggct tctgaggaaa      60
ggacttctgg atctcacttg g                                               81

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Tyr Cys Lys Asn Asp Phe Phe Arg Ser Leu Pro Cys His Leu Leu
1               5                   10                  15

<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tactgcaaga acgacttctt ccggtcactg ccttgccacc ttctt                     45

<210> SEQ ID NO 91
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Ser Gln Asp Leu Gln Glu Gly Phe Ser Ala Pro Ser Arg Ile Ser
1               5                   10                  15

Ala Trp Phe Gly Pro Pro
            20

<210> SEQ ID NO 92
<211> LENGTH: 66
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 92
tggagccagg acctgcagga aggcttctcc gctccttcta ggatctccgc ctggttcggc    60
ccgcct                                                               66

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Ser Glu Ala Ala Val Ala Gln Asp Lys Lys Gln Leu Gln Glu Glu
1               5                  10                  15

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cagagcgagg cggctgtggc ccaggacaag aagcagctgc aggaggag               48

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln His Leu Gln Gln Glu Ala Cys Val Thr Ser Ala Gly Lys Gln Ser
1               5                  10                  15

<210> SEQ ID NO 96
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cagcacctgc agcaggaagc ctgtgtcacg tcggcgggga agcagtca               48

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ala Phe Pro Arg Glu Leu Lys Lys Gly Gln Arg Met Ser Ser Gln
1               5                  10                  15
```

```
<210> SEQ ID NO 98
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cgggcttttc ccagagagct aaaaaagggc cagagaatgt cgtcccag            48

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Met Lys Met Lys Lys Phe Gln Asp Leu Thr Val Asn Phe Thr Gln
1               5                   10                  15

<210> SEQ ID NO 100
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
atgaaaatga aaaaatttca ggacctgact gtgaacttca cccaa               45

<210> SEQ ID NO 101
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Pro Thr Ala Thr Glu Arg Val Gln Arg Gly Val Lys His Lys Ala Pro
1               5                   10                  15

Val Gln Ala Ala Gln Ser Ser Asp Gly Pro Leu Leu Lys Asp Leu Leu
            20                  25                  30

Arg Arg Pro Arg Arg Ser
        35

<210> SEQ ID NO 102
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
ccaacagcaa cagagagagt ccagaggggt gtgaagcaca aggctccagt ccaggccgca      60
cagagcagcg atgggcccct cctgaaggac ctcctacggc ggccaaggcg cagt           114

<210> SEQ ID NO 103
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 103

Ala Leu Met Glu Val Ser Val Ser Gly Gln Arg Gly
1               5                   10

<210> SEQ ID NO 104
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gcgctcatgg aggtgtctgt gtctgggcaa cgtggc                                  36

<210> SEQ ID NO 105
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Val Asn Ala Asp Asp Ser Leu Glu Ala Gly Leu Gln Leu Gln Ala Ser
1               5                   10                  15

Ser Asp Pro Leu Ala Ser Ala Ser
            20

<210> SEQ ID NO 106
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtgaatgctg atgactctct ggaggctggt ctccaactcc aggcctcaag tgatcctctt        60
gcctcggcct cc                                                            72

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Met Ala Thr Lys Arg Leu Ala Arg Lys Gly Thr Leu Ala Ser Ser Phe
1               5                   10                  15

Ala Arg Arg Val His
            20

<210> SEQ ID NO 108
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 108
atggcgacca agcggctcgc gcgaaagggt acactcgcca gcagttttgc caggagagta    60
cac    63

<210> SEQ ID NO 109
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gly Ser Leu Leu Ser Ser Gly Ser Gly Ala Arg Arg His Cys Ile Leu
1               5                   10                  15

Leu Pro Gly Gly Phe Leu Arg Leu Leu Lys Met Arg Asn Thr Leu Ser
            20                  25                  30

Ile Val Ser Gln Gly Met Ile Ser Pro Phe Ser Ala Phe
        35                  40                  45

<210> SEQ ID NO 110
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
ggcagcctgc tgtcttcagg atctggtgcc aggagacact gcattctact cccaggtggg    60
tttctccggc ttttaaaaat gcggaatact ctctccatcg tgtcgcaggg catgatttct   120
ccattcagtg cctttt    135

<210> SEQ ID NO 111
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Phe Lys Ile Pro Lys Phe Ser Ile Val Leu Ser Ser Asn Ser Ala Phe
1               5                   10                  15

Arg Cys Asp Pro Leu Ser Ser Arg Pro Arg Cys Phe Gly Gly Ser Leu
            20                  25                  30

Glu Ala Pro
        35

<210> SEQ ID NO 112
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
tttaaaattc ctaagttttc tattgttctt tcctccaaca gtgctttcag gtgtgacccg    60
ctgtcttctc gcccacgttg ttttgggggg tcactggagg ctccc    105

<210> SEQ ID NO 113
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Glu Glu Asp Arg Glu Lys Tyr Arg Trp Met Ala Pro Phe Val Pro Gly
1               5                   10                  15

Gln Val Trp Thr Trp Glu Tyr Phe Leu
            20                  25

<210> SEQ ID NO 114
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
gaagaggaca gagaaaaata taggtggatg gctccatttg ttccaggcca agtgtggaca    60
tgggagtatt tcctc                                                    75

<210> SEQ ID NO 115
<211> LENGTH: 79
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Leu Lys Gln Asp Val Arg Ser Gly Gly Pro Gly Ala Arg Gln Leu Arg
1               5                   10                  15

Gly Gly Leu Leu Arg Gln Ala Ala Pro Pro Gly Arg Arg Thr Arg Pro
            20                  25                  30

Phe Pro His Arg Ala Arg Leu His Thr Ala Leu Pro Thr Ala Arg Leu
        35                  40                  45

Pro Gly Gly Pro Ala Ala Ala Ser Arg Pro Ala Phe Arg Ala Ala Pro
    50                  55                  60

Arg Glu Ser Gly Ala Ser Val Pro Gly Pro Ser Ala Ser Pro Gly
65                  70                  75

<210> SEQ ID NO 116
<211> LENGTH: 237
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116
ttgaaacagg acgtccgctc ggggggggccg ggcgcccggc agctacgtgg gggcctgctt    60
cgacaggctg ctccacccgg acgccgtacc cgcccttttc cgcaccgtgc ccgtcttcac   120
actgccctcc caactgccag acttcctggg ggccctgcag cagcctcgcg ccccgcgttc   180
cgggcggctc caagagagag cggagcaagt gtcccgggcc cttcagccag ccctgga      237

<210> SEQ ID NO 117

<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr His Ser Ala Glu Glu Ile Gly Gln Glu Tyr Phe Leu Arg Pro Arg
1               5                   10                  15

Thr Pro Asp Met Arg Trp Gly Lys Ser
            20                  25

<210> SEQ ID NO 118
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
actcattctg ctgaggaaat agggcaagaa tatttctaa gaccccgaac tccagatatg    60
cgatggggca aatcc                                                   75

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Asp Pro Ala Lys Val Val Glu Ile Pro Arg Leu Leu
1               5                   10

<210> SEQ ID NO 120
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ggggatccag ccaaggtcgt cgagatcccg aggcttttg                         39

<210> SEQ ID NO 121
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Arg Ser Trp Ile Ser Thr Thr Ser Thr Pro Met Thr Ser Met Phe Ser
1               5                   10                  15

Pro Arg Pro Leu Val Ser Val Ser Pro Thr Pro Ser Ala Thr Gly Arg
            20                  25                  30

Asn Leu Ala Ser Ser Ser His Glu Thr Ser Ala Ala Ile Gln Trp Leu
        35                  40                  45

Ile Asn Cys Cys Val Val
    50

<210> SEQ ID NO 122
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
cggtcctgga tctccaccac cagcactccg atgacctcca tgttctctcc aaggcctctc    60
gtatctgtga gccccacccc cagcgctaca ggtaggaatc tggcttccag ctcccatgaa   120
acgtcggctg ccattcagtg gctgattaat tgctgtgtgg tc                      162

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Arg Ser Leu Asp Asp Leu Glu Lys Leu Asp Thr Leu Cys Cys Lys
1               5                   10                  15

Leu Ser Val His Val Thr
            20

<210> SEQ ID NO 124
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
actcgctccc ttgatgatct tgagaaattg gacaccttgt gctgtaagct gtccgtccat    60
gttaca                                                               66

<210> SEQ ID NO 125
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Thr Ala Trp Arg Ala Ala Arg Ile Arg Ala Pro Gly Pro Gly Ser
1               5                   10                  15

Ser Arg Lys Gly Phe Val Ala Val Tyr Ser Leu Ser Phe Lys Asn Gly
            20                  25                  30

Lys Ser Ala Glu Val Ser Gln Arg Gln Ile Ser Ile Thr
        35                  40                  45

<210> SEQ ID NO 126
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
gccacggcgt ggagagcggc aagaatccgc gctcctggtc caggctccag cagaaaagga      60
tttgtggcag tttacagttt atcttttaaa aatgggaaaa gtgcagaagt gagccaaagg     120
caaataagta taacg                                                      135
```

<210> SEQ ID NO 127
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Lys Gln Tyr Gln Leu Thr Val Gln Met Glu Ser His Ser Leu Pro Gln
1               5                   10                  15

Ala Gly Val Gln Trp His Asp Phe Val Ser Pro Gln Pro Leu Pro Pro
            20                  25                  30

Gly Phe Lys Arg Phe Ser Cys Leu Ser Phe Leu Ser Ser Trp Asp Tyr
        35                  40                  45

Arg Leu Gln Pro Pro His Leu Ala Asn Phe Phe Val Phe Leu Val Glu
    50                  55                  60

Thr Gly Phe His His Val Gly Gln Ala Gly Leu Lys Leu Leu Thr Ser
65                  70                  75                  80

Asp Asp Leu Pro Ala Ser Ala Ser Gln Ser Ala Gly Ile Thr Gly Val
                85                  90                  95

Ser His His Ala Arg Pro Asn Phe Phe Phe Ser Leu Leu Leu Ser
            100                 105                 110
```

<210> SEQ ID NO 128
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
aagcaatatc aactaactgt gcagatggag tctcactctc ttccccaggc tggagtgcaa      60
tggcacgatt tcgtctcacc gcaacctctg cctcctgggt tcaagcgatt ctcctgcctt     120
agctttctga gtagctggga ttacaggctc cagccaccac acctggctaa tttttttgtg     180
tttttagtag agacagggtt tcaccatgtt ggccaagctg gtctcaaact cctgacctca     240
gatgatctgc ctgcctcggc ctcccaaagt gctgggatta caggtgtgag ccaccacgcc     300
cggccaaact ttttttttc ccttctcctg tct                                   333
```

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Ile Gly Lys Gly Ser Phe Gly Lys Phe Leu Glu Asp Ala Thr His Met
1               5                   10                  15

Val
```

<210> SEQ ID NO 130
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
attgggaagg gcagctttgg caagtttta gaagatgcaa ctcacatggt a            51

<210> SEQ ID NO 131
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Lys Thr Ala Ile Gly Ile Lys Thr His His Gly Cys
1               5                   10

<210> SEQ ID NO 132
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aagaaaacag caataggcat aaagactcac cacggatgt                         39

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Tyr Leu Gln Leu Ser Leu Glu Glu Cys Thr Gln Lys Cys Leu Phe Cys
1               5                   10                  15

Leu

<210> SEQ ID NO 134
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tatttgcaac tcagcctaga agagtgcaca cagaaatgtc ttttctgcct t           51

<210> SEQ ID NO 135
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Leu Leu Leu Ala Gly Leu Ala Gln Val Met Ala Pro Lys Pro Pro Phe
1               5                   10                  15

Ala Met Phe Glu Gln Arg His Ala Phe Leu Tyr Ile Phe Ile Ala Glu
                20                  25                  30

Pro Lys Ala Gln Pro Gly Thr Val Arg Glu Thr Val Ser Leu His Ala
            35                  40                  45

Ser Ser Arg Arg Arg Leu Asn Phe Pro Leu Leu Phe Ala Lys Cys Ala
        50                  55                  60

Lys Ser Pro Trp Lys Asn Glu Phe
65                  70

<210> SEQ ID NO 136
<211> LENGTH: 216
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
cttctgcttg ctggcctggc acaggtaatg gcaccgaagc ctcctttcgc tatgtttgaa      60
cagcgccacg ctttcctata tattttata gcagagccta aggcacagcc tggcacagtg     120
cgggaaacag tgtctctcca tgccagctcc aggcggaggc tcaactttcc attgctgttt    180
gcaaaatgtg caaagagccc ctggaaaaac gaattt                              216

<210> SEQ ID NO 137
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Asp Ser Asp Phe Arg Gln Arg Ser Leu Thr Leu Leu Pro Ser Leu
1               5                   10                  15

Glu Trp Asn Gly Thr Ile Leu Ala His Ser Asn Leu Gln Leu Pro Gly
                20                  25                  30

Ser Arg Asp Ser Pro Ala Ser Ala Gly Ile Arg Val Ala Arg Ile Arg
            35                  40                  45

Ser Thr His His His Ala
        50

<210> SEQ ID NO 138
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gctgattcag actttagaca aaggagtctc actctgttgc ccagcctgga gtggaatggc      60
accatcttgg ctcacagcaa cctccaactc ccgggttcaa gagattctcc tgcctcagct    120
gggattagag tagctaggat tagaagcaca caccaccacg cc                       162

<210> SEQ ID NO 139
<211> LENGTH: 68
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 139

```
Glu Met Val Asp Glu Pro Pro Gly His Arg Ser Thr Gly Ser Gln Gly
1               5                   10                  15

Arg Arg Ile Phe Leu Ser Thr Glu Gln Asn Glu Lys Ser Pro Met Ser
            20                  25                  30

Thr Ser Phe Tyr Thr Asp Thr Ala Thr Ile Arg Phe Leu Asn Leu Phe
        35                  40                  45

Pro Thr Cys Pro Pro Phe Leu Phe His Lys Thr Ala Ile Val Ile Met
    50                  55                  60

Ala Arg Ser Gln
65
```

<210> SEQ ID NO 140
<211> LENGTH: 204
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
gagatggtgg atgaaccccc aggtcacaga tcaacaggat cccaaggcag aagaattttt    60
cttagtacag aacaaaatga aagtctccc atgtctacct ctttctacac agacacggca    120
accatccgat ttctcaatct tttccccacc tgtccccct ttctattcca caaaaccgcc     180
attgtcatca tggcccgttc tcaa                                           204
```

<210> SEQ ID NO 141
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

```
Glu Ala Val Ala Lys His Pro Gly Val Gln Pro Tyr Tyr Ile Leu His
1               5                   10                  15

Arg Ser Glu Ile Ile Gln Tyr Leu Ser Val Ser Val Met Phe His Ser
            20                  25                  30

Ala
```

<210> SEQ ID NO 142
<211> LENGTH: 99
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142

```
gaggcagtag ccaaacaccc aggagtccaa ccttattata ttctccatag aagtgagatc    60
atacagtatt tgtctgtttc tgtgatgttt cactcggca                           99
```

<210> SEQ ID NO 143
<211> LENGTH: 11
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 143

His Glu Met Val Thr Glu Pro Pro Gly Leu Gln
1               5                   10

<210> SEQ ID NO 144
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
catgagatgg taactgaacc cccaggttta cag                                    33

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Val Leu Thr Val Thr Ser Thr Asp Gln Glu Tyr Leu Asp Leu Ser Ala
1               5                   10                  15

Pro

<210> SEQ ID NO 146
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
gtccttaccg tgacgtccac cgaccaggag tacctggacc tgtcggcgcc t                51

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Lys Arg Leu Thr Val Ala Pro Pro Gly Lys His Phe Phe Leu Gly Cys
1               5                   10                  15

Met

<210> SEQ ID NO 148
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148

```
aaaaggttaa ccgtggctcc accaggtaaa cattttttcc ttgggtgcat g              51
```

<210> SEQ ID NO 149
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Thr Met Thr Leu Cys Leu Gly Gly Glu Arg Arg Ala Arg Leu Gly Cys
1               5                   10                  15

Gly Gly Gly Gly Ala Gly Pro Arg Val Arg Gly Gly Trp Phe Leu Gly
            20                  25                  30

Arg Thr Asp Gln Asp Leu Gly Trp Gly Leu Ala Phe Arg Lys Gly Val
        35                  40                  45

Glu Tyr
    50
```

<210> SEQ ID NO 150
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

```
acaatgacgc tgtgtctggg cggtgagcgc agggcccgtc tgggctgcgg gggaggcggg     60
gctggaccca gagtaagagg tggctggttt ctgggcagga ctgaccagga tctgggttgg    120
gggttggcgt ttaggaaggg ggtcgagtac                                     150
```

<210> SEQ ID NO 151
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

```
Arg Lys Leu Glu Ser Arg Lys Tyr Gly Ile Ser Phe Leu Ser Phe Asp
1               5                   10                  15

Cys Ala Leu Phe Ser Met His Phe Leu Leu Ile Ser Leu His Ile Lys
            20                  25                  30

Trp Ser Leu Glu Lys Asn Gln Ile Ser
        35                  40
```

<210> SEQ ID NO 152
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152

```
aggaaattag aatcaaggaa atacggtatt ccttcctgt cttttgactg tgccctgttt      60
tctatgcact tcttctgat ttctttgcat ataaatggt cactggaaaa gaatcaaatt     120
tct                                                                  123
```

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Lys Gln Arg Ile Ser Arg Gly Lys Gln Pro Ala
1               5                   10

<210> SEQ ID NO 154
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gagaagcaga ggatcagccg gggtaagcaa cctgcc                                36

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Val Glu Met Lys Glu Asp Ser Gly Ile Lys Phe Ile Leu Leu Leu
1               5                   10                  15

Leu Gly Gly Arg
            20

<210> SEQ ID NO 156
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gatgttgaaa tgaaagaaga ttcaggtatt aaattcatac ttttattatt aggggggtagg    60

<210> SEQ ID NO 157
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Ile Val Lys Asn Met Pro Thr Val Ser Ser Gln Ser
1               5                   10

<210> SEQ ID NO 158
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 158
agcatcgtca aaaacatgcc aactgtgagt agccagtca                                39

<210> SEQ ID NO 159
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Cys Val Glu Glu Arg Gly Tyr Glu Val Gly Ala Ser Pro Phe Ser Ser
1               5                   10                  15

His His Cys Ser Leu Phe Cys Ser Leu Gly Phe Lys Ser Leu Gly Pro
            20                  25                  30

Leu Gln Phe Ser Phe Asn Asn Lys Ile Gln Gln Trp Pro Cys Ile Ser
        35                  40                  45

Leu Phe Ser His Cys Tyr Lys Glu Leu Pro Glu Thr Gly
    50                  55                  60

<210> SEQ ID NO 160
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
tgtgtggagg aacgtggcta tgaggtgggg gcttctccct tctcctccca tcactgttcc       60
cttttttgct ctttggggtt caagtctcta gggcctttac aatttcatt taataataag       120 atacaacagt ggccttgtat tagtctgttt tcacactgct ataaagaact acctgagact      180
ggg                                                                    183

<210> SEQ ID NO 161
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Leu Lys Val Gly Met Arg Arg Glu Gly Ile Gly Leu Ser Phe Leu Leu
1               5                   10                  15

Pro Ser Ser Trp Val Pro Gly Ser Trp Val Arg Leu Ala Ser Leu Leu
            20                  25                  30

Trp Val Arg Thr Arg Ser Pro Lys Leu Phe Ser Ser Tyr Cys Ser Gly
        35                  40                  45

Lys Gly Phe Tyr Thr Arg Ser Glu Phe Cys Ile Gly Thr Gln Thr Pro
    50                  55                  60

Asn Pro His Ala Leu Ala Asp
65                  70

<210> SEQ ID NO 162
<211> LENGTH: 213
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 162

```
ctcaaagtgg gcatgagacg ggaaggtatc ggcctctcat ttctccttcc ctcgtcctgg      60
gtcccggggt cctgggtacg tttgctagc ctgctctggg taaggacaag aagccccaag     120
ctcttctctt cgtattgcag cggaaaaggg ttttatacta gaagcgagtt ctgcattgga    180
acccagaccc caaatccgca tgctttggcc gac                                  213
```

<210> SEQ ID NO 163
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 163

```
Leu Glu Gly Glu Met Leu Tyr Leu Val Asn Gly Val Gly Ala Gly Cys
1               5                   10                  15

Leu Gly Glu Gly Pro Pro Ala Ile Arg His Pro Leu Val Gln Thr Arg
            20                  25                  30
```

<210> SEQ ID NO 164
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 164

```
ctggagggag agatgctgta tctggtaaat ggggtggggg ctgggtgtct gggagaaggg      60
cctccagcta taaggcatcc ccttgtccaa accaga                                96
```

<210> SEQ ID NO 165
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

```
Arg Asn Ser Leu Lys Thr Lys Val Thr Asp Ser Thr Gln Arg Glu Gly
1               5                   10                  15

Gly Phe Leu Met Gln Lys Gly Arg Glu
            20                  25
```

<210> SEQ ID NO 166
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166

```
aggaacagcc tgaagaccaa ggtgacagac tccacccagc gagaggggg attccttatg      60 caaaagggga gggaa                                                      75
```

<210> SEQ ID NO 167

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Glu Leu Gln Asp Ser Phe Tyr Ala Gly Thr Thr Leu Pro Tyr Leu
1               5                   10                  15

<210> SEQ ID NO 168
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gagctccaag actcgttcta tgcaggtact accctcccat atcta                    45

<210> SEQ ID NO 169
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Gln Asn Asn Tyr Leu Gln Ser Gly Thr Lys Leu Ile Asn Lys Lys
1               5                   10                  15

Asn Tyr Val Ile Tyr Val Ser Trp
            20

<210> SEQ ID NO 170
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gatcaaaata attatctaca gtcaggtaca aagttaatta ataaaaaaaa ctatgtcata    60
tatgtaagtt gg                                                        72

<210> SEQ ID NO 171
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Leu Ala Ser Leu Glu Glu Gln Val Gly Pro Arg Ser Gly Pro Pro Ser
1               5                   10                  15

Gly Gly Ala Thr Ala Gly Pro Gly Gly Arg Leu Cys His Val Val Ala
            20                  25                  30

Pro Arg Arg Arg Ala Leu Arg Ser Asp Gly Glu Glu Glu Ala Gly Thr
        35                  40                  45

Leu Gly Gln Pro Phe Pro Ala Gly Arg Gly Thr Leu Cys Val Leu Gln
    50                  55                  60
```

Lys Thr Pro Pro Lys Gly Phe Cys Asp
65                  70

<210> SEQ ID NO 172
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
ttggcctccc tggaggagca ggtgggtccg aggtcggggc ctccgtcagg aggtgccact      60
gctgggcctg gtgggcggct ctgccatgtg gtggcaccaa gaaggagggc tctgaggagt     120
gatggtgagg aggaggccgg aacgttgggg cagccattcc cagctggaag aggcaccctg     180
tgtgtcctcc agaaaacccc gcccaagggt ttctgtgac                           219

<210> SEQ ID NO 173
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Ala Ala Gly Ser Arg Thr Pro Gly Gly Pro His Pro His Arg Gln
1               5                   10                  15

His Arg Leu Leu His
            20

<210> SEQ ID NO 174
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gccgccgcgg gcagccggac cccaggcggg cctcatccgc acagacagca ccgacttctt      60
cat                                                                   63

<210> SEQ ID NO 175
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Lys Ala Met Tyr His Ala Leu Glu Arg Thr Arg Leu Glu Asp Ala Gln
1               5                   10                  15

Leu Thr Thr Gln Pro Pro Leu Thr Thr Ala Pro His Pro Ser Ala Ser
            20                  25                  30

Arg Gln Ile Ala Ile Thr Thr Ala Lys Thr Glu Gly Met Lys Ile Arg
        35                  40                  45

Ala Glu Asn Lys Trp Leu Gln Met Leu Pro Thr Thr Arg Ala Ala Trp
    50                  55                  60

Lys Met Ala Val Cys Leu Val Ala Gly Lys Thr Pro Cys Pro Ser Thr

```
            65                  70                  75                  80
Leu Ser Leu Arg Gly Gly Ser Val Arg His Ala Gly Ile Ala Ser Leu
                85                  90                  95

Ser Cys Phe Thr Cys Met Met Thr Met Ala Ile Ser Leu Thr Ala Leu
                100                 105                 110

Cys Ala Ala Arg Ala Glu Ser Cys Cys Phe Ala Ala Thr Arg Ala Ala
                115                 120                 125

Ala Gly Val Ser Val Trp Ser Ala Trp Arg Cys Trp Trp Ala Gln Ala
130                 135                 140

Gln Arg Pro Arg Pro Ser Phe Arg Ser Pro Gly Ala Val Thr Cys Val
145                 150                 155                 160

Ser Arg Ser Ala Val Met Ala Ser Cys Gly Ala Gly Arg Thr Gly Thr
                165                 170                 175

Cys Ala Cys Arg Pro Ser Ser Pro Val Thr Arg Gly Leu Asn Met Lys
                180                 185                 190

Pro Pro Ser Cys Thr Leu Pro Phe Pro Gln Pro Glu Gly Gly Pro Phe
                195                 200                 205

Glu Ser Cys His Cys Leu Met Ala Ser Arg Gln Ala Thr
    210                 215                 220

<210> SEQ ID NO 176
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
aaagccatgt accatgctct ggagagaaca agactcgaag acgcacagct gacgactcag    60
ccacctctga ctactgcccc gcacccaagc gcctcaagac aaattgctat aacaacggca   120
aagaccgagg ggatgaagat cagagccgag aacaaatggc ttcagatgtt gccaacaaca   180
agagcagcct ggaagatggc tgtttgtctt gtggcaggaa aaaccccgtg tccttccacc   240
ctctctttga ggggggctc tgtcagacat gccgggatcg cttccttgag ctgttttaca   300
tgtatgatga cgatggctat cagtcttact gcactgtgtg ctgcgagggc cgagagctgc   360
tgctttgcag caacacgagc tgctgccggt gtttctgtgt ggagtgcctg gaggtgctgg   420
tgggcacagg cacagcggcc gaggccaagc ttcaggagcc ctggagctgt acatgtgtc    480 tcccgcagcg ctgtcatggc gtcctgcggc gccggaagga ctggaacgtg cgcctgcagg   540
ccttcttcac cagtgacacg gggcttgaat atgaagcccc caagctgtac cctgccattc   600
ccgcagcccg aaggcggccc attcgagtcc tgtcattgtt tgatggcatc gcgacaggct   660
acc                                                                 663

<210> SEQ ID NO 177
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Ala Ser Gly Val Pro Pro Pro Gly Leu Pro Trp Gly Pro Gly Pro
1               5                   10                  15

His Leu Gly
```

<210> SEQ ID NO 178
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ctggcttcgg gcgtgccccc tcctggtctt ccctgggggc cgggtcctca ccttggc        57

<210> SEQ ID NO 179
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ile Pro Pro His Leu Gln Trp Glu Ser Thr Arg Gln Thr Glu Trp Ile
1               5                   10                  15

Ser Val Arg Glu Phe His Leu Glu Ser Ser Leu Tyr Pro
            20                  25

<210> SEQ ID NO 180
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
atcccgcctc atttacagtg ggagagcact agacaaactg aatggatttc agttagagaa     60
tttcaccttg aaagtagcct atatccc                                         87

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Pro Gly His Gly Ala Ile Cys Arg Glu Glu Val
1               5                   10

<210> SEQ ID NO 182
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cctgggcacg gggccatttg tagggaagag gtt                                  33

<210> SEQ ID NO 183
<211> LENGTH: 20
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 183

Leu Glu Glu Glu Phe Ile Ser Glu Trp Arg Arg Cys Leu Leu Cys Ser
1               5                   10                  15

Tyr Leu Gln Trp
            20

<210> SEQ ID NO 184
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cttgaagaag aatttatttc agagtggcgt agatgtttac tatgcagtta ccttcaatgg        60

<210> SEQ ID NO 185
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gln Thr Gln Glu Glu Thr Asp Arg Asp Arg Gly Ser Trp Ser Cys Ala
1               5                   10                  15

Val Ala

<210> SEQ ID NO 186
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cagacccagg aagagactga ccgtgacagg ggatcctgga gctgtgctgt ggct             54

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser His Ala Leu Asn Trp Asn Lys Ile Gly Arg Met Phe Arg Ala Ser
1               5                   10                  15

Arg Val

<210> SEQ ID NO 188
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tcccacgccc tcaactggaa caagataggc agaatgtttc gagcttccag agtc    54

<210> SEQ ID NO 189
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Ser Asn Lys Asp Leu Ala Gln Asp Cys Glu Leu Tyr Thr Arg Phe
1               5                   10                  15

Ala Lys Arg Cys Cys
            20

<210> SEQ ID NO 190
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gactccaaca aggatcttgc ccaggattgt gaattataca ccagatttgc caagagatgc    60
tgt    63

<210> SEQ ID NO 191
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Thr Met Glu Val Lys Ser Lys Lys Lys Gln Thr Thr Val Pro Leu
1               5                   10                  15

Val Gln Thr Arg
            20

<210> SEQ ID NO 192
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ggcactatgg aggtgaagag caagaagaag cagactacag tgcctttggt acagacacgc    60

<210> SEQ ID NO 193
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Leu Leu Phe Pro Tyr Asn Gln Leu Asp Leu His Leu His Arg Pro Ser
1               5                   10                  15

Gly Ser Arg Lys Asn Glu Ile His Trp Asp Lys Cys Phe Ser Ser Glu
            20                  25                  30

Asp

<210> SEQ ID NO 194
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ttattgtttc cttataatca gctggactta cacttgcata gaccttctgg atctcgtaag      60
aacgaaatac actgggacaa atgtttctct tcagaggat                            99

<210> SEQ ID NO 195
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Phe Ile Leu Ile Gly Trp Gly Ala Gly Asn Leu Val Leu Glu Thr
1               5                   10                  15

Ser Ser Gly Phe Ile Lys His Arg Ser
            20                  25

<210> SEQ ID NO 196
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ggcttcatct tgataggctg gggtgctggg aacttagtgc tggagacatc aagtggattt      60
atcaagcacc gatct                                                      75

<210> SEQ ID NO 197
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

His Phe Val Arg Ser Gln Asp Lys Gly Met Val Trp Thr Pro Glu Pro
1               5                   10                  15

Ser Ala Leu Pro Arg Thr Pro Arg Arg His Pro Gly Leu Ser Leu Cys
            20                  25                  30

Ser Gln Trp Gly Gly Leu Arg Val Gly Pro Pro Ala Ala Arg Pro Gly
        35                  40                  45

Trp Ser Leu Ala His Val Leu Arg Val Thr Leu Leu Gln Phe His Pro
    50                  55                  60

Asn Pro Gly Lys Glu Thr Gln Lys Lys Gln Arg Cys Pro Lys Glu Asp
65                  70                  75                  80

Pro Ser Arg Ile Trp Arg Ala
                85

<210> SEQ ID NO 198
<211> LENGTH: 261
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
cactttgtcc gttcccagga caagggaatg gtatggaccc cggagccctc tgctctgccc      60
agaacgccaa gaagacatcc tggactctct ctatgctctc aatggggtgg ccttcgagtt     120
ggacctccag cagccagacc tggatggagc ctggcccatg ttctcagagt cacgctgctc     180
cagttccacc caaacccagg gaaggagacc cagaaaaaac aaagatgccc caagaagat     240 cccagccgca tatggagggc c                                              261

<210> SEQ ID NO 199
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Asn Ile Glu Asp Val Ala Thr Glu Asp Gly Arg His Gly Gly Cys His
1               5                   10                  15

His Gly Pro Gly Arg
            20

<210> SEQ ID NO 200
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
aacattgagg atgtggccac agaagatggg aggcatggag gctgtcatca cgggcctggc      60
aga                                                                   63

<210> SEQ ID NO 201
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Arg His Gly Glu Val Gln Gly Leu Leu Glu Arg Glu Lys Thr Ala
1               5                   10                  15

Arg Gly Asn Pro Ser Gly
            20

<210> SEQ ID NO 202
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
aggaggcatg gagaagttca gggattgctt gaaagagaaa aaacagcaag aggaaaccct    60
agtgga    66

<210> SEQ ID NO 203
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Leu Ser Asp Lys Glu Val Glu Gly Lys Ala Leu Leu Gly Asp Ile
1               5                   10                  15

Lys Leu Val Ile Thr Leu Ser Asp Glu
            20                  25

<210> SEQ ID NO 204
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tccttgagtg ataaagaagt agagggaaag gcactcctag gggacataaa attagtgatt    60
actttgagcg acgag    75

<210> SEQ ID NO 205
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Val Leu Arg Lys Thr Ala His Arg Ser Thr Thr Ala Arg Cys Ser Cys
1               5                   10                  15

Pro Pro Trp Leu Thr Cys Trp Pro Arg Val Ala Ala Pro Gly Ala Leu
            20                  25                  30

Ser Thr Val Ala Arg Glu Ala Ser Trp Trp Leu Leu Thr Thr Glu Val
        35                  40                  45

Val

<210> SEQ ID NO 206
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
gtgctgcgga aaaccgccca cagatcaact actgctcggt gctcgtgtcc tccgtggctg    60
acgtgctggc ccagggtggc ggcccccgga gctctcagca ctgtggcgag ggaagccagc    120
tggtggctgc tgaccacaga ggtggtt    147

<210> SEQ ID NO 207
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Met His Arg Lys Leu Gln Ala Arg Ser Pro Ser Leu Cys Thr Gly His
1               5                   10                  15

Pro Pro Gln Ala Ala
            20

<210> SEQ ID NO 208
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
atgcacagga aactgcaggc cagaagcccc tctctgtgca caggccaccc acctcaggct      60
gcc                                                                  63

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Leu Leu Asp Leu Gln Ala Lys Met Ile Tyr Phe Lys Asn Ser Glu Asn
1               5                   10                  15

<210> SEQ ID NO 210
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ctgcttgatc ttcaggccaa aatgatatat tttaagaatt cagagaat                 48

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Ile Ser Leu Thr Asp Asp Glu Ala Glu Leu Pro Leu Leu Asp Leu
1               5                   10                  15

<210> SEQ ID NO 212
<211> LENGTH: 48
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 212
agcatatctt tgactgatga cgaagctgag ctgcccctcc tggacctg                 48

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Leu Pro Pro Leu Asp Ser Glu Ala Gln Val Pro Asp Ser Asp Glu
1               5                   10                  15

<210> SEQ ID NO 214
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tccctgccgc ccctcgactc tgaagctcag gtaccagaca gtgatgag                 48

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ala Pro Ser Cys Gly Val Ser Arg Ala Ile Cys Asp Arg Gly Cys His
1               5                   10                  15

<210> SEQ ID NO 216
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gctcccagct gcggggtgag ccgagccatc tgtgaccgcg gctgccac                 48

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Pro Ser Cys Gly Val Ser Arg Asp Tyr Arg Thr Gly Pro Cys Phe
1               5                   10                  15

<210> SEQ ID NO 218
<211> LENGTH: 48
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 218
gctcccagct gcggggtgag ccgagattac cggacgggac cctgctttt                48

<210> SEQ ID NO 219
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Leu Ser Pro Gly Gly Ala Cys Val Asp Ile Asp Glu Cys Asp Arg Gln
1               5                   10                  15

<210> SEQ ID NO 220
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ctgtcgccag gcggggcttg tgtggacatt gacgagtgtg accggcag                 48

<210> SEQ ID NO 221
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Met Pro Gly His Gly Ala Ile Cys Ser Gly Ser Ser Arg Gln Pro Asp
1               5                   10                  15

<210> SEQ ID NO 222
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
atgcctgggc acggggccat ttgtagtggc tccagcaggc agcctgac                 48

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Val Gln Lys Leu Lys Asn Ala Arg Ser Leu Asn Leu Glu Asp Gln Ile
1               5                   10                  15

<210> SEQ ID NO 224
```

```
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gtccagaagc ttaaaaatgc cagaagcctg aacttggagg accaaatt              48

<210> SEQ ID NO 225
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asn Pro Lys Lys Phe Lys Ile Asn Ser Arg Val Leu Val Glu Asp Asp
1               5                   10                  15

<210> SEQ ID NO 226
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
aatccaaaga agttcaagat caactccaga gtcctggtgg aggacgat              48

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Arg Lys Pro Arg Asn Trp Leu Glu Arg Ala Arg Trp Leu Arg Gly Ile
1               5                   10                  15

<210> SEQ ID NO 228
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
cgaaagccaa ggaactggct ggagagggct cgatggctcc ggggaatc              48

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asp Glu Ala Lys Phe Ile Pro Arg Ala Gln Asp Lys Ala Ala Met Gln
1               5                   10                  15
```

<210> SEQ ID NO 230
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gacgaagcca agttcattcc cagagcccag gacaaggcag ctatgcag            48

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Leu Gln Ala Gln Gln Gln Val Gln Val Ser Ala Gln Arg Ala Thr Pro
1               5                   10                  15

<210> SEQ ID NO 232
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ctgcaggccc agcagcaggt ccaggtgtca gcacagcggg ctactcct             48

<210> SEQ ID NO 233
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Leu Arg Pro Ser Leu Ser Leu Ala Ser Arg Gly Phe Gln Asn Pro
1               5                   10                  15

<210> SEQ ID NO 234
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tgtctccggc ccagcctgag cctggcctcc aggggcttcc agaacccg              48

<210> SEQ ID NO 235
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asn Tyr Gly Asn Leu Phe Ser Leu Ala Gly Ser Leu His Phe Thr Ala

<210> SEQ ID NO 236
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
aactacggaa acctgttctc cttggctggc tctttgcatt ttactgca    48

<210> SEQ ID NO 237
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 237

Val Glu Asp Glu Glu Lys Lys Glu Pro Asp Gly Ala Gln Arg His Leu
1               5                   10                  15

Val Asp Ile Gly Gly Ser His Gln Thr Ser His Ala Glu Lys Phe Leu
            20                  25                  30

Phe Leu Leu Cys Pro Pro Val Val
        35                  40

<210> SEQ ID NO 238
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 238
gttgaagatg aggagaagaa agagcctgat ggagcccaac gccatctagt ggacattggt    60
ggttctcacc agaccagcca tgctgagaaa ttttttgttcc tcctctgccc tccagtggtc   120

<210> SEQ ID NO 239
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 239

Val Glu Asp Glu Glu Lys Lys Glu Ala Gly Thr His Phe Ile His Leu
1               5                   10                  15

Thr Gly Thr Thr Val Ser Ala Gly Val Pro Glu Glu Met Pro Ala Thr
            20                  25                  30

Thr Leu Arg Arg Glu Val Phe
        35

<210> SEQ ID NO 240
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 240
gttgaagatg aggagaagaa agaggcaggg actcatttca tccacctgac tggaaccact    60
gtctcagctg gagtccctga ggagatgcca gccacaactc tccgaagaga agtattc      117

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Val Glu Asp Glu Glu Lys Lys Glu Gly Leu Ile Ser Ser Thr
1               5                   10

<210> SEQ ID NO 242
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gttgaagatg aggagaagaa agagggactc atttcatcca cc                        42

<210> SEQ ID NO 243
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Val Glu Asp Glu Glu Lys Lys Glu Gly Ser Met Leu Val Ala Pro Thr
1               5                   10                  15

Ser Pro Pro Ser Leu Glu Ala Gly Thr His Phe Ile His Leu Thr Gly
            20                  25                  30

Thr Thr Val Ser Ala Gly Val Pro Glu Glu Met Pro Ala Thr Thr Leu
        35                  40                  45

Arg Arg Glu Val Phe
    50

<210> SEQ ID NO 244
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244
gttgaagatg aggagaagaa agagggcagc atgttggttg ctccaacttc tcctccatcc    60
ctggaggcag ggactcattt catccacctg actggaacca ctgtctcagc tggagtccct   120
gaggagatgc cagccacaac tctccgaaga gaagtattc                           159

<210> SEQ ID NO 245
<211> LENGTH: 34
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 245

Ser Met Met Glu Gly Val Ile Gln Leu Ser Phe Lys Ala Ile Val Cys
1               5                   10                  15

Leu Leu Ser Cys Leu Asp Leu Leu Ser Leu Phe Arg Val Val Arg His
            20                  25                  30

Leu Ser

<210> SEQ ID NO 246
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
agcatgatgg agggtgtcat ccagttgtca ttcaaagcca ttgtctgtct tctatcatgt    60
ttggacttac taagcctgtt tcgagttgtg agacacctat ca                      102

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Lys Lys Arg Lys Gln Ser Glu Leu Gln Gln Pro
1               5                   10

<210> SEQ ID NO 248
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
actaagaaaa gaaagcagag tgagctgcag cagcca                             36

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Phe Phe Lys Arg Ser Ile Gln Glu Leu Pro Thr Leu Cys
1               5                   10

<210> SEQ ID NO 250
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gccttcttca agagaagtat tcaagaactt ccaacactat gt        42

<210> SEQ ID NO 251
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Phe Gln Glu Thr Trp Leu Ala Glu Asp Ala Ala Gly Ala Leu Ser
1               5                   10                  15

Pro Cys Thr Ile Pro Thr Pro Pro Gln Pro Pro Leu Leu Ser Leu Pro
                20                  25                  30

Thr Ser Ser Gly Thr Arg Gln
        35

<210> SEQ ID NO 252
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
ttccaggaga cgtggctcgc tgaagatgca gctgccgggg ccctgtcccc ctgcaccatc        60
ccaacaccac cccagcctcc tctcctgtct cttcccacca gctcaggtac cagacag         117

<210> SEQ ID NO 253
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Ser Gln Glu Gln Ser Arg Thr Arg Ala Ile Phe Thr Phe Ile Leu Asp
1               5                   10                  15

Thr Lys Lys Lys Glu Ile Pro Val Glu Ala His Arg Lys Leu Leu Glu
                20                  25                  30

Gln Ser Cys Val Ser Tyr Leu Gln Arg Cys Arg Lys Asn Lys Pro Gly
        35                  40                  45

Thr Ser Ser Phe Leu Phe Leu Ser Ser Leu Thr Ile Leu Arg Ser Tyr
    50                  55                  60

Ala Thr Arg Ser Thr Phe
65                  70

<210> SEQ ID NO 254
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254
agccaggagc agagccggac ccgagctatc ttcacattta tccttgacac aaagaaaaaa        60
gaaatacctg tagaagcgca tcgaaagctc ctggaacaga gttgtgtctc atatttgcaa       120

```
agatgcagaa aaaataaacc cgggacatcc agctttcttt tcctttcttc tttgactatt    180
ctgagaagct atgcgactag gagcacattt                                      210
```

<210> SEQ ID NO 255
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Arg Leu Asp Asp Ser Gly Ile Gly Asn Phe Ile Thr Ser Leu Leu Asn
1               5                   10                  15

Phe Ile Ser Lys Phe Phe Cys Ser Phe Met Gly Ala
            20                  25

<210> SEQ ID NO 256
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256

```
cggttagatg acagtgggat tggtaatttt ataactagct tgttaaattt cataagtaaa    60
ttcttctgca gttttatggg tgca                                            84
```

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asn Ala Asn Ser Arg Leu Pro Glu Ala Cys Glu Lys
1               5                   10

<210> SEQ ID NO 258
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258

```
aatgctaaca gccggctgcc tgaggcctgt gagaag                               36
```

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Asp Gly Asp Gly Ile Phe Ser Pro Glu Leu Ser
1               5                   10

<210> SEQ ID NO 260

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gatggtgatg ggatattttc tcctgagctc tcc                                      33

<210> SEQ ID NO 261
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Met Ser Gln Glu Ser Asp Lys Asn Gly Leu Ser Ser Arg Ser Trp Met
1               5                   10                  15

Asn Thr Trp Ile Leu Pro Glu Val Leu
            20                  25

<210> SEQ ID NO 262
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
atgtcacaag agtcggacaa gaatggtctc agctcccgct cctggatgaa tacttggata        60
ttgccagagg ttttg                                                         75

<210> SEQ ID NO 263
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Leu Asp Leu Ala Gly Asn Ala Arg Pro Cys Arg Ser Gln Ser Pro Thr
1               5                   10                  15

Ser Ser Asp Gln Thr Pro Ser Val Pro Ser Leu Gly Ser Pro Glu Leu
            20                  25                  30

Pro Asp Gly Glu Glu Gly Gly Ser Pro Asp Gly Ser Pro Gln Glu Ser
        35                  40                  45

Glu Gln Val Arg Gln Gly Gln His Val
    50                  55

<210> SEQ ID NO 264
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
cttgaccttg ctgggaatgc tcggccctgc aggtctcagt cccccacaag cagtgatcaa        60
``` accccccagtg tgccaagcct aggatcccca gagctcccag atggtgaaga agggggatcc    120
ccagatggtt cacccccagga gagtgagcag gtcagacaag ggcagcatgt c              171

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Pro Arg Gly Arg Pro Arg Arg Lys Val Asp Val Leu Pro Gln
1               5                   10

<210> SEQ ID NO 266
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ccgcgcgggc gccccccgccg gaaggttgat gtgctacctc aa                         42

<210> SEQ ID NO 267
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Pro Ser Pro Ser Thr Pro Asn His Ser Gln Gln Ala Ile Cys His Pro
1               5                   10                  15

Gly Arg Arg Pro
            20

<210> SEQ ID NO 268
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cccagcccca gcaccccccaa ccacagccag caggcaatat gccaccctgg ccgacgtccc      60

<210> SEQ ID NO 269
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Ser Pro Ser Thr Pro Asn His Arg Pro Ser Gly Ser Ala Thr Glu Lys
1               5                   10                  15

Pro Ser Arg Trp Arg Glu Gly Gly Trp Ser Val Glu Leu Gly Pro Gly
            20                  25                  30

Ala Leu Ala Gly Arg Arg Trp Pro Val Cys Leu Ala Thr Ser Gly Gly

Gly Pro Arg
    50

<210> SEQ ID NO 270
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 270
agccccagca cccccaacca caggccatca ggatcagcca ccgagaagcc ttccaggtgg     60
agagaaggcg gctggagcgt agaactcggg cccggagccc tggcagggag gaggtggccc    120
gtctgtttgg caacgagcgg aggaggtccc agg                                 153

<210> SEQ ID NO 271
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ser Gly Cys Arg Leu Thr Leu Leu Ser Leu Ser Pro Val Ser Ser Leu
1               5                   10                  15

Gly Cys Pro Val Pro Met Pro
            20

<210> SEQ ID NO 272
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tctggctgca gactgacttt gctcagcttg tcacctgtct caagtctagg ctgtcctgtc     60
cccatgcca                                                            69

<210> SEQ ID NO 273
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ser Gln Phe Ser Leu Asp Asp Val Gly Phe Leu Ala Arg Gly Gln Ala
1               5                   10                  15

Arg Val Trp Pro Ser Arg Leu Gln Ala Leu Leu Ser Thr
            20                  25

<210> SEQ ID NO 274
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tcccagtttt ctctggatga cgtggggttt cttgcacggg ggcaggcaag ggtgtggccg    60
tctcgactcc aggccctgct ttccaca                                        87

<210> SEQ ID NO 275
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Cys Pro Cys Glu Tyr Leu Arg Lys Ile Gln Val Asp Gly Arg Met Ala
1               5                   10                  15

Thr Trp Met

<210> SEQ ID NO 276
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tgcccatgcg agtacctgag gaagatacag gttgatggac ggatggctac atggatg      57

<210> SEQ ID NO 277
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Pro Cys Glu Tyr Leu Arg Lys Val Glu Phe Val Pro Glu Pro His Lys
1               5                   10                  15

Ile Ile Thr Ser Met Ile Lys Arg Ser Arg Leu Gln Lys Lys Gln Phe
            20                  25                  30

Gly Arg Met
        35

<210> SEQ ID NO 278
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278
ccatgcgagt acctgaggaa ggtggagttt gtcccagagc cgcacaaaat catcaccagc    60
atgattaaac ggagtagact tcagaaaaag cagtttggtc ggatg                   105

<210> SEQ ID NO 279
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Trp Leu Leu Arg Thr Trp Glu Arg Ala Asp Ser Gly Leu
1               5                   10

<210> SEQ ID NO 280
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tggctcctgc gcacctggga gagagctgac agtggcctt                              39

<210> SEQ ID NO 281
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Pro Asp Leu Gly His Trp Leu Thr Arg Ala Val Trp Gly Asn Ser Ala
1               5                   10                  15

Thr Ser

<210> SEQ ID NO 282
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
cctgacctcg gccactggct caccagagcc gtgtggggga attcagccac ctcc            54

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Thr Ile Lys Leu Ile Val Gly Arg Thr Ser Ala Leu Gly Gln Tyr
1               5                   10                  15

<210> SEQ ID NO 284
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
actattaaat taatagtggg aaggacctca gctttgggtc agtat                      45

<210> SEQ ID NO 285
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 285

Phe Ile Gln Leu Arg Lys Glu Leu Asn Phe Thr Ser Thr Pro Asp Ala
1               5                   10                  15

<210> SEQ ID NO 286
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tttattcaac ttagaaaaga attgaacttt accagcaccc cagatgct                   48

<210> SEQ ID NO 287
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Glu Glu Glu Glu Glu Glu Glu Pro Leu Arg Leu His Arg Gly Pro
1               5                   10                  15

Glu Ala Ala Gly Val Gly Leu Ser Gly Pro Gln Trp Gly Arg Pro Gly
                20                  25                  30

Val Thr Ser Ser Pro Asn Pro Ser Ser His Ser Leu Val Leu Cys Pro
            35                  40                  45

Ala Thr Thr Gly Pro Cys Val Arg Leu Gly
        50                  55

<210> SEQ ID NO 288
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288
gaagaggagg aggaagaaga agagcccctt cgactccacc ggggccctga ggcggctggg      60
gtggggctgt ctgggcccca gtgggggaga cctggggtca ccagctcccc caacccttcc    120
tcgcactcgc tggtactatg ccctgccacc acaggcccct gtgtccgtct ggga           174

<210> SEQ ID NO 289
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Phe Gln Val Leu Pro Gly Asp Arg Glu Thr Gly Phe His His Val Gly
1               5                   10                  15

Gln Thr Gly Leu Glu Phe Leu Thr Ser Ser Asp Pro Pro Thr Ser Ala
                20                  25                  30
```

Ser Gln Ser Ala Gly Ile Thr Gly Thr Arg His Arg Ala Arg Pro Val
        35                  40                  45

Cys Ser Asn Phe Tyr Cys Arg Leu Pro Cys Leu Tyr Gly Glu Gly Glu
    50                  55                  60

Asn Ile Arg Arg Leu Pro Arg Leu Met Ile Arg Glu Gly Met Arg Trp
65                  70                  75                  80

Cys Lys Phe Ser Ser Glu Lys Ser Ser Arg Phe Pro Val Thr Ala Glu
                85                  90                  95

<210> SEQ ID NO 290
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290
tttcaagtcc ttcctgggga ccgggagacg gggtttcacc atgttggcca gactggtctc      60
gaattcctga cctcaagtga tccacccact tcggcctccc aaagcgctgg gattacaggc     120
acgaggcatc gcgcccggcc agtttgctca aactttact gcaggttgcc ttgtctctat      180
ggtgaggggg agaatattag gaggttgccc aggcttatga taagggaagg catgaggtgg     240
tgcaagtttt caagtgagaa gtcgtccagg ttcccagtga cagcagaa                 288

<210> SEQ ID NO 291
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Cys Asp Leu Glu Cys Ser Glu Gln Arg Gln Gly Phe Ala Met Leu Ala
1               5                   10                  15

Ser Ser

<210> SEQ ID NO 292
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
tgtgacctgg agtgcagcga gcagagacag ggtttcgcca tgttggccag ctcc          54

<210> SEQ ID NO 293
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asn Leu Gln Leu Leu Thr Gln Gly Tyr Ser Gly Ile Trp Arg Tyr Pro
1               5                   10                  15

<210> SEQ ID NO 294

```
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
aatctacagt tactcacaca aggatattca ggaatatgga gatatccc                 48

<210> SEQ ID NO 295
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

His Phe Ser Arg Leu Cys Gly Pro Val Ser His Leu Ser Ala His Leu
1               5                   10                  15

Ala His Leu Arg
            20

<210> SEQ ID NO 296
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
cacttcagcc ggctctgcgg gcccgtgtcc cacctgagtg cccaccttgc ccacctgagg    60

<210> SEQ ID NO 297
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Lys His His Leu Trp Ala Leu Glu Ala Ala Trp Leu Ser Gly Arg Ser
1               5                   10                  15

Pro Leu Ser Glu Pro Gln Leu Pro Leu Gln Pro Ser Gly Asn Ser Ser
            20                  25                  30

Ser Val

<210> SEQ ID NO 298
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 298
aagcaccatc tgtgggctct ggaagcagca tggctgtctg ggcgaagccc tctctctgag    60
cctcagcttc ctccttcagcc cagtgggaac agttcttctg tc                    102

<210> SEQ ID NO 299
<211> LENGTH: 22
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 299

Thr Glu His Glu Asn Thr Glu Thr Gly Ala Pro Leu His Cys Ser Ser
1               5                   10                  15

Cys Phe Ile Asn Pro Tyr
            20

<210> SEQ ID NO 300
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 300
accgagcatg aaaacactga gactggtgct cccttgcatt gttcatcctg cttcatcaac     60
ccctat                                                               66

<210> SEQ ID NO 301
<211> LENGTH: 73
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 301

Cys Gly Ile Ser Val Tyr Leu Ala Gly Arg Thr Arg Trp Leu Thr Pro
1               5                   10                  15

Val Ile Pro Ala Leu Trp Glu Thr Glu Ala Gly Arg Ser Arg Gly Gln
            20                  25                  30

Glu Ile Glu Thr Ile Leu Ala Asn Lys His Cys Pro Ser Met Pro Cys
        35                  40                  45

Tyr Phe Ser Arg Ser Arg Gln Ala Gln Gln Leu Leu Pro Ser Ser Ala
    50                  55                  60

Arg Ala Pro Trp Phe Trp Trp Leu Cys
65                  70

<210> SEQ ID NO 302
<211> LENGTH: 219
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 302
tgtgggatct ccgtctattt agcaggccgg acgcggtggc tcacgcctgt aatcccagca     60
ctttgggaga ccgaggcggg cagatcacga ggtcaggaga tcgagaccat cctggctaac    120
aagcactgtc catctatgcc ttgctacttt tcgagatcga acaggcgca gcagctgctt     180 ccatcctcgg ctcgggcacc ctggttctgg tggctgtgc                           219

<210> SEQ ID NO 303
<211> LENGTH: 35
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 303

Lys Leu Cys Ser Arg Gln Arg Pro Asp Cys Gln Pro Val Asp Ser Arg
1               5                   10                  15

His Gly Pro Ile Leu Ser Ile Gln His Leu Ile Ser Ala Leu His Thr
            20                  25                  30

Gly Asp Gly
        35

<210> SEQ ID NO 304
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 304
aagctgtgca gccggcagcg gccagactgt cagcctgttg acagcaggca tgggcccatt      60
ttgtccatac agcatctaat tagtgccctg catactgggg atgga                     105

<210> SEQ ID NO 305
<211> LENGTH: 97
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 305

Glu Glu Met Glu Thr Asp Met Asp Val Ala Met Glu Ser Ser Pro
1               5                   10                  15

Gly Ser Ser Ile Ser Met Glu His Arg Leu Asp Val Glu Leu Arg Ala
            20                  25                  30

Ser Gly Ser Ser Ser Ser Thr Asn Ile Ser Ser Gly Pro Ser Pro Gly
        35                  40                  45

Pro Ser Pro Gly Pro Gly Thr Gly Pro Gly Pro Gly Pro Gly Pro Gly
    50                  55                  60

Pro Gly Pro Gly Pro Gly Pro Gly Pro Gly Pro Gly Pro Gly Pro Gly
65                  70                  75                  80

Pro Gly Pro Gly Pro Gly Pro Arg Pro Gly Val Gln Cys Ile Pro Gln
                85                  90                  95

Arg

<210> SEQ ID NO 306
<211> LENGTH: 291
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 306
gaggaaatgg aaactgatat ggatgatgtg gctatggaaa gcagtccagg ctcatccatc      60
tctatggagc acaggctgga tgttgaatta agggcatcag gttccagcag cagcactaac     120
atctcttctg gccccagccc tggtcccagt cccggcccg gcaccggccc tggccccggc     180 cccggcccg gccccggccc tggccccggc cccggcccg gtcctggtcc cggccctggc     240

```
cccggccctg gccctggccc ccgtcctgga gtccagtgta ttccacaacg a            291
```

<210> SEQ ID NO 307
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Arg Asp Leu Gln Cys Pro Lys Lys Thr Gln Thr Pro Gln Ala Gln Ser
1               5                   10                  15
Arg Leu Glu Ser Glu Arg Lys Lys Asn Thr Leu Thr Trp Leu Val Pro
            20                  25                  30
Thr Pro Trp Asp Trp Arg Gln Trp Ser Thr Ala Pro Ser Arg Gly Leu
        35                  40                  45
Val Trp Pro Pro Pro Val Asp Tyr Glu Leu Trp Lys Ser Ser
    50                  55                  60

<210> SEQ ID NO 308
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 308

```
cgggacctgc agtgcccaa gaagacccag accccgcagg cgcagtctcg cttggagagt      60
gagaggaaga agaacacgct gacctggctt gttcctactc cctgggattg gcgtcagtgg     120
agcacggctc cctcgagggg cctggtctgg cctcctcccc ctgtggacta tgagctctgg     180
aagtcctcg                                                             189
```

<210> SEQ ID NO 309
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

His Gln Tyr Ile Val Val Gln Asp Ile His Thr Glu Thr Gln His Ser
1               5                   10                  15
Ala Leu Gly Ala Gln Pro Ala Asp Ser Ile Pro Pro Phe Leu Gln His
            20                  25                  30
Thr Leu Gln His Leu Ala Cys Pro Ser Leu Glu Leu Pro Gly Asn Glu
        35                  40                  45
Gln Ala Arg Arg Glu Lys Arg Arg Asp Asp Ala Phe Ser Asp Ser
    50                  55                  60
Leu
65

<210> SEQ ID NO 310
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 310
catcagtaca tagttgtaca ggacattcac acagagactc agcactcagc cctcggtgct    60
cagcctgcgg actccatccc cccatttctc aacacaccc tgcagcattt agcttgtcct   120
agcctggagc tgcctgggaa tgaacaagct agaagagaaa aaaggaggag ggatgatgcc   180
ttctccgaca gcctg                                                    195

<210> SEQ ID NO 311
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Ile Asp Pro Ser Ser Pro Leu His Thr Tyr Tyr Glu Arg Ile Thr Lys
1               5                   10                  15

Gly Arg Asn Pro Glu Arg Arg Tyr Met Lys Pro Glu Arg Ile Ser Pro
            20                  25                  30

Gly His Glu Ala Met Glu Lys Asn Leu Glu Asp Asn Leu
        35                  40                  45

<210> SEQ ID NO 312
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 312
attgatccaa gctctcccctt acatacctac tatgaaagaa ttactaaagg acgtaatcca    60
gaaagaagat atatgaaacc ggaacgaatc agtccgggac acgaggccat ggaaaaaaac   120
cttgaagata actta                                                    135

<210> SEQ ID NO 313
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Val Gly Asn Lys Met Phe Val Lys Val Arg Asn Arg Asn Val Pro Gln
1               5                   10                  15

Pro Pro Leu Leu Pro Thr Pro Ser His Leu Ser Leu Pro Trp Lys Glu
            20                  25                  30

Ser Gly Gly Leu
        35

<210> SEQ ID NO 314
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 314
gtgggcaaca agatgtttgt caaggtcaga aatcggaatg tgcctcagcc ccctcttctt    60
```
cctactccta gccacctgtc actgccctgg aaggaaagtg gtggtctc 108

<210> SEQ ID NO 315
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Trp Asp Lys Asn Ala Pro Asp Glu Gly Lys Trp Gly Leu Cys Gly Gly
1               5                   10                  15

Ser Glu Val Gly Glu Thr Glu Arg Glu Asp Gly Leu Gly Gln Gly
            20                  25                  30

Tyr Asn Ala Ser Gln Gly Gln Ala Gly Asp Lys Leu Val Gly Gln
        35                  40                  45

<210> SEQ ID NO 316
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316
tgggacaaga atgcccctga tgaaggcaag tggggtctat gtgggggcag tgaggtggga      60
gagacagaaa gagaggatgg gggattaggt cagggttaca atgcctccca gggccaggca     120
ggtgacaaac tagtggggca a                                               141

<210> SEQ ID NO 317
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Gly Lys Val Ser Pro Gly Tyr Arg Met Leu Ser Leu Gly Pro Asn
1               5                   10                  15

Ala Val Ala Ser Val Gly Ala Asn His Ser Met Leu Pro His Leu Pro
            20                  25                  30

Phe Phe Arg Ser Pro Ser Thr Arg Thr Gly Pro Ser Arg Ala Ala Ala
        35                  40                  45

Thr Asn Ala Pro Leu Thr Ala Pro Thr Tyr Asn Pro Ile Ser Ala Ala
    50                  55                  60

Ala Thr Pro Ser Gly Trp Arg Ala Ala Ala Gly
65                  70                  75

<210> SEQ ID NO 318
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 318
atgggaaagg taagtcctgg gtaccggatg ctcagccttg gccctaatgc agtggcctca      60

```
gtgggggcca atcactccat gctcccacat cttccatttt tcagatcacc ttctacgagg      120
acagggcctt ccagggccgc agctacgaat gcaccactga ctgccccaac ctacaaccct      180
atttcagccg ctgcaactcc atcagggtgg agagcggctg ctgga                      225
```

<210> SEQ ID NO 319
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

```
Tyr Gly Met Pro His Asn Asn Gln Val Gly Gly Gly Arg Leu Pro Ser
1               5                   10                  15

Pro Ile Leu Pro Pro Met Pro Glu Pro Val Gly Ser Arg Arg Gly Ser
            20                  25                  30

Ser Val Gly Phe Leu Asp Ile Ser Met Leu Phe Gln Arg Leu His Arg
        35                  40                  45

Ser Leu Met
    50
```

<210> SEQ ID NO 320
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 320

```
tacggaatgc ctcacaacaa ccaggtaggt ggagggcggc tcccctcgcc catcctcccc      60
cccatgccag aacccgtggg cagccggcgt ggctccagtg tgggctttct ggacataagc      120
atgcttttcc agcgactcca caggagtctg atg                                   153
```

<210> SEQ ID NO 321
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

```
Met Val Ser Glu Glu Leu Ala Leu Ala Ser Pro Leu Ala Asn Leu Gly
1               5                   10                  15

Leu
```

<210> SEQ ID NO 322
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322

```
atggtaagtg aggaactggc gttagctagt ccgctggcaa acttgggtct c                51
```

<210> SEQ ID NO 323
<211> LENGTH: 48
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 323

Cys Asp Pro Ala Ala Pro Arg Ala Val Ser Leu Pro Gly Arg Gln Gly
1               5                   10                  15

Ser Glu Gly Gly Glu Gly Arg Gly Leu Gly Ser Arg Pro Ala Val Leu
            20                  25                  30

Gly Arg His Ser Ser Gly Glu Gly Gly Pro Trp Gly Glu Leu Pro
        35                  40                  45

<210> SEQ ID NO 324
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 324
tgtgacccag cggcccctcg cgctgtaagt ctcccgggac ggcagggcag tgagggaggc     60
gagggccggg gtctgggctc acgccctgca gtcctgggcc gacacagctc cggggaaggc    120
ggaggtcctt ggggagagct gccc                                           144

<210> SEQ ID NO 325
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Ala Arg Leu Arg Glu Leu Arg Gln Cys Gly Gly Gly Arg Gly Lys Arg
1               5                   10                  15

Gly Gln Gly Trp Gly Val Arg Asp Glu Thr Ile Thr Gly Arg Pro Ala
            20                  25                  30

Val Leu Gly Ser Pro Phe Leu Ser Pro Ala Leu Ala Pro Pro Ser Arg
        35                  40                  45

Leu Met Gly Asp Leu Trp Asp Gly Gln Ser Ala Gly Trp Ser Pro Gly
    50                  55                  60

Ser Pro Ala Ser Pro Phe Cys Gly Gly Trp
65                  70

<210> SEQ ID NO 326
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326
gcgcggctgc gggagctcag gcagtgcggg ggcgggcggg gaaagagggg acagggtgg     60 ggggttcggg atgagaccat aactggccgg ccagcagttc tgggcagccc cttcctctct    120
cctgccttgg cgcctccatc tagacttatg ggcgatctct gggatggcca gtcagcgggg    180
tggtctcctg ggtccccagc ctcgccattc tgtgggggt gg                        222
```

```
<210> SEQ ID NO 327
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Leu His Cys Leu Glu Lys Thr Thr Val Arg Arg Gln His Asp Cys Leu
1               5                   10                  15

Pro Leu Leu Ser Asp Ser Asn Ser Ile Cys Phe Cys Ala Tyr Leu Met
            20                  25                  30

Leu Pro Ser Val Ile Ser Leu Ser Ala Leu Leu Glu Asn Met Leu Lys
        35                  40                  45

Asn Lys Gln Thr Lys Thr Pro Gln Tyr Leu Lys Leu Leu
    50                  55                  60

<210> SEQ ID NO 328
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 328
cttcactgcc tggaaaaaac cacggtaagg agacagcatg actgccttcc cttgctctct     60
gacagtaatt ccatttgctt ttgtgcatac ttaatgcttc cgagtgtgat ttcactgtct    120
gcattactgg aaaacatgct aaaaaacaaa caaaccaaaa ccccacaata tttgaaatta    180
ctt                                                                  183

<210> SEQ ID NO 329
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Arg Val Arg Gly Ala Pro Gly Arg Gly Glu Ser Leu Pro Pro Arg Gly
1               5                   10                  15

Lys Lys Arg Ala His Gly Trp Glu Ala Lys Gly
            20                  25

<210> SEQ ID NO 330
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
agggtccgtg gggctccagg cagaggtgag tccctccctc cccggggaaa gaagagggca     60
catgggtggg aggcaaaggg c                                               81

<210> SEQ ID NO 331
<211> LENGTH: 87
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 331

Leu Cys Gly Thr Pro Gln Ala Ala Gly Lys Gly Gln Glu Val Arg Asp
1               5                   10                  15

Ser Leu Ala Ile Cys Lys Val Gly Glu Gly Leu Leu Leu Phe Leu Leu
            20                  25                  30

Gly Ala Trp Arg Arg His Leu Thr Gln Glu Asp Arg Ile Thr Pro Thr
        35                  40                  45

Asn Leu Leu Pro Leu Thr Leu Gly Lys Thr Gln Arg Gln Arg Gly
    50                  55                  60

Ser Arg Leu Cys Ser Phe Leu Tyr Lys Ile Arg Arg Met Ser Lys Cys
65                  70                  75                  80

Phe Gln Lys Ser Arg Asn Glu
                85

<210> SEQ ID NO 332
<211> LENGTH: 261
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 332
ctatgtggaa ctccccaggc tgcaggtaag gggcaagagg tacgggattc cttagctatt      60
tgcaaggttg gggagggact actgctcttt ctcctaggag cctggcgaag gcatctgact     120
caagaagata gaattacccc aaccaacctc ctcctgcctc tgacactagg aagacccag     180 aggcaacgag ggtccaggtt atgcagtttc ctttataaaa taagaagaat gagtaaatgc     240
ttccagaaaa gtagaaatga g                                                261

<210> SEQ ID NO 333
<211> LENGTH: 24
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 333

Tyr Asp Val Leu Val Leu Lys Gly Glu Trp Gly His Ala Asp Gln Gly
1               5                   10                  15

Leu Leu Trp Pro Arg Lys Ser Arg
            20

<210> SEQ ID NO 334
<211> LENGTH: 72
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 334
tacgacgtct tggtgctcaa aggtgagtgg gggcatgcag accaggggct actgtggccc      60
aggaagtcca gg                                                          72

<210> SEQ ID NO 335
<211> LENGTH: 24

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Arg Ser Ser Val Pro Thr Thr Ser Ser Glu Tyr Ser Thr Asp Val Pro
1               5                   10                  15

Met Ala Pro Ile Leu Gln Gln Thr
            20

<210> SEQ ID NO 336
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
cggagctctg tgcccaccac cagcagtgag tattctactg atgttcccat ggccccaatc    60
ttacaacaaa ct                                                       72

<210> SEQ ID NO 337
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Pro Ser Ser Leu Pro Gly Pro Thr Gly Lys Tyr Gln Ser Met Val Phe
1               5                   10                  15

Gly Ala Trp Leu Met Ser Val Asn Ile Ser Val Tyr Thr Leu Leu Glu
            20                  25                  30

His Gly

<210> SEQ ID NO 338
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 338
ccatcatccc tccctggccc cacaggtaaa taccagtcaa tggtatttgg agcatggttg    60
atgagtgtaa acatctctgt ttatactctg ttagagcatg gt                      102

<210> SEQ ID NO 339
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Arg Ser Ser Gly Leu Thr Thr Ser Ser Glu Tyr Ser Thr His Val His
1               5                   10                  15

Met Pro Leu Ile Leu His Gln Ala Glu Gln Glu Leu Leu Leu Leu Ile
            20                  25                  30
```

Asn Pro

<210> SEQ ID NO 340
<211> LENGTH: 102
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 340
cggagctctg ggctcaccac cagcagtgag tattcaactc atgtccacat gcccctgatt    60
ctacaccaag cggaacagga gctactcctc ctcataaacc ca    102

<210> SEQ ID NO 341
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 341

Trp Ile Pro Val Pro Thr Ser Ser Ser Glu Tyr Ser Thr His Val Gln
1               5                   10                  15

Met Pro Leu Ile Leu His Gln Val Glu Gln Glu Leu Ala Pro Pro Leu
            20                  25                  30

<210> SEQ ID NO 342
<211> LENGTH: 96
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 342
tggatccctg tgcccaccag cagcagtgag tattcaactc atgtccagat gcccctgatc    60
ctacatcaag tggagcaaga gctggcccct cctctt    96

<210> SEQ ID NO 343
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 343

Arg Tyr Trp Thr Pro Ala Thr Ser Ser Glu Tyr Ser Asn Leu
1               5                   10

<210> SEQ ID NO 344
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 344
cggtactgga cccctgccac cagcagtgag tattcaaacc tg    42

<210> SEQ ID NO 345

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Pro Thr Thr Thr Thr Phe Leu Lys Val Arg Leu Ser Ser Pro Ala Leu
1               5                   10                  15

Gly Gln Leu Pro
            20

<210> SEQ ID NO 346
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ccgaccacta cgaccttcct gaaggtgagg ctttcttccc cagccctggg ccagcttccc    60

<210> SEQ ID NO 347
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gln Ala Gly Ala Glu Pro Ser Thr Val Arg Thr Gly Lys Lys Gly His
1               5                   10                  15

Leu

<210> SEQ ID NO 348
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
caggctgggg ccgagcctag cacagtgagg acgggaaaga agggacacct t              51

<210> SEQ ID NO 349
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Lys Arg Pro Met Ala Ser Glu Val Ser Phe Ile Leu Ile Gln Trp Leu
1               5                   10                  15

Leu Lys Pro

<210> SEQ ID NO 350
<211> LENGTH: 57
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 350
aagagaccca tggcatctga ggtgagtttc atactgatac aatggttact aaaacct        57

<210> SEQ ID NO 351
<211> LENGTH: 46
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 351

Glu Phe Leu Thr Gln Glu Ser Lys Val Ser Leu Glu Ser Arg Asn Lys
1               5                   10                  15

Leu Ile Phe Gly Tyr Phe Thr Ser Phe Gln Asn Leu Ser Thr Ser Leu
            20                  25                  30

Ser Phe Arg Asn Met Lys Met Asn Leu Met Lys Lys Trp Pro
        35                  40                  45

<210> SEQ ID NO 352
<211> LENGTH: 138
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 352 gaattttaa ctcaggaatc taaggtatca ttagaaagca gaaataagct tatatttggt       60
tactttacgt catttcagaa tctctcaaca agtctttctt ttagaaacat gaaaatgaat     120
ttaatgaaga agtggcct                                                   138

<210> SEQ ID NO 353
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 353

Leu Thr Pro Ala Leu Arg Thr Leu Val Ser Arg Gly Arg Glu Glu Pro
1               5                   10                  15

Gly Gly Ser Trp Arg Arg Gly Trp Val
            20                  25

<210> SEQ ID NO 354
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 354
ctgacccctg ccctccgcac gttggtgagc cgagggaggg aggagcctgg ggggagctgg      60 aggagggct gggtc                                                       75

<210> SEQ ID NO 355
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Tyr Leu Glu Pro Leu Glu Asp Gly Val Arg Gly
1               5                   10

<210> SEQ ID NO 356
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
tacctggaac ccttggagga cggggtgagg ggc                                    33

<210> SEQ ID NO 357
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Ala Gly Ser Pro Gly Glu Glu Gln Val Gln Phe Gln Gly Leu Gly Met
1               5                   10                  15

Asp Thr Asp Pro Leu Ser Pro Glu Ala Asn Pro Thr Pro Pro Ile Trp
            20                  25                  30

Pro Gln Ala Pro Pro His Thr Pro Leu
        35                  40

<210> SEQ ID NO 358
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 358
gcggggagcc ctggcgagga gcaggtacag ttccagggcc ttgggatgga cacagaccct      60
ctgtctcctg aggccaaccc gaccccgccc atctggcctc aggcacctcc ccacacaccc     120
ctg                                                                   123

<210> SEQ ID NO 359
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Arg Ala Met Thr Lys Lys Tyr Glu Val Gly Met Gly Gln Ser Cys Val
1               5                   10                  15

Gly Gly Ala Gly Val Gln Gly Gly Ser Lys Trp Cys Lys Pro Gln Arg
            20                  25                  30

Val Gly Gly Trp Glu Gly Gly Gln Val Gln Ala Ile Trp Leu Ser Leu
```

35                  40                  45

Thr Glu Ala Ser Ser Val Pro Cys Leu Pro
    50                  55

<210> SEQ ID NO 360
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360
cgagccatga caaaaaaata cgaggtgggc atggggcaga gctgcgtggg tggggcaggg      60
gtccagggag gtccaagtg gtgcaaaccc caaagggtgg gagggtggga aggggggccaa    120 gtccaggcca tctggctgag cctcactgag gcctcctctg tgccctgcct gcca          174

<210> SEQ ID NO 361
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

His Lys Asp Phe Asn Ser Gln Leu Gly Arg Arg Ile Pro Gln Arg Ala
1               5                  10                  15

Pro Pro Ile Leu Phe Phe Leu Lys Arg Gly Asn Phe Gln
            20                  25

<210> SEQ ID NO 362
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
cacaaggact tcaacagtca gcttggtagg aggatacccc agagagcacc tccaatcctg      60
ttctttctaa aaagaggaaa cttccaa                                          87

<210> SEQ ID NO 363
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Val Ser Pro Glu Glu Leu Glu Glu Val Gly Gly Ala Trp Gly Gly Gly
1               5                  10                  15

Gly Gly Gly Glu Glu Ser Gly Gly Leu Glu Ala Gly
            20                  25

<210> SEQ ID NO 364
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gtttccccgg aggagttgga ggaggtaggt ggggcctggg gaggtggagg aggtggggag    60
gaatcgggtg ggctggaggc tgga                                          84

<210> SEQ ID NO 365
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Lys Asp Leu Arg Val Ser Asp Lys Val Arg Leu Phe Ser Met
1               5                   10

<210> SEQ ID NO 366
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
aaagatctga gggtgtcgga caaggtaagg ttgttctcca tg                      42

<210> SEQ ID NO 367
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Asp Gln Asn Asn Tyr Leu Gln Ser Gly Thr Lys Leu Ile Asn Lys Lys
1               5                   10                  15

Asn Tyr Val Ile Tyr Val Ser Trp
            20

<210> SEQ ID NO 368
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gatcaaaata attatctaca gtcaggtaca aagttaatta ataaaaaaaa ctatgtcata    60
tatgtaagtt gg                                                       72

<210> SEQ ID NO 369
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Pro Ala Lys Arg His Lys Gln Leu Ser Met Pro Ala Pro Val Pro Leu
1               5                   10                  15

Leu Asn Val Leu Ala Thr Arg Val Gln Arg Gly Trp Arg Trp His Gly
            20                  25                  30

Ser Ser Ala Gln Asn Pro Gly Arg Ser Ala Gly Val Gln Val Thr Gln
        35                  40                  45

Ala Ala Gly Leu Leu Ala Leu Ser Lys Trp Trp Gly Leu Ser Pro
50                  55                  60

Glu Ala Pro Leu Gly Ala Gly Val Arg Trp Ala Leu Pro Ala Thr Gln
65                  70                  75                  80

Asp Trp Pro Pro Pro Thr Gly Pro Pro Arg Trp Val Arg Ala Ser Gly
                    85                  90                  95

Pro Thr Ser

<210> SEQ ID NO 370
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 370
ccggccaaga ggcacaagca gctcagtatg ccagccccag tgcctctcct gaatgtcctg      60
gccacccggg tgcagagggg gtggagatgg catggcagct ctgccagaa ccctggacgc     120 tcagcaggcg tgcaggtcac tcaggctgct ggccttctgc tggccttgag caagtggtgg    180
gggctgagcc cagaggcccc cttgggggca ggtgtgcgat gggctcttcc tgccactcag    240
gactggcccc ctcccacggg gccccccgg tgggtcaggg cttcagggcc cacctcc       297

<210> SEQ ID NO 371
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Arg Asn Thr Leu Lys Glu Ser Ser Lys Leu Lys Ser Ser Phe Glu Tyr
1               5                   10                  15

Trp Phe Ala Gly Phe Phe Ser Ser Ser Ser Phe Phe Phe Leu Ser
            20                  25                  30

Arg Lys Phe Cys Phe Val Phe Cys Leu Cys Trp Val Glu Ser Leu Gly
        35                  40                  45

Gly Val Ser
    50

<210> SEQ ID NO 372
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 372
cgaaacactc ttaaagagtc aagtaagtta aaatcctcct ttgaatattg gtttgctggt      60
ttcttttctt cttcttcttc ttttttttt taagtagga agtttgttt tgtcttttgt       120 ttatgttggg ttgagagttt gggggggagtt tct                                153

<210> SEQ ID NO 373
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Ser Pro Asn Asp Ala His Arg Gly Glu Gly His Lys Lys Gly Leu Arg
1               5                   10                  15

Ser Arg Gln Asp Gly Gly Pro Gly Ser Gly Arg Gly Leu Asp Ser Gly
            20                  25                  30

Gly His Pro Gly Glu Gly Arg Glu Thr Lys Pro Arg Val Leu Lys Gly
        35                  40                  45

Ala Gly Gly Cys Arg Leu Pro Phe Phe Leu
        50                  55

<210> SEQ ID NO 374
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 374
agccccaacg atgctcacag aggtgagggg cacaagaagg ggctgcggtc ccggcaagac      60
ggtggtcccg gctcagggag gggcctggac tctgggggac acccggggga gggaagagag    120
accaaacccc gtgttctgaa aggggctggg ggctgtagac tcccttctt tctg            174

<210> SEQ ID NO 375
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Leu Cys Ala Ile Ser Val Asp Arg Cys Ala Ala Leu Pro Ala Arg Ala
1               5                   10                  15

Pro Ala Pro Pro Arg Pro Ala Arg Arg Pro His Arg Gly Leu Cys Ala
            20                  25                  30

Val Arg Arg Pro Leu Gly Ala Pro Arg Arg Phe Val Ala Val Ala Val
        35                  40                  45

Pro

<210> SEQ ID NO 376
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376
ctgtgcgcca tcagcgtgga caggtgcgcc gccctccccg cccgcgcccc ggcgcccccg      60
cgccccgccc gccgccctca ccgcggcctg tgcgctgtcc ggcgccccct cggcgctccc    120
cgcaggttcg tggccgtggc cgtgccg                                         147

<210> SEQ ID NO 377
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Lys Ile Val Gln Gln Lys Asn Arg Arg His Arg Arg Leu Gly Arg Arg
1               5                   10                  15

Ala Gly Arg Cys Gly Ser Leu Ala Ala Gly Arg Pro Arg Pro Gly Ala
            20                  25                  30

Glu Asp Arg Arg Leu Arg Glu Tyr Asp Phe Ala
        35                  40

<210> SEQ ID NO 378
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 378
aagatcgtgc agcagaagaa caggcgccac cggcggctgg ggcggcgggc gggcaggtgc      60
ggctccctgg cggcggggag gccccggccc ggagctgagg accgcaggct ccgcgagtac     120
gacttcgcc                                                             129

<210> SEQ ID NO 379
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ser Ser Cys Met Gly Gly Met Asn Gln Arg Pro Ile Leu Thr Ile Ile
1               5                   10                  15

Thr

<210> SEQ ID NO 380
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
agttcctgca tgggcggcat gaaccagagg cccatcctca ccatcatcac a               51

<210> SEQ ID NO 381
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ser Ser Cys Met Gly Gly Met Asn Trp Arg Pro Ile Leu Thr Ile Ile
1               5                   10                  15

Thr

<210> SEQ ID NO 382
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
agttcctgca tgggcggcat gaactggagg cccatcctca ccatcatcac a          51

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Leu Gly Arg Asn Ser Phe Glu Val Cys Val Cys Ala Cys Pro Gly Arg
1               5                   10                  15

Asp

<210> SEQ ID NO 384
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
ctgggacgga acagctttga ggtgtgtgtt tgtgcctgtc ctgggagaga c          51

<210> SEQ ID NO 385
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Leu Gly Arg Asn Ser Phe Glu Val His Val Cys Ala Cys Pro Gly Arg
1               5                   10                  15

Asp

<210> SEQ ID NO 386
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ctgggacgga acagctttga ggtgcatgtt tgtgcctgtc ctgggagaga c          51

<210> SEQ ID NO 387
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 387

Leu Gly Arg Asn Ser Phe Glu Val Leu Val Cys Ala Cys Pro Gly Arg
1               5                   10                  15

Asp

<210> SEQ ID NO 388
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
ctgggacgga acagctttga ggtgcttgtt tgtgcctgtc ctgggagaga c          51

<210> SEQ ID NO 389
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gln His Met Thr Glu Val Val Arg His Cys Pro His His Glu Arg Cys
1               5                   10                  15

Ser

<210> SEQ ID NO 390
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
cagcacatga cggaggttgt gaggcactgc ccccaccatg agcgctgctc a          51

<210> SEQ ID NO 391
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gly Leu Ala Pro Pro Gln His Leu Thr Arg Val Glu Gly Asn Leu Arg
1               5                   10                  15

Val

<210> SEQ ID NO 392
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
```

```
ggtctggccc ctcctcagca tcttacccga gtggaaggaa atttgcgtgt g            51
```

<210> SEQ ID NO 393
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

```
Thr Arg Val Arg Ala Met Ala Ile Cys Lys Gln Ser Gln His Met Thr
1               5                   10                  15

Glu
```

<210> SEQ ID NO 394
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394

```
acccgcgtcc gcgccatggc catctgcaag cagtcacagc acatgacgga g            51
```

<210> SEQ ID NO 395
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

```
Phe Arg His Ser Val Val Val Pro Cys Glu Pro Pro Glu Val Gly Ser
1               5                   10                  15

Asp
```

<210> SEQ ID NO 396
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396

```
tttcgacata gtgtggtggt gccctgtgag ccgcctgagg ttggctctga c            51
```

<210> SEQ ID NO 397
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

```
His Met Thr Glu Val Val Arg Arg Tyr Pro His His Glu Arg Cys Ser
1               5                   10                  15

Asp
```

<210> SEQ ID NO 398

```
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
cacatgacgg aggttgtgag gcgctacccc caccatgagc gctgctcaga tagcgat        57

<210> SEQ ID NO 399
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

His Met Thr Glu Val Val Arg Arg Phe Pro His His Glu Arg Cys Ser
1               5                   10                  15

Asp

<210> SEQ ID NO 400
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
cacatgacgg aggttgtgag gcgcttcccc caccatgagc gctgctcaga tagcgat        57

<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

His Tyr Asn Tyr Met Cys Asn Ser Phe Cys Met Gly Gly Met Asn Arg
1               5                   10                  15

Arg

<210> SEQ ID NO 402
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
cactacaact acatgtgtaa cagtttctgc atgggcggca tgaaccggag g              51

<210> SEQ ID NO 403
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403
```

```
Met Cys Asn Ser Ser Cys Met Gly Asp Met Asn Arg Arg Pro Ile Leu
1               5                   10                  15

Thr

<210> SEQ ID NO 404
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
atgtgtaaca gttcctgcat gggcgacatg aaccggaggc ccatcctcac c        51

<210> SEQ ID NO 405
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Glu Asp Ser Ser Gly Asn Leu Leu Arg Arg Asn Ser Phe Glu Val Arg
1               5                   10                  15

Val

<210> SEQ ID NO 406
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gaagactcca gtggtaatct actgagacgg aacagctttg aggtgcgtgt t        51

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Cys Thr Glu Leu Lys Leu Ser Asp Tyr
1               5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Asn Leu Val Pro Met Val Ala Thr Val
1               5

<210> SEQ ID NO 409
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Leu Ile Tyr Arg Arg Arg Leu Met Lys
1               5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Leu Tyr Ser Ala Cys Phe Trp Trp Leu
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Asn Pro Lys Ala Ser Leu Leu Ser Leu
1               5

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Glu Leu Arg Ser Arg Tyr Trp Ala Ile
1               5

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Asn Pro Lys Ala Ser Leu Leu Ser Leu
1               5

<210> SEQ ID NO 414
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Ile Val Thr Asp Phe Ser Val Ile Lys
```

```
1               5
```

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

```
Asn Pro Lys Ala Ser Leu Leu Ser Leu
1               5
```

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

```
Asn Leu Val Pro Met Val Ala Thr Val
1               5
```

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

```
Leu Ile Tyr Arg Arg Arg Leu Met Lys
1               5
```

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

```
Asn Leu Val Pro Met Val Ala Thr Val
1               5
```

<210> SEQ ID NO 419
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

```
Met Ala Cys Pro Gly Phe Leu Trp Ala Leu Val Ile Ser Thr Cys Leu
1               5                   10                  15

Glu Phe Ser Met Ala
            20
```

<210> SEQ ID NO 420
<211> LENGTH: 77
<212> TYPE: PRT

```
<213> ORGANISM: Artificial Sequence
<220> FEATURE:
<223> OTHER INFORMATION: Description of Artificial Sequence: Synthetic
      polynucleotide

<400> SEQUENCE: 420

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Val Arg
65                  70                  75

<210> SEQ ID NO 421
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val
            20                  25
```

NEOANTIGENS EXPRESSED IN OVARIAN CANCER AND THEIR USES

CROSS-REFERENCE TO RELATED APPLICATIONS

This application claims priority to U.S. Provisional Application No. 62/976,384 filed on Feb. 14, 2020, titled "NEOANTIGENS EXPRESSED IN OVARIAN CANCER AND THEIR USES" which is incorporated by reference in its entirety.

SEQUENCE LISTING

The instant application contains a Sequence Listing which has been submitted electronically in ASCII format and is hereby incorporated by reference in its entirety. The ASCII copy, created on Jan. 22, 2021, is named JB16238USNP1_SL.txt and is 156,473 bytes in size.

FIELD

The disclosure relates to ovarian cancer neoantigens, polynucleotides encoding them, vectors, host cells, vaccines comprising the neoantigens, proteinaceous molecules binding the ovarian cancer neoantigens, and methods of making and using them.

BACKGROUND

Ovarian cancer is the fifth leading cause of cancer-related deaths among women. A woman's risk of getting ovarian cancer during her lifetime is about 1 in 78. The American Cancer Society estimates that in 2020, there will be about 21,750 new cases of ovarian cancer and 13,940 death of ovarian cancer in the United States.

Ovarian cancer results from the uncontrolled growth of abnormal cells inside, near, or on the outer layer of the ovaries. Surgery to remove the cancerous growth is the most common treatment for ovarian cancer. Surgery procedures may include the total abdominal hysterectomy, bilateral salpingo-oophorectomy, omentectomy, visualization of all peritoneal surfaces, and random peritoneal biopsies plus peritoneal washing. After surgery, adjuvant chemotherapy is mandatory in cases of suboptimal debulking (residual disease of 1 cm or more), advanced stages, or early stages with a high risk of recurrence. From the early 2000s, combination platinum-paclitaxel chemotherapy has been the standard of care in the adjuvant and first-line settings.

Although the first-line treatment with combination platinum-paclitaxel chemotherapy has been shown to have response rates of over 80% in patients with advanced ovarian cancer, most patients eventually relapse, with a median progression-free survival of 18 months. Resistance to platinum-based chemotherapy is the primary cause of the poor overall survival associated with ovarian cancer. Response rates to second-line agents such as liposomal doxorubicin, gemcitabine or topotecan decrease with each subsequent relapse due to chemoresistance, resulting in a five-year overall survival of 30-40%.

Therefore, a need remains for therapies against an ovarian cancer, including relapsed, refractory and/or platinum-resistant ovarian cancers.

BRIEF SUMMARY

The disclosure provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, or fragments thereof.

The disclosure also provides an isolated heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof.

The disclosure also provides an isolated polynucleotide comprising a sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, or 406, or fragments thereof.

The disclosure also provides vectors comprising the polynucleotides encoding for the polypeptides disclosed herein.

The disclosure also provides viruses or recombinant viruses comprising the vectors of the disclosure.

The disclosure also provides a self-replicating RNA molecule comprising the vector of the disclosure The disclosure also provides cells comprising or transduced with the vectors of the disclosure or the recombinant viruses of the disclosure.

The disclosure also provides a vaccine comprising the polynucleotides of the disclosure.

The disclosure also provides a vaccine comprising the polypeptides of the disclosure.

The disclosure also provides a vaccine comprising the vectors of the disclosure.

The disclosure also provides a vaccine comprising recombinant viruses of the disclosure.

The disclosure also provides a vaccine comprising the self-replicating RNA molecule of the disclosure.

The disclosure also provides methods of preventing or treating an ovarian cancer in a subject, comprising administering to the subject a therapeutically effective amount of one or more vaccines of the disclosure, one or more virus or recombinant virus of the disclosure or one or more pharmaceutical composition of the disclosure.

The disclosure also provides methods of inducing an immune response against one or more amino acid sequences of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405 in a subject, comprising administering to the subject one or more recombinant virus of the disclosure comprising the polynucleotides of the disclosure, wherein the recombinant virus is Ad26, GAd20, MVA and/or administering a self-replicating RNA molecule encoding polypeptides of the disclosure.

The disclosure also provides a method of treating or preventing an ovarian cancer in a subject, comprising administering to the subject a therapeutically effective amount of a composition comprising a recombinant virus and/or a composition comprising a self-replicating RNA molecule encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, or 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof. In some embodiments, the recombinant virus is a Ad26, GAd20, or MVA virus. In some embodiments, the administration comprises one or more administrations.

The disclosure also provides a method of treating or preventing an ovarian cancer in a subject, comprising administering to the subject a first composition comprising a first heterologous polynucleotide encoding a first heterologous polypeptide, wherein the first heterologous polypeptide comprises two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof; and a second composition comprising a second heterologous polynucleotide encoding a second heterologous polypeptide, wherein the second heterologous polypeptide comprises two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof; wherein the first heterologous polypeptide and the second heterologous polypeptide have distinct amino acid sequences.

The disclosure also provides a method of treating or preventing an ovarian cancer in a subject, comprising administering to the subject a therapeutically effective amount of a composition comprising a recombinant virus and/or a composition comprising a self-replicating RNA molecule encoding a heterologous polypeptide selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and fragments thereof The disclosure also provides administering an anti-CTLA-4 antibody, an anti-PD-1 or an anti-PD-L1 antibody in combination with any of the compositions comprising polynucleotides, polypeptides, vectors, or viruses disclosed herein.

It is to be understood, that the above embodiments of the invention encompass polypeptides comprising, in addition to the specifically recited polypeptides and fragments thereof, also additional polypeptide sequences, including one or more polypeptides different from those specifically recited. Similarly, the above embodiments of the invention also encompass polynucleotides comprising, in addition to the specifically recited polynucleotides and fragments thereof, also additional polynucleotide sequences, including one or more polynucleotides different from those specifically recited.

DETAILED DESCRIPTION

Definitions

Figure 1:
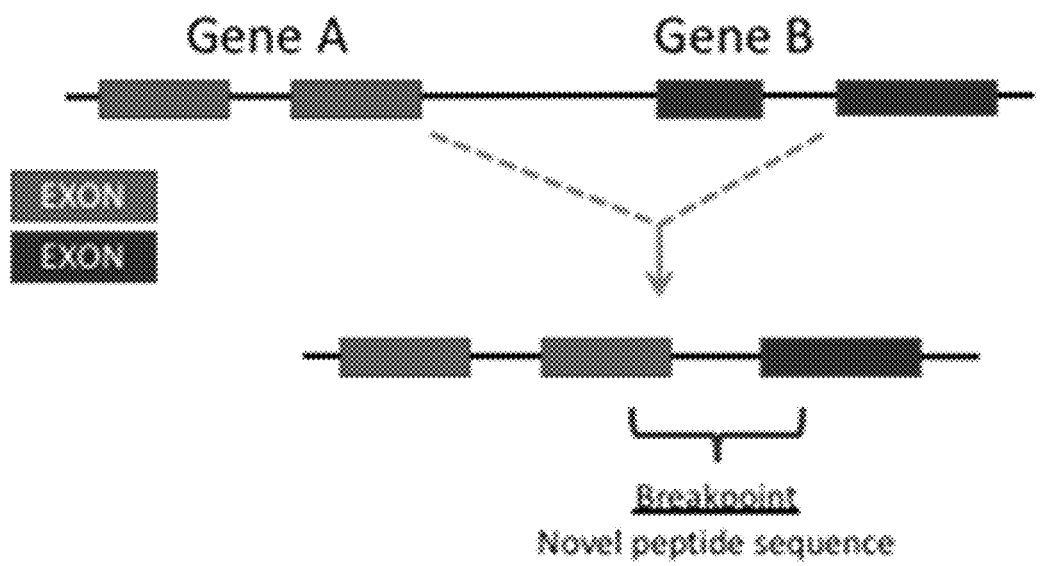
FIG. 1 shows a cartoon of a gene fusion resulting from a chimeric read-through fusion. Neoantigenic peptide sequences arise at the breakpoint junction.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the disclosure pertains.

Although any methods and materials similar or equivalent to those described herein may be used in the practice for testing of the present disclosure, exemplary materials and methods are described herein. In describing and claiming the present disclosure, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed disclosure. Embodiments described in terms of the phrase "comprising" (or its equivalents) also provide as embodiments those independently described in terms of "consisting of" and "consisting essentially of."

As used in this specification and the appended claims, the phrase "and fragments thereof" when appended to a list includes all members of the associated list. The list may comprise a Markush group so that, as an example, the phrase "the group consisting of peptides A, B, and C, and fragments thereof" specifies or recites a Markush group including A, B, C, fragments of A, fragments of B, and fragments of C.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide "Immunogenic fragment" refers to a polypeptide that is recognized by cytotoxic T lymphocytes, helper T lymphocytes or B cells when the fragment is in complex with MHC class I or MHC class II molecules.

"In-frame" refers to the reading frame of codons in a first polynucleotide being the same as the reading frame of codons in a second polynucleotide which are joined together to form a heterologous polynucleotide. In-frame heterologous polynucleotide encodes a heterologous polypeptide encoded by both the first polynucleotide and the second polynucleotide.

"Immunogenic" refers to a polypeptide that comprises one or more immunogenic fragments.

"Heterologous" refers to two or more polynucleotides or two or more polypeptides that are not found in the same relationship to each other in nature.

"Heterologous polynucleotide" refers to a non-naturally occurring polynucleotide that encodes two or more neoantigens as described herein.

"Heterologous polypeptide" refers to a non-naturally occurring polypeptide comprising two or more neoantigen polypeptides as described herein.

"Non-naturally occurring" refers to a molecule that does not exist in nature.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Viral vector" refers to a vector construct that includes at least one polynucleotide element of viral origin and has the capacity to be packaged into a viral vector particle.

"Neoantigen" refers to a polypeptide that is present in ovarian tumor tissue that has at least one alteration that makes it distinct from the corresponding wild-type polypeptide present in non-malignant tissue, e.g., via mutation in a tumor cell or post-translational modification specific to a tumor cell. A mutation can include a frameshift or nonframeshift insertion or deletion, missense or nonsense substitution, splice site alteration, aberrant splice variants, genomic rearrangement or gene fusion, or any genomic or expression alteration giving rise to the neoantigen.

"Prevalence" refers to a percentage of a population studied harboring an ovarian neoantigen.

"Recombinant" refers to polynucleotides, polypeptides, vectors, viruses and other macromolecules that are prepared, expressed, created or isolated by recombinant means.

"Vaccine" refers to a composition that comprises one or more immunogenic polypeptides, immunogenic polynucleotides or fragments, or any combination thereof intentionally administered to induce acquired immunity in the recipient (e.g. subject).

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Prevent", "preventing", "prevention", or "prophylaxis" of a disease or disorder means preventing that a disorder occurs in subject.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

"Replicon" refers to a viral nucleic acid that is capable of directing the generation of copies of itself and includes RNA as well as DNA. For example, double-stranded DNA versions of arterivirus genomes can be used to generate a single-stranded RNA transcript that constitutes an arterivirus replicon. Generally, a viral replicon contains the complete genome of the virus. "Sub-genomic replicon" refers to a viral nucleic acid that contains something less than the full complement of genes and other features of the viral genome yet is still capable of directing the generation of copies of itself. For example, the sub-genomic replicons of arterivirus may contain most of the genes for the non-structural proteins of the virus but are missing most of the genes coding for the structural proteins. Sub-genomic replicons are capable of directing the expression of all of the viral genes necessary for the replication of the viral sub-genome (replication of the sub-genomic replicon), without the production of viral particles.

"RNA replicon" (or "self-replicating RNA molecule") refer to RNA which contains all of the genetic information required for directing its own amplification or self-replication within a permissive cell. To direct its own replication, the RNA molecule 1) encodes polymerase, replicase, or other proteins which may interact with viral or host cell-derived proteins, nucleic acids or ribonucleoproteins to catalyze the RNA amplification process; and 2) contain cis-acting RNA sequences required for replication and transcription of the replicon-encoded RNA. Self-replicating RNA is typically derived from the genomes of positive strand RNA viruses and can be used as basis of introducing foreign sequences to host cells by replacing viral sequences encoding structural or non-structural genes or inserting the foreign sequences 5' or 3' of the sequences encoding the structural or non-structural genes. Foreign sequences may also be introduced into the subgenomic regions of alphaviruses. Self-replicating RNA may be packaged into recombinant virus particles, such as recombinant alphavirus particles or alternatively delivered to the host using lipid nanoparticles (LNP). Self-replicating RNA may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size. Self-replicating RNAs are described, for example, in WO2017/180770, WO2018/075235, WO2019143949A2, "Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"In combination with" means that two or more therapeutic agents are be administered to a subject together in a mixture, concurrently as single agents or sequentially as single agents in any order.

"Enhance" or "induce" when in reference to an immune response refers to increasing the scale and/or efficiency of an immune response or extending the duration of the immune response. The terms are used interchangeably with "augment".

"Immune response" refers to any response to an immunogenic polypeptide or polynucleotide or fragment by the immune system of a vertebrate subject. Exemplary immune responses include local and systemic cellular as well as humoral immunity, such as cytotoxic T lymphocyte (CTL) responses, including antigen-specific induction of CD8$^+$ CTLs, helper T-cell responses including T-cell proliferative responses and cytokine release, and B-cell responses including antibody response.

"Specifically binds", "specific binding", "specifically binding" or "binds" refer to a proteinaceous molecule binding to an antigen or an epitope within the antigen (e.g. to ovarian neoantigen) with greater affinity than for other antigens. Typically, the proteinaceous molecule binds to the antigen or the epitope within the antigen with an equilibrium dissociation constant ($K_D$) of about $1\times10^{-7}$ M or less, for example about $5\times10^{-8}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein). In the context of the ovarian neoantigens described here, "specific binding" refers to binding of the proteinaceous molecule to the ovarian neoantigen without detectable binding to a wild-type protein the neoantigen is a variant of.

"Variant", "mutant" or "altered" refers to a polypeptide or a polynucleotide that differs from a reference polypeptide or a reference polynucleotide by one or more modifications, for example one or more substitutions, insertions or deletions.

"Antibody" refers to an immunoglobulin molecule including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity.

"Alternative scaffold" refers to a single chain protein framework that contains a structured core associated with variable domains of high conformational tolerance. The variable domains tolerate variation to be introduced without compromising scaffold integrity, and hence the variable domains can be engineered and selected for binding to a specific antigen.

"Chimeric antigen receptor" or "CAR" refers to engineered T cell receptors which graft a ligand or antigen specificity onto T cells (for example naïve T cells central memory T cells effector memory T cells or combinations thereof). CARs are also known as artificial T-cell receptors, chimeric T-cell receptors or chimeric immunoreceptors. CARs comprise an extracellular domain capable of binding to an antigen, a transmembrane domain and at least one intracellular domain. CAR intracellular domain comprises a polypeptide known to function as a domain that transmits a signal to cause activation or inhibition of a biological process in a cell. The transmembrane domain comprises any peptide or polypeptide known to span the cell membrane and that can function to link the extracellular and signaling domains. A chimeric antigen receptor may optionally comprise a hinge domain which serves as a linker between the extracellular and transmembrane domains.

"T cell receptor" or "TCR" refers to a molecule capable of recognizing a peptide when presented by an MHC molecule. Naturally occurring TCR heterodimer consists of an alpha (α) and beta (β) chain in around 95% of T-cells, whereas around 5% of T-cells have TCRs consisting of gamma (γ) and delta (δ) chains. Each chain of a natural TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end. The variable domain of both the TCR α chain and β chain have three hypervariable or complementarity determining regions (CDRs), CDR1, CDR2 and CDR3, which are responsible for recognizing processed antigens presented on MHC.

TCR may be a full length α/β or γ/δ heterodimer or a soluble molecule comprising a portion of the extracellular domain of the TCR that retains binding the peptide/MHC complex. TCR may be engineered into a single chain TCR.

"T cell receptor complex" or "TCR complex" refers to a known TCR complex comprising of a TCRα and TCRβ chains, CD3ε, CD3γ, CD3δ and CD3ζ molecules. In some instances, TCRα and TCRβ chains are replaced by TCRγ and TCRδ chains. The amino acid sequences of the various proteins forming the TCR complex are well-known.

"T cell" and "T lymphocyte" are interchangeable and used synonymously herein. T cell includes thymocytes, naïve T lymphocytes, memory T cells, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), a tumor infiltrating cytotoxic T cell (TIL; CD8$^+$ T cell), CD4$^+$CD8$^+$ T cell, or any other subset of T cells. Also included are "NKT cells", which refer to a specialized population of T cells that express a semi-invariant up T-cell receptor, but also express a variety of molecular markers that are typically associated with NK cells, such as NK1.1. NKT cells include NK1.1$^+$ and NK1.1$^-$, as well as CD4$^+$, CD4$^-$, CD8$^+$ and CD8$^-$ cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs" which refer to T cells that suppress an abnormal or excessive immune response and play a role in immune tolerance. Tregs are typically transcription factor Foxp3-positive CD4+T cells and can also include transcription factor Foxp3-negative regulatory T cells that are IL-10-producing CD4+T cells.

"Natural killer cell" or "NK cell" refers to a differentiated lymphocyte with a CD 16+ CD56+ and/or CD57+ TCR- phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Antigen presenting cell" (APC) refers to any cell that presents on its surface an antigen in association with a major histocompatibility complex molecule, either MHC class I or MHC class II molecule, or both.

"Prime-boost" or "prime-boost regimen" refers to a method of treating a subject involving priming a T-cell response with a first vaccine followed by boosting the immune response with a second vaccine. The first vaccine and the second vaccine are typically distinct. These prime- boost immunizations elicit immune responses of greater height and breadth than can be achieved by priming and boosting with the same vaccine. The priming step initiates memory cells and the boost step expands the memory response. Boosting can occur once or multiple times.

"Facilitator element" refers to any polynucleotide or polypeptide element that is operably linked to a polynucle- otide or a polypeptide, and include promoters, enhancers, polyadenylation signals, stop codons, protein tags, such as histidine tag, and the like. Facilitator elements herein include regulatory elements.

"Distinct" in the context of polypeptide or polynucleotide sequences refers to polypeptide or polynucleotide sequences that are not identical.

Compositions of Matter

The disclosure relates to ovarian cancer neoantigens, polynucleotides encoding them, vectors, host cells, vaccines comprising the neoantigens or polynucleotides encoding the neoantigens, proteinaceous molecules binding the ovarian neoantigens, and methods of making and using them. The disclosure also provides vaccines comprising the ovarian cancer neoantigens of the disclosure that are prevalent in a population of ovarian cancer patients, thereby providing a pan-vaccine that may be useful to treating a broad popula- tion of patients having diagnosed with various stages of ovarian cancer, such as localized or metastasized ovarian cancer.

Cancer cells produce neoantigens that result from genomic alterations and aberrant transcriptional programs. Neoantigen burden in patients has been associated with response to immunotherapy (Snyder et al., N Engl J Med. 2014 Dec. 4; 371(23):2189-2199; Le et al., N Engl J Med. 2015 Jun. 25; 372(26):2509-20; Rizvi et al., Science. 2015 Apr. 3; 348(6230):124-8; Van Allen et al., Science. 2015 Oct. 9; 350(6257):207-211. The disclosure is based, at least in part, on the identification of ovarian cancer neoantigens that are common in ovarian cancer patients and hence can be utilized to develop a therapy amenable to treatment of a spectrum of ovarian cancer patients. One or more neoanti- gens or polynucleotides encoding the neoantigens of the disclosure may also be used for diagnostic or prognostic purposes.

Polypeptides

Disclosed herein are polypeptides comprising ovarian cancer neoantigen sequences that may elicit an immune response in a subject.

In some embodiments, the disclosure provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, or fragments thereof. In some embodiments, the isolated poly- peptide may comprise at least two or more ovarian cancer neoantigen sequences.

In some embodiments, the disclosure provides an isolated heterologous polypeptide comprising two or more polypep- tides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof. In some embodiments, the two or more polypeptides disclosed herein may be present in tandem repeats in any order.

The disclosure also provides an isolated polypeptide comprising an amino acid sequence of SEQ ID NO: 1 or fragments thereof.

The disclosure also provides an isolated polypeptide comprising an amino acid sequence of SEQ ID NO: 3 or fragments thereof.

The disclosure also provides an isolated polypeptide comprising an amino acid sequence of SEQ ID NO: 5 or fragments thereof.

The disclosure also provides an isolated polypeptide comprising an amino acid sequence of SEQ ID NO: 7 or fragments thereof.

The disclosure also provides an isolated polypeptide comprising an amino acid sequence of SEQ ID NO: 9 or fragments thereof.

The disclosure also provides an isolated polypeptide comprising an amino acid sequence of SEQ ID NO: 11 or fragments thereof.

The disclosure also provides an isolated polypeptide comprising an amino acid sequence of SEQ ID NO: 13 or fragments thereof.

The disclosure also provides an isolated polypeptide comprising an amino acid sequence of SEQ ID NO: 15 or fragments thereof.

The disclosure also provides an isolated polypeptide comprising an amino acid sequence of SEQ ID NO: 17 or fragments thereof.

The disclosure also provides an isolated polypeptide comprising an amino acid sequence of SEQ ID NO: 19 or fragments thereof.

The disclosure also provides an isolated polypeptide comprising an amino acid sequence of SEQ ID NO: 21 or fragments thereof.

The disclosure also provides an isolated polypeptide comprising an amino acid sequence of SEQ ID NO: 23 or fragments thereof.

The disclosure also provides an isolated polypeptide comprising an amino acid sequence of SEQ ID NO: 25 or fragments thereof.

The disclosure also provides an isolated polypeptide comprising an amino acid sequence of SEQ ID NO: 27 or fragments thereof.

The disclosure also provides an isolated polypeptide comprising an amino acid sequence of SEQ ID NO: 29 or fragments thereof.

The disclosure also provides an isolated polypeptide comprising an amino acid sequence of SEQ ID NO: 31 or fragments thereof.

The disclosure also provides an isolated polypeptide comprising an amino acid sequence of SEQ ID NO: 33 or fragments thereof.

The disclosure also provides an isolated polypeptide comprising an amino acid sequence of SEQ ID NO: 35 or fragments thereof.

The disclosure also provides an isolated polypeptide comprising an amino acid sequence of SEQ ID NO: 37 or fragments thereof.

The disclosure also provides an isolated polypeptide comprising an amino acid sequence of SEQ ID NO: 39 or fragments thereof.

The disclosure also provides an isolated polypeptide comprising an amino acid sequence of SEQ ID NO: 41 or fragments thereof.

The disclosure also provides an isolated polypeptide comprising an amino acid sequence of SEQ ID NO: 43 or fragments thereof.

The disclosure also provides an isolated polypeptide comprising an amino acid sequence of SEQ ID NO: 45 or fragments thereof.

The disclosure also provides an isolated polypeptide comprising an amino acid sequence of SEQ ID NO: 47 or fragments thereof.

The disclosure also provides an isolated polypeptide comprising an amino acid sequence of SEQ ID NO: 49 or fragments thereof.

The disclosure also provides an isolated polypeptide comprising an amino acid sequence of SEQ ID NO: 51 or fragments thereof.

The disclosure also provides an isolated polypeptide comprising an amino acid sequence of SEQ ID NO: 53 or fragments thereof.

The disclosure also provides an isolated polypeptide comprising an amino acid sequence of SEQ ID NO: 55 or fragments thereof.

The disclosure also provides an isolated polypeptide comprising an amino acid sequence of SEQ ID NO: 57 or fragments thereof.

The disclosure also provides an isolated polypeptide comprising an amino acid sequence of SEQ ID NO: 59 or fragments thereof.

The disclosure also provides an isolated polypeptide comprising an amino acid sequence of SEQ ID NO: 61 or fragments thereof.

The disclosure also provides an isolated polypeptide comprising an amino acid sequence of SEQ ID NO: 63 or fragments thereof.

The disclosure also provides an isolated polypeptide comprising an amino acid sequence of SEQ ID NO: 65 or fragments thereof.

The disclosure also provides an isolated polypeptide comprising an amino acid sequence of SEQ ID NO: 67 or fragments thereof.

The disclosure also provides an isolated polypeptide comprising an amino acid sequence of SEQ ID NO: 69 or fragments thereof.

The disclosure also provides an isolated polypeptide comprising an amino acid sequence of SEQ ID NO: 71 or fragments thereof.

The disclosure also provides an isolated polypeptide comprising an amino acid sequence of SEQ ID NO: 73 or fragments thereof.

The disclosure also provides an isolated polypeptide comprising an amino acid sequence of SEQ ID NO: 75 or fragments thereof.

The disclosure also provides an isolated polypeptide comprising an amino acid sequence of SEQ ID NO: 77 or fragments thereof.

The disclosure also provides an isolated polypeptide comprising an amino acid sequence of SEQ ID NO: 79 or fragments thereof.

The disclosure also provides an isolated polypeptide comprising an amino acid sequence of SEQ ID NO: 81 or fragments thereof.

The disclosure also provides an isolated polypeptide comprising an amino acid sequence of SEQ ID NO: 83 or fragments thereof.

The disclosure also provides an isolated polypeptide comprising an amino acid sequence of SEQ ID NO: 85 or fragments thereof.

The disclosure also provides an isolated polypeptide comprising an amino acid sequence of SEQ ID NO: 87 or fragments thereof.

The disclosure also provides an isolated polypeptide comprising an amino acid sequence of SEQ ID NO: 89 or fragments thereof.

The disclosure also provides an isolated polypeptide comprising an amino acid sequence of SEQ ID NO: 91 or fragments thereof.

The disclosure also provides an isolated polypeptide comprising an amino acid sequence of SEQ ID NO: 93 or fragments thereof.

The disclosure also provides an isolated polypeptide comprising an amino acid sequence of SEQ ID NO: 95 or fragments thereof.

The disclosure also provides an isolated polypeptide comprising an amino acid sequence of SEQ ID NO: 97 or fragments thereof.

The disclosure also provides an isolated polypeptide comprising an amino acid sequence of SEQ ID NO: 99 or fragments thereof.

The disclosure also provides an isolated polypeptide comprising an amino acid sequence of SEQ ID NO: 101 or fragments thereof.

The disclosure also provides an isolated polypeptide comprising an amino acid sequence of SEQ ID NO: 103 or fragments thereof.

The disclosure also provides an isolated polypeptide comprising an amino acid sequence of SEQ ID NO: 105 or fragments thereof.

The disclosure also provides an isolated polypeptide comprising an amino acid sequence of SEQ ID NO: 107 or fragments thereof.

The disclosure also provides an isolated polypeptide comprising an amino acid sequence of SEQ ID NO: 109 or fragments thereof.

The disclosure also provides an isolated polypeptide comprising an amino acid sequence of SEQ ID NO: 111 or fragments thereof.

The disclosure also provides an isolated polypeptide comprising an amino acid sequence of SEQ ID NO: 113 or fragments thereof.

The disclosure also provides an isolated polypeptide comprising an amino acid sequence of SEQ ID NO: 115 or fragments thereof.

The disclosure also provides an isolated polypeptide comprising an amino acid sequence of SEQ ID NO: 117 or fragments thereof.

The disclosure also provides an isolated polypeptide comprising an amino acid sequence of SEQ ID NO: 119 or fragments thereof.

The disclosure also provides an isolated polypeptide comprising an amino acid sequence of SEQ ID NO: 121 or fragments thereof.

The disclosure also provides an isolated polypeptide comprising an amino acid sequence of SEQ ID NO: 123 or fragments thereof.

The disclosure also provides an isolated polypeptide comprising an amino acid sequence of SEQ ID NO: 125 or fragments thereof.

The disclosure also provides an isolated polypeptide comprising an amino acid sequence of SEQ ID NO: 127 or fragments thereof.

The disclosure also provides an isolated polypeptide comprising an amino acid sequence of SEQ ID NO: 129 or fragments thereof.

The disclosure also provides an isolated polypeptide comprising an amino acid sequence of SEQ ID NO: 131 or fragments thereof.

The disclosure also provides an isolated polypeptide comprising an amino acid sequence of SEQ ID NO: 133 or fragments thereof.

The disclosure also provides an isolated polypeptide comprising an amino acid sequence of SEQ ID NO: 135 or fragments thereof.

The disclosure also provides an isolated polypeptide comprising an amino acid sequence of SEQ ID NO: 137 or fragments thereof.

The disclosure also provides an isolated polypeptide comprising an amino acid sequence of SEQ ID NO: 139 or fragments thereof.

The disclosure also provides an isolated polypeptide comprising an amino acid sequence of SEQ ID NO: 141 or fragments thereof.

The disclosure also provides an isolated polypeptide comprising an amino acid sequence of SEQ ID NO: 143 or fragments thereof.

The disclosure also provides an isolated polypeptide comprising an amino acid sequence of SEQ ID NO: 145 or fragments thereof.

The disclosure also provides an isolated polypeptide comprising an amino acid sequence of SEQ ID NO: 147 or fragments thereof.

The disclosure also provides an isolated polypeptide comprising an amino acid sequence of SEQ ID NO: 149 or fragments thereof.

The disclosure also provides an isolated polypeptide comprising an amino acid sequence of SEQ ID NO: 151 or fragments thereof.

The disclosure also provides an isolated polypeptide comprising an amino acid sequence of SEQ ID NO: 153 or fragments thereof.

The disclosure also provides an isolated polypeptide comprising an amino acid sequence of SEQ ID NO: 155 or fragments thereof.

The disclosure also provides an isolated polypeptide comprising an amino acid sequence of SEQ ID NO: 157 or fragments thereof.

The disclosure also provides an isolated polypeptide comprising an amino acid sequence of SEQ ID NO: 159 or fragments thereof.

The disclosure also provides an isolated polypeptide comprising an amino acid sequence of SEQ ID NO: 161 or fragments thereof.

The disclosure also provides an isolated polypeptide comprising an amino acid sequence of SEQ ID NO: 163 or fragments thereof.

The disclosure also provides an isolated polypeptide comprising an amino acid sequence of SEQ ID NO: 165 or fragments thereof.

The disclosure also provides an isolated polypeptide comprising an amino acid sequence of SEQ ID NO: 167 or fragments thereof.

The disclosure also provides an isolated polypeptide comprising an amino acid sequence of SEQ ID NO: 169 or fragments thereof.

The disclosure also provides an isolated polypeptide comprising an amino acid sequence of SEQ ID NO: 171 or fragments thereof.

The disclosure also provides an isolated polypeptide comprising an amino acid sequence of SEQ ID NO: 173 or fragments thereof.

The disclosure also provides an isolated polypeptide comprising an amino acid sequence of SEQ ID NO: 175 or fragments thereof.

The disclosure also provides an isolated polypeptide comprising an amino acid sequence of SEQ ID NO: 177 or fragments thereof.

The disclosure also provides an isolated polypeptide comprising an amino acid sequence of SEQ ID NO: 179 or fragments thereof.

The disclosure also provides an isolated polypeptide comprising an amino acid sequence of SEQ ID NO: 181 or fragments thereof.

The disclosure also provides an isolated polypeptide comprising an amino acid sequence of SEQ ID NO: 183 or fragments thereof.

The disclosure also provides an isolated polypeptide comprising an amino acid sequence of SEQ ID NO: 185 or fragments thereof.

The disclosure also provides an isolated polypeptide comprising an amino acid sequence of SEQ ID NO: 187 or fragments thereof.

The disclosure also provides an isolated polypeptide comprising an amino acid sequence of SEQ ID NO: 189 or fragments thereof.

The disclosure also provides an isolated polypeptide comprising an amino acid sequence of SEQ ID NO: 191 or fragments thereof.

The disclosure also provides an isolated polypeptide comprising an amino acid sequence of SEQ ID NO: 193 or fragments thereof.

The disclosure also provides an isolated polypeptide comprising an amino acid sequence of SEQ ID NO: 195 or fragments thereof.

The disclosure also provides an isolated polypeptide comprising an amino acid sequence of SEQ ID NO: 197 or fragments thereof.

The disclosure also provides an isolated polypeptide comprising an amino acid sequence of SEQ ID NO: 199 or fragments thereof.

The disclosure also provides an isolated polypeptide comprising an amino acid sequence of SEQ ID NO: 201 or fragments thereof.

The disclosure also provides an isolated polypeptide comprising an amino acid sequence of SEQ ID NO: 203 or fragments thereof.

The disclosure also provides an isolated polypeptide comprising an amino acid sequence of SEQ ID NO: 205 or fragments thereof.

The disclosure also provides an isolated polypeptide comprising an amino acid sequence of SEQ ID NO: 207 or fragments thereof.

The disclosure also provides an isolated polypeptide comprising an amino acid sequence of SEQ ID NO: 209 or fragments thereof.

The disclosure also provides an isolated polypeptide comprising an amino acid sequence of SEQ ID NO: 211 or fragments thereof.

The disclosure also provides an isolated polypeptide comprising an amino acid sequence of SEQ ID NO: 213 or fragments thereof.

The disclosure also provides an isolated polypeptide comprising an amino acid sequence of SEQ ID NO: 215 or fragments thereof.

The disclosure also provides an isolated polypeptide comprising an amino acid sequence of SEQ ID NO: 217 or fragments thereof.

The disclosure also provides an isolated polypeptide comprising an amino acid sequence of SEQ ID NO: 219 or fragments thereof.

The disclosure also provides an isolated polypeptide comprising an amino acid sequence of SEQ ID NO: 221 or fragments thereof.

The disclosure also provides an isolated polypeptide comprising an amino acid sequence of SEQ ID NO: 223 or fragments thereof.

The disclosure also provides an isolated polypeptide comprising an amino acid sequence of SEQ ID NO: 225 or fragments thereof.

The disclosure also provides an isolated polypeptide comprising an amino acid sequence of SEQ ID NO: 227 or fragments thereof.

The disclosure also provides an isolated polypeptide comprising an amino acid sequence of SEQ ID NO: 229 or fragments thereof.

The disclosure also provides an isolated polypeptide comprising an amino acid sequence of SEQ ID NO: 231 or fragments thereof.

The disclosure also provides an isolated polypeptide comprising an amino acid sequence of SEQ ID NO: 233 or fragments thereof.

The disclosure also provides an isolated polypeptide comprising an amino acid sequence of SEQ ID NO: 235 or fragments thereof.

The disclosure also provides an isolated polypeptide comprising an amino acid sequence of SEQ ID NO: 237 or fragments thereof.

The disclosure also provides an isolated polypeptide comprising an amino acid sequence of SEQ ID NO: 239 or fragments thereof.

The disclosure also provides an isolated polypeptide comprising an amino acid sequence of SEQ ID NO: 241 or fragments thereof.

The disclosure also provides an isolated polypeptide comprising an amino acid sequence of SEQ ID NO: 243 or fragments thereof.

The disclosure also provides an isolated polypeptide comprising an amino acid sequence of SEQ ID NO: 245 or fragments thereof.

The disclosure also provides an isolated polypeptide comprising an amino acid sequence of SEQ ID NO: 247 or fragments thereof.

The disclosure also provides an isolated polypeptide comprising an amino acid sequence of SEQ ID NO: 249 or fragments thereof.

The disclosure also provides an isolated polypeptide comprising an amino acid sequence of SEQ ID NO: 251 or fragments thereof.

The disclosure also provides an isolated polypeptide comprising an amino acid sequence of SEQ ID NO: 253 or fragments thereof.

The disclosure also provides an isolated polypeptide comprising an amino acid sequence of SEQ ID NO: 255 or fragments thereof.

The disclosure also provides an isolated polypeptide comprising an amino acid sequence of SEQ ID NO: 257 or fragments thereof.

The disclosure also provides an isolated polypeptide comprising an amino acid sequence of SEQ ID NO: 259 or fragments thereof.

The disclosure also provides an isolated polypeptide comprising an amino acid sequence of SEQ ID NO: 261 or fragments thereof.

The disclosure also provides an isolated polypeptide comprising an amino acid sequence of SEQ ID NO: 263 or fragments thereof.

The disclosure also provides an isolated polypeptide comprising an amino acid sequence of SEQ ID NO: 265 or fragments thereof.

The disclosure also provides an isolated polypeptide comprising an amino acid sequence of SEQ ID NO: 267 or fragments thereof.

The disclosure also provides an isolated polypeptide comprising an amino acid sequence of SEQ ID NO: 269 or fragments thereof.

The disclosure also provides an isolated polypeptide comprising an amino acid sequence of SEQ ID NO: 271 or fragments thereof.

The disclosure also provides an isolated polypeptide comprising an amino acid sequence of SEQ ID NO: 273 or fragments thereof.

The disclosure also provides an isolated polypeptide comprising an amino acid sequence of SEQ ID NO: 275 or fragments thereof.

The disclosure also provides an isolated polypeptide comprising an amino acid sequence of SEQ ID NO: 277 or fragments thereof.

The disclosure also provides an isolated polypeptide comprising an amino acid sequence of SEQ ID NO: 279 or fragments thereof.

The disclosure also provides an isolated polypeptide comprising an amino acid sequence of SEQ ID NO: 281 or fragments thereof.

The disclosure also provides an isolated polypeptide comprising an amino acid sequence of SEQ ID NO: 283 or fragments thereof.

The disclosure also provides an isolated polypeptide comprising an amino acid sequence of SEQ ID NO: 285 or fragments thereof.

The disclosure also provides an isolated polypeptide comprising an amino acid sequence of SEQ ID NO: 287 or fragments thereof.

The disclosure also provides an isolated polypeptide comprising an amino acid sequence of SEQ ID NO: 289 or fragments thereof.

The disclosure also provides an isolated polypeptide comprising an amino acid sequence of SEQ ID NO: 291 or fragments thereof.

The disclosure also provides an isolated polypeptide comprising an amino acid sequence of SEQ ID NO: 293 or fragments thereof.

The disclosure also provides an isolated polypeptide comprising an amino acid sequence of SEQ ID NO: 295 or fragments thereof.

The disclosure also provides an isolated polypeptide comprising an amino acid sequence of SEQ ID NO: 297 or fragments thereof.

The disclosure also provides an isolated polypeptide comprising an amino acid sequence of SEQ ID NO: 299 or fragments thereof.

The disclosure also provides an isolated polypeptide comprising an amino acid sequence of SEQ ID NO: 301 or fragments thereof.

The disclosure also provides an isolated polypeptide comprising an amino acid sequence of SEQ ID NO: 303 or fragments thereof.

The disclosure also provides an isolated polypeptide comprising an amino acid sequence of SEQ ID NO: 305 or fragments thereof.

The disclosure also provides an isolated polypeptide comprising an amino acid sequence of SEQ ID NO: 307 or fragments thereof.

The disclosure also provides an isolated polypeptide comprising an amino acid sequence of SEQ ID NO: 309 or fragments thereof.

The disclosure also provides an isolated polypeptide comprising an amino acid sequence of SEQ ID NO: 311 or fragments thereof.

The disclosure also provides an isolated polypeptide comprising an amino acid sequence of SEQ ID NO: 313 or fragments thereof.

The disclosure also provides an isolated polypeptide comprising an amino acid sequence of SEQ ID NO: 315 or fragments thereof.

The disclosure also provides an isolated polypeptide comprising an amino acid sequence of SEQ ID NO: 317 or fragments thereof.

The disclosure also provides an isolated polypeptide comprising an amino acid sequence of SEQ ID NO: 319 or fragments thereof.

The disclosure also provides an isolated polypeptide comprising an amino acid sequence of SEQ ID NO: 321 or fragments thereof.

The disclosure also provides an isolated polypeptide comprising an amino acid sequence of SEQ ID NO: 323 or fragments thereof.

The disclosure also provides an isolated polypeptide comprising an amino acid sequence of SEQ ID NO: 325 or fragments thereof.

The disclosure also provides an isolated polypeptide comprising an amino acid sequence of SEQ ID NO: 327 or fragments thereof.

The disclosure also provides an isolated polypeptide comprising an amino acid sequence of SEQ ID NO: 329 or fragments thereof.

The disclosure also provides an isolated polypeptide comprising an amino acid sequence of SEQ ID NO: 331 or fragments thereof.

The disclosure also provides an isolated polypeptide comprising an amino acid sequence of SEQ ID NO: 333 or fragments thereof.

The disclosure also provides an isolated polypeptide comprising an amino acid sequence of SEQ ID NO: 335 or fragments thereof.

The disclosure also provides an isolated polypeptide comprising an amino acid sequence of SEQ ID NO: 337 or fragments thereof.

The disclosure also provides an isolated polypeptide comprising an amino acid sequence of SEQ ID NO: 339 or fragments thereof.

The disclosure also provides an isolated polypeptide comprising an amino acid sequence of SEQ ID NO: 341 or fragments thereof.

The disclosure also provides an isolated polypeptide comprising an amino acid sequence of SEQ ID NO: 343 or fragments thereof.

The disclosure also provides an isolated polypeptide comprising an amino acid sequence of SEQ ID NO: 345 or fragments thereof.

The disclosure also provides an isolated polypeptide comprising an amino acid sequence of SEQ ID NO: 347 or fragments thereof.

The disclosure also provides an isolated polypeptide comprising an amino acid sequence of SEQ ID NO: 349 or fragments thereof.

The disclosure also provides an isolated polypeptide comprising an amino acid sequence of SEQ ID NO: 351 or fragments thereof.

The disclosure also provides an isolated polypeptide comprising an amino acid sequence of SEQ ID NO: 353 or fragments thereof.

The disclosure also provides an isolated polypeptide comprising an amino acid sequence of SEQ ID NO: 355 or fragments thereof.

The disclosure also provides an isolated polypeptide comprising an amino acid sequence of SEQ ID NO: 357 or fragments thereof.

The disclosure also provides an isolated polypeptide comprising an amino acid sequence of SEQ ID NO: 359 or fragments thereof.

The disclosure also provides an isolated polypeptide comprising an amino acid sequence of SEQ ID NO: 361 or fragments thereof.

The disclosure also provides an isolated polypeptide comprising an amino acid sequence of SEQ ID NO: 363 or fragments thereof.

The disclosure also provides an isolated polypeptide comprising an amino acid sequence of SEQ ID NO: 365 or fragments thereof.

The disclosure also provides an isolated polypeptide comprising an amino acid sequence of SEQ ID NO: 367 or fragments thereof.

The disclosure also provides an isolated polypeptide comprising an amino acid sequence of SEQ ID NO: 369 or fragments thereof.

The disclosure also provides an isolated polypeptide comprising an amino acid sequence of SEQ ID NO: 371 or fragments thereof.

The disclosure also provides an isolated polypeptide comprising an amino acid sequence of SEQ ID NO: 373 or fragments thereof.

The disclosure also provides an isolated polypeptide comprising an amino acid sequence of SEQ ID NO: 375 or fragments thereof.

The disclosure also provides an isolated polypeptide comprising an amino acid sequence of SEQ ID NO: 377 or fragments thereof.

The disclosure also provides an isolated polypeptide comprising an amino acid sequence of SEQ ID NO: 379 or fragments thereof.

The disclosure also provides an isolated polypeptide comprising an amino acid sequence of SEQ ID NO: 381 or fragments thereof.

The disclosure also provides an isolated polypeptide comprising an amino acid sequence of SEQ ID NO: 383 or fragments thereof.

The disclosure also provides an isolated polypeptide comprising an amino acid sequence of SEQ ID NO: 385 or fragments thereof.

The disclosure also provides an isolated polypeptide comprising an amino acid sequence of SEQ ID NO: 387 or fragments thereof.

The disclosure also provides an isolated polypeptide comprising an amino acid sequence of SEQ ID NO: 389 or fragments thereof.

The disclosure also provides an isolated polypeptide comprising an amino acid sequence of SEQ ID NO: 391 or fragments thereof.

The disclosure also provides an isolated polypeptide comprising an amino acid sequence of SEQ ID NO: 393 or fragments thereof.

The disclosure also provides an isolated polypeptide comprising an amino acid sequence of SEQ ID NO: 395 or fragments thereof.

The disclosure also provides an isolated polypeptide comprising an amino acid sequence of SEQ ID NO: 397 or fragments thereof.

The disclosure also provides an isolated polypeptide comprising an amino acid sequence of SEQ ID NO: 399 or fragments thereof.

The disclosure also provides an isolated polypeptide comprising an amino acid sequence of SEQ ID NO: 401 or fragments thereof.

The disclosure also provides an isolated polypeptide comprising an amino acid sequence of SEQ ID NO: 403 or fragments thereof.

The disclosure also provides an isolated polypeptide comprising an amino acid sequence of SEQ ID NO: 405 or fragments thereof.

In some embodiments, the fragments comprise about 6-24 amino acids in length.

In some embodiments, the fragments comprise at least 6 amino acids. In some embodiments, the fragments comprise at least 7 amino acids. In some embodiments, the fragments comprise at least 8 amino acids. In some embodiments, the fragments comprise at least 9 amino acids. In some embodiments, the fragments comprise at least 10 amino acids. In some embodiments, the fragments comprise at least 11 amino acids. In some embodiments, the fragments comprise at least 12 amino acids. In some embodiments, the fragments comprise at least 13 amino acids. In some embodiments, the fragments comprise at least 14 amino acids. In some embodiments, the fragments comprise at least 15 amino acids. In some embodiments, the fragments comprise at least 16 amino acids. In some embodiments, the fragments comprise at least 17 amino acids. In some embodiments, the fragments comprise at least 18 amino acids. In some embodiments, the fragments comprise at least 19 amino acids. In some embodiments, the fragments comprise at least 20 amino acids. In some embodiments, the fragments comprise at least 21 amino acids. In some embodiments, the fragments comprise at least 22 amino acids. In some embodiments, the fragments comprise at least 23 amino acids. In some embodiments, the fragments comprise at least 24 amino acids. In some embodiments, the fragments comprise at least 25 amino acids. In some embodiments, the fragments comprise about 6 amino acids. In some embodiments, the fragments comprise about 7 amino acids. In some embodiments, the fragments comprise about 8 amino acids. In some embodiments, the fragments comprise about 9 amino acids. In some embodiments, the fragments comprise about 10 amino acids. In some embodiments, the fragments comprise about 11 amino acids. In some embodiments, the fragments comprise about 12 amino acids. In some embodiments, the fragments comprise about 13 amino acids. In some embodiments, the fragments comprise about 14 amino acids. In some embodiments, the fragments comprise about 15 amino acids. In some embodiments, the fragments comprise about 16 amino acids. In some embodiments, the fragments comprise about 17 amino acids. In some embodiments, the fragments comprise about 18 amino acids. In some embodiments, the fragments comprise about 19 amino acids. In some embodiments, the fragments comprise about 20 amino acids. In some embodiments, the fragments comprise about 21 amino acids. In some embodiments, the fragments comprise about 22 amino acids. In some embodiments, the fragments comprise about 23 amino acids. In some embodiments, the fragments comprise about 24 amino acids. In some embodiments, the fragments comprise about 25 amino acids. In some embodiments, the fragments comprise about 6-25 amino acids. In some embodiments, the fragments comprise about 7-25 amino acids. In some embodiments, the fragments comprise about 8-25 amino acids. In some embodiments, the fragments comprise about 8-24 amino acids. In some embodiments, the fragments comprise about 8-23 amino acids. In some embodiments, the fragments comprise about 8-22 amino acids. In some embodiments, the fragments comprise about 8-21 amino acids. In some embodiments, the fragments comprise about 8-20 amino acids. In some embodiments, the fragments comprise about 8-19 amino acids. In some embodiments, the fragments comprise about 8-18 amino acids. In some embodiments, the fragments comprise about 8-17 amino acids. In some embodiments, the fragments comprise about 8-16 amino acids. In some embodiments, the fragments comprise about 8-15 amino acids. In some embodiments, the fragments comprise about 8-14 amino acids. In some embodiments, the fragments comprise about 9-14 amino acids. In some embodiments, the fragments comprise about 9-13 amino acids. In some embodiments, the fragments comprise about 9-12 amino acids. In some embodiments, the fragments comprise about 9-11 amino acids. In some embodiments, the fragments comprise about 9-10 amino acids.

In some embodiments, the fragments are immunogenic fragments.

Immunogenic fragments in general are peptides that activate T cells, for example those that induce cytotoxic T cells when presented on MHC. Methods for assessing activation of T cells and/or induction of cytotoxic T lymphocytes are well known. In an exemplary assay, PBMCs isolated from an ovarian cancer patient are cultured in vitro in the presence of a test neoantigen or fragments thereof and IL-25. The cultures may be replenished periodically with IL-15 and IL-2 and cultured for an additional 12 days. On day 12, the cultures are re-stimulated with the test neoantigen or fragments thereof and the following day T cell activation may be assessed by measuring a percentage of IFNγ$^+$TNAα$^+$ CD8$^+$ cells when compared to a control culture.

The polypeptides and the heterologous polypeptides of the disclosure are useful in generating the recombinant viruses, the cells and the vaccines of the disclosure and proteinaceous molecules that specifically bind the one or more ovarian neoantigens of the disclosure or may be used directly as therapeutic agents by delivering them to a subject having an ovarian cancer using various technologies. The two or more neoantigens (e.g. polypeptides) may be incorporated into the vaccine in any order using standard cloning methods.

Through the validation process, 95 neoantigen polypeptides of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375 were identified as particularly useful to be included into a ovarian cancer vaccine based on their expression profile, prevalence and in vitro immunogenicity. It is expected that any combination of two or more of the 95 neoantigens can be utilized to generate an ovarian cancer vaccine that can be delivered to a subject utilizing any available delivery vehicles and any form available, such as peptides, DNA, RNA, replicons, or using viral delivery. The two or more neoantigens (e.g. polypeptides) may be incorporated into the vaccine in any order using standard cloning methods.

The two or more of the 95 polypeptides may be assembled into heterologous polynucleotides encoding heterologous polypeptides in any order, and the polypeptide order may differ between the various delivery options. In general, assembly of the polypeptides into a particular order may be based on generating a minimum number of junctional epitopes utilizing known algorithms.

In some embodiments, the disclosure provides a polypeptide comprising one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

The disclosure also provides a polypeptide comprising two or more tandem repeats of SEQ ID NOS; 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375 or fragments thereof. In some embodiments, the polypeptide comprises 2, 3, 4, 5, or more than 5 repeats of the polypeptides of the disclosure.

In some embodiments, the polypeptides are joined head to tail.

In some embodiment, the polypeptides can be separated by a linker.

Exemplary linker sequences include AAY, RR, DPP, HHAA, HHA, HHL, RKSYL, RKSY, SSL, or REKR. In some embodiments, the linkers disclosed herein may comprise a protease cleavage site such that the heterologous polypeptides may be cleaved in vivo in a subject into peptide fragments comprising neoantigen sequences, resulting in improved immune response.

In some embodiment the polypeptides are joined to each other directly without a linker without a linker.

In some embodiments, the polypeptides of the disclosure may further comprise a leader sequence or T-cell enhancer sequence (TCE) at the N-terminus. Leader sequences can increase the expression and/or increase immunological response. Exemplary leader sequences include the α chain of the TCR receptor of T$^2$ lymphocytes (HAVT20) (MACPGFLWALVISTC LEFSMA; SEQ ID NO: 419), a ubiquitin signal sequence (Ubiq) (MQIFVKTLTGKTITLEVEP SDTIENVKAKIQDKEGIPPDQQRLIFAGKQLEDGRTLSDYNIQKESTLHLVLRLRGVR; SEQ ID NO: 420), or a T cell enhancer (TCE) sequence, such as a peptide fragment of length of 28aa from the mandarin fish invariant chain (MGQKEQIHTLQKNSERMSKQLTRSSQAV; SEQ ID NO: 421). It is believed that the leader sequences may help in increasing an immune response to the epitopes disclosed herein.

Polynucleotides

The disclosure also provides polynucleotides that encode any of the polypeptides disclosed herein.

In some embodiments, the disclosure provides an isolated polynucleotide encoding a polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, or fragments thereof.

The disclosure also provides an isolated polynucleotide encoding a polypeptide that is at least 90% identical to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, or fragments thereof;

The disclosure also provides an isolated polynucleotide comprising a polynucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, or 406, or fragments thereof.

The disclosure also provides an isolated polynucleotide comprising a polynucleotide sequence that is at least 90% identical to the polynucleotide sequence of SEQ ID NOs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, or 406, or fragments thereof.

The disclosure also provides an isolated heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, and 406, and fragments thereof.

The disclosure also provides an isolated heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof.

In some embodiments, the fragments comprise at least 18 nucleotides. In some embodiments, the fragments comprise at least 21 nucleotides. In some embodiments, the fragments comprise at least 24 nucleotides. In some embodiments, the fragments comprise at least 27 nucleotides. In some embodiments, the fragments comprise at least 30 nucleotides. In some embodiments, the fragments comprise at least 33 nucleotides. In some embodiments, the fragments comprise at least 36 nucleotides. In some embodiments, the fragments comprise at least 39 nucleotides. In some embodiments, the fragments comprise at least 42 nucleotides. In some embodiments, the fragments comprise at least 45 nucleotides. In some embodiments, the fragments comprise at least 48 nucleotides. In some embodiments, the fragments comprise at least 51 nucleotides. In some embodiments, the fragments comprise at least 54 nucleotides. In some embodiments, the fragments comprise at least 57 nucleotides. In some embodiments, the fragments comprise at least 60 nucleotides. In some embodiments, the fragments comprise at least 63 nucleotides. In some embodiments, the fragments comprise at least 66 nucleotides. In some embodiments, the fragments comprise at least 69 nucleotides. In some embodiments, the fragments comprise at least 72 nucleotides. In some embodiments, the fragments comprise at least 75 nucleotides. In some embodiments, the fragments comprise about 18 nucleotides. In some embodiments, the fragments comprise about 21 nucleotides. In some embodiments, the fragments comprise about 24 nucleotides. In some embodiments, the fragments comprise about 27 nucleotides. In some embodiments, the fragments comprise about 30 nucleotides. In some embodiments, the fragments comprise about 33 nucleotides. In some embodiments, the fragments comprise about 36 nucleotides. In some embodiments, the fragments comprise about 39 nucleotides. In some embodiments, the fragments comprise about 42 nucleotides. In some embodiments, the fragments comprise about 45 nucleotides. In some embodiments, the fragments comprise about 48 nucleotides. In some embodiments, the fragments comprise about 51 nucleotides. In some embodiments, the fragments comprise about 54 nucleotides. In some embodiments, the fragments comprise about 57 nucleotides. In some embodiments, the fragments comprise about 60 nucleotides. In some embodiments, the fragments comprise about 63 nucleotides. In some embodiments, the fragments comprise about 66 nucleotides. In some embodiments, the fragments comprise about 69 nucleotides. In some embodiments, the fragments comprise about 72 nucleotides. In some embodiments, the fragments comprise about 75 nucleotides. In some embodiments, the fragments comprise about 18-75 nucleotides. In some embodiments, the fragments comprise about 21-75 nucleotides. In some embodiments, the fragments comprise about 24-75 nucleotides. In some embodiments, the fragments comprise about 24-72 nucleotides. In some embodiments, the fragments comprise about 24-69 nucleotides. In some embodiments, the fragments comprise about 24-66 nucleotides. In some embodiments, the fragments comprise about 24-63 nucleotides. In some embodiments, the fragments comprise about 24-60 nucleotides. In some embodiments, the fragments comprise about 24-57 nucleotides. In some embodiments, the fragments comprise about 24-54 nucleotides. In some embodiments, the fragments comprise about 24-51 nucleotides. In some embodiments, the fragments comprise about 24-48 nucleotides. In some embodiments, the fragments comprise about 24-45 nucleotides. In some embodiments, the fragments comprise about 24-42 nucleotides. In some embodiments, the fragments comprise about 27-42 nucleotides. In some embodiments, the fragments comprise about 27-39 nucleotides. In some embodiments, the fragments comprise about 27-36 nucleotides. In some embodiments, the fragments comprise about 27-33 nucleotides. In some embodiments, the fragments comprise about 27-30 nucleotides.

The polynucleotides and the heterologous polynucleotides of the disclosure encode the ovarian neoantigens and heterologous polypeptides comprising two or more ovarian neoantigens described herein. The polynucleotides and the heterologous polynucleotides of the disclosure are useful in generating the polypeptides, the heterologous polypeptides, the vectors, the recombinant viruses, the cells and the vaccines of the disclosure. The polynucleotides and the heterologous polynucleotides of the disclosure may be utilized as therapeutics by delivering them to a subject having an ovarian cancer using various technologies, including viral vectors as described herein or other delivery technologies as also described herein.

The disclosure also provides an isolated polynucleotide encoding the polypeptide of SEQ ID NO: 1 or fragments thereof. In some embodiments, the polypeptide of SEQ ID NO: 1, or a fragment thereof, is encoded by the polynucleotide of SEQ ID NO: 2 or fragments thereof.

The disclosure also provides an isolated polynucleotide encoding the polypeptide of SEQ ID NO: 3 or fragments thereof. In some embodiments, the polypeptide of SEQ ID NO: 3, or a fragment thereof, is encoded by the polynucleotide of SEQ ID NO: 4 or fragments thereof.

The disclosure also provides an isolated polynucleotide encoding the polypeptide of SEQ ID NO: 5 or fragments thereof. In some embodiments, the polypeptide of SEQ ID NO: 5, or a fragment thereof, is encoded by the polynucleotide of SEQ ID NO: 6 or fragments thereof.

The disclosure also provides an isolated polynucleotide encoding the polypeptide of SEQ ID NO: 7 or fragments thereof. In some embodiments, the polypeptide of SEQ ID NO: 7, or a fragment thereof, is encoded by the polynucleotide of SEQ ID NO: 8 or fragments thereof.

The disclosure also provides an isolated polynucleotide encoding the polypeptide of SEQ ID NO: 9 or fragments thereof. In some embodiments, the polypeptide of SEQ ID NO: 9, or a fragment thereof, is encoded by the polynucleotide of SEQ ID NO: 10 or fragments thereof.

The disclosure also provides an isolated polynucleotide encoding the polypeptide of SEQ ID NO: 11 or fragments thereof. In some embodiments, the polypeptide of SEQ ID NO: 11, or a fragment thereof, is encoded by the polynucleotide of SEQ ID NO: 12 or fragments thereof.

The disclosure also provides an isolated polynucleotide encoding the polypeptide of SEQ ID NO: 13 or fragments thereof. In some embodiments, the polypeptide of SEQ ID NO: 13, or a fragment thereof, is encoded by the polynucleotide of SEQ ID NO: 14 or fragments thereof.

The disclosure also provides an isolated polynucleotide encoding the polypeptide of SEQ ID NO: 15 or fragments thereof. In some embodiments, the polypeptide of SEQ ID NO: 15, or a fragment thereof, is encoded by the polynucleotide of SEQ ID NO: 16 or fragments thereof.

The disclosure also provides an isolated polynucleotide encoding the polypeptide of SEQ ID NO: 17 or fragments thereof. In some embodiments, the polypeptide of SEQ ID NO: 17, or a fragment thereof, is encoded by the polynucleotide of SEQ ID NO: 18 or fragments thereof.

The disclosure also provides an isolated polynucleotide encoding the polypeptide of SEQ ID NO: 19 or fragments thereof. In some embodiments, the polypeptide of SEQ ID NO: 19, or a fragment thereof, is encoded by the polynucleotide of SEQ ID NO: 20 or fragments thereof.

The disclosure also provides an isolated polynucleotide encoding the polypeptide of SEQ ID NO: 21 or fragments thereof. In some embodiments, the polypeptide of SEQ ID NO: 21, or a fragment thereof, is encoded by the polynucleotide of SEQ ID NO: 22 or fragments thereof.

The disclosure also provides an isolated polynucleotide encoding the polypeptide of SEQ ID NO: 23 or fragments thereof. In some embodiments, the polypeptide of SEQ ID NO: 23, or a fragment thereof, is encoded by the polynucleotide of SEQ ID NO: 24 or fragments thereof.

The disclosure also provides an isolated polynucleotide encoding the polypeptide of SEQ ID NO: 25 or fragments thereof. In some embodiments, the polypeptide of SEQ ID NO: 25, or a fragment thereof, is encoded by the polynucleotide of SEQ ID NO: 26 or fragments thereof.

The disclosure also provides an isolated polynucleotide encoding the polypeptide of SEQ ID NO: 27 or fragments thereof. In some embodiments, the polypeptide of SEQ ID NO: 27, or a fragment thereof, is encoded by the polynucleotide of SEQ ID NO: 28 or fragments thereof.

The disclosure also provides an isolated polynucleotide encoding the polypeptide of SEQ ID NO: 29 or fragments thereof. In some embodiments, the polypeptide of SEQ ID NO: 29, or a fragment thereof, is encoded by the polynucleotide of SEQ ID NO: 30 or fragments thereof.

The disclosure also provides an isolated polynucleotide encoding the polypeptide of SEQ ID NO: 31 or fragments thereof. In some embodiments, the polypeptide of SEQ ID NO: 31, or a fragment thereof, is encoded by the polynucleotide of SEQ ID NO: 32 or fragments thereof.

The disclosure also provides an isolated polynucleotide encoding the polypeptide of SEQ ID NO: 33 or fragments thereof. In some embodiments, the polypeptide of SEQ ID NO: 33, or a fragment thereof, is encoded by the polynucleotide of SEQ ID NO: 34 or fragments thereof.

The disclosure also provides an isolated polynucleotide encoding the polypeptide of SEQ ID NO: 35 or fragments thereof. In some embodiments, the polypeptide of SEQ ID NO: 35, or a fragment thereof, is encoded by the polynucleotide of SEQ ID NO: 36 or fragments thereof.

The disclosure also provides an isolated polynucleotide encoding the polypeptide of SEQ ID NO: 37 or fragments thereof. In some embodiments, the polypeptide of SEQ ID NO: 37, or a fragment thereof, is encoded by the polynucleotide of SEQ ID NO: 38 or fragments thereof.

The disclosure also provides an isolated polynucleotide encoding the polypeptide of SEQ ID NO: 39 or fragments thereof. In some embodiments, the polypeptide of SEQ ID NO: 39, or a fragment thereof, is encoded by the polynucleotide of SEQ ID NO: 40 or fragments thereof.

The disclosure also provides an isolated polynucleotide encoding the polypeptide of SEQ ID NO: 41 or fragments thereof. In some embodiments, the polypeptide of SEQ ID NO: 41, or a fragment thereof, is encoded by the polynucleotide of SEQ ID NO: 42 or fragments thereof.

The disclosure also provides an isolated polynucleotide encoding the polypeptide of SEQ ID NO: 43 or fragments thereof. In some embodiments, the polypeptide of SEQ ID NO: 43, or a fragment thereof, is encoded by the polynucleotide of SEQ ID NO: 44 or fragments thereof.

The disclosure also provides an isolated polynucleotide encoding the polypeptide of SEQ ID NO: 45 or fragments thereof. In some embodiments, the polypeptide of SEQ ID NO: 45, or a fragment thereof, is encoded by the polynucleotide of SEQ ID NO: 46 or fragments thereof.

The disclosure also provides an isolated polynucleotide encoding the polypeptide of SEQ ID NO: 47 or fragments thereof. In some embodiments, the polypeptide of SEQ ID NO: 47, or a fragment thereof, is encoded by the polynucleotide of SEQ ID NO: 48 or fragments thereof.

The disclosure also provides an isolated polynucleotide encoding the polypeptide of SEQ ID NO: 49 or fragments thereof. In some embodiments, the polypeptide of SEQ ID NO: 49, or a fragment thereof, is encoded by the polynucleotide of SEQ ID NO: 50 or fragments thereof.

The disclosure also provides an isolated polynucleotide encoding the polypeptide of SEQ ID NO: 51 or fragments thereof. In some embodiments, the polypeptide of SEQ ID NO: 51, or a fragment thereof, is encoded by the polynucleotide of SEQ ID NO: 52 or fragments thereof.

The disclosure also provides an isolated polynucleotide encoding the polypeptide of SEQ ID NO: 53 or fragments thereof. In some embodiments, the polypeptide of SEQ ID NO: 53, or a fragment thereof, is encoded by the polynucleotide of SEQ ID NO: 54 or fragments thereof.

The disclosure also provides an isolated polynucleotide encoding the polypeptide of SEQ ID NO: 55 or fragments thereof. In some embodiments, the polypeptide of SEQ ID NO: 55, or a fragment thereof, is encoded by the polynucleotide of SEQ ID NO: 56 or fragments thereof.

The disclosure also provides an isolated polynucleotide encoding the polypeptide of SEQ ID NO: 57 or fragments thereof. In some embodiments, the polypeptide of SEQ ID NO: 57, or a fragment thereof, is encoded by the polynucleotide of SEQ ID NO: 58 or fragments thereof.

The disclosure also provides an isolated polynucleotide encoding the polypeptide of SEQ ID NO: 59 or fragments thereof. In some embodiments, the polypeptide of SEQ ID NO: 59, or a fragment thereof, is encoded by the polynucleotide of SEQ ID NO: 60 or fragments thereof.

The disclosure also provides an isolated polynucleotide encoding the polypeptide of SEQ ID NO: 61 or fragments thereof. In some embodiments, the polypeptide of SEQ ID NO: 61, or a fragment thereof, is encoded by the polynucleotide of SEQ ID NO: 62 or fragments thereof.

The disclosure also provides an isolated polynucleotide encoding the polypeptide of SEQ ID NO: 63 or fragments thereof. In some embodiments, the polypeptide of SEQ ID NO: 63, or a fragment thereof, is encoded by the polynucleotide of SEQ ID NO: 64 or fragments thereof.

The disclosure also provides an isolated polynucleotide encoding the polypeptide of SEQ ID NO: 65 or fragments thereof. In some embodiments, the polypeptide of SEQ ID NO: 65, or a fragment thereof, is encoded by the polynucleotide of SEQ ID NO: 66 or fragments thereof.

The disclosure also provides an isolated polynucleotide encoding the polypeptide of SEQ ID NO: 67 or fragments thereof. In some embodiments, the polypeptide of SEQ ID NO: 67, or a fragment thereof, is encoded by the polynucleotide of SEQ ID NO: 68 or fragments thereof.

The disclosure also provides an isolated polynucleotide encoding the polypeptide of SEQ ID NO: 69 or fragments thereof. In some embodiments, the polypeptide of SEQ ID NO: 69, or a fragment thereof, is encoded by the polynucleotide of SEQ ID NO: 70 or fragments thereof.

The disclosure also provides an isolated polynucleotide encoding the polypeptide of SEQ ID NO: 71 or fragments thereof. In some embodiments, the polypeptide of SEQ ID NO: 71, or a fragment thereof, is encoded by the polynucleotide of SEQ ID NO: 72 or fragments thereof.

The disclosure also provides an isolated polynucleotide encoding the polypeptide of SEQ ID NO: 73 or fragments thereof. In some embodiments, the polypeptide of SEQ ID NO: 73, or a fragment thereof, is encoded by the polynucleotide of SEQ ID NO: 74 or fragments thereof.

The disclosure also provides an isolated polynucleotide encoding the polypeptide of SEQ ID NO: 75 or fragments thereof. In some embodiments, the polypeptide of SEQ ID NO: 75, or a fragment thereof, is encoded by the polynucleotide of SEQ ID NO: 76 or fragments thereof.

The disclosure also provides an isolated polynucleotide encoding the polypeptide of SEQ ID NO: 77 or fragments thereof. In some embodiments, the polypeptide of SEQ ID NO: 77, or a fragment thereof, is encoded by the polynucleotide of SEQ ID NO: 78 or fragments thereof.

The disclosure also provides an isolated polynucleotide encoding the polypeptide of SEQ ID NO: 79 or fragments thereof. In some embodiments, the polypeptide of SEQ ID NO: 79, or a fragment thereof, is encoded by the polynucleotide of SEQ ID NO: 80 or fragments thereof.

The disclosure also provides an isolated polynucleotide encoding the polypeptide of SEQ ID NO: 81 or fragments thereof. In some embodiments, the polypeptide of SEQ ID NO: 81, or a fragment thereof, is encoded by the polynucleotide of SEQ ID NO: 82 or fragments thereof.

The disclosure also provides an isolated polynucleotide encoding the polypeptide of SEQ ID NO: 83 or fragments thereof. In some embodiments, the polypeptide of SEQ ID NO: 83, or a fragment thereof, is encoded by the polynucleotide of SEQ ID NO: 84 or fragments thereof.

The disclosure also provides an isolated polynucleotide encoding the polypeptide of SEQ ID NO: 85 or fragments thereof. In some embodiments, the polypeptide of SEQ ID NO: 85, or a fragment thereof, is encoded by the polynucleotide of SEQ ID NO: 86 or fragments thereof.

The disclosure also provides an isolated polynucleotide encoding the polypeptide of SEQ ID NO: 87 or fragments thereof. In some embodiments, the polypeptide of SEQ ID NO: 87, or a fragment thereof, is encoded by the polynucleotide of SEQ ID NO: 88 or fragments thereof.

The disclosure also provides an isolated polynucleotide encoding the polypeptide of SEQ ID NO: 89 or fragments thereof. In some embodiments, the polypeptide of SEQ ID NO: 89, or a fragment thereof, is encoded by the polynucleotide of SEQ ID NO: 90 or fragments thereof.

The disclosure also provides an isolated polynucleotide encoding the polypeptide of SEQ ID NO: 91 or fragments thereof. In some embodiments, the polypeptide of SEQ ID NO: 91, or a fragment thereof, is encoded by the polynucleotide of SEQ ID NO: 92 or fragments thereof.

The disclosure also provides an isolated polynucleotide encoding the polypeptide of SEQ ID NO: 93 or fragments thereof. In some embodiments, the polypeptide of SEQ ID NO: 93, or a fragment thereof, is encoded by the polynucleotide of SEQ ID NO: 94 or fragments thereof.

The disclosure also provides an isolated polynucleotide encoding the polypeptide of SEQ ID NO: 95 or fragments thereof. In some embodiments, the polypeptide of SEQ ID NO: 95, or a fragment thereof, is encoded by the polynucleotide of SEQ ID NO: 96 or fragments thereof.

The disclosure also provides an isolated polynucleotide encoding the polypeptide of SEQ ID NO: 97 or fragments thereof. In some embodiments, the polypeptide of SEQ ID NO: 97, or a fragment thereof, is encoded by the polynucleotide of SEQ ID NO: 98 or fragments thereof.

The disclosure also provides an isolated polynucleotide encoding the polypeptide of SEQ ID NO: 99 or fragments thereof. In some embodiments, the polypeptide of SEQ ID NO: 99, or a fragment thereof, is encoded by the polynucleotide of SEQ ID NO: 100 or fragments thereof.

The disclosure also provides an isolated polynucleotide encoding the polypeptide of SEQ ID NO: 101 or fragments thereof. In some embodiments, the polypeptide of SEQ ID NO: 101, or a fragment thereof, is encoded by the polynucleotide of SEQ ID NO: 102 or fragments thereof.

The disclosure also provides an isolated polynucleotide encoding the polypeptide of SEQ ID NO: 103 or fragments thereof. In some embodiments, the polypeptide of SEQ ID NO: 103, or a fragment thereof, is encoded by the polynucleotide of SEQ ID NO: 104 or fragments thereof.

The disclosure also provides an isolated polynucleotide encoding the polypeptide of SEQ ID NO: 105 or fragments thereof. In some embodiments, the polypeptide of SEQ ID NO: 105, or a fragment thereof, is encoded by the polynucleotide of SEQ ID NO: 106 or fragments thereof.

The disclosure also provides an isolated polynucleotide encoding the polypeptide of SEQ ID NO: 107 or fragments thereof. In some embodiments, the polypeptide of SEQ ID NO: 107, or a fragment thereof, is encoded by the polynucleotide of SEQ ID NO: 108 or fragments thereof.

The disclosure also provides an isolated polynucleotide encoding the polypeptide of SEQ ID NO: 109 or fragments thereof. In some embodiments, the polypeptide of SEQ ID NO: 109, or a fragment thereof, is encoded by the polynucleotide of SEQ ID NO: 110 or fragments thereof.

The disclosure also provides an isolated polynucleotide encoding the polypeptide of SEQ ID NO: 111 or fragments thereof. In some embodiments, the polypeptide of SEQ ID NO: 111, or a fragment thereof, is encoded by the polynucleotide of SEQ ID NO: 112 or fragments thereof.

The disclosure also provides an isolated polynucleotide encoding the polypeptide of SEQ ID NO: 113 or fragments thereof. In some embodiments, the polypeptide of SEQ ID NO: 113, or a fragment thereof, is encoded by the polynucleotide of SEQ ID NO: 114 or fragments thereof.

The disclosure also provides an isolated polynucleotide encoding the polypeptide of SEQ ID NO: 115 or fragments thereof. In some embodiments, the polypeptide of SEQ ID NO: 115, or a fragment thereof, is encoded by the polynucleotide of SEQ ID NO: 116 or fragments thereof.

The disclosure also provides an isolated polynucleotide encoding the polypeptide of SEQ ID NO: 117 or fragments thereof. In some embodiments, the polypeptide of SEQ ID NO: 117, or a fragment thereof, is encoded by the polynucleotide of SEQ ID NO: 118 or fragments thereof.

The disclosure also provides an isolated polynucleotide encoding the polypeptide of SEQ ID NO: 119 or fragments thereof. In some embodiments, the polypeptide of SEQ ID NO: 119, or a fragment thereof, is encoded by the polynucleotide of SEQ ID NO: 120 or fragments thereof.

The disclosure also provides an isolated polynucleotide encoding the polypeptide of SEQ ID NO: 121 or fragments thereof. In some embodiments, the polypeptide of SEQ ID NO: 121, or a fragment thereof, is encoded by the polynucleotide of SEQ ID NO: 122 or fragments thereof.

The disclosure also provides an isolated polynucleotide encoding the polypeptide of SEQ ID NO: 123 or fragments thereof. In some embodiments, the polypeptide of SEQ ID NO: 123, or a fragment thereof, is encoded by the polynucleotide of SEQ ID NO: 124 or fragments thereof.

The disclosure also provides an isolated polynucleotide encoding the polypeptide of SEQ ID NO: 125 or fragments thereof. In some embodiments, the polypeptide of SEQ ID NO: 125, or a fragment thereof, is encoded by the polynucleotide of SEQ ID NO: 126 or fragments thereof.

The disclosure also provides an isolated polynucleotide encoding the polypeptide of SEQ ID NO: 127 or fragments thereof. In some embodiments, the polypeptide of SEQ ID NO: 127, or a fragment thereof, is encoded by the polynucleotide of SEQ ID NO: 128 or fragments thereof.

The disclosure also provides an isolated polynucleotide encoding the polypeptide of SEQ ID NO: 129 or fragments thereof. In some embodiments, the polypeptide of SEQ ID NO: 129, or a fragment thereof, is encoded by the polynucleotide of SEQ ID NO: 130 or fragments thereof.

The disclosure also provides an isolated polynucleotide encoding the polypeptide of SEQ ID NO: 131 or fragments thereof. In some embodiments, the polypeptide of SEQ ID NO: 131, or a fragment thereof, is encoded by the polynucleotide of SEQ ID NO: 132 or fragments thereof.

The disclosure also provides an isolated polynucleotide encoding the polypeptide of SEQ ID NO: 133 or fragments thereof. In some embodiments, the polypeptide of SEQ ID NO: 133, or a fragment thereof, is encoded by the polynucleotide of SEQ ID NO: 134 or fragments thereof.

The disclosure also provides an isolated polynucleotide encoding the polypeptide of SEQ ID NO: 135 or fragments thereof. In some embodiments, the polypeptide of SEQ ID NO: 135, or a fragment thereof, is encoded by the polynucleotide of SEQ ID NO: 136 or fragments thereof.

The disclosure also provides an isolated polynucleotide encoding the polypeptide of SEQ ID NO: 137 or fragments thereof. In some embodiments, the polypeptide of SEQ ID NO: 137, or a fragment thereof, is encoded by the polynucleotide of SEQ ID NO: 138 or fragments thereof.

The disclosure also provides an isolated polynucleotide encoding the polypeptide of SEQ ID NO: 139 or fragments thereof. In some embodiments, the polypeptide of SEQ ID NO: 139, or a fragment thereof, is encoded by the polynucleotide of SEQ ID NO: 140 or fragments thereof.

The disclosure also provides an isolated polynucleotide encoding the polypeptide of SEQ ID NO: 141 or fragments thereof. In some embodiments, the polypeptide of SEQ ID NO: 141, or a fragment thereof, is encoded by the polynucleotide of SEQ ID NO: 142 or fragments thereof.

The disclosure also provides an isolated polynucleotide encoding the polypeptide of SEQ ID NO: 143 or fragments thereof. In some embodiments, the polypeptide of SEQ ID NO: 143, or a fragment thereof, is encoded by the polynucleotide of SEQ ID NO: 144 or fragments thereof.

The disclosure also provides an isolated polynucleotide encoding the polypeptide of SEQ ID NO: 145 or fragments thereof. In some embodiments, the polypeptide of SEQ ID NO: 145, or a fragment thereof, is encoded by the polynucleotide of SEQ ID NO: 146 or fragments thereof.

The disclosure also provides an isolated polynucleotide encoding the polypeptide of SEQ ID NO: 147 or fragments thereof. In some embodiments, the polypeptide of SEQ ID NO: 147, or a fragment thereof, is encoded by the polynucleotide of SEQ ID NO: 148 or fragments thereof.

The disclosure also provides an isolated polynucleotide encoding the polypeptide of SEQ ID NO: 149 or fragments thereof. In some embodiments, the polypeptide of SEQ ID NO: 149, or a fragment thereof, is encoded by the polynucleotide of SEQ ID NO: 150 or fragments thereof.

The disclosure also provides an isolated polynucleotide encoding the polypeptide of SEQ ID NO: 151 or fragments thereof. In some embodiments, the polypeptide of SEQ ID NO: 151, or a fragment thereof, is encoded by the polynucleotide of SEQ ID NO: 152 or fragments thereof.

The disclosure also provides an isolated polynucleotide encoding the polypeptide of SEQ ID NO: 153 or fragments thereof. In some embodiments, the polypeptide of SEQ ID NO: 153, or a fragment thereof, is encoded by the polynucleotide of SEQ ID NO: 154 or fragments thereof.

The disclosure also provides an isolated polynucleotide encoding the polypeptide of SEQ ID NO: 155 or fragments thereof. In some embodiments, the polypeptide of SEQ ID NO: 155, or a fragment thereof, is encoded by the polynucleotide of SEQ ID NO: 156 or fragments thereof.

The disclosure also provides an isolated polynucleotide encoding the polypeptide of SEQ ID NO: 157 or fragments thereof. In some embodiments, the polypeptide of SEQ ID NO: 157, or a fragment thereof, is encoded by the polynucleotide of SEQ ID NO: 158 or fragments thereof.

The disclosure also provides an isolated polynucleotide encoding the polypeptide of SEQ ID NO: 159 or fragments thereof. In some embodiments, the polypeptide of SEQ ID NO: 159, or a fragment thereof, is encoded by the polynucleotide of SEQ ID NO: 160 or fragments thereof.

The disclosure also provides an isolated polynucleotide encoding the polypeptide of SEQ ID NO: 161 or fragments thereof. In some embodiments, the polypeptide of SEQ ID NO: 161, or a fragment thereof, is encoded by the polynucleotide of SEQ ID NO: 162 or fragments thereof.

The disclosure also provides an isolated polynucleotide encoding the polypeptide of SEQ ID NO: 163 or fragments thereof. In some embodiments, the polypeptide of SEQ ID NO: 163, or a fragment thereof, is encoded by the polynucleotide of SEQ ID NO: 164 or fragments thereof.

The disclosure also provides an isolated polynucleotide encoding the polypeptide of SEQ ID NO: 165 or fragments thereof. In some embodiments, the polypeptide of SEQ ID NO: 165, or a fragment thereof, is encoded by the polynucleotide of SEQ ID NO: 166 or fragments thereof.

The disclosure also provides an isolated polynucleotide encoding the polypeptide of SEQ ID NO: 167 or fragments thereof. In some embodiments, the polypeptide of SEQ ID NO: 167, or a fragment thereof, is encoded by the polynucleotide of SEQ ID NO: 168 or fragments thereof.

The disclosure also provides an isolated polynucleotide encoding the polypeptide of SEQ ID NO: 169 or fragments thereof. In some embodiments, the polypeptide of SEQ ID NO: 169, or a fragment thereof, is encoded by the polynucleotide of SEQ ID NO: 170 or fragments thereof.

The disclosure also provides an isolated polynucleotide encoding the polypeptide of SEQ ID NO: 171 or fragments thereof. In some embodiments, the polypeptide of SEQ ID NO: 171, or a fragment thereof, is encoded by the polynucleotide of SEQ ID NO: 172 or fragments thereof.

The disclosure also provides an isolated polynucleotide encoding the polypeptide of SEQ ID NO: 173 or fragments thereof. In some embodiments, the polypeptide of SEQ ID NO: 173, or a fragment thereof, is encoded by the polynucleotide of SEQ ID NO: 174 or fragments thereof.

The disclosure also provides an isolated polynucleotide encoding the polypeptide of SEQ ID NO: 175 or fragments thereof. In some embodiments, the polypeptide of SEQ ID NO: 175, or a fragment thereof, is encoded by the polynucleotide of SEQ ID NO: 176 or fragments thereof.

The disclosure also provides an isolated polynucleotide encoding the polypeptide of SEQ ID NO: 177 or fragments thereof. In some embodiments, the polypeptide of SEQ ID NO: 177, or a fragment thereof, is encoded by the polynucleotide of SEQ ID NO: 178 or fragments thereof.

The disclosure also provides an isolated polynucleotide encoding the polypeptide of SEQ ID NO: 179 or fragments thereof. In some embodiments, the polypeptide of SEQ ID NO: 179, or a fragment thereof, is encoded by the polynucleotide of SEQ ID NO: 180 or fragments thereof.

The disclosure also provides an isolated polynucleotide encoding the polypeptide of SEQ ID NO: 181 or fragments thereof. In some embodiments, the polypeptide of SEQ ID NO: 181, or a fragment thereof, is encoded by the polynucleotide of SEQ ID NO: 182 or fragments thereof.

The disclosure also provides an isolated polynucleotide encoding the polypeptide of SEQ ID NO: 183 or fragments thereof. In some embodiments, the polypeptide of SEQ ID NO: 183, or a fragment thereof, is encoded by the polynucleotide of SEQ ID NO: 184 or fragments thereof.

The disclosure also provides an isolated polynucleotide encoding the polypeptide of SEQ ID NO: 185 or fragments thereof. In some embodiments, the polypeptide of SEQ ID NO: 185, or a fragment thereof, is encoded by the polynucleotide of SEQ ID NO: 186 or fragments thereof.

The disclosure also provides an isolated polynucleotide encoding the polypeptide of SEQ ID NO: 187 or fragments thereof. In some embodiments, the polypeptide of SEQ ID NO: 187, or a fragment thereof, is encoded by the polynucleotide of SEQ ID NO: 188 or fragments thereof.

The disclosure also provides an isolated polynucleotide encoding the polypeptide of SEQ ID NO: 189 or fragments thereof. In some embodiments, the polypeptide of SEQ ID NO: 189, or a fragment thereof, is encoded by the polynucleotide of SEQ ID NO: 190 or fragments thereof.

The disclosure also provides an isolated polynucleotide encoding the polypeptide of SEQ ID NO: 191 or fragments thereof. In some embodiments, the polypeptide of SEQ ID NO: 191, or a fragment thereof, is encoded by the polynucleotide of SEQ ID NO: 192 or fragments thereof.

The disclosure also provides an isolated polynucleotide encoding the polypeptide of SEQ ID NO: 193 or fragments thereof. In some embodiments, the polypeptide of SEQ ID NO: 193, or a fragment thereof, is encoded by the polynucleotide of SEQ ID NO: 194 or fragments thereof.

The disclosure also provides an isolated polynucleotide encoding the polypeptide of SEQ ID NO: 195 or fragments thereof. In some embodiments, the polypeptide of SEQ ID NO: 195, or a fragment thereof, is encoded by the polynucleotide of SEQ ID NO: 196 or fragments thereof.

The disclosure also provides an isolated polynucleotide encoding the polypeptide of SEQ ID NO: 197 or fragments thereof. In some embodiments, the polypeptide of SEQ ID NO: 197, or a fragment thereof, is encoded by the polynucleotide of SEQ ID NO: 198 or fragments thereof.

The disclosure also provides an isolated polynucleotide encoding the polypeptide of SEQ ID NO: 199 or fragments thereof. In some embodiments, the polypeptide of SEQ ID NO: 199, or a fragment thereof, is encoded by the polynucleotide of SEQ ID NO: 200 or fragments thereof.

The disclosure also provides an isolated polynucleotide encoding the polypeptide of SEQ ID NO: 201 or fragments thereof. In some embodiments, the polypeptide of SEQ ID NO: 201, or a fragment thereof, is encoded by the polynucleotide of SEQ ID NO: 202 or fragments thereof.

The disclosure also provides an isolated polynucleotide encoding the polypeptide of SEQ ID NO: 203 or fragments thereof. In some embodiments, the polypeptide of SEQ ID NO: 203, or a fragment thereof, is encoded by the polynucleotide of SEQ ID NO: 204 or fragments thereof.

The disclosure also provides an isolated polynucleotide encoding the polypeptide of SEQ ID NO: 205 or fragments thereof. In some embodiments, the polypeptide of SEQ ID NO: 205, or a fragment thereof, is encoded by the polynucleotide of SEQ ID NO: 206 or fragments thereof.

The disclosure also provides an isolated polynucleotide encoding the polypeptide of SEQ ID NO: 207 or fragments thereof. In some embodiments, the polypeptide of SEQ ID NO: 207, or a fragment thereof, is encoded by the polynucleotide of SEQ ID NO: 208 or fragments thereof.

The disclosure also provides an isolated polynucleotide encoding the polypeptide of SEQ ID NO: 209 or fragments thereof. In some embodiments, the polypeptide of SEQ ID NO: 209, or a fragment thereof, is encoded by the polynucleotide of SEQ ID NO: 210 or fragments thereof.

The disclosure also provides an isolated polynucleotide encoding the polypeptide of SEQ ID NO: 211 or fragments thereof. In some embodiments, the polypeptide of SEQ ID NO: 211, or a fragment thereof, is encoded by the polynucleotide of SEQ ID NO: 212 or fragments thereof.

The disclosure also provides an isolated polynucleotide encoding the polypeptide of SEQ ID NO: 213 or fragments thereof. In some embodiments, the polypeptide of SEQ ID NO: 213, or a fragment thereof, is encoded by the polynucleotide of SEQ ID NO: 214 or fragments thereof.

The disclosure also provides an isolated polynucleotide encoding the polypeptide of SEQ ID NO: 215 or fragments thereof. In some embodiments, the polypeptide of SEQ ID NO: 215, or a fragment thereof, is encoded by the polynucleotide of SEQ ID NO: 216 or fragments thereof.

The disclosure also provides an isolated polynucleotide encoding the polypeptide of SEQ ID NO: 217 or fragments thereof. In some embodiments, the polypeptide of SEQ ID NO: 217, or a fragment thereof, is encoded by the polynucleotide of SEQ ID NO: 218 or fragments thereof.

The disclosure also provides an isolated polynucleotide encoding the polypeptide of SEQ ID NO: 219 or fragments thereof. In some embodiments, the polypeptide of SEQ ID NO: 219, or a fragment thereof, is encoded by the polynucleotide of SEQ ID NO: 220 or fragments thereof.

The disclosure also provides an isolated polynucleotide encoding the polypeptide of SEQ ID NO: 221 or fragments thereof. In some embodiments, the polypeptide of SEQ ID NO: 221, or a fragment thereof, is encoded by the polynucleotide of SEQ ID NO: 222 or fragments thereof.

The disclosure also provides an isolated polynucleotide encoding the polypeptide of SEQ ID NO: 223 or fragments thereof. In some embodiments, the polypeptide of SEQ ID NO: 223, or a fragment thereof, is encoded by the polynucleotide of SEQ ID NO: 224 or fragments thereof.

The disclosure also provides an isolated polynucleotide encoding the polypeptide of SEQ ID NO: 225 or fragments thereof. In some embodiments, the polypeptide of SEQ ID NO: 225, or a fragment thereof, is encoded by the polynucleotide of SEQ ID NO: 226 or fragments thereof.

The disclosure also provides an isolated polynucleotide encoding the polypeptide of SEQ ID NO: 227 or fragments thereof. In some embodiments, the polypeptide of SEQ ID NO: 227, or a fragment thereof, is encoded by the polynucleotide of SEQ ID NO: 228 or fragments thereof.

The disclosure also provides an isolated polynucleotide encoding the polypeptide of SEQ ID NO: 229 or fragments thereof. In some embodiments, the polypeptide of SEQ ID NO: 229, or a fragment thereof, is encoded by the polynucleotide of SEQ ID NO: 230 or fragments thereof.

The disclosure also provides an isolated polynucleotide encoding the polypeptide of SEQ ID NO: 231 or fragments thereof. In some embodiments, the polypeptide of SEQ ID NO: 231, or a fragment thereof, is encoded by the polynucleotide of SEQ ID NO: 232 or fragments thereof.

The disclosure also provides an isolated polynucleotide encoding the polypeptide of SEQ ID NO: 233 or fragments thereof. In some embodiments, the polypeptide of SEQ ID NO: 233, or a fragment thereof, is encoded by the polynucleotide of SEQ ID NO: 234 or fragments thereof.

The disclosure also provides an isolated polynucleotide encoding the polypeptide of SEQ ID NO: 235 or fragments thereof. In some embodiments, the polypeptide of SEQ ID NO: 235, or a fragment thereof, is encoded by the polynucleotide of SEQ ID NO: 236 or fragments thereof.

The disclosure also provides an isolated polynucleotide encoding the polypeptide of SEQ ID NO: 237 or fragments thereof. In some embodiments, the polypeptide of SEQ ID NO: 237, or a fragment thereof, is encoded by the polynucleotide of SEQ ID NO: 238 or fragments thereof.

The disclosure also provides an isolated polynucleotide encoding the polypeptide of SEQ ID NO: 239 or fragments thereof. In some embodiments, the polypeptide of SEQ ID NO: 239, or a fragment thereof, is encoded by the polynucleotide of SEQ ID NO: 240 or fragments thereof.

The disclosure also provides an isolated polynucleotide encoding the polypeptide of SEQ ID NO: 241 or fragments thereof. In some embodiments, the polypeptide of SEQ ID NO: 241, or a fragment thereof, is encoded by the polynucleotide of SEQ ID NO: 242 or fragments thereof.

The disclosure also provides an isolated polynucleotide encoding the polypeptide of SEQ ID NO: 243 or fragments thereof. In some embodiments, the polypeptide of SEQ ID NO: 243, or a fragment thereof, is encoded by the polynucleotide of SEQ ID NO: 244 or fragments thereof.

The disclosure also provides an isolated polynucleotide encoding the polypeptide of SEQ ID NO: 245 or fragments thereof. In some embodiments, the polypeptide of SEQ ID NO: 245, or a fragment thereof, is encoded by the polynucleotide of SEQ ID NO: 246 or fragments thereof.

The disclosure also provides an isolated polynucleotide encoding the polypeptide of SEQ ID NO: 247 or fragments thereof. In some embodiments, the polypeptide of SEQ ID NO: 247, or a fragment thereof, is encoded by the polynucleotide of SEQ ID NO: 248 or fragments thereof.

The disclosure also provides an isolated polynucleotide encoding the polypeptide of SEQ ID NO: 249 or fragments thereof. In some embodiments, the polypeptide of SEQ ID NO: 249, or a fragment thereof, is encoded by the polynucleotide of SEQ ID NO: 250 or fragments thereof.

The disclosure also provides an isolated polynucleotide encoding the polypeptide of SEQ ID NO: 251 or fragments thereof. In some embodiments, the polypeptide of SEQ ID NO: 251, or a fragment thereof, is encoded by the polynucleotide of SEQ ID NO: 252 or fragments thereof.

The disclosure also provides an isolated polynucleotide encoding the polypeptide of SEQ ID NO: 253 or fragments thereof. In some embodiments, the polypeptide of SEQ ID NO: 253, or a fragment thereof, is encoded by the polynucleotide of SEQ ID NO: 254 or fragments thereof.

The disclosure also provides an isolated polynucleotide encoding the polypeptide of SEQ ID NO: 255 or fragments thereof. In some embodiments, the polypeptide of SEQ ID NO: 255, or a fragment thereof, is encoded by the polynucleotide of SEQ ID NO: 256 or fragments thereof.

The disclosure also provides an isolated polynucleotide encoding the polypeptide of SEQ ID NO: 257 or fragments thereof. In some embodiments, the polypeptide of SEQ ID NO: 257, or a fragment thereof, is encoded by the polynucleotide of SEQ ID NO: 258 or fragments thereof.

The disclosure also provides an isolated polynucleotide encoding the polypeptide of SEQ ID NO: 259 or fragments thereof. In some embodiments, the polypeptide of SEQ ID NO: 259, or a fragment thereof, is encoded by the polynucleotide of SEQ ID NO: 260 or fragments thereof.

The disclosure also provides an isolated polynucleotide encoding the polypeptide of SEQ ID NO: 261 or fragments thereof. In some embodiments, the polypeptide of SEQ ID NO: 261, or a fragment thereof, is encoded by the polynucleotide of SEQ ID NO: 262 or fragments thereof.

The disclosure also provides an isolated polynucleotide encoding the polypeptide of SEQ ID NO: 263 or fragments thereof. In some embodiments, the polypeptide of SEQ ID NO: 263, or a fragment thereof, is encoded by the polynucleotide of SEQ ID NO: 264 or fragments thereof.

The disclosure also provides an isolated polynucleotide encoding the polypeptide of SEQ ID NO: 265 or fragments thereof. In some embodiments, the polypeptide of SEQ ID NO: 265, or a fragment thereof, is encoded by the polynucleotide of SEQ ID NO: 266 or fragments thereof.

The disclosure also provides an isolated polynucleotide encoding the polypeptide of SEQ ID NO: 267 or fragments thereof. In some embodiments, the polypeptide of SEQ ID NO: 267, or a fragment thereof, is encoded by the polynucleotide of SEQ ID NO: 268 or fragments thereof.

The disclosure also provides an isolated polynucleotide encoding the polypeptide of SEQ ID NO: 269 or fragments thereof. In some embodiments, the polypeptide of SEQ ID NO: 269, or a fragment thereof, is encoded by the polynucleotide of SEQ ID NO: 270 or fragments thereof.

The disclosure also provides an isolated polynucleotide encoding the polypeptide of SEQ ID NO: 271 or fragments thereof. In some embodiments, the polypeptide of SEQ ID NO: 271, or a fragment thereof, is encoded by the polynucleotide of SEQ ID NO: 272 or fragments thereof.

The disclosure also provides an isolated polynucleotide encoding the polypeptide of SEQ ID NO: 273 or fragments thereof. In some embodiments, the polypeptide of SEQ ID NO: 273, or a fragment thereof, is encoded by the polynucleotide of SEQ ID NO: 274 or fragments thereof.

The disclosure also provides an isolated polynucleotide encoding the polypeptide of SEQ ID NO: 275 or fragments thereof. In some embodiments, the polypeptide of SEQ ID NO: 275, or a fragment thereof, is encoded by the polynucleotide of SEQ ID NO: 276 or fragments thereof.

The disclosure also provides an isolated polynucleotide encoding the polypeptide of SEQ ID NO: 277 or fragments thereof. In some embodiments, the polypeptide of SEQ ID NO: 277, or a fragment thereof, is encoded by the polynucleotide of SEQ ID NO: 278 or fragments thereof.

The disclosure also provides an isolated polynucleotide encoding the polypeptide of SEQ ID NO: 279 or fragments thereof. In some embodiments, the polypeptide of SEQ ID NO: 279, or a fragment thereof, is encoded by the polynucleotide of SEQ ID NO: 280 or fragments thereof.

The disclosure also provides an isolated polynucleotide encoding the polypeptide of SEQ ID NO: 281 or fragments thereof. In some embodiments, the polypeptide of SEQ ID NO: 281, or a fragment thereof, is encoded by the polynucleotide of SEQ ID NO: 282 or fragments thereof.

The disclosure also provides an isolated polynucleotide encoding the polypeptide of SEQ ID NO: 283 or fragments thereof. In some embodiments, the polypeptide of SEQ ID NO: 283, or a fragment thereof, is encoded by the polynucleotide of SEQ ID NO: 284 or fragments thereof.

The disclosure also provides an isolated polynucleotide encoding the polypeptide of SEQ ID NO: 285 or fragments thereof. In some embodiments, the polypeptide of SEQ ID NO: 285, or a fragment thereof, is encoded by the polynucleotide of SEQ ID NO: 286 or fragments thereof.

The disclosure also provides an isolated polynucleotide encoding the polypeptide of SEQ ID NO: 287 or fragments thereof. In some embodiments, the polypeptide of SEQ ID NO: 287, or a fragment thereof, is encoded by the polynucleotide of SEQ ID NO: 288 or fragments thereof.

The disclosure also provides an isolated polynucleotide encoding the polypeptide of SEQ ID NO: 289 or fragments thereof. In some embodiments, the polypeptide of SEQ ID NO: 289, or a fragment thereof, is encoded by the polynucleotide of SEQ ID NO: 290 or fragments thereof.

The disclosure also provides an isolated polynucleotide encoding the polypeptide of SEQ ID NO: 291 or fragments thereof. In some embodiments, the polypeptide of SEQ ID NO: 291, or a fragment thereof, is encoded by the polynucleotide of SEQ ID NO: 292 or fragments thereof.

The disclosure also provides an isolated polynucleotide encoding the polypeptide of SEQ ID NO: 293 or fragments thereof. In some embodiments, the polypeptide of SEQ ID NO: 293, or a fragment thereof, is encoded by the polynucleotide of SEQ ID NO: 294 or fragments thereof.

The disclosure also provides an isolated polynucleotide encoding the polypeptide of SEQ ID NO: 295 or fragments thereof. In some embodiments, the polypeptide of SEQ ID NO: 295, or a fragment thereof, is encoded by the polynucleotide of SEQ ID NO: 296 or fragments thereof.

The disclosure also provides an isolated polynucleotide encoding the polypeptide of SEQ ID NO: 297 or fragments thereof. In some embodiments, the polypeptide of SEQ ID NO: 297, or a fragment thereof, is encoded by the polynucleotide of SEQ ID NO: 298 or fragments thereof.

The disclosure also provides an isolated polynucleotide encoding the polypeptide of SEQ ID NO: 299 or fragments thereof. In some embodiments, the polypeptide of SEQ ID NO: 299, or a fragment thereof, is encoded by the polynucleotide of SEQ ID NO: 300 or fragments thereof.

The disclosure also provides an isolated polynucleotide encoding the polypeptide of SEQ ID NO: 301 or fragments thereof. In some embodiments, the polypeptide of SEQ ID NO: 301, or a fragment thereof, is encoded by the polynucleotide of SEQ ID NO: 302 or fragments thereof.

The disclosure also provides an isolated polynucleotide encoding the polypeptide of SEQ ID NO: 303 or fragments thereof. In some embodiments, the polypeptide of SEQ ID NO: 303, or a fragment thereof, is encoded by the polynucleotide of SEQ ID NO: 304 or fragments thereof.

The disclosure also provides an isolated polynucleotide encoding the polypeptide of SEQ ID NO: 305 or fragments thereof. In some embodiments, the polypeptide of SEQ ID NO: 305, or a fragment thereof, is encoded by the polynucleotide of SEQ ID NO: 306 or fragments thereof.

The disclosure also provides an isolated polynucleotide encoding the polypeptide of SEQ ID NO: 307 or fragments thereof. In some embodiments, the polypeptide of SEQ ID NO: 307, or a fragment thereof, is encoded by the polynucleotide of SEQ ID NO: 308 or fragments thereof.

The disclosure also provides an isolated polynucleotide encoding the polypeptide of SEQ ID NO: 309 or fragments thereof. In some embodiments, the polypeptide of SEQ ID NO: 309, or a fragment thereof, is encoded by the polynucleotide of SEQ ID NO: 310 or fragments thereof.

The disclosure also provides an isolated polynucleotide encoding the polypeptide of SEQ ID NO: 311 or fragments thereof. In some embodiments, the polypeptide of SEQ ID NO: 311, or a fragment thereof, is encoded by the polynucleotide of SEQ ID NO: 312 or fragments thereof.

The disclosure also provides an isolated polynucleotide encoding the polypeptide of SEQ ID NO: 313 or fragments thereof. In some embodiments, the polypeptide of SEQ ID NO: 313, or a fragment thereof, is encoded by the polynucleotide of SEQ ID NO: 314 or fragments thereof.

The disclosure also provides an isolated polynucleotide encoding the polypeptide of SEQ ID NO: 315 or fragments thereof. In some embodiments, the polypeptide of SEQ ID NO: 315, or a fragment thereof, is encoded by the polynucleotide of SEQ ID NO: 316 or fragments thereof.

The disclosure also provides an isolated polynucleotide encoding the polypeptide of SEQ ID NO: 317 or fragments thereof. In some embodiments, the polypeptide of SEQ ID NO: 317, or a fragment thereof, is encoded by the polynucleotide of SEQ ID NO: 318 or fragments thereof.

The disclosure also provides an isolated polynucleotide encoding the polypeptide of SEQ ID NO: 319 or fragments thereof. In some embodiments, the polypeptide of SEQ ID NO: 319, or a fragment thereof, is encoded by the polynucleotide of SEQ ID NO: 320 or fragments thereof.

The disclosure also provides an isolated polynucleotide encoding the polypeptide of SEQ ID NO: 321 or fragments thereof. In some embodiments, the polypeptide of SEQ ID NO: 321, or a fragment thereof, is encoded by the polynucleotide of SEQ ID NO: 322 or fragments thereof.

The disclosure also provides an isolated polynucleotide encoding the polypeptide of SEQ ID NO: 323 or fragments thereof. In some embodiments, the polypeptide of SEQ ID NO: 323, or a fragment thereof, is encoded by the polynucleotide of SEQ ID NO: 324 or fragments thereof.

The disclosure also provides an isolated polynucleotide encoding the polypeptide of SEQ ID NO: 325 or fragments thereof. In some embodiments, the polypeptide of SEQ ID NO: 325, or a fragment thereof, is encoded by the polynucleotide of SEQ ID NO: 326 or fragments thereof.

The disclosure also provides an isolated polynucleotide encoding the polypeptide of SEQ ID NO: 327 or fragments thereof. In some embodiments, the polypeptide of SEQ ID NO: 327, or a fragment thereof, is encoded by the polynucleotide of SEQ ID NO: 328 or fragments thereof.

The disclosure also provides an isolated polynucleotide encoding the polypeptide of SEQ ID NO: 329 or fragments thereof. In some embodiments, the polypeptide of SEQ ID NO: 329, or a fragment thereof, is encoded by the polynucleotide of SEQ ID NO: 330 or fragments thereof.

The disclosure also provides an isolated polynucleotide encoding the polypeptide of SEQ ID NO: 331 or fragments thereof. In some embodiments, the polypeptide of SEQ ID NO: 331, or a fragment thereof, is encoded by the polynucleotide of SEQ ID NO: 332 or fragments thereof.

The disclosure also provides an isolated polynucleotide encoding the polypeptide of SEQ ID NO: 333 or fragments thereof. In some embodiments, the polypeptide of SEQ ID NO: 333, or a fragment thereof, is encoded by the polynucleotide of SEQ ID NO: 334 or fragments thereof.

The disclosure also provides an isolated polynucleotide encoding the polypeptide of SEQ ID NO: 335 or fragments thereof. In some embodiments, the polypeptide of SEQ ID NO: 335, or a fragment thereof, is encoded by the polynucleotide of SEQ ID NO: 336 or fragments thereof.

The disclosure also provides an isolated polynucleotide encoding the polypeptide of SEQ ID NO: 337 or fragments thereof. In some embodiments, the polypeptide of SEQ ID NO: 337, or a fragment thereof, is encoded by the polynucleotide of SEQ ID NO: 338 or fragments thereof.

The disclosure also provides an isolated polynucleotide encoding the polypeptide of SEQ ID NO: 339 or fragments thereof. In some embodiments, the polypeptide of SEQ ID NO: 339, or a fragment thereof, is encoded by the polynucleotide of SEQ ID NO: 340 or fragments thereof.

The disclosure also provides an isolated polynucleotide encoding the polypeptide of SEQ ID NO: 341 or fragments thereof. In some embodiments, the polypeptide of SEQ ID NO: 341, or a fragment thereof, is encoded by the polynucleotide of SEQ ID NO: 342 or fragments thereof.

The disclosure also provides an isolated polynucleotide encoding the polypeptide of SEQ ID NO: 343 or fragments thereof. In some embodiments, the polypeptide of SEQ ID NO: 343, or a fragment thereof, is encoded by the polynucleotide of SEQ ID NO: 344 or fragments thereof.

The disclosure also provides an isolated polynucleotide encoding the polypeptide of SEQ ID NO: 345 or fragments thereof. In some embodiments, the polypeptide of SEQ ID NO: 345, or a fragment thereof, is encoded by the polynucleotide of SEQ ID NO: 346 or fragments thereof.

The disclosure also provides an isolated polynucleotide encoding the polypeptide of SEQ ID NO: 347 or fragments thereof. In some embodiments, the polypeptide of SEQ ID NO: 347, or a fragment thereof, is encoded by the polynucleotide of SEQ ID NO: 348 or fragments thereof.

The disclosure also provides an isolated polynucleotide encoding the polypeptide of SEQ ID NO: 349 or fragments thereof. In some embodiments, the polypeptide of SEQ ID NO: 349, or a fragment thereof, is encoded by the polynucleotide of SEQ ID NO: 350 or fragments thereof.

The disclosure also provides an isolated polynucleotide encoding the polypeptide of SEQ ID NO: 351 or fragments thereof. In some embodiments, the polypeptide of SEQ ID NO: 351, or a fragment thereof, is encoded by the polynucleotide of SEQ ID NO: 352 or fragments thereof.

The disclosure also provides an isolated polynucleotide encoding the polypeptide of SEQ ID NO: 353 or fragments thereof. In some embodiments, the polypeptide of SEQ ID NO: 353, or a fragment thereof, is encoded by the polynucleotide of SEQ ID NO: 354 or fragments thereof.

The disclosure also provides an isolated polynucleotide encoding the polypeptide of SEQ ID NO: 355 or fragments thereof. In some embodiments, the polypeptide of SEQ ID NO: 355, or a fragment thereof, is encoded by the polynucleotide of SEQ ID NO: 356 or fragments thereof.

The disclosure also provides an isolated polynucleotide encoding the polypeptide of SEQ ID NO: 357 or fragments thereof. In some embodiments, the polypeptide of SEQ ID NO: 357, or a fragment thereof, is encoded by the polynucleotide of SEQ ID NO: 358 or fragments thereof.

The disclosure also provides an isolated polynucleotide encoding the polypeptide of SEQ ID NO: 359 or fragments thereof. In some embodiments, the polypeptide of SEQ ID NO: 359, or a fragment thereof, is encoded by the polynucleotide of SEQ ID NO: 360 or fragments thereof.

The disclosure also provides an isolated polynucleotide encoding the polypeptide of SEQ ID NO: 361 or fragments thereof. In some embodiments, the polypeptide of SEQ ID NO: 361, or a fragment thereof, is encoded by the polynucleotide of SEQ ID NO: 362 or fragments thereof.

The disclosure also provides an isolated polynucleotide encoding the polypeptide of SEQ ID NO: 363 or fragments thereof. In some embodiments, the polypeptide of SEQ ID NO: 363, or a fragment thereof, is encoded by the polynucleotide of SEQ ID NO: 364 or fragments thereof.

The disclosure also provides an isolated polynucleotide encoding the polypeptide of SEQ ID NO: 365 or fragments thereof. In some embodiments, the polypeptide of SEQ ID NO: 365, or a fragment thereof, is encoded by the polynucleotide of SEQ ID NO: 366 or fragments thereof.

The disclosure also provides an isolated polynucleotide encoding the polypeptide of SEQ ID NO: 367 or fragments thereof. In some embodiments, the polypeptide of SEQ ID NO: 367, or a fragment thereof, is encoded by the polynucleotide of SEQ ID NO: 368 or fragments thereof.

The disclosure also provides an isolated polynucleotide encoding the polypeptide of SEQ ID NO: 369 or fragments thereof. In some embodiments, the polypeptide of SEQ ID NO: 369, or a fragment thereof, is encoded by the polynucleotide of SEQ ID NO: 370 or fragments thereof.

The disclosure also provides an isolated polynucleotide encoding the polypeptide of SEQ ID NO: 371 or fragments thereof. In some embodiments, the polypeptide of SEQ ID NO: 371, or a fragment thereof, is encoded by the polynucleotide of SEQ ID NO: 372 or fragments thereof.

The disclosure also provides an isolated polynucleotide encoding the polypeptide of SEQ ID NO: 373 or fragments thereof. In some embodiments, the polypeptide of SEQ ID NO: 373, or a fragment thereof, is encoded by the polynucleotide of SEQ ID NO: 374 or fragments thereof.

The disclosure also provides an isolated polynucleotide encoding the polypeptide of SEQ ID NO: 375 or fragments thereof. In some embodiments, the polypeptide of SEQ ID NO: 375, or a fragment thereof, is encoded by the polynucleotide of SEQ ID NO: 376 or fragments thereof.

The disclosure also provides an isolated polynucleotide encoding the polypeptide of SEQ ID NO: 377 or fragments thereof. In some embodiments, the polypeptide of SEQ ID NO: 377, or a fragment thereof, is encoded by the polynucleotide of SEQ ID NO: 378 or fragments thereof.

The disclosure also provides an isolated polynucleotide encoding the polypeptide of SEQ ID NO: 379 or fragments thereof. In some embodiments, the polypeptide of SEQ ID NO: 379, or a fragment thereof, is encoded by the polynucleotide of SEQ ID NO: 380 or fragments thereof.

The disclosure also provides an isolated polynucleotide encoding the polypeptide of SEQ ID NO: 381 or fragments thereof. In some embodiments, the polypeptide of SEQ ID NO: 381, or a fragment thereof, is encoded by the polynucleotide of SEQ ID NO: 382 or fragments thereof.

The disclosure also provides an isolated polynucleotide encoding the polypeptide of SEQ ID NO: 383 or fragments thereof. In some embodiments, the polypeptide of SEQ ID NO: 383, or a fragment thereof, is encoded by the polynucleotide of SEQ ID NO: 384 or fragments thereof.

The disclosure also provides an isolated polynucleotide encoding the polypeptide of SEQ ID NO: 385 or fragments thereof. In some embodiments, the polypeptide of SEQ ID NO: 385, or a fragment thereof, is encoded by the polynucleotide of SEQ ID NO: 386 or fragments thereof.

The disclosure also provides an isolated polynucleotide encoding the polypeptide of SEQ ID NO: 387 or fragments thereof. In some embodiments, the polypeptide of SEQ ID NO: 387, or a fragment thereof, is encoded by the polynucleotide of SEQ ID NO: 388 or fragments thereof.

The disclosure also provides an isolated polynucleotide encoding the polypeptide of SEQ ID NO: 389 or fragments thereof. In some embodiments, the polypeptide of SEQ ID NO: 389, or a fragment thereof, is encoded by the polynucleotide of SEQ ID NO: 390 or fragments thereof.

The disclosure also provides an isolated polynucleotide encoding the polypeptide of SEQ ID NO: 391 or fragments thereof. In some embodiments, the polypeptide of SEQ ID NO: 391, or a fragment thereof, is encoded by the polynucleotide of SEQ ID NO: 392 or fragments thereof.

The disclosure also provides an isolated polynucleotide encoding the polypeptide of SEQ ID NO: 393 or fragments thereof. In some embodiments, the polypeptide of SEQ ID NO: 393, or a fragment thereof, is encoded by the polynucleotide of SEQ ID NO: 394 or fragments thereof.

The disclosure also provides an isolated polynucleotide encoding the polypeptide of SEQ ID NO: 395 or fragments thereof. In some embodiments, the polypeptide of SEQ ID NO: 395, or a fragment thereof, is encoded by the polynucleotide of SEQ ID NO: 396 or fragments thereof.

The disclosure also provides an isolated polynucleotide encoding the polypeptide of SEQ ID NO: 397 or fragments thereof. In some embodiments, the polypeptide of SEQ ID NO: 397, or a fragment thereof, is encoded by the polynucleotide of SEQ ID NO: 398 or fragments thereof.

The disclosure also provides an isolated polynucleotide encoding the polypeptide of SEQ ID NO: 399 or fragments thereof. In some embodiments, the polypeptide of SEQ ID NO: 399, or a fragment thereof, is encoded by the polynucleotide of SEQ ID NO: 400 or fragments thereof.

The disclosure also provides an isolated polynucleotide encoding the polypeptide of SEQ ID NO: 401 or fragments thereof. In some embodiments, the polypeptide of SEQ ID NO: 401, or a fragment thereof, is encoded by the polynucleotide of SEQ ID NO: 402 or fragments thereof.

The disclosure also provides an isolated polynucleotide encoding the polypeptide of SEQ ID NO: 403 or fragments thereof. In some embodiments, the polypeptide of SEQ ID NO: 403, or a fragment thereof, is encoded by the polynucleotide of SEQ ID NO: 404 or fragments thereof.

The disclosure also provides an isolated polynucleotide encoding the polypeptide of SEQ ID NO: 405 or fragments thereof. In some embodiments, the polypeptide of SEQ ID NO: 405, or a fragment thereof, is encoded by the polynucleotide of SEQ ID NO: 406 or fragments thereof.

In some embodiments, the heterologous polynucleotide is an in-frame heterologous polynucleotide.

For expression in various hosts, the polynucleotides may be codon-optimized utilizing known methods.

In some embodiments, the isolated heterologous polynucleotide is an in-frame heterologous polynucleotide.

In some embodiments, the polynucleotide comprises DNA or RNA.

In some embodiments, the polynucleotide comprises RNA.

In some embodiments, RNA is mRNA.

Variants of and Engineered Polynucleotides, Polypeptides, Heterologous Polynucleotides and Heterologous Polypeptides of the Disclosure Variants of the polynucleotides, polypeptides, heterologous polynucleotides and heterologous polypeptides or fragments thereof are within the scope of the disclosure. For example, variants may comprise one or more substitutions, deletions or insertions, as long as the variants retain or have improved characteristics (such as immunogenicity or stability) when compared to the parent. In some embodiments, the sequence identity may be about 80%, 81%, 82%, 83%, 84%, 85%, 86%, 87%, 88%, 89%, 90%, 91%, 92%, 93%, 94%, 95%, 96%, 97%, 98% or 99% between the parent and the variant. In some embodiments, variants are generated by conservative substitutions.

In some embodiments, the identity is about 80%. In some embodiments, the identity is about 85%. In some embodiments, the identity is about 90%. In some embodiments, the identity is about 91%. In some embodiments, the identity is about 91%. In some embodiments, the identity is about 92%. In some embodiments, the identity is about 93%. In some embodiments, the identity is about 94%. In some embodiments, the identity is 94%. In some embodiments, the identity is about 95%. In some embodiments, the identity is about 96%. In some embodiments, the identity is about 97%. In some embodiments, the identity is about 98%. In some embodiments, the identity is about 99%.

The percent identity between the two sequences is a function of the number of identical positions shared by the sequences (i.e., % identity=number of identical positions/total number of positions×100), taking into account the number of gaps, and the length of each gap, which need to be introduced for optimal alignment of the two sequences. The percent identity between two amino acid sequences may be determined using the algorithm of E. Meyers and W. Miller (ComputAppl Biosci 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J Mol Biol* 48:444-453 (1970)) algorithm which has been incorporated into the GAP program in the GCG software package (available at http_//_www_gcg_com), using either a Blossum 62 matrix or a PAM250 matrix, and a gap weight of 16, 14, 12, 10, 8, 6, or 4 and a length weight of 1, 2, 3, 4, 5, or 6.

The variants of the polypeptides or the heterologous polypeptides or fragments thereof containing one amino acid alteration generally retain similar tertiary structure and antigenicity relative to the parent. In some instances, the variant may also contain at least one amino acid alteration that causes the variant to have increased antigenicity, increased binding affinity to TCR or to antibody, or both. The variants of the polypeptides or the heterologous polypeptides may also have improved ability to bind to a HLA molecule.

The variants of the disclosure may be engineered to contain conservative substitutions. Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gin); Group 3-polar, positively charged residues (His, Arg, Lys); Group 4-large, aliphatic, nonpolar residues (Met, Leu, lie, Val, Cys); and Group 5-large, aromatic residues (Phe, Tyr, Trp).

The variants of the disclosure may be engineered to contain less conservative substitutions, such as the replacement of one amino acid by another that has similar characteristics but is somewhat different in size, such as replacement of an alanine by an isoleucine residue. The variants of the disclosure may also be engineered to contain highly non-conservative substitutions which may involve substituting an acidic amino acid for one that is polar, or even for one that is basic in character.

Additional substitutions that may be made to generate variants of the disclosure include substitutions may involve structures other than the common L-amino acids. Thus, D-amino and non-standard amino acids (i.e., other than the common naturally occurring proteinogenic amino acids) may also be used for substitution purposes to produce variants with enhanced immunogenicity when compared to the parent.

If substitutions at more than one position are found to result in polypeptides or heterologous polypeptides with substantially equivalent or greater immunogenicity, then combinations of those substitutions may be tested to determine if the combined substitutions result in additive or synergistic effects on the immunogenicity of the variant.

The amino acid residues that do not substantially contribute to interactions with the TCR may be modified by replacement with other amino acid whose incorporation does not substantially affect T-cell reactivity and does not eliminate binding to the relevant MHC. The amino acid residues that do not substantially contribute to interactions with the TCR may also be deleted as long as the deletion does not substantially affect T-cell reactivity and does not eliminate binding to the relevant MHC.

In addition, the polypeptides or the heterologous polypeptides or fragments thereof or variants may be further modified to improve stability and/or binding to MHC molecules in order to elicit a stronger immune response. Methods for such an optimization of a peptide sequence are well known in the art and include, for example, the introduction of reverse peptide bonds or non-peptide bonds. In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997). This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis. Additional non-peptide bond that may be used are, for example, —CH$_2$—NH, —CH$_2$S—, —CH$_2$CH$_2$—, —CH=CH—, —COCH$_2$—, —CH(OH)CH$_2$—, and —CH$_2$SO—.

The polypeptides or the heterologous polypeptides or fragments thereof, or variants of the disclosure may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the amino terminus. Likewise, an acetyl group or a 9-fluorenyl-methoxy-carbonyl group may be placed at the amino termini. Additionally, the hydrophobic group, t-butyloxycarbonyl, or an amido group may be added to the carboxy termini.

Further, the polypeptides or the heterologous polypeptides or fragments thereof, or variants of the disclosure may be synthesized to alter their steric configuration. For example, the D-isomer of one or more of the amino acid residues of the peptide may be used, rather than the usual L-isomer.

Similarly, the polypeptides or the heterologous polypeptides or fragments thereof, or variants of the disclosure may be modified chemically by reacting specific amino acids either before or after synthesis of the polypeptides or the heterologous polypeptides or fragments thereof, or variants of the disclosure. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http://www.sigma-aldrich.com) provide information on specific reagents. Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T. Tetranitromethane and N-acetylimidazole can be used for the modification of tyrosyl residues. Cross-linking via the formation of dityrosine can be accomplished with hydrogen peroxide/copper ions. Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole). Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

The disclosure provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405.

The disclosure also provides an isolated polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polynucleotide of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, or 406.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, and fragments thereof, wherein the polypeptide comprises one or more reverse peptide bonds.

In some embodiments, the reverse peptide bond comprises NH—CO bond.

In some embodiments, the reverse peptide bond comprises CH$_2$—NH, —CH$_2$S—, —CH$_2$CH$_2$—, —CH=CH—, —COCH$_2$—, —CH(OH)CH$_2$—, or —CH$_2$SO— bond.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, wherein the polypeptide comprises one or more chemical modifications.

In some embodiments, the one or more chemical modification comprises modification with carbobenzoxyl, dansyl, t-butyloxycarbonyl, 9-fluorenylmethoxy-carbonyl or D-isomer of an amino acid.

Methods of Making Polynucleotides and Polypeptides of the Disclosure

The polynucleotides of the disclosure or variants may be in the form of RNA or in the form of DNA obtained by cloning or produced synthetically. The DNA may be double-stranded or single-stranded.

Methods of generating polynucleotides and heterologous polynucleotides of the disclosure or variants are known in the art and include chemical synthesis, enzymatic synthesis (e.g. in vitro transcription), enzymatic or chemical cleavage of a longer precursor, chemical synthesis of smaller fragments of the polynucleotides followed by ligation of the fragments or known PCR methods. The polynucleotide sequence to be synthesized may be designed with the appropriate codons for the desired amino acid sequence. In general, preferred codons may be selected for the intended host in which the sequence will be used for expression.

Methods of making polypeptides and heterologous polypeptides of the disclosure are known in the art and include standard molecular biology techniques for cloning and expression of the polypeptides and chemical synthesis of the polypeptides.

Peptides may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoro-acetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Vectors and Recombinant Viruses of the Disclosure

The disclosure also provides a vector comprising a polynucleotide or a heterologous polynucleotide of the disclosure. The disclosure also provides vectors comprising a polynucleotide encoding for one or more of the polypeptides disclosed herein.

The disclosure also provides a vector comprising a polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, or fragments thereof.

The disclosure also provides a vector comprising one or more polynucleotides of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, or 406, or fragments thereof.

The disclosure also provides a vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof.

The disclosure also provides a vector comprising a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, and 406, and fragments thereof.

The disclosure also provides a vector comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, or 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof.

The disclosure also provides a vector comprising a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, or 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, and 406, and fragments thereof.

In some embodiments, the vector is an expression vector. In some embodiments, the vector is a viral vector.

In some embodiments, the vector is an expression vector. The vector may be a vector intended for expression of the polynucleotide or the heterologous polynucleotide of the disclosure in any host, such as bacteria, yeast or a mammal. Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed or transduced with the desired DNA sequences. Exemplary vectors are plasmids, cosmids, phages, viral vectors, transposons or artificial chromosomes.

Suitable vectors are known; many are commercially available for generating recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene), pSVK3, pBPV, pMSG and pSVL (Pharmacia). Transposon vectors: Sleeping Beauty transposon and PiggyBac transposon.

In some embodiments, the vector is a viral vector. The vectors of the disclosure may be utilized to generate recombinant viruses comprising the vectors of the disclosure or to express the polypeptides of the disclosure. Viral vectors are derived from naturally occurring virus genomes, which typically are modified to be replication incompetent, e.g. non-replicating. Non-replicating viruses require the provision of proteins in trans for replication. Typically, those proteins are stably or transiently expressed in a viral producer cell line, thereby allowing replication of the virus. The viral vectors are, thus, typically infectious and non-replicating. Viral vectors may be adenovirus vectors, adeno-associated virus (AAV) vectors (e.g., AAV type 5 and type 2), alphavirus vectors (e.g., Venezuelan equine encephalitis virus (VEE), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus vectors, lentivirus vectors, viral like particles, baculoviral vectors and bacterial spores.

The vectors of the disclosure may be generated using known techniques. The disclosure also provides a recombinant virus comprising the vector of the disclosure.

Adenovirus Vectors

In some embodiments, the viral vector is derived from an adenovirus. In some embodiments, the recombinant virus comprising the vector is derived from an adenovirus.

Adenovirus vectors may be derived from human adenovirus (Ad) but also from adenoviruses that infect other species, such as bovine adenovirus (e.g. bovine adenovirus 3, BAdV3), a canine adenovirus (e.g. CAdV2), a porcine adenovirus (e.g. PAdV3 or 5), or great apes, such as Chimpanzee (*Pan*), Gorilla (*Gorilla*), Orangutan (*Pongo*), Bonobo (*Pan paniscus*) and common chimpanzee (*Pan troglodytes*). Typically, naturally occurring great ape adenoviruses are isolated from stool samples of the respective great ape.

Human adenovirus vectors may be derived from various adenovirus serotypes, for example from human adenovirus serotypes hAd5, hAd7, hAd11, hAd26, hAd34, hAd35, hAd48, hAd49 or hAd50 (the serotypes are also referred to as Ad5, Ad7, Ad11, Ad26, Ad34, Ad35, Ad48, Ad49 or Ad50).

Great ape adenovirus vectors may be derived from various adenovirus serotypes, for example from great ape adenovirus serotypes GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, or PanAd3.

Adenovirus vectors are known in the art. The sequences of most of the human and non-human adenoviruses are known, and for others can be obtained using routine procedures. An exemplary genome sequence of Ad26 is found in GenBank Accession number EF153474 and in SEQ ID NO: 1 of Int. Pat. Publ. No. WO2007/104792. An exemplary genome sequence of Ad35 is found in FIG. 6 of Int. Pat. Publ. No. WO2000/70071. Vectors based on Ad26 are described for example, in Int. Pat. Publ. No. WO2007/104792. Vectors based on Ad35 are described for example in U.S. Pat. No. 7,270,811 and Int. Pat. Publ. No. WO2000/70071. Vectors based on ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in WO2005/071093. Vectors based on PanAd1, PanAd2, PanAd3, ChAd55, ChAd73, ChAd83, ChAd146, and ChAd147 are described in Int. Pat. Publ. No. WO2010/086189.

Adenovirus vectors are engineered to comprise at least one functional deletion or a complete removal of a gene product that is essential for viral replication, such as one or more of the adenoviral regions E1, E2 and E4, therefore rendering the adenovirus to be incapable of replication. The deletion of the E1 region may comprise deletion of EIA, EIB 55K or EIB 21K, or any combination thereof. Replication deficient adenoviruses are propagated by providing the proteins encoded by the deleted region(s) in trans by the producer cell by utilizing helper plasmids or engineering the produce cell to express the required proteins. Adenovirus vectors may also have a deletion in the E3 region, which is dispensable for replication, and hence such a deletion does not have to be complemented. The adenovirus vector of the disclosure may comprise a functional deletion or a complete removal of the E1 region and at least part of the E3 region. The adenovirus vector of the disclosure may further comprise a functional deletion or a complete removal of the E4 region and/or the E2 region. Suitable producer cells that can be utilized are human retina cells immortalized by E1, e.g. 911 or PER.C6 cells (see, e.g., U.S. Pat. No. 5,994,128), E1-transformed amniocytes (See, e.g., EP 1230354), E 1-transformed A549 cells (see e.g. Int. Pat. Publ. No. WO1998/39411, U.S. Pat. No. 5,891,690). Exemplary vectors that may be used are Ad26 comprising a functional E1 coding region that is sufficient for viral replication, a deletion in the E3 coding region and a deletion in the E4 coding region, provided that E4 open reading frame 6/7 is not deleted (see e.g. U.S. Pat. No. 9,750,801).

In some embodiments, the adenovirus vector is a human adenovirus (Ad) vector. In some embodiments, the Ad vector is derived from Ad5. In some embodiments, the Ad vector is derived from Ad11. In some embodiments, the Ad vector is derived from Ad26. In some embodiments, the Ad vector is derived from Ad34. In some embodiments, the Ad vector is derived from Ad35. In some embodiments, the Ad vector is derived from Ad48. In some embodiments, the Ad vector is derived from Ad49. In some embodiments, the Ad vector is derived from Ad50.

In some embodiments, the adenovirus vector is a great ape adenovirus (GAd) vector. In some embodiments, the GAd vector is derived from GAd20. In some embodiments, the GAd vector is derived from GAd19. In some embodiments, the GAd vector is derived from GAd21. In some embodiments, the GAd vector is derived from GAd25. In some embodiments, the GAd vector is derived from GAd26. In some embodiments, the GAd vector is derived from GAd27. In some embodiments, the GAd vector is derived from GAd28. In some embodiments, the GAd vector is derived from GAd29. In some embodiments, the GAd vector is derived from GAd30. In some embodiments, the GAd vector is derived from GAd31. In some embodiments, the GAd vector is derived from ChAd4. In some embodiments, the GAd vector is derived from ChAd5. In some embodiments, the GAd vector is derived from ChAd6. In some embodiments, the GAd vector is derived from ChAd7. In some embodiments, the GAd vector is derived from ChAd8. In some embodiments, the GAd vector is derived from ChAd9. In some embodiments, the GAd vector is derived from ChAd20. In some embodiments, the GAd vector is derived from ChAd22. In some embodiments, the GAd vector is derived from ChAd24. In some embodiments, the GAd vector is derived from ChAd26. In some embodiments, the GAd vector is derived from ChAd30. In some embodiments, the GAd vector is derived from ChAd31. In some embodiments, the GAd vector is derived from ChAd32. In some embodiments, the GAd vector is derived from ChAd33. In some embodiments, the GAd vector is derived from ChAd37. In some embodiments, the GAd vector is derived from ChAd38. In some embodiments, the GAd vector is derived from ChAd44. In some embodiments, the GAd vector is derived from ChAd55. In some embodiments, the GAd vector is derived from ChAd63. In some embodiments, the GAd vector is derived from ChAd68. In some embodiments, the GAd vector is derived from ChAd73. In some embodiments, the GAd vector is derived from ChAd82. In some embodiments, the GAd vector is derived from ChAd83.

The polypeptide or the heterologous polypeptide of the disclosure may be inserted into a site or region (insertion region) in the vector that does not affect virus viability of the resultant recombinant virus. The polypeptide or the heterologous polypeptide of the disclosure may be inserted into the deleted E1 region in parallel (transcribed 5' to 3') or anti-parallel (transcribed in a 3' to 5' direction relative to the vector backbone) orientation. In addition, appropriate transcriptional regulatory elements that are capable of directing expression of the polypeptide or the heterologous polypeptide of the disclosure in the mammalian host cells that the vector is being prepared for use may be operatively linked to the polypeptide or the heterologous polypeptide of the disclosure. "Operatively linked" sequences include both expression control sequences that are contiguous with the nucleic acid sequences that they regulate and regulatory sequences that act in trans, or at a distance to control the regulated nucleic acid sequence.

Recombinant adenoviral particles may be prepared and propagated according to any conventional technique in the field of the art (e.g., Int. Pat. Publ. No. WO1996/17070) using a complementation cell line or a helper virus, which supplies in trans the missing viral genes necessary for viral replication. The cell lines 293 (Graham et al., 1977, J. Gen. Virol. 36: 59-72), PER.C6 (see e.g. U.S. Pat. No. 5,994,128), E1 A549 and 911 are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and Int. Pat. Publ. No. WO1997/04119). The adenoviral particles may be recovered from the culture supernatant but also from the cells after lysis and optionally further purified according to standard techniques (e.g., chromatography, ultracentrifugation, as described in Int. Pat. Publ. No. WO1996/27677, Int. Pat. Publ. No. WO1998/00524, Int. Pat. Publ. No. WO1998/26048 and Int. Pat. Publ. No. WO2000/50573). The construction and methods for propagating adenoviral vectors are also described in for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

The disclosure provides a recombinant adenovirus comprising the vector of the disclosure. The disclosure also provides a recombinant human adenovirus (rAd) comprising the vector of the disclosure. The disclosure also provides a recombinant human adenovirus derived from serotype 26 (rAd26) comprising the vector of the disclosure.

Provided herein is a viral vector comprising any of the polynucleotides of the disclosure, wherein the vector is derived from hAd26 (also referred to has Ad26).

In some embodiments, the Ad26 vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the Ad26 vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the Ad26 vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the Ad26 vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the Ad26 vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the Ad26 vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the Ad26 vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the Ad26 vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the Ad26 vector comprises a polynucleotide encoding an amino acid sequence of SEQ ID NO: 17 or having at least 90% sequence identity, or at least 95% sequence identity, or at least 99% sequence identity to SEQ ID NO: 17.

In some embodiments, the Ad26 vector comprises a polynucleotide encoding for a polypeptide of SEQ ID NO: 19 or having at least 90% sequence identity to SEQ ID NO: 19, or at least 95% sequence identity, or at least 99% sequence identity to SEQ ID NO: 19.

In some embodiments, the Ad26 vector comprises a polynucleotide encoding for a polypeptide of SEQ ID NO: 21 or having at least 90% sequence identity, or at least 95% sequence identity, or at least 99% sequence identity to SEQ ID NO: 21.

In some embodiments, the Ad26 vector comprises a polynucleotide encoding for a polypeptide of SEQ ID NO: 23 or having at least 90% sequence identity, or at least 95% sequence identity, or at least 99% sequence identity to SEQ ID NO: 23.

In some embodiments, the Ad26 vector comprises a polynucleotide encoding for a polypeptide encoding an amino acid sequence of SEQ ID NO: 25 or having at least 90% sequence identity, or at least 95% sequence identity, or at least 99% sequence identity to SEQ ID NO: 25.

In some embodiments, the Ad26 vector comprises a polynucleotide encoding for a polypeptide encoding an amino acid sequence of SEQ ID NO: 27 or having at least 90% sequence identity, or at least 95% sequence identity, or at least 99% sequence identity to SEQ ID NO: 27.

In some embodiments, the Ad26 vector comprises a polynucleotide encoding for a polypeptide encoding an amino acid sequence of SEQ ID NO: 29 or having at least 90% sequence identity, or at least 95% sequence identity, or at least 99% sequence identity to SEQ ID NO: 29.

In some embodiments, the Ad26 vector comprises a polynucleotide encoding for a polypeptide encoding an amino acid sequence of SEQ ID NO: 31 or having at least 90% sequence identity, or at least 95% sequence identity, or at least 99% sequence identity to SEQ ID NO: 31.

In some embodiments, the Ad26 vector comprises a polynucleotide encoding an amino acid sequence of SEQ ID NO: 33 or having at least 90% sequence identity, or at least 95% sequence identity, or at least 99% sequence identity to SEQ ID NO: 33.

In some embodiments, the Ad26 vector comprises a polynucleotide encoding an amino acid sequence of SEQ ID NO: 35 or having at least 90% sequence identity, or at least 95% sequence identity, or at least 99% sequence identity to SEQ ID NO: 35.

In some embodiments, the Ad26 vector comprises a polynucleotide encoding an amino acid sequence of SEQ ID NO: 37 or having at least 90% sequence identity, or at least 95% sequence identity, or at least 99% sequence identity to SEQ ID NO: 37.

In some embodiments, the Ad26 vector comprises a polynucleotide encoding an amino acid sequence of SEQ ID NO: 39 or having at least 90% sequence identity, or at least 95% sequence identity, or at least 99% sequence identity to SEQ ID NO: 39.

In some embodiments, the Ad26 vector comprises a polynucleotide encoding an amino acid sequence of SEQ ID NO: 41 or having at least 90% sequence identity, or at least 95% sequence identity, or at least 99% sequence identity to SEQ ID NO: 41.

In some embodiments, the Ad26 vector comprises a polynucleotide encoding an amino acid sequence of SEQ ID NO: 43 or having at least 90% sequence identity, or at least 95% sequence identity, or at least 99% sequence identity to SEQ ID NO: 43.

In some embodiments, the Ad26 vector comprises a polynucleotide encoding an amino acid sequence of SEQ ID NO: 45 or having at least 90% sequence identity, or at least 95% sequence identity, or at least 99% sequence identity to SEQ ID NO: 45.

In some embodiments, the Ad26 vector comprises a polynucleotide encoding an amino acid sequence of SEQ ID NO: 47 or having at least 90% sequence identity, or at least 95% sequence identity, or at least 99% sequence identity to SEQ ID NO: 47.

In some embodiments, the Ad26 vector comprises a polynucleotide encoding an amino acid sequence of SEQ ID NO: 49 or having at least 90% sequence identity, or at least 95% sequence identity, or at least 99% sequence identity to SEQ ID NO: 49.

In some embodiments, the Ad26 vector comprises a polynucleotide encoding an amino acid sequence of SEQ ID NO: 51 or having at least 90% sequence identity, or at least 95% sequence identity, or at least 99% sequence identity to SEQ ID NO: 51.

In some embodiments, the Ad26 vector comprises a polynucleotide encoding an amino acid sequence of SEQ ID NO: 53 or having at least 90% sequence identity, or at least 95% sequence identity, or at least 99% sequence identity to SEQ ID NO: 53.

In some embodiments, the Ad26 vector comprises a polynucleotide encoding an amino acid sequence of SEQ ID NO: 55 or having at least 90% sequence identity, or at least 95% sequence identity, or at least 99% sequence identity to SEQ ID NO: 55.

In some embodiments, the Ad26 vector comprises a polynucleotide encoding an amino acid sequence of SEQ ID NO: 57 or having at least 90% sequence identity, or at least 95% sequence identity, or at least 99% sequence identity to SEQ ID NO: 57.

In some embodiments, the Ad26 vector comprises a polynucleotide encoding an amino acid sequence of SEQ ID NO: 59 or having at least 90% sequence identity, or at least 95% sequence identity, or at least 99% sequence identity to SEQ ID NO: 59.

In some embodiments, the Ad26 vector comprises a polynucleotide encoding an amino acid sequence of SEQ ID NO: 61 or having at least 90% sequence identity, or at least 95% sequence identity, or at least 99% sequence identity to SEQ ID NO: 61.

In some embodiments, the Ad26 vector comprises a polynucleotide encoding an amino acid sequence of SEQ ID NO: 63 or having at least 90% sequence identity, or at least 95% sequence identity, or at least 99% sequence identity to SEQ ID NO: 63.

In some embodiments, the Ad26 vector comprises a polynucleotide encoding an amino acid sequence of SEQ ID NO: 65 or having at least 90% sequence identity, or at least 95% sequence identity, or at least 99% sequence identity to SEQ ID NO: 65.

In some embodiments, the Ad26 vector comprises a polynucleotide encoding an amino acid sequence of SEQ ID NO: 67 or having at least 90% sequence identity, or at least 95% sequence identity, or at least 99% sequence identity to SEQ ID NO: 67.

In some embodiments, the Ad26 vector comprises a polynucleotide encoding an amino acid sequence of SEQ ID NO: 69 or having at least 90% sequence identity, or at least 95% sequence identity, or at least 99% sequence identity to SEQ ID NO: 69.

In some embodiments, the Ad26 vector comprises a polynucleotide encoding an amino acid sequence of SEQ ID NO: 71 or having at least 90% sequence identity, or at least 95% sequence identity, or at least 99% sequence identity to SEQ ID NO: 71.

In some embodiments, the Ad26 vector comprises a polynucleotide encoding an amino acid sequence of SEQ ID NO: 73 or having at least 90% sequence identity, or at least 95% sequence identity, or at least 99% sequence identity to SEQ ID NO: 73.

In some embodiments, the Ad26 vector comprises a polynucleotide encoding an amino acid sequence of SEQ ID NO: 75 or having at least 90% sequence identity, or at least 95% sequence identity, or at least 99% sequence identity to SEQ ID NO: 75.

In some embodiments, the Ad26 vector comprises a polynucleotide encoding an amino acid sequence of SEQ ID NO: 77 or having at least 90% sequence identity, or at least 95% sequence identity, or at least 99% sequence identity to SEQ ID NO: 77.

In some embodiments, the Ad26 vector comprises a polynucleotide encoding an amino acid sequence of SEQ ID NO: 79 or having at least 90% sequence identity, or at least 95% sequence identity, or at least 99% sequence identity to SEQ ID NO: 79.

In some embodiments, the Ad26 vector comprises a polynucleotide encoding an amino acid sequence of SEQ ID NO: 81 or having at least 90% sequence identity, or at least 95% sequence identity, or at least 99% sequence identity to SEQ ID NO: 81.

In some embodiments, the Ad26 vector comprises a polynucleotide encoding an amino acid sequence of SEQ ID NO: 83 or having at least 90% sequence identity, or at least 95% sequence identity, or at least 99% sequence identity to SEQ ID NO: 83.

In some embodiments, the Ad26 vector comprises a polynucleotide encoding an amino acid sequence of SEQ ID NO: 85 or having at least 90% sequence identity, or at least 95% sequence identity, or at least 99% sequence identity to SEQ ID NO: 85.

In some embodiments, the Ad26 vector comprises a polynucleotide encoding an amino acid sequence of SEQ ID NO: 87 or having at least 90% sequence identity, or at least 95% sequence identity, or at least 99% sequence identity to SEQ ID NO: 87.

In some embodiments, the Ad26 vector comprises a polynucleotide encoding an amino acid sequence of SEQ ID NO: 89 or having at least 90% sequence identity, or at least 95% sequence identity, or at least 99% sequence identity to SEQ ID NO: 89.

In some embodiments, the Ad26 vector comprises a polynucleotide encoding an amino acid sequence of SEQ ID NO: 91 or having at least 90% sequence identity, or at least 95% sequence identity, or at least 99% sequence identity to SEQ ID NO: 91.

In some embodiments, the Ad26 vector comprises a polynucleotide encoding an amino acid sequence of SEQ ID NO: 93 or having at least 90% sequence identity, or at least 95% sequence identity, or at least 99% sequence identity to SEQ ID NO: 93.

In some embodiments, the Ad26 vector comprises a polynucleotide encoding an amino acid sequence of SEQ ID NO: 95 or having at least 90% sequence identity, or at least 95% sequence identity, or at least 99% sequence identity to SEQ ID NO: 95.

In some embodiments, the Ad26 vector comprises a polynucleotide encoding an amino acid sequence of SEQ ID NO: 97 or having at least 90% sequence identity, or at least 95% sequence identity, or at least 99% sequence identity to SEQ ID NO: 97.

In some embodiments, the Ad26 vector comprises a polynucleotide encoding an amino acid sequence of SEQ ID NO: 99 or having at least 90% sequence identity, or at least 95% sequence identity, or at least 99% sequence identity to SEQ ID NO: 99.

In some embodiments, the Ad26 vector comprises a polynucleotide encoding an amino acid sequence of SEQ ID NO: 101 or having at least 90% sequence identity, or at least 95% sequence identity, or at least 99% sequence identity to SEQ ID NO: 101.

In some embodiments, the Ad26 vector comprises a polynucleotide encoding an amino acid sequence of SEQ ID NO: 103 or having at least 90% sequence identity, or at least 95% sequence identity, or at least 99% sequence identity to SEQ ID NO: 103.

In some embodiments, the Ad26 vector comprises a polynucleotide encoding an amino acid sequence of SEQ ID NO: 105 or having at least 90% sequence identity, or at least 95% sequence identity, or at least 99% sequence identity to SEQ ID NO: 105.

In some embodiments, the Ad26 vector comprises a polynucleotide encoding an amino acid sequence of SEQ ID NO: 107 or having at least 90% sequence identity, or at least 95% sequence identity, or at least 99% sequence identity to SEQ ID NO: 107.

In some embodiments, the Ad26 vector comprises a polynucleotide encoding an amino acid sequence of SEQ ID NO: 109 or having at least 90% sequence identity, or at least 95% sequence identity, or at least 99% sequence identity to SEQ ID NO: 109.

In some embodiments, the Ad26 vector comprises a polynucleotide encoding an amino acid sequence of SEQ ID NO: 111 or having at least 90% sequence identity, or at least 95% sequence identity, or at least 99% sequence identity to SEQ ID NO: 111.

In some embodiments, the Ad26 vector comprises a polynucleotide encoding an amino acid sequence of SEQ ID NO: 113 or having at least 90% sequence identity, or at least 95% sequence identity, or at least 99% sequence identity to SEQ ID NO: 113.

In some embodiments, the Ad26 vector comprises a polynucleotide encoding an amino acid sequence of SEQ ID NO: 115 or having at least 90% sequence identity, or at least 95% sequence identity, or at least 99% sequence identity to SEQ ID NO: 115.

In some embodiments, the Ad26 vector comprises a polynucleotide encoding an amino acid sequence of SEQ ID In some embodiments, the Ad26 vector comprises a polynucleotide encoding an amino acid sequence of SEQ ID NO: 117 or having at least 90% sequence identity, or at least 95% sequence identity, or at least 99% sequence identity to SEQ ID NO: 117.

In some embodiments, the Ad26 vector comprises a polynucleotide encoding an amino acid sequence of SEQ ID NO: 119 or having at least 90% sequence identity, or at least 95% sequence identity, or at least 99% sequence identity to SEQ ID NO: 119.

In some embodiments, the Ad26 vector comprises a polynucleotide encoding an amino acid sequence of SEQ ID NO: 121 or having at least 90% sequence identity, or at least 95% sequence identity, or at least 99% sequence identity to SEQ ID NO: 121.

In some embodiments, the Ad26 vector comprises a polynucleotide encoding an amino acid sequence of SEQ ID NO: 123 or having at least 90% sequence identity, or at least 95% sequence identity, or at least 99% sequence identity to SEQ ID NO: 123.

In some embodiments, the Ad26 vector comprises a polynucleotide encoding an amino acid sequence of SEQ ID NO: 125 or having at least 90% sequence identity, or at least 95% sequence identity, or at least 99% sequence identity to SEQ ID NO: 125.

In some embodiments, the Ad26 vector comprises a polynucleotide encoding an amino acid sequence of SEQ ID NO: 127 or having at least 90% sequence identity, or at least 95% sequence identity, or at least 99% sequence identity to SEQ ID NO: 127.

In some embodiments, the Ad26 vector comprises a polynucleotide encoding an amino acid sequence of SEQ ID NO: 129 or having at least 90% sequence identity, or at least 95% sequence identity, or at least 99% sequence identity to SEQ ID NO: 129.

In some embodiments, the Ad26 vector comprises a polynucleotide encoding an amino acid sequence of SEQ ID NO: 131 or having at least 90% sequence identity, or at least 95% sequence identity, or at least 99% sequence identity to SEQ ID NO: 131.

In some embodiments, the Ad26 vector comprises a polynucleotide encoding an amino acid sequence of SEQ ID NO: 133 or having at least 90% sequence identity, or at least 95% sequence identity, or at least 99% sequence identity to SEQ ID NO: 133.

In some embodiments, the Ad26 vector comprises a polynucleotide encoding an amino acid sequence of SEQ ID NO: 135 or having at least 90% sequence identity, or at least 95% sequence identity, or at least 99% sequence identity to SEQ ID NO: 135.

In some embodiments, the Ad26 vector comprises a polynucleotide encoding an amino acid sequence of SEQ ID NO: 137 or having at least 90% sequence identity, or at least 95% sequence identity, or at least 99% sequence identity to SEQ ID NO: 137.

In some embodiments, the Ad26 vector comprises a polynucleotide encoding an amino acid sequence of SEQ ID NO: 139 or having at least 90% sequence identity, or at least 95% sequence identity, or at least 99% sequence identity to SEQ ID NO: 139.

In some embodiments, the Ad26 vector comprises a polynucleotide encoding an amino acid sequence of SEQ ID NO: 141 or having at least 90% sequence identity, or at least 95% sequence identity, or at least 99% sequence identity to SEQ ID NO: 141.

In some embodiments, the Ad26 vector comprises a polynucleotide encoding an amino acid sequence of SEQ ID NO: 143 or having at least 90% sequence identity, or at least 95% sequence identity, or at least 99% sequence identity to SEQ ID NO: 143.

In some embodiments, the Ad26 vector comprises a polynucleotide encoding an amino acid sequence of SEQ ID NO: 145 or having at least 90% sequence identity, or at least 95% sequence identity, or at least 99% sequence identity to SEQ ID NO: 145.

In some embodiments, the Ad26 vector comprises a polynucleotide encoding an amino acid sequence of SEQ ID NO: 147 or having at least 90% sequence identity, or at least 95% sequence identity, or at least 99% sequence identity to SEQ ID NO: 147.

In some embodiments, the Ad26 vector comprises a polynucleotide encoding an amino acid sequence of SEQ ID NO: 149 or having at least 90% sequence identity, or at least 95% sequence identity, or at least 99% sequence identity to SEQ ID NO: 149.

In some embodiments, the Ad26 vector comprises a polynucleotide encoding an amino acid sequence of SEQ ID NO: 151 or having at least 90% sequence identity, or at least 95% sequence identity, or at least 99% sequence identity to SEQ ID NO: 151.

In some embodiments, the Ad26 vector comprises a polynucleotide encoding an amino acid sequence of SEQ ID NO: 153 or having at least 90% sequence identity, or at least 95% sequence identity, or at least 99% sequence identity to SEQ ID NO: 153.

In some embodiments, the Ad26 vector comprises a polynucleotide encoding an amino acid sequence of SEQ ID NO: 155 or having at least 90% sequence identity, or at least 95% sequence identity, or at least 99% sequence identity to SEQ ID NO: 155.

In some embodiments, the Ad26 vector comprises a polynucleotide encoding an amino acid sequence of SEQ ID NO: 157 or having at least 90% sequence identity, or at least 95% sequence identity, or at least 99% sequence identity to SEQ ID NO: 157.

In some embodiments, the Ad26 vector comprises a polynucleotide encoding an amino acid sequence of SEQ ID NO: 159 or having at least 90% sequence identity, or at least 95% sequence identity, or at least 99% sequence identity to SEQ ID NO: 159.

In some embodiments, the Ad26 vector comprises a polynucleotide encoding an amino acid sequence of SEQ ID NO: 161 or having at least 90% sequence identity, or at least 95% sequence identity, or at least 99% sequence identity to SEQ ID NO: 161.

In some embodiments, the Ad26 vector comprises a polynucleotide encoding an amino acid sequence of SEQ ID NO: 163 or having at least 90% sequence identity, or at least 95% sequence identity, or at least 99% sequence identity to SEQ ID NO: 163.

In some embodiments, the Ad26 vector comprises a polynucleotide encoding an amino acid sequence of SEQ ID NO: 165 or having at least 90% sequence identity, or at least 95% sequence identity, or at least 99% sequence identity to SEQ ID NO: 165.

In some embodiments, the Ad26 vector comprises a polynucleotide encoding an amino acid sequence of SEQ ID NO: 167 or having at least 90% sequence identity, or at least 95% sequence identity, or at least 99% sequence identity to SEQ ID NO: 167.

In some embodiments, the Ad26 vector comprises a polynucleotide encoding an amino acid sequence of SEQ ID In some embodiments, the Ad26 vector comprises a polynucleotide encoding an amino acid sequence of SEQ ID NO: 169 or having at least 90% sequence identity, or at least 95% sequence identity, or at least 99% sequence identity to SEQ ID NO: 169.

In some embodiments, the Ad26 vector comprises a polynucleotide encoding an amino acid sequence of SEQ ID NO: 171 or having at least 90% sequence identity, or at least 95% sequence identity, or at least 99% sequence identity to SEQ ID NO: 171.

In some embodiments, the Ad26 vector comprises a polynucleotide encoding an amino acid sequence of SEQ ID NO: 173 or having at least 90% sequence identity, or at least 95% sequence identity, or at least 99% sequence identity to SEQ ID NO: 173.

In some embodiments, the Ad26 vector comprises a polynucleotide encoding an amino acid sequence of SEQ ID NO: 175 or having at least 90% sequence identity, or at least 95% sequence identity, or at least 99% sequence identity to SEQ ID NO: 175.

In some embodiments, the Ad26 vector comprises a polynucleotide encoding an amino acid sequence of SEQ ID NO: 177 or having at least 90% sequence identity, or at least 95% sequence identity, or at least 99% sequence identity to SEQ ID NO: 177.

In some embodiments, the Ad26 vector comprises a polynucleotide encoding an amino acid sequence of SEQ ID NO: 179 or having at least 90% sequence identity, or at least 95% sequence identity, or at least 99% sequence identity to SEQ ID NO: 179.

In some embodiments, the Ad26 vector comprises a polynucleotide encoding an amino acid sequence of SEQ ID NO: 181 or having at least 90% sequence identity, or at least 95% sequence identity, or at least 99% sequence identity to SEQ ID NO: 181.

In some embodiments, the Ad26 vector comprises a polynucleotide encoding an amino acid sequence of SEQ ID NO: 183 or having at least 90% sequence identity, or at least 95% sequence identity, or at least 99% sequence identity to SEQ ID NO: 183.

In some embodiments, the Ad26 vector comprises a polynucleotide encoding an amino acid sequence of SEQ ID NO: 185 or having at least 90% sequence identity, or at least 95% sequence identity, or at least 99% sequence identity to SEQ ID NO: 185.

In some embodiments, the Ad26 vector comprises a polynucleotide encoding an amino acid sequence of SEQ ID NO: 187 or having at least 90% sequence identity, or at least 95% sequence identity, or at least 99% sequence identity to SEQ ID NO: 187.

In some embodiments, the Ad26 vector comprises a polynucleotide encoding an amino acid sequence of SEQ ID NO: 189 or having at least 90% sequence identity, or at least 95% sequence identity, or at least 99% sequence identity to SEQ ID NO: 189.

In some embodiments, the Ad26 vector comprises a polynucleotide encoding an amino acid sequence of SEQ ID NO: 191 or having at least 90% sequence identity, or at least 95% sequence identity, or at least 99% sequence identity to SEQ ID NO: 191.

In some embodiments, the Ad26 vector comprises a polynucleotide encoding an amino acid sequence of SEQ ID NO: 193 or having at least 90% sequence identity, or at least 95% sequence identity, or at least 99% sequence identity to SEQ ID NO: 193.

In some embodiments, the Ad26 vector comprises a polynucleotide encoding an amino acid sequence of SEQ ID NO: 195 or having at least 90% sequence identity, or at least 95% sequence identity, or at least 99% sequence identity to SEQ ID NO: 195.

In some embodiments, the Ad26 vector comprises a polynucleotide encoding an amino acid sequence of SEQ ID NO: 197 or having at least 90% sequence identity, or at least 95% sequence identity, or at least 99% sequence identity to SEQ ID NO: 197.

In some embodiments, the Ad26 vector comprises a polynucleotide encoding an amino acid sequence of SEQ ID NO: 199 or having at least 90% sequence identity, or at least 95% sequence identity, or at least 99% sequence identity to SEQ ID NO: 199.

In some embodiments, the Ad26 vector comprises a polynucleotide encoding an amino acid sequence of SEQ ID NO: 201 or having at least 90% sequence identity, or at least 95% sequence identity, or at least 99% sequence identity to SEQ ID NO: 201.

In some embodiments, the Ad26 vector comprises a polynucleotide encoding an amino acid sequence of SEQ ID NO: 203 or having at least 90% sequence identity, or at least 95% sequence identity, or at least 99% sequence identity to SEQ ID NO: 203.

In some embodiments, the Ad26 vector comprises a polynucleotide encoding an amino acid sequence of SEQ ID NO: 205 or having at least 90% sequence identity, or at least 95% sequence identity, or at least 99% sequence identity to SEQ ID NO: 205.

In some embodiments, the Ad26 vector comprises a polynucleotide encoding an amino acid sequence of SEQ ID NO: 207 or having at least 90% sequence identity, or at least 95% sequence identity, or at least 99% sequence identity to SEQ ID NO: 207.

In some embodiments, the Ad26 vector comprises a polynucleotide encoding an amino acid sequence of SEQ ID NO: 209 or having at least 90% sequence identity, or at least 95% sequence identity, or at least 99% sequence identity to SEQ ID NO: 209.

In some embodiments, the Ad26 vector comprises a polynucleotide encoding an amino acid sequence of SEQ ID NO: 211 or having at least 90% sequence identity, or at least 95% sequence identity, or at least 99% sequence identity to SEQ ID NO: 211.

In some embodiments, the Ad26 vector comprises a polynucleotide encoding an amino acid sequence of SEQ ID NO: 213 or having at least 90% sequence identity, or at least 95% sequence identity, or at least 99% sequence identity to SEQ ID NO: 213.

In some embodiments, the Ad26 vector comprises a polynucleotide encoding an amino acid sequence of SEQ ID NO: 215 or having at least 90% sequence identity, or at least 95% sequence identity, or at least 99% sequence identity to SEQ ID NO: 215.

In some embodiments, the Ad26 vector comprises a polynucleotide encoding an amino acid sequence of SEQ ID NO: 217 or having at least 90% sequence identity, or at least 95% sequence identity, or at least 99% sequence identity to SEQ ID NO: 217.

In some embodiments, the Ad26 vector comprises a polynucleotide encoding an amino acid sequence of SEQ ID NO: 219 or having at least 90% sequence identity, or at least 95% sequence identity, or at least 99% sequence identity to SEQ ID NO: 219.

In some embodiments, the Ad26 vector comprises a polynucleotide encoding an amino acid sequence of SEQ ID In some embodiments, the Ad26 vector comprises a polynucleotide encoding an amino acid sequence of SEQ ID NO: 221 or having at least 90% sequence identity, or at least 95% sequence identity, or at least 99% sequence identity to SEQ ID NO: 221.

In some embodiments, the Ad26 vector comprises a polynucleotide encoding an amino acid sequence of SEQ ID NO: 223 or having at least 90% sequence identity, or at least 95% sequence identity, or at least 99% sequence identity to SEQ ID NO: 223.

In some embodiments, the Ad26 vector comprises a polynucleotide encoding an amino acid sequence of SEQ ID NO: 225 or having at least 90% sequence identity, or at least 95% sequence identity, or at least 99% sequence identity to SEQ ID NO: 225.

In some embodiments, the Ad26 vector comprises a polynucleotide encoding an amino acid sequence of SEQ ID NO: 227 or having at least 90% sequence identity, or at least 95% sequence identity, or at least 99% sequence identity to SEQ ID NO: 227.

In some embodiments, the Ad26 vector comprises a polynucleotide encoding an amino acid sequence of SEQ ID NO: 229 or having at least 90% sequence identity, or at least 95% sequence identity, or at least 99% sequence identity to SEQ ID NO: 229.

In some embodiments, the Ad26 vector comprises a polynucleotide encoding an amino acid sequence of SEQ ID NO: 231 or having at least 90% sequence identity, or at least 95% sequence identity, or at least 99% sequence identity to SEQ ID NO: 231.

In some embodiments, the Ad26 vector comprises a polynucleotide encoding an amino acid sequence of SEQ ID NO: 233 or having at least 90% sequence identity, or at least 95% sequence identity, or at least 99% sequence identity to SEQ ID NO: 233.

In some embodiments, the Ad26 vector comprises a polynucleotide encoding an amino acid sequence of SEQ ID NO: 235 or having at least 90% sequence identity, or at least 95% sequence identity, or at least 99% sequence identity to SEQ ID NO: 235.

In some embodiments, the Ad26 vector comprises a polynucleotide encoding an amino acid sequence of SEQ ID NO: 237 or having at least 90% sequence identity, or at least 95% sequence identity, or at least 99% sequence identity to SEQ ID NO: 237.

In some embodiments, the Ad26 vector comprises a polynucleotide encoding an amino acid sequence of SEQ ID NO: 239 or having at least 90% sequence identity, or at least 95% sequence identity, or at least 99% sequence identity to SEQ ID NO: 239.

In some embodiments, the Ad26 vector comprises a polynucleotide encoding an amino acid sequence of SEQ ID NO: 241 or having at least 90% sequence identity, or at least 95% sequence identity, or at least 99% sequence identity to SEQ ID NO: 241.

In some embodiments, the Ad26 vector comprises a polynucleotide encoding an amino acid sequence of SEQ ID NO: 243 or having at least 90% sequence identity, or at least 95% sequence identity, or at least 99% sequence identity to SEQ ID NO: 243.

In some embodiments, the Ad26 vector comprises a polynucleotide encoding an amino acid sequence of SEQ ID NO: 245 or having at least 90% sequence identity, or at least 95% sequence identity, or at least 99% sequence identity to SEQ ID NO: 245.

In some embodiments, the Ad26 vector comprises a polynucleotide encoding an amino acid sequence of SEQ ID NO: 247 or having at least 90% sequence identity, or at least 95% sequence identity, or at least 99% sequence identity to SEQ ID NO: 247.

In some embodiments, the Ad26 vector comprises a polynucleotide encoding an amino acid sequence of SEQ ID NO: 249 or having at least 90% sequence identity, or at least 95% sequence identity, or at least 99% sequence identity to SEQ ID NO: 249.

In some embodiments, the Ad26 vector comprises a polynucleotide encoding an amino acid sequence of SEQ ID NO: 251 or having at least 90% sequence identity, or at least 95% sequence identity, or at least 99% sequence identity to SEQ ID NO: 251.

In some embodiments, the Ad26 vector comprises a polynucleotide encoding an amino acid sequence of SEQ ID NO: 253 or having at least 90% sequence identity, or at least 95% sequence identity, or at least 99% sequence identity to SEQ ID NO: 253.

In some embodiments, the Ad26 vector comprises a polynucleotide encoding an amino acid sequence of SEQ ID NO: 255 or having at least 90% sequence identity, or at least 95% sequence identity, or at least 99% sequence identity to SEQ ID NO: 255.

In some embodiments, the Ad26 vector comprises a polynucleotide encoding an amino acid sequence of SEQ ID NO: 257 or having at least 90% sequence identity, or at least 95% sequence identity, or at least 99% sequence identity to SEQ ID NO: 257.

In some embodiments, the Ad26 vector comprises a polynucleotide encoding an amino acid sequence of SEQ ID NO: 259 or having at least 90% sequence identity, or at least 95% sequence identity, or at least 99% sequence identity to SEQ ID NO: 259.

In some embodiments, the Ad26 vector comprises a polynucleotide encoding an amino acid sequence of SEQ ID NO: 261 or having at least 90% sequence identity, or at least 95% sequence identity, or at least 99% sequence identity to SEQ ID NO: 261.

In some embodiments, the Ad26 vector comprises a polynucleotide encoding an amino acid sequence of SEQ ID NO: 263 or having at least 90% sequence identity, or at least 95% sequence identity, or at least 99% sequence identity to SEQ ID NO: 263.

In some embodiments, the Ad26 vector comprises a polynucleotide encoding an amino acid sequence of SEQ ID NO: 265 or having at least 90% sequence identity, or at least 95% sequence identity, or at least 99% sequence identity to SEQ ID NO: 265.

In some embodiments, the Ad26 vector comprises a polynucleotide encoding an amino acid sequence of SEQ ID NO: 267 or having at least 90% sequence identity, or at least 95% sequence identity, or at least 99% sequence identity to SEQ ID NO: 267.

In some embodiments, the Ad26 vector comprises a polynucleotide encoding an amino acid sequence of SEQ ID NO: 269 or having at least 90% sequence identity, or at least 95% sequence identity, or at least 99% sequence identity to SEQ ID NO: 269.

In some embodiments, the Ad26 vector comprises a polynucleotide encoding an amino acid sequence of SEQ ID NO: 271 or having at least 90% sequence identity, or at least 95% sequence identity, or at least 99% sequence identity to SEQ ID NO: 271.

In some embodiments, the Ad26 vector comprises a polynucleotide encoding an amino acid sequence of SEQ ID NO: 273 or having at least 90% sequence identity, or at least 95% sequence identity, or at least 99% sequence identity to SEQ ID NO: 273.

In some embodiments, the Ad26 vector comprises a polynucleotide encoding an amino acid sequence of SEQ ID NO: 275 or having at least 90% sequence identity, or at least 95% sequence identity, or at least 99% sequence identity to SEQ ID NO: 275.

In some embodiments, the Ad26 vector comprises a polynucleotide encoding an amino acid sequence of SEQ ID NO: 277 or having at least 90% sequence identity, or at least 95% sequence identity, or at least 99% sequence identity to SEQ ID NO: 277.

In some embodiments, the Ad26 vector comprises a polynucleotide encoding an amino acid sequence of SEQ ID NO: 279 or having at least 90% sequence identity, or at least 95% sequence identity, or at least 99% sequence identity to SEQ ID NO: 279.

In some embodiments, the Ad26 vector comprises a polynucleotide encoding an amino acid sequence of SEQ ID NO: 281 or having at least 90% sequence identity, or at least 95% sequence identity, or at least 99% sequence identity to SEQ ID NO: 281.

In some embodiments, the Ad26 vector comprises a polynucleotide encoding an amino acid sequence of SEQ ID NO: 283 or having at least 90% sequence identity, or at least 95% sequence identity, or at least 99% sequence identity to SEQ ID NO: 283.

In some embodiments, the Ad26 vector comprises a polynucleotide encoding an amino acid sequence of SEQ ID NO: 285 or having at least 90% sequence identity, or at least 95% sequence identity, or at least 99% sequence identity to SEQ ID NO: 285.

In some embodiments, the Ad26 vector comprises a polynucleotide encoding an amino acid sequence of SEQ ID NO: 287 or having at least 90% sequence identity, or at least 95% sequence identity, or at least 99% sequence identity to SEQ ID NO: 287.

In some embodiments, the Ad26 vector comprises a polynucleotide encoding an amino acid sequence of SEQ ID NO: 289 or having at least 90% sequence identity, or at least 95% sequence identity, or at least 99% sequence identity to SEQ ID NO: 289.

In some embodiments, the Ad26 vector comprises a polynucleotide encoding an amino acid sequence of SEQ ID NO: 291 or having at least 90% sequence identity, or at least 95% sequence identity, or at least 99% sequence identity to SEQ ID NO: 291.

In some embodiments, the Ad26 vector comprises a polynucleotide encoding an amino acid sequence of SEQ ID NO: 293 or having at least 90% sequence identity, or at least 95% sequence identity, or at least 99% sequence identity to SEQ ID NO: 293.

In some embodiments, the Ad26 vector comprises a polynucleotide encoding an amino acid sequence of SEQ ID NO: 295 or having at least 90% sequence identity, or at least 95% sequence identity, or at least 99% sequence identity to SEQ ID NO: 295.

In some embodiments, the Ad26 vector comprises a polynucleotide encoding an amino acid sequence of SEQ ID NO: 297 or having at least 90% sequence identity, or at least 95% sequence identity, or at least 99% sequence identity to SEQ ID NO: 297.

In some embodiments, the Ad26 vector comprises a polynucleotide encoding an amino acid sequence of SEQ ID NO: 299 or having at least 90% sequence identity, or at least 95% sequence identity, or at least 99% sequence identity to SEQ ID NO: 299.

In some embodiments, the Ad26 vector comprises a polynucleotide encoding an amino acid sequence of SEQ ID NO: 301 or having at least 90% sequence identity, or at least 95% sequence identity, or at least 99% sequence identity to SEQ ID NO: 301.

In some embodiments, the Ad26 vector comprises a polynucleotide encoding an amino acid sequence of SEQ ID NO: 303 or having at least 90% sequence identity, or at least 95% sequence identity, or at least 99% sequence identity to SEQ ID NO: 303.

In some embodiments, the Ad26 vector comprises a polynucleotide encoding an amino acid sequence of SEQ ID NO: 305 or having at least 90% sequence identity, or at least 95% sequence identity, or at least 99% sequence identity to SEQ ID NO: 305.

In some embodiments, the Ad26 vector comprises a polynucleotide encoding an amino acid sequence of SEQ ID NO: 307 or having at least 90% sequence identity, or at least 95% sequence identity, or at least 99% sequence identity to SEQ ID NO: 307.

In some embodiments, the Ad26 vector comprises a polynucleotide encoding an amino acid sequence of SEQ ID NO: 309 or having at least 90% sequence identity, or at least 95% sequence identity, or at least 99% sequence identity to SEQ ID NO: 309.

In some embodiments, the Ad26 vector comprises a polynucleotide encoding an amino acid sequence of SEQ ID NO: 311 or having at least 90% sequence identity, or at least 95% sequence identity, or at least 99% sequence identity to SEQ ID NO: 311.

In some embodiments, the Ad26 vector comprises a polynucleotide encoding an amino acid sequence of SEQ ID NO: 313 or having at least 90% sequence identity, or at least 95% sequence identity, or at least 99% sequence identity to SEQ ID NO: 313.

In some embodiments, the Ad26 vector comprises a polynucleotide encoding an amino acid sequence of SEQ ID NO: 315 or having at least 90% sequence identity, or at least 95% sequence identity, or at least 99% sequence identity to SEQ ID NO: 315.

In some embodiments, the Ad26 vector comprises a polynucleotide encoding an amino acid sequence of SEQ ID NO: 317 or having at least 90% sequence identity, or at least 95% sequence identity, or at least 99% sequence identity to SEQ ID NO: 317.

In some embodiments, the Ad26 vector comprises a polynucleotide encoding an amino acid sequence of SEQ ID NO: 319 or having at least 90% sequence identity, or at least 95% sequence identity, or at least 99% sequence identity to SEQ ID NO: 319.

In some embodiments, the Ad26 vector comprises a polynucleotide encoding an amino acid sequence of SEQ ID NO: 321 or having at least 90% sequence identity, or at least 95% sequence identity, or at least 99% sequence identity to SEQ ID NO: 321.

In some embodiments, the Ad26 vector comprises a polynucleotide encoding an amino acid sequence of SEQ ID NO: 323 or having at least 90% sequence identity, or at least 95% sequence identity, or at least 99% sequence identity to SEQ ID NO: 323.

In some embodiments, the Ad26 vector comprises a polynucleotide encoding an amino acid sequence of SEQ ID NO: 325 or having at least 90% sequence identity, or at least 95% sequence identity, or at least 99% sequence identity to SEQ ID NO: 325.

In some embodiments, the Ad26 vector comprises a polynucleotide encoding an amino acid sequence of SEQ ID NO: 327 or having at least 90% sequence identity, or at least 95% sequence identity, or at least 99% sequence identity to SEQ ID NO: 327.

In some embodiments, the Ad26 vector comprises a polynucleotide encoding an amino acid sequence of SEQ ID NO: 329 or having at least 90% sequence identity, or at least 95% sequence identity, or at least 99% sequence identity to SEQ ID NO: 329.

In some embodiments, the Ad26 vector comprises a polynucleotide encoding an amino acid sequence of SEQ ID NO: 331 or having at least 90% sequence identity, or at least 95% sequence identity, or at least 99% sequence identity to SEQ ID NO: 331.

In some embodiments, the Ad26 vector comprises a polynucleotide encoding an amino acid sequence of SEQ ID NO: 333 or having at least 90% sequence identity, or at least 95% sequence identity, or at least 99% sequence identity to SEQ ID NO: 333.

In some embodiments, the Ad26 vector comprises a polynucleotide encoding an amino acid sequence of SEQ ID NO: 335 or having at least 90% sequence identity, or at least 95% sequence identity, or at least 99% sequence identity to SEQ ID NO: 335.

In some embodiments, the Ad26 vector comprises a polynucleotide encoding an amino acid sequence of SEQ ID NO: 337 or having at least 90% sequence identity, or at least 95% sequence identity, or at least 99% sequence identity to SEQ ID NO: 337.

In some embodiments, the Ad26 vector comprises a polynucleotide encoding an amino acid sequence of SEQ ID NO: 339 or having at least 90% sequence identity, or at least 95% sequence identity, or at least 99% sequence identity to SEQ ID NO: 339.

In some embodiments, the Ad26 vector comprises a polynucleotide encoding an amino acid sequence of SEQ ID NO: 341 or having at least 90% sequence identity, or at least 95% sequence identity, or at least 99% sequence identity to SEQ ID NO: 341.

In some embodiments, the Ad26 vector comprises a polynucleotide encoding an amino acid sequence of SEQ ID NO: 343 or having at least 90% sequence identity, or at least 95% sequence identity, or at least 99% sequence identity to SEQ ID NO: 343.

In some embodiments, the Ad26 vector comprises a polynucleotide encoding an amino acid sequence of SEQ ID NO: 345 or having at least 90% sequence identity, or at least 95% sequence identity, or at least 99% sequence identity to SEQ ID NO: 345.

In some embodiments, the Ad26 vector comprises a polynucleotide encoding an amino acid sequence of SEQ ID NO: 347 or having at least 90% sequence identity, or at least 95% sequence identity, or at least 99% sequence identity to SEQ ID NO: 347.

In some embodiments, the Ad26 vector comprises a polynucleotide encoding an amino acid sequence of SEQ ID NO: 349 or having at least 90% sequence identity, or at least 95% sequence identity, or at least 99% sequence identity to SEQ ID NO: 349.

In some embodiments, the Ad26 vector comprises a polynucleotide encoding an amino acid sequence of SEQ ID NO: 351 or having at least 90% sequence identity, or at least 95% sequence identity, or at least 99% sequence identity to SEQ ID NO: 351.

In some embodiments, the Ad26 vector comprises a polynucleotide encoding an amino acid sequence of SEQ ID NO: 353 or having at least 90% sequence identity, or at least 95% sequence identity, or at least 99% sequence identity to SEQ ID NO: 353.

In some embodiments, the Ad26 vector comprises a polynucleotide encoding an amino acid sequence of SEQ ID NO: 355 or having at least 90% sequence identity, or at least 95% sequence identity, or at least 99% sequence identity to SEQ ID NO: 355.

In some embodiments, the Ad26 vector comprises a polynucleotide encoding an amino acid sequence of SEQ ID NO: 357 or having at least 90% sequence identity, or at least 95% sequence identity, or at least 99% sequence identity to SEQ ID NO: 357.

In some embodiments, the Ad26 vector comprises a polynucleotide encoding an amino acid sequence of SEQ ID NO: 359 or having at least 90% sequence identity, or at least 95% sequence identity, or at least 99% sequence identity to SEQ ID NO: 359.

In some embodiments, the Ad26 vector comprises a polynucleotide encoding an amino acid sequence of SEQ ID NO: 361 or having at least 90% sequence identity, or at least 95% sequence identity, or at least 99% sequence identity to SEQ ID NO: 361.

In some embodiments, the Ad26 vector comprises a polynucleotide encoding an amino acid sequence of SEQ ID NO: 363 or having at least 90% sequence identity, or at least 95% sequence identity, or at least 99% sequence identity to SEQ ID NO: 363.

In some embodiments, the Ad26 vector comprises a polynucleotide encoding an amino acid sequence of SEQ ID NO: 365 or having at least 90% sequence identity, or at least 95% sequence identity, or at least 99% sequence identity to SEQ ID NO: 365.

In some embodiments, the Ad26 vector comprises a polynucleotide encoding an amino acid sequence of SEQ ID NO: 367 or having at least 90% sequence identity, or at least 95% sequence identity, or at least 99% sequence identity to SEQ ID NO: 367.

In some embodiments, the Ad26 vector comprises a polynucleotide encoding an amino acid sequence of SEQ ID NO: 369 or having at least 90% sequence identity, or at least 95% sequence identity, or at least 99% sequence identity to SEQ ID NO: 369.

In some embodiments, the Ad26 vector comprises a polynucleotide encoding an amino acid sequence of SEQ ID NO: 371 or having at least 90% sequence identity, or at least 95% sequence identity, or at least 99% sequence identity to SEQ ID NO: 371.

In some embodiments, the Ad26 vector comprises a polynucleotide encoding an amino acid sequence of SEQ ID NO: 373 or having at least 90% sequence identity, or at least 95% sequence identity, or at least 99% sequence identity to SEQ ID NO: 373.

In some embodiments, the Ad26 vector comprises a polynucleotide encoding an amino acid sequence of SEQ ID NO: 375 or having at least 90% sequence identity, or at least 95% sequence identity, or at least 99% sequence identity to SEQ ID NO: 375.

In some embodiments, the Ad26 vector comprises a polynucleotide encoding an amino acid sequence of SEQ ID NO: 377 or having at least 90% sequence identity, or at least 95% sequence identity, or at least 99% sequence identity to SEQ ID NO: 377.

In some embodiments, the Ad26 vector comprises a polynucleotide encoding an amino acid sequence of SEQ ID NO: 379 or having at least 90% sequence identity, or at least 95% sequence identity, or at least 99% sequence identity to SEQ ID NO: 379.

In some embodiments, the Ad26 vector comprises a polynucleotide encoding an amino acid sequence of SEQ ID NO: 381 or having at least 90% sequence identity, or at least 95% sequence identity, or at least 99% sequence identity to SEQ ID NO: 381.

In some embodiments, the Ad26 vector comprises a polynucleotide encoding an amino acid sequence of SEQ ID NO: 383 or having at least 90% sequence identity, or at least 95% sequence identity, or at least 99% sequence identity to SEQ ID NO: 383.

In some embodiments, the Ad26 vector comprises a polynucleotide encoding an amino acid sequence of SEQ ID NO: 385 or having at least 90% sequence identity, or at least 95% sequence identity, or at least 99% sequence identity to SEQ ID NO: 385.

In some embodiments, the Ad26 vector comprises a polynucleotide encoding an amino acid sequence of SEQ ID NO: 387 or having at least 90% sequence identity, or at least 95% sequence identity, or at least 99% sequence identity to SEQ ID NO: 387.

In some embodiments, the Ad26 vector comprises a polynucleotide encoding an amino acid sequence of SEQ ID NO: 389 or having at least 90% sequence identity, or at least 95% sequence identity, or at least 99% sequence identity to SEQ ID NO: 389.

In some embodiments, the Ad26 vector comprises a polynucleotide encoding an amino acid sequence of SEQ ID NO: 391 or having at least 90% sequence identity, or at least 95% sequence identity, or at least 99% sequence identity to SEQ ID NO: 391.

In some embodiments, the Ad26 vector comprises a polynucleotide encoding an amino acid sequence of SEQ ID NO: 393 or having at least 90% sequence identity, or at least 95% sequence identity, or at least 99% sequence identity to SEQ ID NO: 393.

In some embodiments, the Ad26 vector comprises a polynucleotide encoding an amino acid sequence of SEQ ID NO: 395 or having at least 90% sequence identity, or at least 95% sequence identity, or at least 99% sequence identity to SEQ ID NO: 395.

In some embodiments, the Ad26 vector comprises a polynucleotide encoding an amino acid sequence of SEQ ID NO: 397 or having at least 90% sequence identity, or at least 95% sequence identity, or at least 99% sequence identity to SEQ ID NO: 397.

In some embodiments, the Ad26 vector comprises a polynucleotide encoding an amino acid sequence of SEQ ID NO: 399 or having at least 90% sequence identity, or at least 95% sequence identity, or at least 99% sequence identity to SEQ ID NO: 399.

In some embodiments, the Ad26 vector comprises a polynucleotide encoding an amino acid sequence of SEQ ID NO: 401 or having at least 90% sequence identity, or at least 95% sequence identity, or at least 99% sequence identity to SEQ ID NO: 401.

In some embodiments, the Ad26 vector comprises a polynucleotide encoding an amino acid sequence of SEQ ID NO: 403 or having at least 90% sequence identity, or at least 95% sequence identity, or at least 99% sequence identity to SEQ ID NO: 403.

In some embodiments, the Ad26 vector comprises a polynucleotide encoding an amino acid sequence of SEQ ID NO: 405 or having at least 90% sequence identity, or at least 95% sequence identity, or at least 99% sequence identity to SEQ ID NO: 405.

In some embodiments, the Ad26 vector comprises a polynucleotide encoding an amino acid sequence of two or more of the polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and fragments thereof.

The disclosure also provides a recombinant great ape adenovirus (rGAd) comprising the vector of the disclosure. In some embodiments, the rGAd is derived from GAd20. In some embodiments, the rGAd is derived from GAd19. In some embodiments, the rGAd is derived from GAd21. In some embodiments, the rGAd is derived from GAd25. In some embodiments, the rGAd is derived from GAd26. In some embodiments, the rGAd is derived from GAd27. In some embodiments, the rGAd is derived from GAd28. In some embodiments, the rGAd is derived from GAd29. In some embodiments, the rGAd is derived from GAd30. In some embodiments, the rGAd is derived from GAd31. GAd19-21 and GAd25-31 are described in Int. Pat. Publ. No. WO2019/008111 and represent strains with high immunogenicity and no pre-existing immunity in the general human population. The polynucleotide sequence of GAd20 genome is disclosed in WO2019/008111.

Provided herein is a recombinant chimpanzee adenovirus derived from serotype 20 (rChAd20) comprising the vector of the disclosure. In some embodiments, the viral vector comprising any of the polynucleotides of the disclosure, is a vector derived from GAd20.

In some embodiments, the GAd20 vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the GAd20 vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the GAd20 vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the GAd20 vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the GAd20 vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the GAd20 vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the GAd20 vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the GAd20 vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the GAd20 vector comprises a polynucleotide encoding an amino acid sequence of SEQ ID NO: 17 or having at least 90% sequence identity, or at least 95% sequence identity, or at least 99% sequence identity to SEQ ID NO: 17.

In some embodiments, the GAd20 vector comprises a polynucleotide encoding an amino acid sequence of SEQ ID NO: 19 or having at least 90% sequence identity to SEQ ID NO: 19, or at least 95% sequence identity, or at least 99% sequence identity to SEQ ID NO: 19.

In some embodiments, the GAd20 vector comprises a polynucleotide encoding an amino acid sequence of SEQ ID NO: 21 or having at least 90% sequence identity, or at least 95% sequence identity, or at least 99% sequence identity to SEQ ID NO: 21.

In some embodiments, the GAd20 vector comprises a polynucleotide encoding an amino acid sequence of SEQ ID NO: 23 or having at least 90% sequence identity, or at least 95% sequence identity, or at least 99% sequence identity to SEQ ID NO: 23.

In some embodiments, the GAd20 vector comprises a polynucleotide encoding an amino acid sequence of SEQ ID NO: 25 or having at least 90% sequence identity, or at least 95% sequence identity, or at least 99% sequence identity to SEQ ID NO: 25.

In some embodiments, the GAd20 vector comprises a polynucleotide encoding an amino acid sequence of SEQ ID NO: 27 or having at least 90% sequence identity, or at least 95% sequence identity, or at least 99% sequence identity to SEQ ID NO: 27.

In some embodiments, the GAd20 vector comprises a polynucleotide encoding an amino acid sequence of SEQ ID NO: 29 or having at least 90% sequence identity, or at least 95% sequence identity, or at least 99% sequence identity to SEQ ID NO: 29.

In some embodiments, the GAd20 vector comprises a polynucleotide encoding an amino acid sequence of SEQ ID NO: 31 or having at least 90% sequence identity, or at least 95% sequence identity, or at least 99% sequence identity to SEQ ID NO: 31.

In some embodiments, the GAd20 vector comprises a polynucleotide encoding an amino acid sequence of SEQ ID NO: 33 or having at least 90% sequence identity, or at least 95% sequence identity, or at least 99% sequence identity to SEQ ID NO: 33.

In some embodiments, the GAd20 vector comprises a polynucleotide encoding an amino acid sequence of SEQ ID NO: 35 or having at least 90% sequence identity, or at least 95% sequence identity, or at least 99% sequence identity to SEQ ID NO: 35.

In some embodiments, the GAd20 vector comprises a polynucleotide encoding an amino acid sequence of SEQ ID NO: 37 or having at least 90% sequence identity, or at least 95% sequence identity, or at least 99% sequence identity to SEQ ID NO: 37.

In some embodiments, the GAd20 vector comprises a polynucleotide encoding an amino acid sequence of SEQ ID NO: 39 or having at least 90% sequence identity, or at least 95% sequence identity, or at least 99% sequence identity to SEQ ID NO: 39.

In some embodiments, the GAd20 vector comprises a polynucleotide encoding an amino acid sequence of SEQ ID NO: 41 or having at least 90% sequence identity, or at least 95% sequence identity, or at least 99% sequence identity to SEQ ID NO: 41.

In some embodiments, the GAd20 vector comprises a polynucleotide encoding an amino acid sequence of SEQ ID NO: 43 or having at least 90% sequence identity, or at least 95% sequence identity, or at least 99% sequence identity to SEQ ID NO: 43.

In some embodiments, the GAd20 vector comprises a polynucleotide encoding an amino acid sequence of SEQ ID NO: 45 or having at least 90% sequence identity, or at least 95% sequence identity, or at least 99% sequence identity to SEQ ID NO: 45.

In some embodiments, the GAd20 vector comprises a polynucleotide encoding an amino acid sequence of SEQ ID NO: 47 or having at least 90% sequence identity, or at least 95% sequence identity, or at least 99% sequence identity to SEQ ID NO: 47.

In some embodiments, the GAd20 vector comprises a polynucleotide encoding an amino acid sequence of SEQ ID NO: 49 or having at least 90% sequence identity, or at least 95% sequence identity, or at least 99% sequence identity to SEQ ID NO: 49.

In some embodiments, the GAd20 vector comprises a polynucleotide encoding an amino acid sequence of SEQ ID NO: 51 or having at least 90% sequence identity, or at least 95% sequence identity, or at least 99% sequence identity to SEQ ID NO: 51.

In some embodiments, the GAd20 vector comprises a polynucleotide encoding an amino acid sequence of SEQ ID NO: 53 or having at least 90% sequence identity, or at least 95% sequence identity, or at least 99% sequence identity to SEQ ID NO: 53.

In some embodiments, the GAd20 vector comprises a polynucleotide encoding an amino acid sequence of SEQ ID NO: 55 or having at least 90% sequence identity, or at least 95% sequence identity, or at least 99% sequence identity to SEQ ID NO: 55.

In some embodiments, the GAd20 vector comprises a polynucleotide encoding an amino acid sequence of SEQ ID NO: 57 or having at least 90% sequence identity, or at least 95% sequence identity, or at least 99% sequence identity to SEQ ID NO: 57.

In some embodiments, the GAd20 vector comprises a polynucleotide encoding an amino acid sequence of SEQ ID NO: 59 or having at least 90% sequence identity, or at least 95% sequence identity, or at least 99% sequence identity to SEQ ID NO: 59.

In some embodiments, the GAd20 vector comprises a polynucleotide encoding an amino acid sequence of SEQ ID NO: 61 or having at least 90% sequence identity, or at least 95% sequence identity, or at least 99% sequence identity to SEQ ID NO: 61.

In some embodiments, the GAd20 vector comprises a polynucleotide encoding an amino acid sequence of SEQ ID NO: 63 or having at least 90% sequence identity, or at least 95% sequence identity, or at least 99% sequence identity to SEQ ID NO: 63.

In some embodiments, the GAd20 vector comprises a polynucleotide encoding an amino acid sequence of SEQ ID NO: 65 or having at least 90% sequence identity, or at least 95% sequence identity, or at least 99% sequence identity to SEQ ID NO: 65.

In some embodiments, the GAd20 vector comprises a polynucleotide encoding an amino acid sequence of SEQ ID NO: 67 or having at least 90% sequence identity, or at least 95% sequence identity, or at least 99% sequence identity to SEQ ID NO: 67.

In some embodiments, the GAd20 vector comprises a polynucleotide encoding an amino acid sequence of SEQ ID NO: 69 or having at least 90% sequence identity, or at least 95% sequence identity, or at least 99% sequence identity to SEQ ID NO: 69.

In some embodiments, the GAd20 vector comprises a polynucleotide encoding an amino acid sequence of SEQ ID NO: 71 or having at least 90% sequence identity, or at least 95% sequence identity, or at least 99% sequence identity to SEQ ID NO: 71.

In some embodiments, the GAd20 vector comprises a polynucleotide encoding an amino acid sequence of SEQ ID NO: 73 or having at least 90% sequence identity, or at least 95% sequence identity, or at least 99% sequence identity to SEQ ID NO: 73.

In some embodiments, the GAd20 vector comprises a polynucleotide encoding an amino acid sequence of SEQ ID NO: 75 or having at least 90% sequence identity, or at least 95% sequence identity, or at least 99% sequence identity to SEQ ID NO: 75.

In some embodiments, the GAd20 vector comprises a polynucleotide encoding an amino acid sequence of SEQ ID NO: 77 or having at least 90% sequence identity, or at least 95% sequence identity, or at least 99% sequence identity to SEQ ID NO: 77.

In some embodiments, the GAd20 vector comprises a polynucleotide encoding an amino acid sequence of SEQ ID NO: 79 or having at least 90% sequence identity, or at least 95% sequence identity, or at least 99% sequence identity to SEQ ID NO: 79.

In some embodiments, the GAd20 vector comprises a polynucleotide encoding an amino acid sequence of SEQ ID NO: 81 or having at least 90% sequence identity, or at least 95% sequence identity, or at least 99% sequence identity to SEQ ID NO: 81.

In some embodiments, the GAd20 vector comprises a polynucleotide encoding an amino acid sequence of SEQ ID NO: 83 or having at least 90% sequence identity, or at least 95% sequence identity, or at least 99% sequence identity to SEQ ID NO: 83.

In some embodiments, the GAd20 vector comprises a polynucleotide encoding an amino acid sequence of SEQ ID NO: 85 or having at least 90% sequence identity, or at least 95% sequence identity, or at least 99% sequence identity to SEQ ID NO: 85.

In some embodiments, the GAd20 vector comprises a polynucleotide encoding an amino acid sequence of SEQ ID NO: 87 or having at least 90% sequence identity, or at least 95% sequence identity, or at least 99% sequence identity to SEQ ID NO: 87.

In some embodiments, the GAd20 vector comprises a polynucleotide encoding an amino acid sequence of SEQ ID NO: 89 or having at least 90% sequence identity, or at least 95% sequence identity, or at least 99% sequence identity to SEQ ID NO: 89.

In some embodiments, the GAd20 vector comprises a polynucleotide encoding an amino acid sequence of SEQ ID NO: 91 or having at least 90% sequence identity, or at least 95% sequence identity, or at least 99% sequence identity to SEQ ID NO: 91.

In some embodiments, the GAd20 vector comprises a polynucleotide encoding an amino acid sequence of SEQ ID NO: 93 or having at least 90% sequence identity, or at least 95% sequence identity, or at least 99% sequence identity to SEQ ID NO: 93.

In some embodiments, the GAd20 vector comprises a polynucleotide encoding an amino acid sequence of SEQ ID NO: 95 or having at least 90% sequence identity, or at least 95% sequence identity, or at least 99% sequence identity to SEQ ID NO: 95.

In some embodiments, the GAd20 vector comprises a polynucleotide encoding an amino acid sequence of SEQ ID NO: 97 or having at least 90% sequence identity, or at least 95% sequence identity, or at least 99% sequence identity to SEQ ID NO: 97.

In some embodiments, the GAd20 vector comprises a polynucleotide encoding an amino acid sequence of SEQ ID NO: 99 or having at least 90% sequence identity, or at least 95% sequence identity, or at least 99% sequence identity to SEQ ID NO: 99.

In some embodiments, the GAd20 vector comprises a polynucleotide encoding an amino acid sequence of SEQ ID NO: 101 or having at least 90% sequence identity, or at least 95% sequence identity, or at least 99% sequence identity to SEQ ID NO: 101.

In some embodiments, the GAd20 vector comprises a polynucleotide encoding an amino acid sequence of SEQ ID NO: 103 or having at least 90% sequence identity, or at least 95% sequence identity, or at least 99% sequence identity to SEQ ID NO: 103.

In some embodiments, the GAd20 vector comprises a polynucleotide encoding an amino acid sequence of SEQ ID NO: 105 or having at least 90% sequence identity, or at least 95% sequence identity, or at least 99% sequence identity to SEQ ID NO: 105.

In some embodiments, the GAd20 vector comprises a polynucleotide encoding an amino acid sequence of SEQ ID NO: 107 or having at least 90% sequence identity, or at least 95% sequence identity, or at least 99% sequence identity to SEQ ID NO: 107.

In some embodiments, the GAd20 vector comprises a polynucleotide encoding an amino acid sequence of SEQ ID NO: 109 or having at least 90% sequence identity, or at least 95% sequence identity, or at least 99% sequence identity to SEQ ID NO: 109.

In some embodiments, the GAd20 vector comprises a polynucleotide encoding an amino acid sequence of SEQ ID NO: 111 or having at least 90% sequence identity, or at least 95% sequence identity, or at least 99% sequence identity to SEQ ID NO: 111.

In some embodiments, the GAd20 vector comprises a polynucleotide encoding an amino acid sequence of SEQ ID NO: 113 or having at least 90% sequence identity, or at least 95% sequence identity, or at least 99% sequence identity to SEQ ID NO: 113.

In some embodiments, the GAd20 vector comprises a polynucleotide encoding an amino acid sequence of SEQ ID NO: 115 or having at least 90% sequence identity, or at least 95% sequence identity, or at least 99% sequence identity to SEQ ID NO: 115.

In some embodiments, the GAd20 vector comprises a polynucleotide encoding an amino acid sequence of SEQ ID NO: 117 or having at least 90% sequence identity, or at least 95% sequence identity, or at least 99% sequence identity to SEQ ID NO: 117.

In some embodiments, the GAd20 vector comprises a polynucleotide encoding an amino acid sequence of SEQ ID NO: 119 or having at least 90% sequence identity, or at least 95% sequence identity, or at least 99% sequence identity to SEQ ID NO: 119.

In some embodiments, the GAd20 vector comprises a polynucleotide encoding an amino acid sequence of SEQ ID NO: 121 or having at least 90% sequence identity, or at least 95% sequence identity, or at least 99% sequence identity to SEQ ID NO: 121.

In some embodiments, the GAd20 vector comprises a polynucleotide encoding an amino acid sequence of SEQ ID NO: 123 or having at least 90% sequence identity, or at least 95% sequence identity, or at least 99% sequence identity to SEQ ID NO: 123.

In some embodiments, the GAd20 vector comprises a polynucleotide encoding an amino acid sequence of SEQ ID NO: 125 or having at least 90% sequence identity, or at least 95% sequence identity, or at least 99% sequence identity to SEQ ID NO: 125.

In some embodiments, the GAd20 vector comprises a polynucleotide encoding an amino acid sequence of SEQ ID NO: 127 or having at least 90% sequence identity, or at least 95% sequence identity, or at least 99% sequence identity to SEQ ID NO: 127.

In some embodiments, the GAd20 vector comprises a polynucleotide encoding an amino acid sequence of SEQ ID NO: 129 or having at least 90% sequence identity, or at least 95% sequence identity, or at least 99% sequence identity to SEQ ID NO: 129.

In some embodiments, the GAd20 vector comprises a polynucleotide encoding an amino acid sequence of SEQ ID NO: 131 or having at least 90% sequence identity, or at least 95% sequence identity, or at least 99% sequence identity to SEQ ID NO: 131.

In some embodiments, the GAd20 vector comprises a polynucleotide encoding an amino acid sequence of SEQ ID NO: 133 or having at least 90% sequence identity, or at least 95% sequence identity, or at least 99% sequence identity to SEQ ID NO: 133.

In some embodiments, the GAd20 vector comprises a polynucleotide encoding an amino acid sequence of SEQ ID NO: 135 or having at least 90% sequence identity, or at least 95% sequence identity, or at least 99% sequence identity to SEQ ID NO: 135.

In some embodiments, the GAd20 vector comprises a polynucleotide encoding an amino acid sequence of SEQ ID NO: 137 or having at least 90% sequence identity, or at least 95% sequence identity, or at least 99% sequence identity to SEQ ID NO: 137.

In some embodiments, the GAd20 vector comprises a polynucleotide encoding an amino acid sequence of SEQ ID NO: 139 or having at least 90% sequence identity, or at least 95% sequence identity, or at least 99% sequence identity to SEQ ID NO: 139.

In some embodiments, the GAd20 vector comprises a polynucleotide encoding an amino acid sequence of SEQ ID NO: 141 or having at least 90% sequence identity, or at least 95% sequence identity, or at least 99% sequence identity to SEQ ID NO: 141.

In some embodiments, the GAd20 vector comprises a polynucleotide encoding an amino acid sequence of SEQ ID NO: 143 or having at least 90% sequence identity, or at least 95% sequence identity, or at least 99% sequence identity to SEQ ID NO: 143.

In some embodiments, the GAd20 vector comprises a polynucleotide encoding an amino acid sequence of SEQ ID NO: 145 or having at least 90% sequence identity, or at least 95% sequence identity, or at least 99% sequence identity to SEQ ID NO: 145.

In some embodiments, the GAd20 vector comprises a polynucleotide encoding an amino acid sequence of SEQ ID NO: 147 or having at least 90% sequence identity, or at least 95% sequence identity, or at least 99% sequence identity to SEQ ID NO: 147.

In some embodiments, the GAd20 vector comprises a polynucleotide encoding an amino acid sequence of SEQ ID NO: 149 or having at least 90% sequence identity, or at least 95% sequence identity, or at least 99% sequence identity to SEQ ID NO: 149.

In some embodiments, the GAd20 vector comprises a polynucleotide encoding an amino acid sequence of SEQ ID NO: 151 or having at least 90% sequence identity, or at least 95% sequence identity, or at least 99% sequence identity to SEQ ID NO: 151.

In some embodiments, the GAd20 vector comprises a polynucleotide encoding an amino acid sequence of SEQ ID NO: 153 or having at least 90% sequence identity, or at least 95% sequence identity, or at least 99% sequence identity to SEQ ID NO: 153.

In some embodiments, the GAd20 vector comprises a polynucleotide encoding an amino acid sequence of SEQ ID NO: 155 or having at least 90% sequence identity, or at least 95% sequence identity, or at least 99% sequence identity to SEQ ID NO: 155.

In some embodiments, the GAd20 vector comprises a polynucleotide encoding an amino acid sequence of SEQ ID NO: 157 or having at least 90% sequence identity, or at least 95% sequence identity, or at least 99% sequence identity to SEQ ID NO: 157.

In some embodiments, the GAd20 vector comprises a polynucleotide encoding an amino acid sequence of SEQ ID NO: 159 or having at least 90% sequence identity, or at least 95% sequence identity, or at least 99% sequence identity to SEQ ID NO: 159.

In some embodiments, the GAd20 vector comprises a polynucleotide encoding an amino acid sequence of SEQ ID NO: 161 or having at least 90% sequence identity, or at least 95% sequence identity, or at least 99% sequence identity to SEQ ID NO: 161.

In some embodiments, the GAd20 vector comprises a polynucleotide encoding an amino acid sequence of SEQ ID NO: 163 or having at least 90% sequence identity, or at least 95% sequence identity, or at least 99% sequence identity to SEQ ID NO: 163.

In some embodiments, the GAd20 vector comprises a polynucleotide encoding an amino acid sequence of SEQ ID NO: 165 or having at least 90% sequence identity, or at least 95% sequence identity, or at least 99% sequence identity to SEQ ID NO: 165.

In some embodiments, the GAd20 vector comprises a polynucleotide encoding an amino acid sequence of SEQ ID NO: 167 or having at least 90% sequence identity, or at least 95% sequence identity, or at least 99% sequence identity to SEQ ID NO: 167.

In some embodiments, the GAd20 vector comprises a polynucleotide encoding an amino acid sequence of SEQ ID NO: 169 or having at least 90% sequence identity, or at least 95% sequence identity, or at least 99% sequence identity to SEQ ID NO: 169.

In some embodiments, the GAd20 vector comprises a polynucleotide encoding an amino acid sequence of SEQ ID NO: 171 or having at least 90% sequence identity, or at least 95% sequence identity, or at least 99% sequence identity to SEQ ID NO: 171.

In some embodiments, the GAd20 vector comprises a polynucleotide encoding an amino acid sequence of SEQ ID NO: 173 or having at least 90% sequence identity, or at least 95% sequence identity, or at least 99% sequence identity to SEQ ID NO: 173.

In some embodiments, the GAd20 vector comprises a polynucleotide encoding an amino acid sequence of SEQ ID NO: 175 or having at least 90% sequence identity, or at least 95% sequence identity, or at least 99% sequence identity to SEQ ID NO: 175.

In some embodiments, the GAd20 vector comprises a polynucleotide encoding an amino acid sequence of SEQ ID NO: 177 or having at least 90% sequence identity, or at least 95% sequence identity, or at least 99% sequence identity to SEQ ID NO: 177.

In some embodiments, the GAd20 vector comprises a polynucleotide encoding an amino acid sequence of SEQ ID NO: 179 or having at least 90% sequence identity, or at least 95% sequence identity, or at least 99% sequence identity to SEQ ID NO: 179.

In some embodiments, the GAd20 vector comprises a polynucleotide encoding an amino acid sequence of SEQ ID NO: 181 or having at least 90% sequence identity, or at least 95% sequence identity, or at least 99% sequence identity to SEQ ID NO: 181.

In some embodiments, the GAd20 vector comprises a polynucleotide encoding an amino acid sequence of SEQ ID NO: 183 or having at least 90% sequence identity, or at least 95% sequence identity, or at least 99% sequence identity to SEQ ID NO: 183.

In some embodiments, the GAd20 vector comprises a polynucleotide encoding an amino acid sequence of SEQ ID NO: 185 or having at least 90% sequence identity, or at least 95% sequence identity, or at least 99% sequence identity to SEQ ID NO: 185.

In some embodiments, the GAd20 vector comprises a polynucleotide encoding an amino acid sequence of SEQ ID NO: 187 or having at least 90% sequence identity, or at least 95% sequence identity, or at least 99% sequence identity to SEQ ID NO: 187.

In some embodiments, the GAd20 vector comprises a polynucleotide encoding an amino acid sequence of SEQ ID NO: 189 or having at least 90% sequence identity, or at least 95% sequence identity, or at least 99% sequence identity to SEQ ID NO: 189.

In some embodiments, the GAd20 vector comprises a polynucleotide encoding an amino acid sequence of SEQ ID NO: 191 or having at least 90% sequence identity, or at least 95% sequence identity, or at least 99% sequence identity to SEQ ID NO: 191.

In some embodiments, the GAd20 vector comprises a polynucleotide encoding an amino acid sequence of SEQ ID NO: 193 or having at least 90% sequence identity, or at least 95% sequence identity, or at least 99% sequence identity to SEQ ID NO: 193.

In some embodiments, the GAd20 vector comprises a polynucleotide encoding an amino acid sequence of SEQ ID NO: 195 or having at least 90% sequence identity, or at least 95% sequence identity, or at least 99% sequence identity to SEQ ID NO: 195.

In some embodiments, the GAd20 vector comprises a polynucleotide encoding an amino acid sequence of SEQ ID NO: 197 or having at least 90% sequence identity, or at least 95% sequence identity, or at least 99% sequence identity to SEQ ID NO: 197.

In some embodiments, the GAd20 vector comprises a polynucleotide encoding an amino acid sequence of SEQ ID NO: 199 or having at least 90% sequence identity, or at least 95% sequence identity, or at least 99% sequence identity to SEQ ID NO: 199.

In some embodiments, the GAd20 vector comprises a polynucleotide encoding an amino acid sequence of SEQ ID NO: 201 or having at least 90% sequence identity, or at least 95% sequence identity, or at least 99% sequence identity to SEQ ID NO: 201.

In some embodiments, the GAd20 vector comprises a polynucleotide encoding an amino acid sequence of SEQ ID NO: 203 or having at least 90% sequence identity, or at least 95% sequence identity, or at least 99% sequence identity to SEQ ID NO: 203.

In some embodiments, the GAd20 vector comprises a polynucleotide encoding an amino acid sequence of SEQ ID NO: 205 or having at least 90% sequence identity, or at least 95% sequence identity, or at least 99% sequence identity to SEQ ID NO: 205.

In some embodiments, the GAd20 vector comprises a polynucleotide encoding an amino acid sequence of SEQ ID NO: 207 or having at least 90% sequence identity, or at least 95% sequence identity, or at least 99% sequence identity to SEQ ID NO: 207.

In some embodiments, the GAd20 vector comprises a polynucleotide encoding an amino acid sequence of SEQ ID NO: 209 or having at least 90% sequence identity, or at least 95% sequence identity, or at least 99% sequence identity to SEQ ID NO: 209.

In some embodiments, the GAd20 vector comprises a polynucleotide encoding an amino acid sequence of SEQ ID NO: 211 or having at least 90% sequence identity, or at least 95% sequence identity, or at least 99% sequence identity to SEQ ID NO: 211.

In some embodiments, the GAd20 vector comprises a polynucleotide encoding an amino acid sequence of SEQ ID NO: 213 or having at least 90% sequence identity, or at least 95% sequence identity, or at least 99% sequence identity to SEQ ID NO: 213.

In some embodiments, the GAd20 vector comprises a polynucleotide encoding an amino acid sequence of SEQ ID NO: 215 or having at least 90% sequence identity, or at least 95% sequence identity, or at least 99% sequence identity to SEQ ID NO: 215.

In some embodiments, the GAd20 vector comprises a polynucleotide encoding an amino acid sequence of SEQ ID NO: 217 or having at least 90% sequence identity, or at least 95% sequence identity, or at least 99% sequence identity to SEQ ID NO: 217.

In some embodiments, the GAd20 vector comprises a polynucleotide encoding an amino acid sequence of SEQ ID NO: 219 or having at least 90% sequence identity, or at least 95% sequence identity, or at least 99% sequence identity to SEQ ID NO: 219.

In some embodiments, the GAd20 vector comprises a polynucleotide encoding an amino acid sequence of SEQ ID NO: 221 or having at least 90% sequence identity, or at least 95% sequence identity, or at least 99% sequence identity to SEQ ID NO: 221.

In some embodiments, the GAd20 vector comprises a polynucleotide encoding an amino acid sequence of SEQ ID NO: 223 or having at least 90% sequence identity, or at least 95% sequence identity, or at least 99% sequence identity to SEQ ID NO: 223.

In some embodiments, the GAd20 vector comprises a polynucleotide encoding an amino acid sequence of SEQ ID NO: 225 or having at least 90% sequence identity, or at least 95% sequence identity, or at least 99% sequence identity to SEQ ID NO: 225.

In some embodiments, the GAd20 vector comprises a polynucleotide encoding an amino acid sequence of SEQ ID NO: 227 or having at least 90% sequence identity, or at least 95% sequence identity, or at least 99% sequence identity to SEQ ID NO: 227.

In some embodiments, the GAd20 vector comprises a polynucleotide encoding an amino acid sequence of SEQ ID NO: 229 or having at least 90% sequence identity, or at least 95% sequence identity, or at least 99% sequence identity to SEQ ID NO: 229.

In some embodiments, the GAd20 vector comprises a polynucleotide encoding an amino acid sequence of SEQ ID NO: 231 or having at least 90% sequence identity, or at least 95% sequence identity, or at least 99% sequence identity to SEQ ID NO: 231.

In some embodiments, the GAd20 vector comprises a polynucleotide encoding an amino acid sequence of SEQ ID NO: 233 or having at least 90% sequence identity, or at least 95% sequence identity, or at least 99% sequence identity to SEQ ID NO: 233.

In some embodiments, the GAd20 vector comprises a polynucleotide encoding an amino acid sequence of SEQ ID NO: 235 or having at least 90% sequence identity, or at least 95% sequence identity, or at least 99% sequence identity to SEQ ID NO: 235.

In some embodiments, the GAd20 vector comprises a polynucleotide encoding an amino acid sequence of SEQ ID NO: 237 or having at least 90% sequence identity, or at least 95% sequence identity, or at least 99% sequence identity to SEQ ID NO: 237.

In some embodiments, the GAd20 vector comprises a polynucleotide encoding an amino acid sequence of SEQ ID NO: 239 or having at least 90% sequence identity, or at least 95% sequence identity, or at least 99% sequence identity to SEQ ID NO: 239.

In some embodiments, the GAd20 vector comprises a polynucleotide encoding an amino acid sequence of SEQ ID NO: 241 or having at least 90% sequence identity, or at least 95% sequence identity, or at least 99% sequence identity to SEQ ID NO: 241.

In some embodiments, the GAd20 vector comprises a polynucleotide encoding an amino acid sequence of SEQ ID NO: 243 or having at least 90% sequence identity, or at least 95% sequence identity, or at least 99% sequence identity to SEQ ID NO: 243.

In some embodiments, the GAd20 vector comprises a polynucleotide encoding an amino acid sequence of SEQ ID NO: 245 or having at least 90% sequence identity, or at least 95% sequence identity, or at least 99% sequence identity to SEQ ID NO: 245.

In some embodiments, the GAd20 vector comprises a polynucleotide encoding an amino acid sequence of SEQ ID NO: 247 or having at least 90% sequence identity, or at least 95% sequence identity, or at least 99% sequence identity to SEQ ID NO: 247.

In some embodiments, the GAd20 vector comprises a polynucleotide encoding an amino acid sequence of SEQ ID NO: 249 or having at least 90% sequence identity, or at least 95% sequence identity, or at least 99% sequence identity to SEQ ID NO: 249.

In some embodiments, the GAd20 vector comprises a polynucleotide encoding an amino acid sequence of SEQ ID NO: 251 or having at least 90% sequence identity, or at least 95% sequence identity, or at least 99% sequence identity to SEQ ID NO: 251.

In some embodiments, the GAd20 vector comprises a polynucleotide encoding an amino acid sequence of SEQ ID NO: 253 or having at least 90% sequence identity, or at least 95% sequence identity, or at least 99% sequence identity to SEQ ID NO: 253.

In some embodiments, the GAd20 vector comprises a polynucleotide encoding an amino acid sequence of SEQ ID NO: 255 or having at least 90% sequence identity, or at least 95% sequence identity, or at least 99% sequence identity to SEQ ID NO: 255.

In some embodiments, the GAd20 vector comprises a polynucleotide encoding an amino acid sequence of SEQ ID NO: 257 or having at least 90% sequence identity, or at least 95% sequence identity, or at least 99% sequence identity to SEQ ID NO: 257.

In some embodiments, the GAd20 vector comprises a polynucleotide encoding an amino acid sequence of SEQ ID NO: 259 or having at least 90% sequence identity, or at least 95% sequence identity, or at least 99% sequence identity to SEQ ID NO: 259.

In some embodiments, the GAd20 vector comprises a polynucleotide encoding an amino acid sequence of SEQ ID NO: 261 or having at least 90% sequence identity, or at least 95% sequence identity, or at least 99% sequence identity to SEQ ID NO: 261.

In some embodiments, the GAd20 vector comprises a polynucleotide encoding an amino acid sequence of SEQ ID NO: 263 or having at least 90% sequence identity, or at least 95% sequence identity, or at least 99% sequence identity to SEQ ID NO: 263.

In some embodiments, the GAd20 vector comprises a polynucleotide encoding an amino acid sequence of SEQ ID NO: 265 or having at least 90% sequence identity, or at least 95% sequence identity, or at least 99% sequence identity to SEQ ID NO: 265.

In some embodiments, the GAd20 vector comprises a polynucleotide encoding an amino acid sequence of SEQ ID NO: 267 or having at least 90% sequence identity, or at least 95% sequence identity, or at least 99% sequence identity to SEQ ID NO: 267.

In some embodiments, the GAd20 vector comprises a polynucleotide encoding an amino acid sequence of SEQ ID NO: 269 or having at least 90% sequence identity, or at least 95% sequence identity, or at least 99% sequence identity to SEQ ID NO: 269.

In some embodiments, the GAd20 vector comprises a polynucleotide encoding an amino acid sequence of SEQ ID NO: 271 or having at least 90% sequence identity, or at least 95% sequence identity, or at least 99% sequence identity to SEQ ID NO: 271.

In some embodiments, the GAd20 vector comprises a polynucleotide encoding an amino acid sequence of SEQ ID NO: 273 or having at least 90% sequence identity, or at least 95% sequence identity, or at least 99% sequence identity to SEQ ID NO: 273.

In some embodiments, the GAd20 vector comprises a polynucleotide encoding an amino acid sequence of SEQ ID NO: 275 or having at least 90% sequence identity, or at least 95% sequence identity, or at least 99% sequence identity to SEQ ID NO: 275.

In some embodiments, the GAd20 vector comprises a polynucleotide encoding an amino acid sequence of SEQ ID NO: 277 or having at least 90% sequence identity, or at least 95% sequence identity, or at least 99% sequence identity to SEQ ID NO: 277.

In some embodiments, the GAd20 vector comprises a polynucleotide encoding an amino acid sequence of SEQ ID NO: 279 or having at least 90% sequence identity, or at least 95% sequence identity, or at least 99% sequence identity to SEQ ID NO: 279.

In some embodiments, the GAd20 vector comprises a polynucleotide encoding an amino acid sequence of SEQ ID NO: 281 or having at least 90% sequence identity, or at least 95% sequence identity, or at least 99% sequence identity to SEQ ID NO: 281.

In some embodiments, the GAd20 vector comprises a polynucleotide encoding an amino acid sequence of SEQ ID NO: 283 or having at least 90% sequence identity, or at least 95% sequence identity, or at least 99% sequence identity to SEQ ID NO: 283.

In some embodiments, the GAd20 vector comprises a polynucleotide encoding an amino acid sequence of SEQ ID NO: 285 or having at least 90% sequence identity, or at least 95% sequence identity, or at least 99% sequence identity to SEQ ID NO: 285.

In some embodiments, the GAd20 vector comprises a polynucleotide encoding an amino acid sequence of SEQ ID NO: 287 or having at least 90% sequence identity, or at least 95% sequence identity, or at least 99% sequence identity to SEQ ID NO: 287.

In some embodiments, the GAd20 vector comprises a polynucleotide encoding an amino acid sequence of SEQ ID NO: 289 or having at least 90% sequence identity, or at least 95% sequence identity, or at least 99% sequence identity to SEQ ID NO: 289.

In some embodiments, the GAd20 vector comprises a polynucleotide encoding an amino acid sequence of SEQ ID NO: 291 or having at least 90% sequence identity, or at least 95% sequence identity, or at least 99% sequence identity to SEQ ID NO: 291.

In some embodiments, the GAd20 vector comprises a polynucleotide encoding an amino acid sequence of SEQ ID NO: 293 or having at least 90% sequence identity, or at least 95% sequence identity, or at least 99% sequence identity to SEQ ID NO: 293.

In some embodiments, the GAd20 vector comprises a polynucleotide encoding an amino acid sequence of SEQ ID NO: 295 or having at least 90% sequence identity, or at least 95% sequence identity, or at least 99% sequence identity to SEQ ID NO: 295.

In some embodiments, the GAd20 vector comprises a polynucleotide encoding an amino acid sequence of SEQ ID NO: 297 or having at least 90% sequence identity, or at least 95% sequence identity, or at least 99% sequence identity to SEQ ID NO: 297.

In some embodiments, the GAd20 vector comprises a polynucleotide encoding an amino acid sequence of SEQ ID NO: 299 or having at least 90% sequence identity, or at least 95% sequence identity, or at least 99% sequence identity to SEQ ID NO: 299.

In some embodiments, the GAd20 vector comprises a polynucleotide encoding an amino acid sequence of SEQ ID NO: 301 or having at least 90% sequence identity, or at least 95% sequence identity, or at least 99% sequence identity to SEQ ID NO: 301.

In some embodiments, the GAd20 vector comprises a polynucleotide encoding an amino acid sequence of SEQ ID NO: 303 or having at least 90% sequence identity, or at least 95% sequence identity, or at least 99% sequence identity to SEQ ID NO: 303.

In some embodiments, the GAd20 vector comprises a polynucleotide encoding an amino acid sequence of SEQ ID NO: 305 or having at least 90% sequence identity, or at least 95% sequence identity, or at least 99% sequence identity to SEQ ID NO: 305.

In some embodiments, the GAd20 vector comprises a polynucleotide encoding an amino acid sequence of SEQ ID NO: 307 or having at least 90% sequence identity, or at least 95% sequence identity, or at least 99% sequence identity to SEQ ID NO: 307.

In some embodiments, the GAd20 vector comprises a polynucleotide encoding an amino acid sequence of SEQ ID NO: 309 or having at least 90% sequence identity, or at least 95% sequence identity, or at least 99% sequence identity to SEQ ID NO: 309.

In some embodiments, the GAd20 vector comprises a polynucleotide encoding an amino acid sequence of SEQ ID NO: 311 or having at least 90% sequence identity, or at least 95% sequence identity, or at least 99% sequence identity to SEQ ID NO: 311.

In some embodiments, the GAd20 vector comprises a polynucleotide encoding an amino acid sequence of SEQ ID NO: 313 or having at least 90% sequence identity, or at least 95% sequence identity, or at least 99% sequence identity to SEQ ID NO: 313.

In some embodiments, the GAd20 vector comprises a polynucleotide encoding an amino acid sequence of SEQ ID NO: 315 or having at least 90% sequence identity, or at least 95% sequence identity, or at least 99% sequence identity to SEQ ID NO: 315.

In some embodiments, the GAd20 vector comprises a polynucleotide encoding an amino acid sequence of SEQ ID NO: 317 or having at least 90% sequence identity, or at least 95% sequence identity, or at least 99% sequence identity to SEQ ID NO: 317.

In some embodiments, the GAd20 vector comprises a polynucleotide encoding an amino acid sequence of SEQ ID NO: 319 or having at least 90% sequence identity, or at least 95% sequence identity, or at least 99% sequence identity to SEQ ID NO: 319.

In some embodiments, the GAd20 vector comprises a polynucleotide encoding an amino acid sequence of SEQ ID NO: 321 or having at least 90% sequence identity, or at least 95% sequence identity, or at least 99% sequence identity to SEQ ID NO: 321.

In some embodiments, the GAd20 vector comprises a polynucleotide encoding an amino acid sequence of SEQ ID NO: 323 or having at least 90% sequence identity, or at least 95% sequence identity, or at least 99% sequence identity to SEQ ID NO: 323.

In some embodiments, the GAd20 vector comprises a polynucleotide encoding an amino acid sequence of SEQ ID NO: 325 or having at least 90% sequence identity, or at least 95% sequence identity, or at least 99% sequence identity to SEQ ID NO: 325.

In some embodiments, the GAd20 vector comprises a polynucleotide encoding an amino acid sequence of SEQ ID NO: 327 or having at least 90% sequence identity, or at least 95% sequence identity, or at least 99% sequence identity to SEQ ID NO: 327.

In some embodiments, the GAd20 vector comprises a polynucleotide encoding an amino acid sequence of SEQ ID NO: 329 or having at least 90% sequence identity, or at least 95% sequence identity, or at least 99% sequence identity to SEQ ID NO: 329.

In some embodiments, the GAd20 vector comprises a polynucleotide encoding an amino acid sequence of SEQ ID NO: 331 or having at least 90% sequence identity, or at least 95% sequence identity, or at least 99% sequence identity to SEQ ID NO: 331.

In some embodiments, the GAd20 vector comprises a polynucleotide encoding an amino acid sequence of SEQ ID NO: 333 or having at least 90% sequence identity, or at least 95% sequence identity, or at least 99% sequence identity to SEQ ID NO: 333.

In some embodiments, the GAd20 vector comprises a polynucleotide encoding an amino acid sequence of SEQ ID NO: 335 or having at least 90% sequence identity, or at least 95% sequence identity, or at least 99% sequence identity to SEQ ID NO: 335.

In some embodiments, the GAd20 vector comprises a polynucleotide encoding an amino acid sequence of SEQ ID NO: 337 or having at least 90% sequence identity, or at least 95% sequence identity, or at least 99% sequence identity to SEQ ID NO: 337.

In some embodiments, the GAd20 vector comprises a polynucleotide encoding an amino acid sequence of SEQ ID NO: 339 or having at least 90% sequence identity, or at least 95% sequence identity, or at least 99% sequence identity to SEQ ID NO: 339.

In some embodiments, the GAd20 vector comprises a polynucleotide encoding an amino acid sequence of SEQ ID NO: 341 or having at least 90% sequence identity, or at least 95% sequence identity, or at least 99% sequence identity to SEQ ID NO: 341.

In some embodiments, the GAd20 vector comprises a polynucleotide encoding an amino acid sequence of SEQ ID NO: 343 or having at least 90% sequence identity, or at least 95% sequence identity, or at least 99% sequence identity to SEQ ID NO: 343.

In some embodiments, the GAd20 vector comprises a polynucleotide encoding an amino acid sequence of SEQ ID NO: 345 or having at least 90% sequence identity, or at least 95% sequence identity, or at least 99% sequence identity to SEQ ID NO: 345.

In some embodiments, the GAd20 vector comprises a polynucleotide encoding an amino acid sequence of SEQ ID NO: 347 or having at least 90% sequence identity, or at least 95% sequence identity, or at least 99% sequence identity to SEQ ID NO: 347.

In some embodiments, the GAd20 vector comprises a polynucleotide encoding an amino acid sequence of SEQ ID NO: 349 or having at least 90% sequence identity, or at least 95% sequence identity, or at least 99% sequence identity to SEQ ID NO: 349.

In some embodiments, the GAd20 vector comprises a polynucleotide encoding an amino acid sequence of SEQ ID NO: 351 or having at least 90% sequence identity, or at least 95% sequence identity, or at least 99% sequence identity to SEQ ID NO: 351.

In some embodiments, the GAd20 vector comprises a polynucleotide encoding an amino acid sequence of SEQ ID NO: 353 or having at least 90% sequence identity, or at least 95% sequence identity, or at least 99% sequence identity to SEQ ID NO: 353.

In some embodiments, the GAd20 vector comprises a polynucleotide encoding an amino acid sequence of SEQ ID NO: 355 or having at least 90% sequence identity, or at least 95% sequence identity, or at least 99% sequence identity to SEQ ID NO: 355.

In some embodiments, the GAd20 vector comprises a polynucleotide encoding an amino acid sequence of SEQ ID NO: 357 or having at least 90% sequence identity, or at least 95% sequence identity, or at least 99% sequence identity to SEQ ID NO: 357.

In some embodiments, the GAd20 vector comprises a polynucleotide encoding an amino acid sequence of SEQ ID NO: 359 or having at least 90% sequence identity, or at least 95% sequence identity, or at least 99% sequence identity to SEQ ID NO: 359.

In some embodiments, the GAd20 vector comprises a polynucleotide encoding an amino acid sequence of SEQ ID NO: 361 or having at least 90% sequence identity, or at least 95% sequence identity, or at least 99% sequence identity to SEQ ID NO: 361.

In some embodiments, the GAd20 vector comprises a polynucleotide encoding an amino acid sequence of SEQ ID NO: 363 or having at least 90% sequence identity, or at least 95% sequence identity, or at least 99% sequence identity to SEQ ID NO: 363.

In some embodiments, the GAd20 vector comprises a polynucleotide encoding an amino acid sequence of SEQ ID NO: 365 or having at least 90% sequence identity, or at least 95% sequence identity, or at least 99% sequence identity to SEQ ID NO: 365.

In some embodiments, the GAd20 vector comprises a polynucleotide encoding an amino acid sequence of SEQ ID NO: 367 or having at least 90% sequence identity, or at least 95% sequence identity, or at least 99% sequence identity to SEQ ID NO: 367.

In some embodiments, the GAd20 vector comprises a polynucleotide encoding an amino acid sequence of SEQ ID NO: 369 or having at least 90% sequence identity, or at least 95% sequence identity, or at least 99% sequence identity to SEQ ID NO: 369.

In some embodiments, the GAd20 vector comprises a polynucleotide encoding an amino acid sequence of SEQ ID NO: 371 or having at least 90% sequence identity, or at least 95% sequence identity, or at least 99% sequence identity to SEQ ID NO: 371.

In some embodiments, the GAd20 vector comprises a polynucleotide encoding an amino acid sequence of SEQ ID NO: 373 or having at least 90% sequence identity, or at least 95% sequence identity, or at least 99% sequence identity to SEQ ID NO: 373.

In some embodiments, the GAd20 vector comprises a polynucleotide encoding an amino acid sequence of SEQ ID NO: 375 or having at least 90% sequence identity, or at least 95% sequence identity, or at least 99% sequence identity to SEQ ID NO: 375.

In some embodiments, the GAd20 vector comprises a polynucleotide encoding an amino acid sequence of SEQ ID NO: 377 or having at least 90% sequence identity, or at least 95% sequence identity, or at least 99% sequence identity to SEQ ID NO: 377.

In some embodiments, the GAd20 vector comprises a polynucleotide encoding an amino acid sequence of SEQ ID NO: 379 or having at least 90% sequence identity, or at least 95% sequence identity, or at least 99% sequence identity to SEQ ID NO: 379.

In some embodiments, the GAd20 vector comprises a polynucleotide encoding an amino acid sequence of SEQ ID NO: 381 or having at least 90% sequence identity, or at least 95% sequence identity, or at least 99% sequence identity to SEQ ID NO: 381.

In some embodiments, the GAd20 vector comprises a polynucleotide encoding an amino acid sequence of SEQ ID NO: 383 or having at least 90% sequence identity, or at least 95% sequence identity, or at least 99% sequence identity to SEQ ID NO: 383.

In some embodiments, the GAd20 vector comprises a polynucleotide encoding an amino acid sequence of SEQ ID NO: 385 or having at least 90% sequence identity, or at least 95% sequence identity, or at least 99% sequence identity to SEQ ID NO: 385.

In some embodiments, the GAd20 vector comprises a polynucleotide encoding an amino acid sequence of SEQ ID NO: 387 or having at least 90% sequence identity, or at least 95% sequence identity, or at least 99% sequence identity to SEQ ID NO: 387.

In some embodiments, the GAd20 vector comprises a polynucleotide encoding an amino acid sequence of SEQ ID NO: 389 or having at least 90% sequence identity, or at least 95% sequence identity, or at least 99% sequence identity to SEQ ID NO: 389.

In some embodiments, the GAd20 vector comprises a polynucleotide encoding an amino acid sequence of SEQ ID NO: 391 or having at least 90% sequence identity, or at least 95% sequence identity, or at least 99% sequence identity to SEQ ID NO: 391.

In some embodiments, the GAd20 vector comprises a polynucleotide encoding an amino acid sequence of SEQ ID NO: 393 or having at least 90% sequence identity, or at least 95% sequence identity, or at least 99% sequence identity to SEQ ID NO: 393.

In some embodiments, the GAd20 vector comprises a polynucleotide encoding an amino acid sequence of SEQ ID NO: 395 or having at least 90% sequence identity, or at least 95% sequence identity, or at least 99% sequence identity to SEQ ID NO: 395.

In some embodiments, the GAd20 vector comprises a polynucleotide encoding an amino acid sequence of SEQ ID NO: 397 or having at least 90% sequence identity, or at least 95% sequence identity, or at least 99% sequence identity to SEQ ID NO: 397.

In some embodiments, the GAd20 vector comprises a polynucleotide encoding an amino acid sequence of SEQ ID NO: 399 or having at least 90% sequence identity, or at least 95% sequence identity, or at least 99% sequence identity to SEQ ID NO: 399.

In some embodiments, the GAd20 vector comprises a polynucleotide encoding an amino acid sequence of SEQ ID NO: 401 or having at least 90% sequence identity, or at least 95% sequence identity, or at least 99% sequence identity to SEQ ID NO: 401.

In some embodiments, the GAd20 vector comprises a polynucleotide encoding an amino acid sequence of SEQ ID NO: 403 or having at least 90% sequence identity, or at least 95% sequence identity, or at least 99% sequence identity to SEQ ID NO: 403.

In some embodiments, the GAd20 vector comprises a polynucleotide encoding an amino acid sequence of SEQ ID NO: 405 or having at least 90% sequence identity, or at least 95% sequence identity, or at least 99% sequence identity to SEQ ID NO: 405.

In some embodiments, the GAd20 vector comprises a polynucleotide encoding an amino acid sequence of two or more of the polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and fragments thereof.

Poxvirus Vectors

In some embodiments, the viral vector is derived from a poxvirus. In some embodiments, the recombinant virus comprising the vector is derived from a poxvirus.

Poxvirus (Poxviridae) vectors may be derived from smallpox virus (variola), vaccinia virus, cowpox virus or monkeypox virus. Exemplary vaccinia viruses are the Copenhagen vaccinia virus (W), New York Attenuated Vaccinia Virus (NYVAC), ALVAC, TROVAC and Modified Vaccinia Ankara (MVA).

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

MVA has been generated by 516 serial passages on chicken embryo fibroblasts of the CVA virus (see Meyer et al., J. Gen. Virol., 72: 1031-1038 (1991) and U.S. Pat. No. 10,035,832). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; Meisinger-Henschel et al., Genomic sequence of chorioallantois vaccinia virus Ankara, the ancestor of modified vaccinia virus Ankara, J. Gen. Virol. 88, 3249-3259, 2007). Comparison of the MVA genome to its parent, CVA, revealed 6 major deletions of genomic DNA (deletion I, II, III, IV, V, and VI), totaling 31,000 basepairs. (Meyer et al., J. Gen. Virol. 72:1031-8 (1991)). It was shown in a variety of animal models that the resulting MVA was significantly avirulent (Mayr, A. & Danner, K. Vaccination against pox diseases under immunosuppressive conditions, Dev. Biol. Stand. 41: 225-34, 1978). Being that many passages were used to attenuate MVA, there are a number of different strains or isolates, depending on the passage number in CEF cells, such as MVA 476 MG/14/78, MVA-571, MVA-572, MVA-574, MVA-575 and MVA-BN. MVA 476 MG/14/78 is described for example in Int. Pat. Publ. No.

WO2019/115816A1. MVA-572 strain was deposited at the European Collection of Animal Cell Cultures ("ECACC"), Health Protection Agency, Microbiology Services, Porton Down, Salisbury SP4 0JG, United Kingdom ("UK"), under the deposit number ECACC 94012707 on Jan. 27, 1994. MVA-575 strain was deposited at the ECACC under deposit number ECACC 00120707 on Dec. 7, 2000; MVA-Bavarian Nordic ("MVA-BN") strain was deposited at the ECACC under deposit number V00080038 on Aug. 30, 2000. The genome sequences of MVA-BN and MVA-572 are available at GenBank (Accession numbers DQ983238 and DQ983237, respectively). The genome sequences of other MVA strains can be obtained using standard sequencing methods.

Vectors and viruses of the disclosure may be derived from any MVA strain or further derivatives of the MVA strain. A further exemplary MVA strain is deposit VR-1508, deposited at the American Type Culture collection (ATCC), Manassas, Va. 20108, USA.

"Derivatives" of MVA refer to viruses exhibiting essentially the same characteristics as the parent MVA but exhibiting differences in one or more parts of their genomes.

In some embodiments, the MVA vector is derived from MVA 476 MG/14/78. In some embodiments, the MVA vector is derived from MVA-571. In some embodiments, the MVA vector is derived from MVA-572. In some embodiments, the MVA vector is derived from MVA-574. In some embodiments, the MVA vector is derived from MVA-575. In some embodiments, the MVA vector is derived from MVA-BN.

The polynucleotide or the heterologous polynucleotide of the disclosure may be inserted into a site or region (insertion region) in the MVA vector that does not affect virus viability of the resultant recombinant virus. Such regions can be readily identified by testing segments of virus DNA for regions that allow recombinant formation without seriously affecting virus viability of the recombinant virus. The thymidine kinase (TK) gene is an insertion region that may be used and is present in many viruses, such as in all examined poxvirus genomes. Additionally, MVA contains 6 natural deletion sites, each of which may be used as insertion sites (e.g. deletion I, II, III, IV, V, and VI; see e.g. U.S. Pat. Nos. 5,185,146 and 6,440,442). One or more intergenic regions (IGR) of the MVA may also be used as an insertion site, such as IGRs IGR07/08, IGR 44/45, IGR 64/65, IGR 88/89, IGR 136/137, and IGR 148/149 (see e.g. U.S. Pat. Publ. No. 2018/0064803). Additional suitable insertion sites are described in Int. Pat. Publ. No. WO2005/048957.

Recombinant poxviral particles such as rMVA are prepared as described in the art (Piccini, et al., 1987, Methods of Enzymology 153: 545-563; U.S. Pat. Nos. 4,769,330; 4,772,848; 4,603,112; 5,100,587 and 5,179,993).

In an exemplary method, the DNA sequence to be inserted into the virus can be placed into an E. coli plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within E. coli bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences. rMVA particles may be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

Provided herein is a viral vector comprising any of the polynucleotides of the disclosure, wherein the vector is derived from MVA. The disclosure also provides a recombinant modified vaccinia Ankara (rMVA) comprising the vector of the disclosure.

In some embodiments, the MVA vector comprises a polynucleotide encoding an amino acid sequence of SEQ ID NO: 1 or having at least 90% sequence identity, or at least 95% sequence identity, or at least 99% sequence identity to SEQ ID NO: 1.

In some embodiments, the MVA vector comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the MVA vector comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the MVA vector comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the MVA vector comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the MVA vector comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the MVA vector comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the MVA vector comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the MVA vector comprises a polynucleotide encoding an amino acid sequence of SEQ ID NO: 17 or having at least 90% sequence identity, or at least 95% sequence identity, or at least 99% sequence identity to SEQ ID NO: 17.

In some embodiments, the MVA vector comprises a polynucleotide encoding an amino acid sequence of SEQ ID NO: 19 or having at least 90% sequence identity to SEQ ID NO: 19, or at least 95% sequence identity, or at least 99% sequence identity to SEQ ID NO: 19.

In some embodiments, the MVA vector comprises a polynucleotide encoding an amino acid sequence of SEQ ID NO: 21 or having at least 90% sequence identity, or at least 95% sequence identity, or at least 99% sequence identity to SEQ ID NO: 21.

In some embodiments, the MVA vector comprises a polynucleotide encoding an amino acid sequence of SEQ ID NO: 23 or having at least 90% sequence identity, or at least 95% sequence identity, or at least 99% sequence identity to SEQ ID NO: 23.

In some embodiments, the MVA vector comprises a polynucleotide encoding an amino acid sequence of SEQ ID NO: 25 or having at least 90% sequence identity, or at least 95% sequence identity, or at least 99% sequence identity to SEQ ID NO: 25.

In some embodiments, the MVA vector comprises a polynucleotide encoding an amino acid sequence of SEQ ID NO: 27 or having at least 90% sequence identity, or at least 95% sequence identity, or at least 99% sequence identity to SEQ ID NO: 27.

In some embodiments, the MVA vector comprises a polynucleotide encoding an amino acid sequence of SEQ ID NO: 29 or having at least 90% sequence identity, or at least 95% sequence identity, or at least 99% sequence identity to SEQ ID NO: 29.

In some embodiments, the MVA vector comprises a polynucleotide encoding an amino acid sequence of SEQ ID NO: 31 or having at least 90% sequence identity, or at least 95% sequence identity, or at least 99% sequence identity to SEQ ID NO: 31.

In some embodiments, the MVA vector comprises a polynucleotide encoding an amino acid sequence of SEQ ID NO: 33 or having at least 90% sequence identity, or at least 95% sequence identity, or at least 99% sequence identity to SEQ ID NO: 33.

In some embodiments, the MVA vector comprises a polynucleotide encoding an amino acid sequence of SEQ ID NO: 35 or having at least 90% sequence identity, or at least 95% sequence identity, or at least 99% sequence identity to SEQ ID NO: 35.

In some embodiments, the MVA vector comprises a polynucleotide encoding an amino acid sequence of SEQ ID NO: 37 or having at least 90% sequence identity, or at least 95% sequence identity, or at least 99% sequence identity to SEQ ID NO: 37.

In some embodiments, the MVA vector comprises a polynucleotide encoding an amino acid sequence of SEQ ID NO: 39 or having at least 90% sequence identity, or at least 95% sequence identity, or at least 99% sequence identity to SEQ ID NO: 39.

In some embodiments, the MVA vector comprises a polynucleotide encoding an amino acid sequence of SEQ ID NO: 41 or having at least 90% sequence identity, or at least 95% sequence identity, or at least 99% sequence identity to SEQ ID NO: 41.

In some embodiments, the MVA vector comprises a polynucleotide encoding an amino acid sequence of SEQ ID NO: 43 or having at least 90% sequence identity, or at least 95% sequence identity, or at least 99% sequence identity to SEQ ID NO: 43.

In some embodiments, the MVA vector comprises a polynucleotide encoding an amino acid sequence of SEQ ID NO: 45 or having at least 90% sequence identity, or at least 95% sequence identity, or at least 99% sequence identity to SEQ ID NO: 45.

In some embodiments, the MVA vector comprises a polynucleotide encoding an amino acid sequence of SEQ ID NO: 47 or having at least 90% sequence identity, or at least 95% sequence identity, or at least 99% sequence identity to SEQ ID NO: 47.

In some embodiments, the MVA vector comprises a polynucleotide encoding an amino acid sequence of SEQ ID NO: 49 or having at least 90% sequence identity, or at least 95% sequence identity, or at least 99% sequence identity to SEQ ID NO: 49.

In some embodiments, the MVA vector comprises a polynucleotide encoding an amino acid sequence of SEQ ID NO: 51 or having at least 90% sequence identity, or at least 95% sequence identity, or at least 99% sequence identity to SEQ ID NO: 51.

In some embodiments, the MVA vector comprises a polynucleotide encoding an amino acid sequence of SEQ ID NO: 53 or having at least 90% sequence identity, or at least 95% sequence identity, or at least 99% sequence identity to SEQ ID NO: 53.

In some embodiments, the MVA vector comprises a polynucleotide encoding an amino acid sequence of SEQ ID NO: 55 or having at least 90% sequence identity, or at least 95% sequence identity, or at least 99% sequence identity to SEQ ID NO: 55.

In some embodiments, the MVA vector comprises a polynucleotide encoding an amino acid sequence of SEQ ID NO: 57 or having at least 90% sequence identity, or at least 95% sequence identity, or at least 99% sequence identity to SEQ ID NO: 57.

In some embodiments, the MVA vector comprises a polynucleotide encoding an amino acid sequence of SEQ ID NO: 59 or having at least 90% sequence identity, or at least 95% sequence identity, or at least 99% sequence identity to SEQ ID NO: 59.

In some embodiments, the MVA vector comprises a polynucleotide encoding an amino acid sequence of SEQ ID NO: 61 or having at least 90% sequence identity, or at least 95% sequence identity, or at least 99% sequence identity to SEQ ID NO: 61.

In some embodiments, the MVA vector comprises a polynucleotide encoding an amino acid sequence of SEQ ID NO: 63 or having at least 90% sequence identity, or at least 95% sequence identity, or at least 99% sequence identity to SEQ ID NO: 63.

In some embodiments, the MVA vector comprises a polynucleotide encoding an amino acid sequence of SEQ ID NO: 65 or having at least 90% sequence identity, or at least 95% sequence identity, or at least 99% sequence identity to SEQ ID NO: 65.

In some embodiments, the MVA vector comprises a polynucleotide encoding an amino acid sequence of SEQ ID NO: 67 or having at least 90% sequence identity, or at least 95% sequence identity, or at least 99% sequence identity to SEQ ID NO: 67.

In some embodiments, the MVA vector comprises a polynucleotide encoding an amino acid sequence of SEQ ID NO: 69 or having at least 90% sequence identity, or at least 95% sequence identity, or at least 99% sequence identity to SEQ ID NO: 69.

In some embodiments, the MVA vector comprises a polynucleotide encoding an amino acid sequence of SEQ ID NO: 71 or having at least 90% sequence identity, or at least 95% sequence identity, or at least 99% sequence identity to SEQ ID NO: 71.

In some embodiments, the MVA vector comprises a polynucleotide encoding an amino acid sequence of SEQ ID NO: 73 or having at least 90% sequence identity, or at least 95% sequence identity, or at least 99% sequence identity to SEQ ID NO: 73.

In some embodiments, the MVA vector comprises a polynucleotide encoding an amino acid sequence of SEQ ID NO: 75 or having at least 90% sequence identity, or at least 95% sequence identity, or at least 99% sequence identity to SEQ ID NO: 75.

In some embodiments, the MVA vector comprises a polynucleotide encoding an amino acid sequence of SEQ ID NO: 77 or having at least 90% sequence identity, or at least 95% sequence identity, or at least 99% sequence identity to SEQ ID NO: 77.

In some embodiments, the MVA vector comprises a polynucleotide encoding an amino acid sequence of SEQ ID NO: 79 or having at least 90% sequence identity, or at least 95% sequence identity, or at least 99% sequence identity to SEQ ID NO: 79.

In some embodiments, the MVA vector comprises a polynucleotide encoding an amino acid sequence of SEQ ID NO: 81 or having at least 90% sequence identity, or at least 95% sequence identity, or at least 99% sequence identity to SEQ ID NO: 81.

In some embodiments, the MVA vector comprises a polynucleotide encoding an amino acid sequence of SEQ ID NO: 83 or having at least 90% sequence identity, or at least 95% sequence identity, or at least 99% sequence identity to SEQ ID NO: 83.

In some embodiments, the MVA vector comprises a polynucleotide encoding an amino acid sequence of SEQ ID NO: 85 or having at least 90% sequence identity, or at least 95% sequence identity, or at least 99% sequence identity to SEQ ID NO: 85.

In some embodiments, the MVA vector comprises a polynucleotide encoding an amino acid sequence of SEQ ID NO: 87 or having at least 90% sequence identity, or at least 95% sequence identity, or at least 99% sequence identity to SEQ ID NO: 87.

In some embodiments, the MVA vector comprises a polynucleotide encoding an amino acid sequence of SEQ ID NO: 89 or having at least 90% sequence identity, or at least 95% sequence identity, or at least 99% sequence identity to SEQ ID NO: 89.

In some embodiments, the MVA vector comprises a polynucleotide encoding an amino acid sequence of SEQ ID NO: 91 or having at least 90% sequence identity, or at least 95% sequence identity, or at least 99% sequence identity to SEQ ID NO: 91.

In some embodiments, the MVA vector comprises a polynucleotide encoding an amino acid sequence of SEQ ID NO: 93 or having at least 90% sequence identity, or at least 95% sequence identity, or at least 99% sequence identity to SEQ ID NO: 93.

In some embodiments, the MVA vector comprises a polynucleotide encoding an amino acid sequence of SEQ ID NO: 95 or having at least 90% sequence identity, or at least 95% sequence identity, or at least 99% sequence identity to SEQ ID NO: 95.

In some embodiments, the MVA vector comprises a polynucleotide encoding an amino acid sequence of SEQ ID NO: 97 or having at least 90% sequence identity, or at least 95% sequence identity, or at least 99% sequence identity to SEQ ID NO: 97.

In some embodiments, the MVA vector comprises a polynucleotide encoding an amino acid sequence of SEQ ID NO: 99 or having at least 90% sequence identity, or at least 95% sequence identity, or at least 99% sequence identity to SEQ ID NO: 99.

In some embodiments, the MVA vector comprises a polynucleotide encoding an amino acid sequence of SEQ ID NO: 101 or having at least 90% sequence identity, or at least 95% sequence identity, or at least 99% sequence identity to SEQ ID NO: 101.

In some embodiments, the MVA vector comprises a polynucleotide encoding an amino acid sequence of SEQ ID NO: 103 or having at least 90% sequence identity, or at least 95% sequence identity, or at least 99% sequence identity to SEQ ID NO: 103.

In some embodiments, the MVA vector comprises a polynucleotide encoding an amino acid sequence of SEQ ID NO: 105 or having at least 90% sequence identity, or at least 95% sequence identity, or at least 99% sequence identity to SEQ ID NO: 105.

In some embodiments, the MVA vector comprises a polynucleotide encoding an amino acid sequence of SEQ ID NO: 107 or having at least 90% sequence identity, or at least 95% sequence identity, or at least 99% sequence identity to SEQ ID NO: 107.

In some embodiments, the MVA vector comprises a polynucleotide encoding an amino acid sequence of SEQ ID NO: 109 or having at least 90% sequence identity, or at least 95% sequence identity, or at least 99% sequence identity to SEQ ID NO: 109.

In some embodiments, the MVA vector comprises a polynucleotide encoding an amino acid sequence of SEQ ID NO: 111 or having at least 90% sequence identity, or at least 95% sequence identity, or at least 99% sequence identity to SEQ ID NO: 111.

In some embodiments, the MVA vector comprises a polynucleotide encoding an amino acid sequence of SEQ ID NO: 113 or having at least 90% sequence identity, or at least 95% sequence identity, or at least 99% sequence identity to SEQ ID NO: 113.

In some embodiments, the MVA vector comprises a polynucleotide encoding an amino acid sequence of SEQ ID NO: 115 or having at least 90% sequence identity, or at least 95% sequence identity, or at least 99% sequence identity to SEQ ID NO: 115.

In some embodiments, the MVA vector comprises a polynucleotide encoding an amino acid sequence of SEQ ID NO: 117 or having at least 90% sequence identity, or at least 95% sequence identity, or at least 99% sequence identity to SEQ ID NO: 117.

In some embodiments, the MVA vector comprises a polynucleotide encoding an amino acid sequence of SEQ ID NO: 119 or having at least 90% sequence identity, or at least 95% sequence identity, or at least 99% sequence identity to SEQ ID NO: 119.

In some embodiments, the MVA vector comprises a polynucleotide encoding an amino acid sequence of SEQ ID NO: 121 or having at least 90% sequence identity, or at least 95% sequence identity, or at least 99% sequence identity to SEQ ID NO: 121.

In some embodiments, the MVA vector comprises a polynucleotide encoding an amino acid sequence of SEQ ID NO: 123 or having at least 90% sequence identity, or at least 95% sequence identity, or at least 99% sequence identity to SEQ ID NO: 123.

In some embodiments, the MVA vector comprises a polynucleotide encoding an amino acid sequence of SEQ ID NO: 125 or having at least 90% sequence identity, or at least 95% sequence identity, or at least 99% sequence identity to SEQ ID NO: 125.

In some embodiments, the MVA vector comprises a polynucleotide encoding an amino acid sequence of SEQ ID NO: 127 or having at least 90% sequence identity, or at least 95% sequence identity, or at least 99% sequence identity to SEQ ID NO: 127.

In some embodiments, the MVA vector comprises a polynucleotide encoding an amino acid sequence of SEQ ID NO: 129 or having at least 90% sequence identity, or at least 95% sequence identity, or at least 99% sequence identity to SEQ ID NO: 129.

In some embodiments, the MVA vector comprises a polynucleotide encoding an amino acid sequence of SEQ ID NO: 131 or having at least 90% sequence identity, or at least 95% sequence identity, or at least 99% sequence identity to SEQ ID NO: 131.

In some embodiments, the MVA vector comprises a polynucleotide encoding an amino acid sequence of SEQ ID NO: 133 or having at least 90% sequence identity, or at least 95% sequence identity, or at least 99% sequence identity to SEQ ID NO: 133.

In some embodiments, the MVA vector comprises a polynucleotide encoding an amino acid sequence of SEQ ID NO: 135 or having at least 90% sequence identity, or at least 95% sequence identity, or at least 99% sequence identity to SEQ ID NO: 135.

In some embodiments, the MVA vector comprises a polynucleotide encoding an amino acid sequence of SEQ ID NO: 137 or having at least 90% sequence identity, or at least 95% sequence identity, or at least 99% sequence identity to SEQ ID NO: 137.

In some embodiments, the MVA vector comprises a polynucleotide encoding an amino acid sequence of SEQ ID NO: 139 or having at least 90% sequence identity, or at least 95% sequence identity, or at least 99% sequence identity to SEQ ID NO: 139.

In some embodiments, the MVA vector comprises a polynucleotide encoding an amino acid sequence of SEQ ID NO: 141 or having at least 90% sequence identity, or at least 95% sequence identity, or at least 99% sequence identity to SEQ ID NO: 141.

In some embodiments, the MVA vector comprises a polynucleotide encoding an amino acid sequence of SEQ ID NO: 143 or having at least 90% sequence identity, or at least 95% sequence identity, or at least 99% sequence identity to SEQ ID NO: 143.

In some embodiments, the MVA vector comprises a polynucleotide encoding an amino acid sequence of SEQ ID NO: 145 or having at least 90% sequence identity, or at least 95% sequence identity, or at least 99% sequence identity to SEQ ID NO: 145.

In some embodiments, the MVA vector comprises a polynucleotide encoding an amino acid sequence of SEQ ID NO: 147 or having at least 90% sequence identity, or at least 95% sequence identity, or at least 99% sequence identity to SEQ ID NO: 147.

In some embodiments, the MVA vector comprises a polynucleotide encoding an amino acid sequence of SEQ ID NO: 149 or having at least 90% sequence identity, or at least 95% sequence identity, or at least 99% sequence identity to SEQ ID NO: 149.

In some embodiments, the MVA vector comprises a polynucleotide encoding an amino acid sequence of SEQ ID NO: 151 or having at least 90% sequence identity, or at least 95% sequence identity, or at least 99% sequence identity to SEQ ID NO: 151.

In some embodiments, the MVA vector comprises a polynucleotide encoding an amino acid sequence of SEQ ID NO: 153 or having at least 90% sequence identity, or at least 95% sequence identity, or at least 99% sequence identity to SEQ ID NO: 153.

In some embodiments, the MVA vector comprises a polynucleotide encoding an amino acid sequence of SEQ ID NO: 155 or having at least 90% sequence identity, or at least 95% sequence identity, or at least 99% sequence identity to SEQ ID NO: 155.

In some embodiments, the MVA vector comprises a polynucleotide encoding an amino acid sequence of SEQ ID NO: 157 or having at least 90% sequence identity, or at least 95% sequence identity, or at least 99% sequence identity to SEQ ID NO: 157.

In some embodiments, the MVA vector comprises a polynucleotide encoding an amino acid sequence of SEQ ID NO: 159 or having at least 90% sequence identity, or at least 95% sequence identity, or at least 99% sequence identity to SEQ ID NO: 159.

In some embodiments, the MVA vector comprises a polynucleotide encoding an amino acid sequence of SEQ ID NO: 161 or having at least 90% sequence identity, or at least 95% sequence identity, or at least 99% sequence identity to SEQ ID NO: 161.

In some embodiments, the MVA vector comprises a polynucleotide encoding an amino acid sequence of SEQ ID NO: 163 or having at least 90% sequence identity, or at least 95% sequence identity, or at least 99% sequence identity to SEQ ID NO: 163.

In some embodiments, the MVA vector comprises a polynucleotide encoding an amino acid sequence of SEQ ID NO: 165 or having at least 90% sequence identity, or at least 95% sequence identity, or at least 99% sequence identity to SEQ ID NO: 165.

In some embodiments, the MVA vector comprises a polynucleotide encoding an amino acid sequence of SEQ ID NO: 167 or having at least 90% sequence identity, or at least 95% sequence identity, or at least 99% sequence identity to SEQ ID NO: 167.

In some embodiments, the MVA vector comprises a polynucleotide encoding an amino acid sequence of SEQ ID NO: 169 or having at least 90% sequence identity, or at least 95% sequence identity, or at least 99% sequence identity to SEQ ID NO: 169.

In some embodiments, the MVA vector comprises a polynucleotide encoding an amino acid sequence of SEQ ID NO: 171 or having at least 90% sequence identity, or at least 95% sequence identity, or at least 99% sequence identity to SEQ ID NO: 171.

In some embodiments, the MVA vector comprises a polynucleotide encoding an amino acid sequence of SEQ ID NO: 173 or having at least 90% sequence identity, or at least 95% sequence identity, or at least 99% sequence identity to SEQ ID NO: 173.

In some embodiments, the MVA vector comprises a polynucleotide encoding an amino acid sequence of SEQ ID NO: 175 or having at least 90% sequence identity, or at least 95% sequence identity, or at least 99% sequence identity to SEQ ID NO: 175.

In some embodiments, the MVA vector comprises a polynucleotide encoding an amino acid sequence of SEQ ID NO: 177 or having at least 90% sequence identity, or at least 95% sequence identity, or at least 99% sequence identity to SEQ ID NO: 177.

In some embodiments, the MVA vector comprises a polynucleotide encoding an amino acid sequence of SEQ ID NO: 179 or having at least 90% sequence identity, or at least 95% sequence identity, or at least 99% sequence identity to SEQ ID NO: 179.

In some embodiments, the MVA vector comprises a polynucleotide encoding an amino acid sequence of SEQ ID NO: 181 or having at least 90% sequence identity, or at least 95% sequence identity, or at least 99% sequence identity to SEQ ID NO: 181.

In some embodiments, the MVA vector comprises a polynucleotide encoding an amino acid sequence of SEQ ID NO: 183 or having at least 90% sequence identity, or at least 95% sequence identity, or at least 99% sequence identity to SEQ ID NO: 183.

In some embodiments, the MVA vector comprises a polynucleotide encoding an amino acid sequence of SEQ ID NO: 185 or having at least 90% sequence identity, or at least 95% sequence identity, or at least 99% sequence identity to SEQ ID NO: 185.

In some embodiments, the MVA vector comprises a polynucleotide encoding an amino acid sequence of SEQ ID NO: 187 or having at least 90% sequence identity, or at least 95% sequence identity, or at least 99% sequence identity to SEQ ID NO: 187.

In some embodiments, the MVA vector comprises a polynucleotide encoding an amino acid sequence of SEQ ID NO: 189 or having at least 90% sequence identity, or at least 95% sequence identity, or at least 99% sequence identity to SEQ ID NO: 189.

In some embodiments, the MVA vector comprises a polynucleotide encoding an amino acid sequence of SEQ ID NO: 191 or having at least 90% sequence identity, or at least 95% sequence identity, or at least 99% sequence identity to SEQ ID NO: 191.

In some embodiments, the MVA vector comprises a polynucleotide encoding an amino acid sequence of SEQ ID NO: 193 or having at least 90% sequence identity, or at least 95% sequence identity, or at least 99% sequence identity to SEQ ID NO: 193.

In some embodiments, the MVA vector comprises a polynucleotide encoding an amino acid sequence of SEQ ID NO: 195 or having at least 90% sequence identity, or at least 95% sequence identity, or at least 99% sequence identity to SEQ ID NO: 195.

In some embodiments, the MVA vector comprises a polynucleotide encoding an amino acid sequence of SEQ ID NO: 197 or having at least 90% sequence identity, or at least 95% sequence identity, or at least 99% sequence identity to SEQ ID NO: 197.

In some embodiments, the MVA vector comprises a polynucleotide encoding an amino acid sequence of SEQ ID NO: 199 or having at least 90% sequence identity, or at least 95% sequence identity, or at least 99% sequence identity to SEQ ID NO: 199.

In some embodiments, the MVA vector comprises a polynucleotide encoding an amino acid sequence of SEQ ID NO: 201 or having at least 90% sequence identity, or at least 95% sequence identity, or at least 99% sequence identity to SEQ ID NO: 201.

In some embodiments, the MVA vector comprises a polynucleotide encoding an amino acid sequence of SEQ ID NO: 203 or having at least 90% sequence identity, or at least 95% sequence identity, or at least 99% sequence identity to SEQ ID NO: 203.

In some embodiments, the MVA vector comprises a polynucleotide encoding an amino acid sequence of SEQ ID NO: 205 or having at least 90% sequence identity, or at least 95% sequence identity, or at least 99% sequence identity to SEQ ID NO: 205.

In some embodiments, the MVA vector comprises a polynucleotide encoding an amino acid sequence of SEQ ID NO: 207 or having at least 90% sequence identity, or at least 95% sequence identity, or at least 99% sequence identity to SEQ ID NO: 207.

In some embodiments, the MVA vector comprises a polynucleotide encoding an amino acid sequence of SEQ ID NO: 209 or having at least 90% sequence identity, or at least 95% sequence identity, or at least 99% sequence identity to SEQ ID NO: 209.

In some embodiments, the MVA vector comprises a polynucleotide encoding an amino acid sequence of SEQ ID NO: 211 or having at least 90% sequence identity, or at least 95% sequence identity, or at least 99% sequence identity to SEQ ID NO: 211.

In some embodiments, the MVA vector comprises a polynucleotide encoding an amino acid sequence of SEQ ID NO: 213 or having at least 90% sequence identity, or at least 95% sequence identity, or at least 99% sequence identity to SEQ ID NO: 213.

In some embodiments, the MVA vector comprises a polynucleotide encoding an amino acid sequence of SEQ ID NO: 215 or having at least 90% sequence identity, or at least 95% sequence identity, or at least 99% sequence identity to SEQ ID NO: 215.

In some embodiments, the MVA vector comprises a polynucleotide encoding an amino acid sequence of SEQ ID NO: 217 or having at least 90% sequence identity, or at least 95% sequence identity, or at least 99% sequence identity to SEQ ID NO: 217.

In some embodiments, the MVA vector comprises a polynucleotide encoding an amino acid sequence of SEQ ID NO: 219 or having at least 90% sequence identity, or at least 95% sequence identity, or at least 99% sequence identity to SEQ ID NO: 219.

In some embodiments, the MVA vector comprises a polynucleotide encoding an amino acid sequence of SEQ ID NO: 221 or having at least 90% sequence identity, or at least 95% sequence identity, or at least 99% sequence identity to SEQ ID NO: 221.

In some embodiments, the MVA vector comprises a polynucleotide encoding an amino acid sequence of SEQ ID NO: 223 or having at least 90% sequence identity, or at least 95% sequence identity, or at least 99% sequence identity to SEQ ID NO: 223.

In some embodiments, the MVA vector comprises a polynucleotide encoding an amino acid sequence of SEQ ID NO: 225 or having at least 90% sequence identity, or at least 95% sequence identity, or at least 99% sequence identity to SEQ ID NO: 225.

In some embodiments, the MVA vector comprises a polynucleotide encoding an amino acid sequence of SEQ ID NO: 227 or having at least 90% sequence identity, or at least 95% sequence identity, or at least 99% sequence identity to SEQ ID NO: 227.

In some embodiments, the MVA vector comprises a polynucleotide encoding an amino acid sequence of SEQ ID NO: 229 or having at least 90% sequence identity, or at least 95% sequence identity, or at least 99% sequence identity to SEQ ID NO: 229.

In some embodiments, the MVA vector comprises a polynucleotide encoding an amino acid sequence of SEQ ID NO: 231 or having at least 90% sequence identity, or at least 95% sequence identity, or at least 99% sequence identity to SEQ ID NO: 231.

In some embodiments, the MVA vector comprises a polynucleotide encoding an amino acid sequence of SEQ ID NO: 233 or having at least 90% sequence identity, or at least 95% sequence identity, or at least 99% sequence identity to SEQ ID NO: 233.

In some embodiments, the MVA vector comprises a polynucleotide encoding an amino acid sequence of SEQ ID NO: 235 or having at least 90% sequence identity, or at least 95% sequence identity, or at least 99% sequence identity to SEQ ID NO: 235.

In some embodiments, the MVA vector comprises a polynucleotide encoding an amino acid sequence of SEQ ID NO: 237 or having at least 90% sequence identity, or at least 95% sequence identity, or at least 99% sequence identity to SEQ ID NO: 237.

In some embodiments, the MVA vector comprises a polynucleotide encoding an amino acid sequence of SEQ ID NO: 239 or having at least 90% sequence identity, or at least 95% sequence identity, or at least 99% sequence identity to SEQ ID NO: 239.

In some embodiments, the MVA vector comprises a polynucleotide encoding an amino acid sequence of SEQ ID NO: 241 or having at least 90% sequence identity, or at least 95% sequence identity, or at least 99% sequence identity to SEQ ID NO: 241.

In some embodiments, the MVA vector comprises a polynucleotide encoding an amino acid sequence of SEQ ID NO: 243 or having at least 90% sequence identity, or at least 95% sequence identity, or at least 99% sequence identity to SEQ ID NO: 243.

In some embodiments, the MVA vector comprises a polynucleotide encoding an amino acid sequence of SEQ ID NO: 245 or having at least 90% sequence identity, or at least 95% sequence identity, or at least 99% sequence identity to SEQ ID NO: 245.

In some embodiments, the MVA vector comprises a polynucleotide encoding an amino acid sequence of SEQ ID NO: 247 or having at least 90% sequence identity, or at least 95% sequence identity, or at least 99% sequence identity to SEQ ID NO: 247.

In some embodiments, the MVA vector comprises a polynucleotide encoding an amino acid sequence of SEQ ID NO: 249 or having at least 90% sequence identity, or at least 95% sequence identity, or at least 99% sequence identity to SEQ ID NO: 249.

In some embodiments, the MVA vector comprises a polynucleotide encoding an amino acid sequence of SEQ ID NO: 251 or having at least 90% sequence identity, or at least 95% sequence identity, or at least 99% sequence identity to SEQ ID NO: 251.

In some embodiments, the MVA vector comprises a polynucleotide encoding an amino acid sequence of SEQ ID NO: 253 or having at least 90% sequence identity, or at least 95% sequence identity, or at least 99% sequence identity to SEQ ID NO: 253.

In some embodiments, the MVA vector comprises a polynucleotide encoding an amino acid sequence of SEQ ID NO: 255 or having at least 90% sequence identity, or at least 95% sequence identity, or at least 99% sequence identity to SEQ ID NO: 255.

In some embodiments, the MVA vector comprises a polynucleotide encoding an amino acid sequence of SEQ ID NO: 257 or having at least 90% sequence identity, or at least 95% sequence identity, or at least 99% sequence identity to SEQ ID NO: 257.

In some embodiments, the MVA vector comprises a polynucleotide encoding an amino acid sequence of SEQ ID NO: 259 or having at least 90% sequence identity, or at least 95% sequence identity, or at least 99% sequence identity to SEQ ID NO: 259.

In some embodiments, the MVA vector comprises a polynucleotide encoding an amino acid sequence of SEQ ID NO: 261 or having at least 90% sequence identity, or at least 95% sequence identity, or at least 99% sequence identity to SEQ ID NO: 261.

In some embodiments, the MVA vector comprises a polynucleotide encoding an amino acid sequence of SEQ ID NO: 263 or having at least 90% sequence identity, or at least 95% sequence identity, or at least 99% sequence identity to SEQ ID NO: 263.

In some embodiments, the MVA vector comprises a polynucleotide encoding an amino acid sequence of SEQ ID NO: 265 or having at least 90% sequence identity, or at least 95% sequence identity, or at least 99% sequence identity to SEQ ID NO: 265.

In some embodiments, the MVA vector comprises a polynucleotide encoding an amino acid sequence of SEQ ID NO: 267 or having at least 90% sequence identity, or at least 95% sequence identity, or at least 99% sequence identity to SEQ ID NO: 267.

In some embodiments, the MVA vector comprises a polynucleotide encoding an amino acid sequence of SEQ ID NO: 269 or having at least 90% sequence identity, or at least 95% sequence identity, or at least 99% sequence identity to SEQ ID NO: 269.

In some embodiments, the MVA vector comprises a polynucleotide encoding an amino acid sequence of SEQ ID NO: 271 or having at least 90% sequence identity, or at least 95% sequence identity, or at least 99% sequence identity to SEQ ID NO: 271.

In some embodiments, the MVA vector comprises a polynucleotide encoding an amino acid sequence of SEQ ID NO: 273 or having at least 90% sequence identity, or at least 95% sequence identity, or at least 99% sequence identity to SEQ ID NO: 273.

In some embodiments, the MVA vector comprises a polynucleotide encoding an amino acid sequence of SEQ ID NO: 275 or having at least 90% sequence identity, or at least 95% sequence identity, or at least 99% sequence identity to SEQ ID NO: 275.

In some embodiments, the MVA vector comprises a polynucleotide encoding an amino acid sequence of SEQ ID NO: 277 or having at least 90% sequence identity, or at least 95% sequence identity, or at least 99% sequence identity to SEQ ID NO: 277.

In some embodiments, the MVA vector comprises a polynucleotide encoding an amino acid sequence of SEQ ID NO: 279 or having at least 90% sequence identity, or at least 95% sequence identity, or at least 99% sequence identity to SEQ ID NO: 279.

In some embodiments, the MVA vector comprises a polynucleotide encoding an amino acid sequence of SEQ ID NO: 281 or having at least 90% sequence identity, or at least 95% sequence identity, or at least 99% sequence identity to SEQ ID NO: 281.

In some embodiments, the MVA vector comprises a polynucleotide encoding an amino acid sequence of SEQ ID NO: 283 or having at least 90% sequence identity, or at least 95% sequence identity, or at least 99% sequence identity to SEQ ID NO: 283.

In some embodiments, the MVA vector comprises a polynucleotide encoding an amino acid sequence of SEQ ID NO: 285 or having at least 90% sequence identity, or at least 95% sequence identity, or at least 99% sequence identity to SEQ ID NO: 285.

In some embodiments, the MVA vector comprises a polynucleotide encoding an amino acid sequence of SEQ ID NO: 287 or having at least 90% sequence identity, or at least 95% sequence identity, or at least 99% sequence identity to SEQ ID NO: 287.

In some embodiments, the MVA vector comprises a polynucleotide encoding an amino acid sequence of SEQ ID NO: 289 or having at least 90% sequence identity, or at least 95% sequence identity, or at least 99% sequence identity to SEQ ID NO: 289.

In some embodiments, the MVA vector comprises a polynucleotide encoding an amino acid sequence of SEQ ID NO: 291 or having at least 90% sequence identity, or at least 95% sequence identity, or at least 99% sequence identity to SEQ ID NO: 291.

In some embodiments, the MVA vector comprises a polynucleotide encoding an amino acid sequence of SEQ ID NO: 293 or having at least 90% sequence identity, or at least 95% sequence identity, or at least 99% sequence identity to SEQ ID NO: 293.

In some embodiments, the MVA vector comprises a polynucleotide encoding an amino acid sequence of SEQ ID NO: 295 or having at least 90% sequence identity, or at least 95% sequence identity, or at least 99% sequence identity to SEQ ID NO: 295.

In some embodiments, the MVA vector comprises a polynucleotide encoding an amino acid sequence of SEQ ID NO: 297 or having at least 90% sequence identity, or at least 95% sequence identity, or at least 99% sequence identity to SEQ ID NO: 297.

In some embodiments, the MVA vector comprises a polynucleotide encoding an amino acid sequence of SEQ ID NO: 299 or having at least 90% sequence identity, or at least 95% sequence identity, or at least 99% sequence identity to SEQ ID NO: 299.

In some embodiments, the MVA vector comprises a polynucleotide encoding an amino acid sequence of SEQ ID NO: 301 or having at least 90% sequence identity, or at least 95% sequence identity, or at least 99% sequence identity to SEQ ID NO: 301.

In some embodiments, the MVA vector comprises a polynucleotide encoding an amino acid sequence of SEQ ID NO: 303 or having at least 90% sequence identity, or at least 95% sequence identity, or at least 99% sequence identity to SEQ ID NO: 303.

In some embodiments, the MVA vector comprises a polynucleotide encoding an amino acid sequence of SEQ ID NO: 305 or having at least 90% sequence identity, or at least 95% sequence identity, or at least 99% sequence identity to SEQ ID NO: 305.

In some embodiments, the MVA vector comprises a polynucleotide encoding an amino acid sequence of SEQ ID NO: 307 or having at least 90% sequence identity, or at least 95% sequence identity, or at least 99% sequence identity to SEQ ID NO: 307.

In some embodiments, the MVA vector comprises a polynucleotide encoding an amino acid sequence of SEQ ID NO: 309 or having at least 90% sequence identity, or at least 95% sequence identity, or at least 99% sequence identity to SEQ ID NO: 309.

In some embodiments, the MVA vector comprises a polynucleotide encoding an amino acid sequence of SEQ ID NO: 311 or having at least 90% sequence identity, or at least 95% sequence identity, or at least 99% sequence identity to SEQ ID NO: 311.

In some embodiments, the MVA vector comprises a polynucleotide encoding an amino acid sequence of SEQ ID NO: 313 or having at least 90% sequence identity, or at least 95% sequence identity, or at least 99% sequence identity to SEQ ID NO: 313.

In some embodiments, the MVA vector comprises a polynucleotide encoding an amino acid sequence of SEQ ID NO: 315 or having at least 90% sequence identity, or at least 95% sequence identity, or at least 99% sequence identity to SEQ ID NO: 315.

In some embodiments, the MVA vector comprises a polynucleotide encoding an amino acid sequence of SEQ ID NO: 317 or having at least 90% sequence identity, or at least 95% sequence identity, or at least 99% sequence identity to SEQ ID NO: 317.

In some embodiments, the MVA vector comprises a polynucleotide encoding an amino acid sequence of SEQ ID NO: 319 or having at least 90% sequence identity, or at least 95% sequence identity, or at least 99% sequence identity to SEQ ID NO: 319.

In some embodiments, the MVA vector comprises a polynucleotide encoding an amino acid sequence of SEQ ID NO: 321 or having at least 90% sequence identity, or at least 95% sequence identity, or at least 99% sequence identity to SEQ ID NO: 321.

In some embodiments, the MVA vector comprises a polynucleotide encoding an amino acid sequence of SEQ ID NO: 323 or having at least 90% sequence identity, or at least 95% sequence identity, or at least 99% sequence identity to SEQ ID NO: 323.

In some embodiments, the MVA vector comprises a polynucleotide encoding an amino acid sequence of SEQ ID NO: 325 or having at least 90% sequence identity, or at least 95% sequence identity, or at least 99% sequence identity to SEQ ID NO: 325.

In some embodiments, the MVA vector comprises a polynucleotide encoding an amino acid sequence of SEQ ID NO: 327 or having at least 90% sequence identity, or at least 95% sequence identity, or at least 99% sequence identity to SEQ ID NO: 327.

In some embodiments, the MVA vector comprises a polynucleotide encoding an amino acid sequence of SEQ ID NO: 329 or having at least 90% sequence identity, or at least 95% sequence identity, or at least 99% sequence identity to SEQ ID NO: 329.

In some embodiments, the MVA vector comprises a polynucleotide encoding an amino acid sequence of SEQ ID NO: 331 or having at least 90% sequence identity, or at least 95% sequence identity, or at least 99% sequence identity to SEQ ID NO: 331.

In some embodiments, the MVA vector comprises a polynucleotide encoding an amino acid sequence of SEQ ID NO: 333 or having at least 90% sequence identity, or at least 95% sequence identity, or at least 99% sequence identity to SEQ ID NO: 333.

In some embodiments, the MVA vector comprises a polynucleotide encoding an amino acid sequence of SEQ ID NO: 335 or having at least 90% sequence identity, or at least 95% sequence identity, or at least 99% sequence identity to SEQ ID NO: 335.

In some embodiments, the MVA vector comprises a polynucleotide encoding an amino acid sequence of SEQ ID NO: 337 or having at least 90% sequence identity, or at least 95% sequence identity, or at least 99% sequence identity to SEQ ID NO: 337.

In some embodiments, the MVA vector comprises a polynucleotide encoding an amino acid sequence of SEQ ID NO: 339 or having at least 90% sequence identity, or at least 95% sequence identity, or at least 99% sequence identity to SEQ ID NO: 339.

In some embodiments, the MVA vector comprises a polynucleotide encoding an amino acid sequence of SEQ ID NO: 341 or having at least 90% sequence identity, or at least 95% sequence identity, or at least 99% sequence identity to SEQ ID NO: 341.

In some embodiments, the MVA vector comprises a polynucleotide encoding an amino acid sequence of SEQ ID NO: 343 or having at least 90% sequence identity, or at least 95% sequence identity, or at least 99% sequence identity to SEQ ID NO: 343.

In some embodiments, the MVA vector comprises a polynucleotide encoding an amino acid sequence of SEQ ID NO: 345 or having at least 90% sequence identity, or at least 95% sequence identity, or at least 99% sequence identity to SEQ ID NO: 345.

In some embodiments, the MVA vector comprises a polynucleotide encoding an amino acid sequence of SEQ ID NO: 347 or having at least 90% sequence identity, or at least 95% sequence identity, or at least 99% sequence identity to SEQ ID NO: 347.

In some embodiments, the MVA vector comprises a polynucleotide encoding an amino acid sequence of SEQ ID NO: 349 or having at least 90% sequence identity, or at least 95% sequence identity, or at least 99% sequence identity to SEQ ID NO: 349.

In some embodiments, the MVA vector comprises a polynucleotide encoding an amino acid sequence of SEQ ID NO: 351 or having at least 90% sequence identity, or at least 95% sequence identity, or at least 99% sequence identity to SEQ ID NO: 351.

In some embodiments, the MVA vector comprises a polynucleotide encoding an amino acid sequence of SEQ ID NO: 353 or having at least 90% sequence identity, or at least 95% sequence identity, or at least 99% sequence identity to SEQ ID NO: 353.

In some embodiments, the MVA vector comprises a polynucleotide encoding an amino acid sequence of SEQ ID NO: 355 or having at least 90% sequence identity, or at least 95% sequence identity, or at least 99% sequence identity to SEQ ID NO: 355.

In some embodiments, the MVA vector comprises a polynucleotide encoding an amino acid sequence of SEQ ID NO: 357 or having at least 90% sequence identity, or at least 95% sequence identity, or at least 99% sequence identity to SEQ ID NO: 357.

In some embodiments, the MVA vector comprises a polynucleotide encoding an amino acid sequence of SEQ ID NO: 359 or having at least 90% sequence identity, or at least 95% sequence identity, or at least 99% sequence identity to SEQ ID NO: 359.

In some embodiments, the MVA vector comprises a polynucleotide encoding an amino acid sequence of SEQ ID NO: 361 or having at least 90% sequence identity, or at least 95% sequence identity, or at least 99% sequence identity to SEQ ID NO: 361.

In some embodiments, the MVA vector comprises a polynucleotide encoding an amino acid sequence of SEQ ID NO: 363 or having at least 90% sequence identity, or at least 95% sequence identity, or at least 99% sequence identity to SEQ ID NO: 363.

In some embodiments, the MVA vector comprises a polynucleotide encoding an amino acid sequence of SEQ ID NO: 365 or having at least 90% sequence identity, or at least 95% sequence identity, or at least 99% sequence identity to SEQ ID NO: 365.

In some embodiments, the MVA vector comprises a polynucleotide encoding an amino acid sequence of SEQ ID NO: 367 or having at least 90% sequence identity, or at least 95% sequence identity, or at least 99% sequence identity to SEQ ID NO: 367.

In some embodiments, the MVA vector comprises a polynucleotide encoding an amino acid sequence of SEQ ID NO: 369 or having at least 90% sequence identity, or at least 95% sequence identity, or at least 99% sequence identity to SEQ ID NO: 369.

In some embodiments, the MVA vector comprises a polynucleotide encoding an amino acid sequence of SEQ ID NO: 371 or having at least 90% sequence identity, or at least 95% sequence identity, or at least 99% sequence identity to SEQ ID NO: 371.

In some embodiments, the MVA vector comprises a polynucleotide encoding an amino acid sequence of SEQ ID NO: 373 or having at least 90% sequence identity, or at least 95% sequence identity, or at least 99% sequence identity to SEQ ID NO: 373.

In some embodiments, the MVA vector comprises a polynucleotide encoding an amino acid sequence of SEQ ID NO: 375 or having at least 90% sequence identity, or at least 95% sequence identity, or at least 99% sequence identity to SEQ ID NO: 375.

In some embodiments, the MVA vector comprises a polynucleotide encoding an amino acid sequence of SEQ ID NO: 377 or having at least 90% sequence identity, or at least 95% sequence identity, or at least 99% sequence identity to SEQ ID NO: 377.

In some embodiments, the MVA vector comprises a polynucleotide encoding an amino acid sequence of SEQ ID NO: 379 or having at least 90% sequence identity, or at least 95% sequence identity, or at least 99% sequence identity to SEQ ID NO: 379.

In some embodiments, the MVA vector comprises a polynucleotide encoding an amino acid sequence of SEQ ID NO: 381 or having at least 90% sequence identity, or at least 95% sequence identity, or at least 99% sequence identity to SEQ ID NO: 381.

In some embodiments, the MVA vector comprises a polynucleotide encoding an amino acid sequence of SEQ ID NO: 383 or having at least 90% sequence identity, or at least 95% sequence identity, or at least 99% sequence identity to SEQ ID NO: 383.

In some embodiments, the MVA vector comprises a polynucleotide encoding an amino acid sequence of SEQ ID NO: 385 or having at least 90% sequence identity, or at least 95% sequence identity, or at least 99% sequence identity to SEQ ID NO: 385.

In some embodiments, the MVA vector comprises a polynucleotide encoding an amino acid sequence of SEQ ID NO: 387 or having at least 90% sequence identity, or at least 95% sequence identity, or at least 99% sequence identity to SEQ ID NO: 387.

In some embodiments, the MVA vector comprises a polynucleotide encoding an amino acid sequence of SEQ ID NO: 389 or having at least 90% sequence identity, or at least 95% sequence identity, or at least 99% sequence identity to SEQ ID NO: 389.

In some embodiments, the MVA vector comprises a polynucleotide encoding an amino acid sequence of SEQ ID NO: 391 or having at least 90% sequence identity, or at least 95% sequence identity, or at least 99% sequence identity to SEQ ID NO: 391.

In some embodiments, the MVA vector comprises a polynucleotide encoding an amino acid sequence of SEQ ID NO: 393 or having at least 90% sequence identity, or at least 95% sequence identity, or at least 99% sequence identity to SEQ ID NO: 393.

In some embodiments, the MVA vector comprises a polynucleotide encoding an amino acid sequence of SEQ ID NO: 395 or having at least 90% sequence identity, or at least 95% sequence identity, or at least 99% sequence identity to SEQ ID NO: 395.

In some embodiments, the MVA vector comprises a polynucleotide encoding an amino acid sequence of SEQ ID NO: 397 or having at least 90% sequence identity, or at least 95% sequence identity, or at least 99% sequence identity to SEQ ID NO: 397.

In some embodiments, the MVA vector comprises a polynucleotide encoding an amino acid sequence of SEQ ID NO: 399 or having at least 90% sequence identity, or at least 95% sequence identity, or at least 99% sequence identity to SEQ ID NO: 399.

In some embodiments, the MVA vector comprises a polynucleotide encoding an amino acid sequence of SEQ ID NO: 401 or having at least 90% sequence identity, or at least 95% sequence identity, or at least 99% sequence identity to SEQ ID NO: 401.

In some embodiments, the MVA vector comprises a polynucleotide encoding an amino acid sequence of SEQ ID NO: 403 or having at least 90% sequence identity, or at least 95% sequence identity, or at least 99% sequence identity to SEQ ID NO: 403.

In some embodiments, the MVA vector comprises a polynucleotide encoding an amino acid sequence of SEQ ID NO: 405 or having at least 90% sequence identity, or at least 95% sequence identity, or at least 99% sequence identity to SEQ ID NO: 405.

In some embodiments, the MVA vector comprises a polynucleotide encoding an amino acid sequence of two or more of the polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and fragments thereof.

Self-Replicating RNA Molecules

In some embodiments, the viral vector is a self-replicating RMA molecule derived from an alphavirus.

Self-replicating RNA molecules may be derived from alphavirus. Alphaviruses may belong to the VEEV/EEEV group, or the SF group, or the SIN group. Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S. A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV).

The self-replicating RNA molecules can be derived from alphavirus genomes, meaning that they have some of the structural characteristics of alphavirus genomes, or similar to them. The self-replicating RNA molecules can be derived from modified alphavirus genomes.

Self-replicating RNA molecules may be derived from Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. Virulent and avirulent alphavirus strains are both suitable. In some embodiments, the alphavirus RNA replicon is of a Sindbis virus (SIN), a Semliki Forest virus (SFV), a Ross River virus (RRV), a Venezuelan equine encephalitis virus (VEEV), or an Eastern equine encephalitis virus (EEEV).

In some embodiments, the alphavirus-derived self-replicating RNA molecule is a Venezuelan equine encephalitis virus (VEEV).

The self-replicating RNA molecules can contain RNA sequences from (or amino acid sequences encoded by) a wild-type New World or Old World alphavirus genome. Any of the self-replicating RNA molecules disclosed herein can contain RNA sequences "derived from" or "based on" wild type alphavirus genome sequences, meaning that they have at least 60% or at least 65% or at least 68% or at least 70% or at least 80% or at least 85% or at least 90% or at least 95% or at least 97% or at least 98% or at least 99% or 100% or 80-99% or 90-100% or 95-99% or 95-100% or 97-99% or 98-99% sequence identity with an RNA sequence (which can be a corresponding RNA sequence) from a wild type RNA alphavirus genome, which can be a New World or Old World alphavirus genome.

Self-replicating RNA molecules contain all of the genetic information required for directing their own amplification or self-replication within a permissive cell. To direct their own replication, self-replicating RNA molecules encode polymerase, replicase, or other proteins which may interact with viral or host cell-derived proteins, nucleic acids or ribonucleoproteins to catalyze the RNA amplification process; and contain cis-acting RNA sequences required for replication and transcription of the replicon-encoded RNA. Thus, RNA replication leads to the production of multiple daughter RNAs. These daughter RNAs, as well as collinear subgenomic transcripts, can be translated to provide in situ expression of a gene of interest, or can be transcribed to provide further transcripts with the same sense as the delivered RNA which are translated to provide in situ expression of the gene of interest. The overall results of this sequence of transcriptions is a huge amplification in the number of the introduced replicon RNAs and so the encoded gene of interest becomes a major polypeptide product of the cells.

There are two open reading frames (ORF's) in the genome of alphaviruses, non-structural (ns) and structural genes. The ns ORF encodes proteins (nsP1-nsP4) necessary for transcription and replication of viral RNA and are produced as a polyprotein and are the virus replication machinery. The structural ORF encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion. The four ns protein genes are encoded by genes in the 5' two-thirds of the genome, while the three structural proteins are translated from a subgenomic mRNA colinear with the 3' one-third of the genome.

Self-replicating RNA molecules can be used as basis of introducing foreign sequences to host cells by replacing viral sequences encoding structural genes or inserting the foreign sequences 5' or 3' of the sequences encoding the structural genes. They can be engineered to replace the viral structural genes downstream of the replicase, which are under control of a subgenomic promoter, by genes of interest (GOI), e.g. any of the polynucleotides encoding for any of the polypeptides of the disclosure. Upon transfection, the replicase which is translated immediately, interacts with the 5' and 3' termini of the genomic RNA, and synthesizes complementary genomic RNA copies. Those act as templates for the synthesis of novel positive-stranded, capped, and polyadenylated genomic copies, and subgenomic transcripts. Amplification eventually leads to very high RNA copy numbers of up to $2\times10^5$ copies per cell. The result is a uniform and/or enhanced expression of a GOI (e.g. a polynucleotide encoding for one or more of the polypeptides of the disclosure) that can affect vaccine efficacy or therapeutic impact of a treatment. Vaccines based on self-replicating RNA molecules can therefore be dosed at very low levels due to the very high copies of RNA generated compared to conventional viral vector.

The self-replicating RNA molecules of the disclosure comprising the RNA encoding for one or more of the ovarian cancer neoantigens polypeptides of the disclosure may be utilized as therapeutics by delivering them to a subject having ovarian cancer or at risk of ovarian cancer using various technologies, including viral vectors as described herein or other delivery technologies as also described herein.

The ovarian cancer neoantigen polynucleotides of the disclosure can be expressed under the control of a subgenomic promoter. In certain embodiments, instead of the native subgenomic promoter, the subgenomic RNA can be placed under control of internal ribosome entry site (IRES) derived from encephalomyocarditis viruses (EMCV), Bovine Viral Diarrhea Viruses (BVDV), polioviruses, Foot-and-mouth disease viruses (FMD), enterovirus 71, or hepatitis C viruses. Subgenomic promoters range from 24 nucleotide (Sindbis virus) to over 100 nucleotides (Beet necrotic yellow vein virus) and are usually found upstream of the transcription start.

The disclosure provides a self-replicating RNA molecule containing all of the genetic information required for directing its own amplification or self-replication within a permissive cell.

The disclosure also provides a self-replicating RNA molecule that can be used as the basis of introducing foreign sequences to host cells (e.g. the ovarian neoantigen polypeptides of the disclosure) by replacing viral sequences encoding structural genes.

Provided herein is a viral vector comprising any of the polynucleotides of the disclosure, wherein the vector is a self-replicating RNA molecule.

In some embodiments, the self-replicating RNA molecule comprises an RNA sequence encoding an amino acid sequence of SEQ ID NO: 1 or having at least 90% sequence identity, or at least 95% sequence identity, or at least 99% sequence identity to SEQ ID NO: 1.

In some embodiments, the self-replicating RNA molecule comprises a polynucleotide encoding an amino acid sequence of SEQ ID NO: 3 or having at least 90% sequence identity, or at least 95% sequence identity, or at least 99% sequence identity to SEQ ID NO: 3.

In some embodiments, the self-replicating RNA molecule comprises a polynucleotide encoding an amino acid sequence of SEQ ID NO: 5 or having at least 90% sequence identity, or at least 95% sequence identity, or at least 99% sequence identity to SEQ ID NO: 5.

In some embodiments, the self-replicating RNA molecule comprises a polynucleotide encoding an amino acid sequence of SEQ ID NO: 7 or having at least 90% sequence identity, or at least 95% sequence identity, or at least 99% sequence identity to SEQ ID NO: 7.

In some embodiments, the self-replicating RNA molecule comprises a polynucleotide encoding an amino acid sequence of SEQ ID NO: 9 or having at least 90% sequence identity, or at least 95% sequence identity, or at least 99% sequence identity to SEQ ID NO: 9.

In some embodiments, the self-replicating RNA molecule comprises a polynucleotide encoding an amino acid sequence of SEQ ID NO: 11 or having at least 90% sequence identity, or at least 95% sequence identity, or at least 99% sequence identity to SEQ ID NO: 11.

In some embodiments, the self-replicating RNA molecule comprises a polynucleotide encoding an amino acid sequence of SEQ ID NO: 13 or having at least 90% sequence identity, or at least 95% sequence identity, or at least 99% sequence identity to SEQ ID NO: 13.

In some embodiments, the self-replicating RNA molecule comprises a polynucleotide encoding an amino acid sequence of SEQ ID NO: 15 or having at least 90% sequence identity, or at least 95% sequence identity, or at least 99% sequence identity to SEQ ID NO: 15.

In some embodiments, the self-replicating RNA molecule comprises a polynucleotide encoding an amino acid sequence of SEQ ID NO: 17 or having at least 90% sequence identity, or at least 95% sequence identity, or at least 99% sequence identity to SEQ ID NO: 17.

In some embodiments, the self-replicating RNA molecule comprises a polynucleotide encoding an amino acid sequence of SEQ ID NO: 19 or having at least 90% sequence identity, or at least 95% sequence identity, or at least 99% sequence identity to SEQ ID NO: 19.

In some embodiments, the self-replicating RNA molecule comprises a polynucleotide encoding an amino acid sequence of SEQ ID NO: 21 or having at least 90% sequence identity, or at least 95% sequence identity, or at least 99% sequence identity to SEQ ID NO: 21.

In some embodiments, the self-replicating RNA molecule comprises a polynucleotide encoding an amino acid sequence of SEQ ID NO: 23 or having at least 90% sequence identity, or at least 95% sequence identity, or at least 99% sequence identity to SEQ ID NO: 23.

In some embodiments, the self-replicating RNA molecule comprises a polynucleotide encoding an amino acid sequence of SEQ ID NO: 25 or having at least 90% sequence identity, or at least 95% sequence identity, or at least 99% sequence identity to SEQ ID NO: 25.

In some embodiments, the self-replicating RNA molecule comprises a polynucleotide encoding an amino acid sequence of SEQ ID NO: 27 or having at least 90% sequence identity, or at least 95% sequence identity, or at least 99% sequence identity to SEQ ID NO: 27.

In some embodiments, the self-replicating RNA molecule comprises a polynucleotide encoding an amino acid sequence of SEQ ID NO: 29 or having at least 90% sequence identity, or at least 95% sequence identity, or at least 99% sequence identity to SEQ ID NO: 29.

In some embodiments, the self-replicating RNA molecule comprises a polynucleotide encoding an amino acid sequence of SEQ ID NO: 31 or having at least 90% sequence identity, or at least 95% sequence identity, or at least 99% sequence identity to SEQ ID NO: 31.

In some embodiments, the self-replicating RNA molecule comprises a polynucleotide encoding an amino acid sequence of SEQ ID NO: 33 or having at least 90% sequence identity, or at least 95% sequence identity, or at least 99% sequence identity to SEQ ID NO: 33.

In some embodiments, the self-replicating RNA molecule comprises a polynucleotide encoding an amino acid sequence of SEQ ID NO: 35 or having at least 90% sequence identity, or at least 95% sequence identity, or at least 99% sequence identity to SEQ ID NO: 35.

In some embodiments, the self-replicating RNA molecule comprises a polynucleotide encoding an amino acid sequence of SEQ ID NO: 37 or having at least 90% sequence identity, or at least 95% sequence identity, or at least 99% sequence identity to SEQ ID NO: 37.

In some embodiments, the self-replicating RNA molecule comprises a polynucleotide encoding an amino acid sequence of SEQ ID NO: 39 or having at least 90% sequence identity, or at least 95% sequence identity, or at least 99% sequence identity to SEQ ID NO: 39.

In some embodiments, the self-replicating RNA molecule comprises a polynucleotide encoding an amino acid sequence of SEQ ID NO: 41 or having at least 90% sequence identity, or at least 95% sequence identity, or at least 99% sequence identity to SEQ ID NO: 41.

In some embodiments, the self-replicating RNA molecule comprises a polynucleotide encoding an amino acid sequence of SEQ ID NO: 43 or having at least 90% sequence identity, or at least 95% sequence identity, or at least 99% sequence identity to SEQ ID NO: 43.

In some embodiments, the self-replicating RNA molecule comprises a polynucleotide encoding an amino acid sequence of SEQ ID NO: 45 or having at least 90% sequence identity, or at least 95% sequence identity, or at least 99% sequence identity to SEQ ID NO: 45.

In some embodiments, the self-replicating RNA molecule comprises a polynucleotide encoding an amino acid sequence of SEQ ID NO: 47 or having at least 90% sequence identity, or at least 95% sequence identity, or at least 99% sequence identity to SEQ ID NO: 47.

In some embodiments, the self-replicating RNA molecule comprises a polynucleotide encoding an amino acid sequence of SEQ ID NO: 49 or having at least 90% sequence identity, or at least 95% sequence identity, or at least 99% sequence identity to SEQ ID NO: 49.

In some embodiments, the self-replicating RNA molecule comprises a polynucleotide encoding an amino acid sequence of SEQ ID NO: 51 or having at least 90% sequence identity, or at least 95% sequence identity, or at least 99% sequence identity to SEQ ID NO: 51.

In some embodiments, the self-replicating RNA molecule comprises a polynucleotide encoding an amino acid sequence of SEQ ID NO: 53 or having at least 90% sequence identity, or at least 95% sequence identity, or at least 99% sequence identity to SEQ ID NO: 53.

In some embodiments, the self-replicating RNA molecule comprises a polynucleotide encoding an amino acid sequence of SEQ ID NO: 55 or having at least 90% sequence identity, or at least 95% sequence identity, or at least 99% sequence identity to SEQ ID NO: 55.

In some embodiments, the self-replicating RNA molecule comprises a polynucleotide encoding an amino acid sequence of SEQ ID NO: 57 or having at least 90% sequence identity, or at least 95% sequence identity, or at least 99% sequence identity to SEQ ID NO: 57.

In some embodiments, the self-replicating RNA molecule comprises a polynucleotide encoding an amino acid sequence of SEQ ID NO: 59 or having at least 90% sequence identity, or at least 95% sequence identity, or at least 99% sequence identity to SEQ ID NO: 59.

In some embodiments, the self-replicating RNA molecule comprises a polynucleotide encoding an amino acid sequence of SEQ ID NO: 61 or having at least 90% sequence identity, or at least 95% sequence identity, or at least 99% sequence identity to SEQ ID NO: 61.

In some embodiments, the self-replicating RNA molecule comprises a polynucleotide encoding an amino acid sequence of SEQ ID NO: 63 or having at least 90% sequence identity, or at least 95% sequence identity, or at least 99% sequence identity to SEQ ID NO: 63.

In some embodiments, the self-replicating RNA molecule comprises a polynucleotide encoding an amino acid sequence of SEQ ID NO: 65 or having at least 90% sequence identity, or at least 95% sequence identity, or at least 99% sequence identity to SEQ ID NO: 65.

In some embodiments, the self-replicating RNA molecule comprises a polynucleotide encoding an amino acid sequence of SEQ ID NO: 67 or having at least 90% sequence identity, or at least 95% sequence identity, or at least 99% sequence identity to SEQ ID NO: 67.

In some embodiments, the self-replicating RNA molecule comprises a polynucleotide encoding an amino acid sequence of SEQ ID NO: 69 or having at least 90% sequence identity, or at least 95% sequence identity, or at least 99% sequence identity to SEQ ID NO: 69.

In some embodiments, the self-replicating RNA molecule comprises a polynucleotide encoding an amino acid sequence of SEQ ID NO: 71 or having at least 90% sequence identity, or at least 95% sequence identity, or at least 99% sequence identity to SEQ ID NO: 71.

In some embodiments, the self-replicating RNA molecule comprises a polynucleotide encoding an amino acid sequence of SEQ ID NO: 73 or having at least 90% sequence identity, or at least 95% sequence identity, or at least 99% sequence identity to SEQ ID NO: 73.

In some embodiments, the self-replicating RNA molecule comprises a polynucleotide encoding an amino acid sequence of SEQ ID NO: 75 or having at least 90% sequence identity, or at least 95% sequence identity, or at least 99% sequence identity to SEQ ID NO: 75.

In some embodiments, the self-replicating RNA molecule comprises a polynucleotide encoding an amino acid sequence of SEQ ID NO: 77 or having at least 90% sequence identity, or at least 95% sequence identity, or at least 99% sequence identity to SEQ ID NO: 77.

In some embodiments, the self-replicating RNA molecule comprises a polynucleotide encoding an amino acid sequence of SEQ ID NO: 79 or having at least 90% sequence identity, or at least 95% sequence identity, or at least 99% sequence identity to SEQ ID NO: 79.

In some embodiments, the self-replicating RNA molecule comprises a polynucleotide encoding an amino acid sequence of SEQ ID NO: 81 or having at least 90% sequence identity, or at least 95% sequence identity, or at least 99% sequence identity to SEQ ID NO: 81.

In some embodiments, the self-replicating RNA molecule comprises a polynucleotide encoding an amino acid sequence of SEQ ID NO: 83 or having at least 90% sequence identity, or at least 95% sequence identity, or at least 99% sequence identity to SEQ ID NO: 83.

In some embodiments, the self-replicating RNA molecule comprises a polynucleotide encoding an amino acid sequence of SEQ ID NO: 85 or having at least 90% sequence identity, or at least 95% sequence identity, or at least 99% sequence identity to SEQ ID NO: 85.

In some embodiments, the self-replicating RNA molecule comprises a polynucleotide encoding an amino acid sequence of SEQ ID NO: 87 or having at least 90% sequence identity, or at least 95% sequence identity, or at least 99% sequence identity to SEQ ID NO: 87.

In some embodiments, the self-replicating RNA molecule comprises a polynucleotide encoding an amino acid sequence of SEQ ID NO: 89 or having at least 90% sequence identity, or at least 95% sequence identity, or at least 99% sequence identity to SEQ ID NO: 89.

In some embodiments, the self-replicating RNA molecule comprises a polynucleotide encoding an amino acid sequence of SEQ ID NO: 91 or having at least 90% sequence identity, or at least 95% sequence identity, or at least 99% sequence identity to SEQ ID NO: 91.

In some embodiments, the self-replicating RNA molecule comprises a polynucleotide encoding an amino acid sequence of SEQ ID NO: 93 or having at least 90% sequence identity, or at least 95% sequence identity, or at least 99% sequence identity to SEQ ID NO: 93.

In some embodiments, the self-replicating RNA molecule comprises a polynucleotide encoding an amino acid sequence of SEQ ID NO: 95 or having at least 90% sequence identity, or at least 95% sequence identity, or at least 99% sequence identity to SEQ ID NO: 95.

In some embodiments, the self-replicating RNA molecule comprises a polynucleotide encoding an amino acid sequence of SEQ ID NO: 97 or having at least 90% sequence identity, or at least 95% sequence identity, or at least 99% sequence identity to SEQ ID NO: 97.

In some embodiments, the self-replicating RNA molecule comprises a polynucleotide encoding an amino acid sequence of SEQ ID NO: 99 or having at least 90% sequence identity, or at least 95% sequence identity, or at least 99% sequence identity to SEQ ID NO: 99.

In some embodiments, the self-replicating RNA molecule comprises a polynucleotide encoding an amino acid sequence of SEQ ID NO: 101 or having at least 90% sequence identity, or at least 95% sequence identity, or at least 99% sequence identity to SEQ ID NO: 101.

In some embodiments, the self-replicating RNA molecule comprises a polynucleotide encoding an amino acid sequence of SEQ ID NO: 103 or having at least 90% sequence identity, or at least 95% sequence identity, or at least 99% sequence identity to SEQ ID NO: 103.

In some embodiments, the self-replicating RNA molecule comprises a polynucleotide encoding an amino acid sequence of SEQ ID NO: 105 or having at least 90% sequence identity, or at least 95% sequence identity, or at least 99% sequence identity to SEQ ID NO: 105.

In some embodiments, the self-replicating RNA molecule comprises a polynucleotide encoding an amino acid sequence of SEQ ID NO: 107 or having at least 90% sequence identity, or at least 95% sequence identity, or at least 99% sequence identity to SEQ ID NO: 107.

In some embodiments, the self-replicating RNA molecule comprises a polynucleotide encoding an amino acid sequence of SEQ ID NO: 109 or having at least 90% sequence identity, or at least 95% sequence identity, or at least 99% sequence identity to SEQ ID NO: 109.

In some embodiments, the self-replicating RNA molecule comprises a polynucleotide encoding an amino acid sequence of SEQ ID NO: 111 or having at least 90% sequence identity, or at least 95% sequence identity, or at least 99% sequence identity to SEQ ID NO: 111.

In some embodiments, the self-replicating RNA molecule comprises a polynucleotide encoding an amino acid sequence of SEQ ID NO: 113 or having at least 90% sequence identity, or at least 95% sequence identity, or at least 99% sequence identity to SEQ ID NO: 113.

In some embodiments, the self-replicating RNA molecule comprises a polynucleotide encoding an amino acid sequence of SEQ ID NO: 115 or having at least 90% sequence identity, or at least 95% sequence identity, or at least 99% sequence identity to SEQ ID NO: 115.

In some embodiments, the self-replicating RNA molecule comprises a polynucleotide encoding an amino acid sequence of SEQ ID NO: 117 or having at least 90% sequence identity, or at least 95% sequence identity, or at least 99% sequence identity to SEQ ID NO: 117.

In some embodiments, the self-replicating RNA molecule comprises a polynucleotide encoding an amino acid sequence of SEQ ID NO: 119 or having at least 90% sequence identity, or at least 95% sequence identity, or at least 99% sequence identity to SEQ ID NO: 119.

In some embodiments, the self-replicating RNA molecule comprises a polynucleotide encoding an amino acid sequence of SEQ ID NO: 121 or having at least 90% sequence identity, or at least 95% sequence identity, or at least 99% sequence identity to SEQ ID NO: 121.

In some embodiments, the self-replicating RNA molecule comprises a polynucleotide encoding an amino acid sequence of SEQ ID NO: 123 or having at least 90% sequence identity, or at least 95% sequence identity, or at least 99% sequence identity to SEQ ID NO: 123.

In some embodiments, the self-replicating RNA molecule comprises a polynucleotide encoding an amino acid sequence of SEQ ID NO: 125 or having at least 90% sequence identity, or at least 95% sequence identity, or at least 99% sequence identity to SEQ ID NO: 125.

In some embodiments, the self-replicating RNA molecule comprises a polynucleotide encoding an amino acid sequence of SEQ ID NO: 127 or having at least 90% sequence identity, or at least 95% sequence identity, or at least 99% sequence identity to SEQ ID NO: 127.

In some embodiments, the self-replicating RNA molecule comprises a polynucleotide encoding an amino acid sequence of SEQ ID NO: 129 or having at least 90% sequence identity, or at least 95% sequence identity, or at least 99% sequence identity to SEQ ID NO: 129.

In some embodiments, the self-replicating RNA molecule comprises a polynucleotide encoding an amino acid sequence of SEQ ID NO: 131 or having at least 90% sequence identity, or at least 95% sequence identity, or at least 99% sequence identity to SEQ ID NO: 131.

In some embodiments, the self-replicating RNA molecule comprises a polynucleotide encoding an amino acid sequence of SEQ ID NO: 133 or having at least 90% sequence identity, or at least 95% sequence identity, or at least 99% sequence identity to SEQ ID NO: 133.

In some embodiments, the self-replicating RNA molecule comprises a polynucleotide encoding an amino acid sequence of SEQ ID NO: 135 or having at least 90% sequence identity, or at least 95% sequence identity, or at least 99% sequence identity to SEQ ID NO: 135.

In some embodiments, the self-replicating RNA molecule comprises a polynucleotide encoding an amino acid sequence of SEQ ID NO: 137 or having at least 90% sequence identity, or at least 95% sequence identity, or at least 99% sequence identity to SEQ ID NO: 137.

In some embodiments, the self-replicating RNA molecule comprises a polynucleotide encoding an amino acid sequence of SEQ ID NO: 139 or having at least 90% sequence identity, or at least 95% sequence identity, or at least 99% sequence identity to SEQ ID NO: 139.

In some embodiments, the self-replicating RNA molecule comprises a polynucleotide encoding an amino acid sequence of SEQ ID NO: 141 or having at least 90% sequence identity, or at least 95% sequence identity, or at least 99% sequence identity to SEQ ID NO: 141.

In some embodiments, the self-replicating RNA molecule comprises a polynucleotide encoding an amino acid sequence of SEQ ID NO: 143 or having at least 90% sequence identity, or at least 95% sequence identity, or at least 99% sequence identity to SEQ ID NO: 143.

In some embodiments, the self-replicating RNA molecule comprises a polynucleotide encoding an amino acid sequence of SEQ ID NO: 145 or having at least 90% sequence identity, or at least 95% sequence identity, or at least 99% sequence identity to SEQ ID NO: 145.

In some embodiments, the self-replicating RNA molecule comprises a polynucleotide encoding an amino acid sequence of SEQ ID NO: 147 or having at least 90% sequence identity, or at least 95% sequence identity, or at least 99% sequence identity to SEQ ID NO: 147.

In some embodiments, the self-replicating RNA molecule comprises a polynucleotide encoding an amino acid sequence of SEQ ID NO: 149 or having at least 90% sequence identity, or at least 95% sequence identity, or at least 99% sequence identity to SEQ ID NO: 149.

In some embodiments, the self-replicating RNA molecule comprises a polynucleotide encoding an amino acid sequence of SEQ ID NO: 151 or having at least 90% sequence identity, or at least 95% sequence identity, or at least 99% sequence identity to SEQ ID NO: 151.

In some embodiments, the self-replicating RNA molecule comprises a polynucleotide encoding an amino acid sequence of SEQ ID NO: 153 or having at least 90% sequence identity, or at least 95% sequence identity, or at least 99% sequence identity to SEQ ID NO: 153.

In some embodiments, the self-replicating RNA molecule comprises a polynucleotide encoding an amino acid sequence of SEQ ID NO: 155 or having at least 90% sequence identity, or at least 95% sequence identity, or at least 99% sequence identity to SEQ ID NO: 155.

In some embodiments, the self-replicating RNA molecule comprises a polynucleotide encoding an amino acid sequence of SEQ ID NO: 157 or having at least 90% sequence identity, or at least 95% sequence identity, or at least 99% sequence identity to SEQ ID NO: 157.

In some embodiments, the self-replicating RNA molecule comprises a polynucleotide encoding an amino acid sequence of SEQ ID NO: 159 or having at least 90% sequence identity, or at least 95% sequence identity, or at least 99% sequence identity to SEQ ID NO: 159.

In some embodiments, the self-replicating RNA molecule comprises a polynucleotide encoding an amino acid sequence of SEQ ID NO: 161 or having at least 90% sequence identity, or at least 95% sequence identity, or at least 99% sequence identity to SEQ ID NO: 161.

In some embodiments, the self-replicating RNA molecule comprises a polynucleotide encoding an amino acid sequence of SEQ ID NO: 163 or having at least 90% sequence identity, or at least 95% sequence identity, or at least 99% sequence identity to SEQ ID NO: 163.

In some embodiments, the self-replicating RNA molecule comprises a polynucleotide encoding an amino acid sequence of SEQ ID NO: 165 or having at least 90% sequence identity, or at least 95% sequence identity, or at least 99% sequence identity to SEQ ID NO: 165.

In some embodiments, the self-replicating RNA molecule comprises a polynucleotide encoding an amino acid sequence of SEQ ID NO: 167 or having at least 90% sequence identity, or at least 95% sequence identity, or at least 99% sequence identity to SEQ ID NO: 167.

In some embodiments, the self-replicating RNA molecule comprises a polynucleotide encoding an amino acid sequence of SEQ ID NO: 169 or having at least 90% sequence identity, or at least 95% sequence identity, or at least 99% sequence identity to SEQ ID NO: 169.

In some embodiments, the self-replicating RNA molecule comprises a polynucleotide encoding an amino acid sequence of SEQ ID NO: 171 or having at least 90% sequence identity, or at least 95% sequence identity, or at least 99% sequence identity to SEQ ID NO: 171.

In some embodiments, the self-replicating RNA molecule comprises a polynucleotide encoding an amino acid sequence of SEQ ID NO: 173 or having at least 90% sequence identity, or at least 95% sequence identity, or at least 99% sequence identity to SEQ ID NO: 173.

In some embodiments, the self-replicating RNA molecule comprises a polynucleotide encoding an amino acid sequence of SEQ ID NO: 175 or having at least 90% sequence identity, or at least 95% sequence identity, or at least 99% sequence identity to SEQ ID NO: 175.

In some embodiments, the self-replicating RNA molecule comprises a polynucleotide encoding an amino acid sequence of SEQ ID NO: 177 or having at least 90% sequence identity, or at least 95% sequence identity, or at least 99% sequence identity to SEQ ID NO: 177.

In some embodiments, the self-replicating RNA molecule comprises a polynucleotide encoding an amino acid sequence of SEQ ID NO: 179 or having at least 90% sequence identity, or at least 95% sequence identity, or at least 99% sequence identity to SEQ ID NO: 179.

In some embodiments, the self-replicating RNA molecule comprises a polynucleotide encoding an amino acid sequence of SEQ ID NO: 181 or having at least 90% sequence identity, or at least 95% sequence identity, or at least 99% sequence identity to SEQ ID NO: 181.

In some embodiments, the self-replicating RNA molecule comprises a polynucleotide encoding an amino acid sequence of SEQ ID NO: 183 or having at least 90% sequence identity, or at least 95% sequence identity, or at least 99% sequence identity to SEQ ID NO: 183.

In some embodiments, the self-replicating RNA molecule comprises a polynucleotide encoding an amino acid sequence of SEQ ID NO: 185 or having at least 90% sequence identity, or at least 95% sequence identity, or at least 99% sequence identity to SEQ ID NO: 185.

In some embodiments, the self-replicating RNA molecule comprises a polynucleotide encoding an amino acid sequence of SEQ ID NO: 187 or having at least 90% sequence identity, or at least 95% sequence identity, or at least 99% sequence identity to SEQ ID NO: 187.

In some embodiments, the self-replicating RNA molecule comprises a polynucleotide encoding an amino acid sequence of SEQ ID NO: 189 or having at least 90% sequence identity, or at least 95% sequence identity, or at least 99% sequence identity to SEQ ID NO: 189.

In some embodiments, the self-replicating RNA molecule comprises a polynucleotide encoding an amino acid sequence of SEQ ID NO: 191 or having at least 90% sequence identity, or at least 95% sequence identity, or at least 99% sequence identity to SEQ ID NO: 191.

In some embodiments, the self-replicating RNA molecule comprises a polynucleotide encoding an amino acid sequence of SEQ ID NO: 193 or having at least 90% sequence identity, or at least 95% sequence identity, or at least 99% sequence identity to SEQ ID NO: 193.

In some embodiments, the self-replicating RNA molecule comprises a polynucleotide encoding an amino acid sequence of SEQ ID NO: 195 or having at least 90% sequence identity, or at least 95% sequence identity, or at least 99% sequence identity to SEQ ID NO: 195.

In some embodiments, the self-replicating RNA molecule comprises a polynucleotide encoding an amino acid sequence of SEQ ID NO: 197 or having at least 90% sequence identity, or at least 95% sequence identity, or at least 99% sequence identity to SEQ ID NO: 197.

In some embodiments, the self-replicating RNA molecule comprises a polynucleotide encoding an amino acid sequence of SEQ ID NO: 199 or having at least 90% sequence identity, or at least 95% sequence identity, or at least 99% sequence identity to SEQ ID NO: 199.

In some embodiments, the self-replicating RNA molecule comprises a polynucleotide encoding an amino acid sequence of SEQ ID NO: 201 or having at least 90% sequence identity, or at least 95% sequence identity, or at least 99% sequence identity to SEQ ID NO: 201.

In some embodiments, the self-replicating RNA molecule comprises a polynucleotide encoding an amino acid sequence of SEQ ID NO: 203 or having at least 90% sequence identity, or at least 95% sequence identity, or at least 99% sequence identity to SEQ ID NO: 203.

In some embodiments, the self-replicating RNA molecule comprises a polynucleotide encoding an amino acid sequence of SEQ ID NO: 205 or having at least 90% sequence identity, or at least 95% sequence identity, or at least 99% sequence identity to SEQ ID NO: 205.

In some embodiments, the self-replicating RNA molecule comprises a polynucleotide encoding an amino acid sequence of SEQ ID NO: 207 or having at least 90% sequence identity, or at least 95% sequence identity, or at least 99% sequence identity to SEQ ID NO: 207.

In some embodiments, the self-replicating RNA molecule comprises a polynucleotide encoding an amino acid sequence of SEQ ID NO: 209 or having at least 90% sequence identity, or at least 95% sequence identity, or at least 99% sequence identity to SEQ ID NO: 209.

In some embodiments, the self-replicating RNA molecule comprises a polynucleotide encoding an amino acid sequence of SEQ ID NO: 211 or having at least 90% sequence identity, or at least 95% sequence identity, or at least 99% sequence identity to SEQ ID NO: 211.

In some embodiments, the self-replicating RNA molecule comprises a polynucleotide encoding an amino acid sequence of SEQ ID NO: 213 or having at least 90% sequence identity, or at least 95% sequence identity, or at least 99% sequence identity to SEQ ID NO: 213.

In some embodiments, the self-replicating RNA molecule comprises a polynucleotide encoding an amino acid sequence of SEQ ID NO: 215 or having at least 90% sequence identity, or at least 95% sequence identity, or at least 99% sequence identity to SEQ ID NO: 215.

In some embodiments, the self-replicating RNA molecule comprises a polynucleotide encoding an amino acid sequence of SEQ ID NO: 217 or having at least 90% sequence identity, or at least 95% sequence identity, or at least 99% sequence identity to SEQ ID NO: 217.

In some embodiments, the self-replicating RNA molecule comprises a polynucleotide encoding an amino acid sequence of SEQ ID NO: 219 or having at least 90% sequence identity, or at least 95% sequence identity, or at least 99% sequence identity to SEQ ID NO: 219.

In some embodiments, the self-replicating RNA molecule comprises a polynucleotide encoding an amino acid sequence of SEQ ID NO: 221 or having at least 90% sequence identity, or at least 95% sequence identity, or at least 99% sequence identity to SEQ ID NO: 221.

In some embodiments, the self-replicating RNA molecule comprises a polynucleotide encoding an amino acid sequence of SEQ ID NO: 223 or having at least 90% sequence identity, or at least 95% sequence identity, or at least 99% sequence identity to SEQ ID NO: 223.

In some embodiments, the self-replicating RNA molecule comprises a polynucleotide encoding an amino acid sequence of SEQ ID NO: 225 or having at least 90% sequence identity, or at least 95% sequence identity, or at least 99% sequence identity to SEQ ID NO: 225.

In some embodiments, the self-replicating RNA molecule comprises a polynucleotide encoding an amino acid sequence of SEQ ID NO: 227 or having at least 90% sequence identity, or at least 95% sequence identity, or at least 99% sequence identity to SEQ ID NO: 227.

In some embodiments, the self-replicating RNA molecule comprises a polynucleotide encoding an amino acid sequence of SEQ ID NO: 229 or having at least 90% sequence identity, or at least 95% sequence identity, or at least 99% sequence identity to SEQ ID NO: 229.

In some embodiments, the self-replicating RNA molecule comprises a polynucleotide encoding an amino acid sequence of SEQ ID NO: 231 or having at least 90% sequence identity, or at least 95% sequence identity, or at least 99% sequence identity to SEQ ID NO: 231.

In some embodiments, the self-replicating RNA molecule comprises a polynucleotide encoding an amino acid sequence of SEQ ID NO: 233 or having at least 90% sequence identity, or at least 95% sequence identity, or at least 99% sequence identity to SEQ ID NO: 233.

In some embodiments, the self-replicating RNA molecule comprises a polynucleotide encoding an amino acid sequence of SEQ ID NO: 235 or having at least 90% sequence identity, or at least 95% sequence identity, or at least 99% sequence identity to SEQ ID NO: 235.

In some embodiments, the self-replicating RNA molecule comprises a polynucleotide encoding an amino acid sequence of SEQ ID NO: 237 or having at least 90% sequence identity, or at least 95% sequence identity, or at least 99% sequence identity to SEQ ID NO: 237.

In some embodiments, the self-replicating RNA molecule comprises a polynucleotide encoding an amino acid sequence of SEQ ID NO: 239 or having at least 90% sequence identity, or at least 95% sequence identity, or at least 99% sequence identity to SEQ ID NO: 239.

In some embodiments, the self-replicating RNA molecule comprises a polynucleotide encoding an amino acid sequence of SEQ ID NO: 241 or having at least 90% sequence identity, or at least 95% sequence identity, or at least 99% sequence identity to SEQ ID NO: 241.

In some embodiments, the self-replicating RNA molecule comprises a polynucleotide encoding an amino acid sequence of SEQ ID NO: 243 or having at least 90% sequence identity, or at least 95% sequence identity, or at least 99% sequence identity to SEQ ID NO: 243.

In some embodiments, the self-replicating RNA molecule comprises a polynucleotide encoding an amino acid sequence of SEQ ID NO: 245 or having at least 90% sequence identity, or at least 95% sequence identity, or at least 99% sequence identity to SEQ ID NO: 245.

In some embodiments, the self-replicating RNA molecule comprises a polynucleotide encoding an amino acid sequence of SEQ ID NO: 247 or having at least 90% sequence identity, or at least 95% sequence identity, or at least 99% sequence identity to SEQ ID NO: 247.

In some embodiments, the self-replicating RNA molecule comprises a polynucleotide encoding an amino acid sequence of SEQ ID NO: 249 or having at least 90% sequence identity, or at least 95% sequence identity, or at least 99% sequence identity to SEQ ID NO: 249.

In some embodiments, the self-replicating RNA molecule comprises a polynucleotide encoding an amino acid sequence of SEQ ID NO: 251 or having at least 90% sequence identity, or at least 95% sequence identity, or at least 99% sequence identity to SEQ ID NO: 251.

In some embodiments, the self-replicating RNA molecule comprises a polynucleotide encoding an amino acid sequence of SEQ ID NO: 253 or having at least 90% sequence identity, or at least 95% sequence identity, or at least 99% sequence identity to SEQ ID NO: 253.

In some embodiments, the self-replicating RNA molecule comprises a polynucleotide encoding an amino acid sequence of SEQ ID NO: 255 or having at least 90% sequence identity, or at least 95% sequence identity, or at least 99% sequence identity to SEQ ID NO: 255.

In some embodiments, the self-replicating RNA molecule comprises a polynucleotide encoding an amino acid sequence of SEQ ID NO: 257 or having at least 90% sequence identity, or at least 95% sequence identity, or at least 99% sequence identity to SEQ ID NO: 257.

In some embodiments, the self-replicating RNA molecule comprises a polynucleotide encoding an amino acid sequence of SEQ ID NO: 259 or having at least 90% sequence identity, or at least 95% sequence identity, or at least 99% sequence identity to SEQ ID NO: 259.

In some embodiments, the self-replicating RNA molecule comprises a polynucleotide encoding an amino acid sequence of SEQ ID NO: 261 or having at least 90% sequence identity, or at least 95% sequence identity, or at least 99% sequence identity to SEQ ID NO: 261.

In some embodiments, the self-replicating RNA molecule comprises a polynucleotide encoding an amino acid sequence of SEQ ID NO: 263 or having at least 90% sequence identity, or at least 95% sequence identity, or at least 99% sequence identity to SEQ ID NO: 263.

In some embodiments, the self-replicating RNA molecule comprises a polynucleotide encoding an amino acid sequence of SEQ ID NO: 265 or having at least 90% sequence identity, or at least 95% sequence identity, or at least 99% sequence identity to SEQ ID NO: 265.

In some embodiments, the self-replicating RNA molecule comprises a polynucleotide encoding an amino acid sequence of SEQ ID NO: 267 or having at least 90% sequence identity, or at least 95% sequence identity, or at least 99% sequence identity to SEQ ID NO: 267.

In some embodiments, the self-replicating RNA molecule comprises a polynucleotide encoding an amino acid sequence of SEQ ID NO: 269 or having at least 90% sequence identity, or at least 95% sequence identity, or at least 99% sequence identity to SEQ ID NO: 269.

In some embodiments, the self-replicating RNA molecule comprises a polynucleotide encoding an amino acid sequence of SEQ ID NO: 271 or having at least 90% sequence identity, or at least 95% sequence identity, or at least 99% sequence identity to SEQ ID NO: 271.

In some embodiments, the self-replicating RNA molecule comprises a polynucleotide encoding an amino acid sequence of SEQ ID NO: 273 or having at least 90% sequence identity, or at least 95% sequence identity, or at least 99% sequence identity to SEQ ID NO: 273.

In some embodiments, the self-replicating RNA molecule comprises a polynucleotide encoding an amino acid sequence of SEQ ID NO: 275 or having at least 90% sequence identity, or at least 95% sequence identity, or at least 99% sequence identity to SEQ ID NO: 275.

In some embodiments, the self-replicating RNA molecule comprises a polynucleotide encoding an amino acid sequence of SEQ ID NO: 277 or having at least 90% sequence identity, or at least 95% sequence identity, or at least 99% sequence identity to SEQ ID NO: 277.

In some embodiments, the self-replicating RNA molecule comprises a polynucleotide encoding an amino acid sequence of SEQ ID NO: 279 or having at least 90% sequence identity, or at least 95% sequence identity, or at least 99% sequence identity to SEQ ID NO: 279.

In some embodiments, the self-replicating RNA molecule comprises a polynucleotide encoding an amino acid sequence of SEQ ID NO: 281 or having at least 90% sequence identity, or at least 95% sequence identity, or at least 99% sequence identity to SEQ ID NO: 281.

In some embodiments, the self-replicating RNA molecule comprises a polynucleotide encoding an amino acid sequence of SEQ ID NO: 283 or having at least 90% sequence identity, or at least 95% sequence identity, or at least 99% sequence identity to SEQ ID NO: 283.

In some embodiments, the self-replicating RNA molecule comprises a polynucleotide encoding an amino acid sequence of SEQ ID NO: 285 or having at least 90% sequence identity, or at least 95% sequence identity, or at least 99% sequence identity to SEQ ID NO: 285.

In some embodiments, the self-replicating RNA molecule comprises a polynucleotide encoding an amino acid sequence of SEQ ID NO: 287 or having at least 90% sequence identity, or at least 95% sequence identity, or at least 99% sequence identity to SEQ ID NO: 287.

In some embodiments, the self-replicating RNA molecule comprises a polynucleotide encoding an amino acid sequence of SEQ ID NO: 289 or having at least 90% sequence identity, or at least 95% sequence identity, or at least 99% sequence identity to SEQ ID NO: 289.

In some embodiments, the self-replicating RNA molecule comprises a polynucleotide encoding an amino acid sequence of SEQ ID NO: 291 or having at least 90% sequence identity, or at least 95% sequence identity, or at least 99% sequence identity to SEQ ID NO: 291.

In some embodiments, the self-replicating RNA molecule comprises a polynucleotide encoding an amino acid sequence of SEQ ID NO: 293 or having at least 90% sequence identity, or at least 95% sequence identity, or at least 99% sequence identity to SEQ ID NO: 293.

In some embodiments, the self-replicating RNA molecule comprises a polynucleotide encoding an amino acid sequence of SEQ ID NO: 295 or having at least 90% sequence identity, or at least 95% sequence identity, or at least 99% sequence identity to SEQ ID NO: 295.

In some embodiments, the self-replicating RNA molecule comprises a polynucleotide encoding an amino acid sequence of SEQ ID NO: 297 or having at least 90% sequence identity, or at least 95% sequence identity, or at least 99% sequence identity to SEQ ID NO: 297.

In some embodiments, the self-replicating RNA molecule comprises a polynucleotide encoding an amino acid sequence of SEQ ID NO: 299 or having at least 90% sequence identity, or at least 95% sequence identity, or at least 99% sequence identity to SEQ ID NO: 299.

In some embodiments, the self-replicating RNA molecule comprises a polynucleotide encoding an amino acid sequence of SEQ ID NO: 301 or having at least 90% sequence identity, or at least 95% sequence identity, or at least 99% sequence identity to SEQ ID NO: 301.

In some embodiments, the self-replicating RNA molecule comprises a polynucleotide encoding an amino acid sequence of SEQ ID NO: 303 or having at least 90% sequence identity, or at least 95% sequence identity, or at least 99% sequence identity to SEQ ID NO: 303.

In some embodiments, the self-replicating RNA molecule comprises a polynucleotide encoding an amino acid sequence of SEQ ID NO: 305 or having at least 90% sequence identity, or at least 95% sequence identity, or at least 99% sequence identity to SEQ ID NO: 305.

In some embodiments, the self-replicating RNA molecule comprises a polynucleotide encoding an amino acid sequence of SEQ ID NO: 307 or having at least 90% sequence identity, or at least 95% sequence identity, or at least 99% sequence identity to SEQ ID NO: 307.

In some embodiments, the self-replicating RNA molecule comprises a polynucleotide encoding an amino acid sequence of SEQ ID NO: 309 or having at least 90% sequence identity, or at least 95% sequence identity, or at least 99% sequence identity to SEQ ID NO: 309.

In some embodiments, the self-replicating RNA molecule comprises a polynucleotide encoding an amino acid sequence of SEQ ID NO: 311 or having at least 90% sequence identity, or at least 95% sequence identity, or at least 99% sequence identity to SEQ ID NO: 311.

In some embodiments, the self-replicating RNA molecule comprises a polynucleotide encoding an amino acid sequence of SEQ ID NO: 313 or having at least 90% sequence identity, or at least 95% sequence identity, or at least 99% sequence identity to SEQ ID NO: 313.

In some embodiments, the self-replicating RNA molecule comprises a polynucleotide encoding an amino acid sequence of SEQ ID NO: 315 or having at least 90% sequence identity, or at least 95% sequence identity, or at least 99% sequence identity to SEQ ID NO: 315.

In some embodiments, the self-replicating RNA molecule comprises a polynucleotide encoding an amino acid sequence of SEQ ID NO: 317 or having at least 90% sequence identity, or at least 95% sequence identity, or at least 99% sequence identity to SEQ ID NO: 317.

In some embodiments, the self-replicating RNA molecule comprises a polynucleotide encoding an amino acid sequence of SEQ ID NO: 319 or having at least 90% sequence identity, or at least 95% sequence identity, or at least 99% sequence identity to SEQ ID NO: 319.

In some embodiments, the self-replicating RNA molecule comprises a polynucleotide encoding an amino acid sequence of SEQ ID NO: 321 or having at least 90% sequence identity, or at least 95% sequence identity, or at least 99% sequence identity to SEQ ID NO: 321.

In some embodiments, the self-replicating RNA molecule comprises a polynucleotide encoding an amino acid sequence of SEQ ID NO: 323 or having at least 90% sequence identity, or at least 95% sequence identity, or at least 99% sequence identity to SEQ ID NO: 323.

In some embodiments, the self-replicating RNA molecule comprises a polynucleotide encoding an amino acid sequence of SEQ ID NO: 325 or having at least 90% sequence identity, or at least 95% sequence identity, or at least 99% sequence identity to SEQ ID NO: 325.

In some embodiments, the self-replicating RNA molecule comprises a polynucleotide encoding an amino acid sequence of SEQ ID NO: 327 or having at least 90% sequence identity, or at least 95% sequence identity, or at least 99% sequence identity to SEQ ID NO: 327.

In some embodiments, the self-replicating RNA molecule comprises a polynucleotide encoding an amino acid sequence of SEQ ID NO: 329 or having at least 90% sequence identity, or at least 95% sequence identity, or at least 99% sequence identity to SEQ ID NO: 329.

In some embodiments, the self-replicating RNA molecule comprises a polynucleotide encoding an amino acid sequence of SEQ ID NO: 331 or having at least 90% sequence identity, or at least 95% sequence identity, or at least 99% sequence identity to SEQ ID NO: 331.

In some embodiments, the self-replicating RNA molecule comprises a polynucleotide encoding an amino acid sequence of SEQ ID NO: 333 or having at least 90% sequence identity, or at least 95% sequence identity, or at least 99% sequence identity to SEQ ID NO: 333.

In some embodiments, the self-replicating RNA molecule comprises a polynucleotide encoding an amino acid sequence of SEQ ID NO: 335 or having at least 90% sequence identity, or at least 95% sequence identity, or at least 99% sequence identity to SEQ ID NO: 335.

In some embodiments, the self-replicating RNA molecule comprises a polynucleotide encoding an amino acid sequence of SEQ ID NO: 337 or having at least 90% sequence identity, or at least 95% sequence identity, or at least 99% sequence identity to SEQ ID NO: 337.

In some embodiments, the self-replicating RNA molecule comprises a polynucleotide encoding an amino acid sequence of SEQ ID NO: 339 or having at least 90% sequence identity, or at least 95% sequence identity, or at least 99% sequence identity to SEQ ID NO: 339.

In some embodiments, the self-replicating RNA molecule comprises a polynucleotide encoding an amino acid sequence of SEQ ID NO: 341 or having at least 90% sequence identity, or at least 95% sequence identity, or at least 99% sequence identity to SEQ ID NO: 341.

In some embodiments, the self-replicating RNA molecule comprises a polynucleotide encoding an amino acid sequence of SEQ ID NO: 343 or having at least 90% sequence identity, or at least 95% sequence identity, or at least 99% sequence identity to SEQ ID NO: 343.

In some embodiments, the self-replicating RNA molecule comprises a polynucleotide encoding an amino acid sequence of SEQ ID NO: 345 or having at least 90% sequence identity, or at least 95% sequence identity, or at least 99% sequence identity to SEQ ID NO: 345.

In some embodiments, the self-replicating RNA molecule comprises a polynucleotide encoding an amino acid sequence of SEQ ID NO: 347 or having at least 90% sequence identity, or at least 95% sequence identity, or at least 99% sequence identity to SEQ ID NO: 347.

In some embodiments, the self-replicating RNA molecule comprises a polynucleotide encoding an amino acid sequence of SEQ ID NO: 349 or having at least 90% sequence identity, or at least 95% sequence identity, or at least 99% sequence identity to SEQ ID NO: 349.

In some embodiments, the self-replicating RNA molecule comprises a polynucleotide encoding an amino acid sequence of SEQ ID NO: 351 or having at least 90% sequence identity, or at least 95% sequence identity, or at least 99% sequence identity to SEQ ID NO: 351.

In some embodiments, the self-replicating RNA molecule comprises a polynucleotide encoding an amino acid sequence of SEQ ID NO: 353 or having at least 90% sequence identity, or at least 95% sequence identity, or at least 99% sequence identity to SEQ ID NO: 353.

In some embodiments, the self-replicating RNA molecule comprises a polynucleotide encoding an amino acid sequence of SEQ ID NO: 355 or having at least 90% sequence identity, or at least 95% sequence identity, or at least 99% sequence identity to SEQ ID NO: 355.

In some embodiments, the self-replicating RNA molecule comprises a polynucleotide encoding an amino acid sequence of SEQ ID NO: 357 or having at least 90% sequence identity, or at least 95% sequence identity, or at least 99% sequence identity to SEQ ID NO: 357.

In some embodiments, the self-replicating RNA molecule comprises a polynucleotide encoding an amino acid sequence of SEQ ID NO: 359 or having at least 90% sequence identity, or at least 95% sequence identity, or at least 99% sequence identity to SEQ ID NO: 359.

In some embodiments, the self-replicating RNA molecule comprises a polynucleotide encoding an amino acid sequence of SEQ ID NO: 361 or having at least 90% sequence identity, or at least 95% sequence identity, or at least 99% sequence identity to SEQ ID NO: 361.

In some embodiments, the self-replicating RNA molecule comprises a polynucleotide encoding an amino acid sequence of SEQ ID NO: 363 or having at least 90% sequence identity, or at least 95% sequence identity, or at least 99% sequence identity to SEQ ID NO: 363.

In some embodiments, the self-replicating RNA molecule comprises a polynucleotide encoding an amino acid sequence of SEQ ID NO: 365 or having at least 90% sequence identity, or at least 95% sequence identity, or at least 99% sequence identity to SEQ ID NO: 365.

In some embodiments, the self-replicating RNA molecule comprises a polynucleotide encoding an amino acid sequence of SEQ ID NO: 367 or having at least 90% sequence identity, or at least 95% sequence identity, or at least 99% sequence identity to SEQ ID NO: 367.

In some embodiments, the self-replicating RNA molecule comprises a polynucleotide encoding an amino acid sequence of SEQ ID NO: 369 or having at least 90% sequence identity, or at least 95% sequence identity, or at least 99% sequence identity to SEQ ID NO: 369.

In some embodiments, the self-replicating RNA molecule comprises a polynucleotide encoding an amino acid sequence of SEQ ID NO: 371 or having at least 90% sequence identity, or at least 95% sequence identity, or at least 99% sequence identity to SEQ ID NO: 371.

In some embodiments, the self-replicating RNA molecule comprises a polynucleotide encoding an amino acid sequence of SEQ ID NO: 373 or having at least 90% sequence identity, or at least 95% sequence identity, or at least 99% sequence identity to SEQ ID NO: 373.

In some embodiments, the self-replicating RNA molecule comprises a polynucleotide encoding an amino acid sequence of SEQ ID NO: 375 or having at least 90% sequence identity, or at least 95% sequence identity, or at least 99% sequence identity to SEQ ID NO: 375.

In some embodiments, the self-replicating RNA molecule comprises a polynucleotide encoding an amino acid sequence of SEQ ID NO: 377 or having at least 90% sequence identity, or at least 95% sequence identity, or at least 99% sequence identity to SEQ ID NO: 377.

In some embodiments, the self-replicating RNA molecule comprises a polynucleotide encoding an amino acid sequence of SEQ ID NO: 379 or having at least 90% sequence identity, or at least 95% sequence identity, or at least 99% sequence identity to SEQ ID NO: 379.

In some embodiments, the self-replicating RNA molecule comprises a polynucleotide encoding an amino acid sequence of SEQ ID NO: 381 or having at least 90% sequence identity, or at least 95% sequence identity, or at least 99% sequence identity to SEQ ID NO: 381.

In some embodiments, the self-replicating RNA molecule comprises a polynucleotide encoding an amino acid sequence of SEQ ID NO: 383 or having at least 90% sequence identity, or at least 95% sequence identity, or at least 99% sequence identity to SEQ ID NO: 383.

In some embodiments, the self-replicating RNA molecule comprises a polynucleotide encoding an amino acid sequence of SEQ ID NO: 385 or having at least 90% sequence identity, or at least 95% sequence identity, or at least 99% sequence identity to SEQ ID NO: 385.

In some embodiments, the self-replicating RNA molecule comprises a polynucleotide encoding an amino acid sequence of SEQ ID NO: 387 or having at least 90% sequence identity, or at least 95% sequence identity, or at least 99% sequence identity to SEQ ID NO: 387.

In some embodiments, the self-replicating RNA molecule comprises a polynucleotide encoding an amino acid sequence of SEQ ID NO: 389 or having at least 90% sequence identity, or at least 95% sequence identity, or at least 99% sequence identity to SEQ ID NO: 389.

In some embodiments, the self-replicating RNA molecule comprises a polynucleotide encoding an amino acid sequence of SEQ ID NO: 391 or having at least 90% sequence identity, or at least 95% sequence identity, or at least 99% sequence identity to SEQ ID NO: 391.

In some embodiments, the self-replicating RNA molecule comprises a polynucleotide encoding an amino acid sequence of SEQ ID NO: 393 or having at least 90% sequence identity, or at least 95% sequence identity, or at least 99% sequence identity to SEQ ID NO: 393.

In some embodiments, the self-replicating RNA molecule comprises a polynucleotide encoding an amino acid sequence of SEQ ID NO: 395 or having at least 90% sequence identity, or at least 95% sequence identity, or at least 99% sequence identity to SEQ ID NO: 395.

In some embodiments, the self-replicating RNA molecule comprises a polynucleotide encoding an amino acid sequence of SEQ ID NO: 397 or having at least 90% sequence identity, or at least 95% sequence identity, or at least 99% sequence identity to SEQ ID NO: 397.

In some embodiments, the self-replicating RNA molecule comprises a polynucleotide encoding an amino acid sequence of SEQ ID NO: 399 or having at least 90% sequence identity, or at least 95% sequence identity, or at least 99% sequence identity to SEQ ID NO: 399.

In some embodiments, the self-replicating RNA molecule comprises a polynucleotide encoding an amino acid sequence of SEQ ID NO: 401 or having at least 90% sequence identity, or at least 95% sequence identity, or at least 99% sequence identity to SEQ ID NO: 401.

In some embodiments, the self-replicating RNA molecule comprises a polynucleotide encoding an amino acid sequence of SEQ ID NO: 403 or having at least 90% sequence identity, or at least 95% sequence identity, or at least 99% sequence identity to SEQ ID NO: 403.

In some embodiments, the self-replicating RNA molecule comprises a polynucleotide encoding an amino acid sequence of SEQ ID NO: 405 or having at least 90% sequence identity, or at least 95% sequence identity, or at least 99% sequence identity to SEQ ID NO: 405.

In some embodiments, the self-replicating RNA molecule comprises a polynucleotide encoding an amino acid sequence of two or more of the polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and fragments thereof.

Any of the above self-replicating RNA molecules can further comprise one or more of the following:
one or more nonstructural genes nsP1, nsP2, nsP3 and nsP4;
at least one of a DLP motif, a 5' UTR, a 3'UTR and a Poly A; and
a subgenomic promoter.

In some embodiments, for example, the self-replicating RNA molecule can comprise one or more of the following:
one or more nonstructural genes nsP1, nsP2, nsP3 and nsP4;
at least one of a DLP motif, a 5' UTR, a 3'UTR and a Poly A; and
a subgenomic promoter; and
an RNA encoding for any of the polypeptides of the disclosure, and operably linked to the subgenomic promoter.

In some embodiments, the self-replicating RNA molecule comprises an RNA sequence encoding a protein or peptide; 5' and 3' alphavirus untranslated regions; RNA sequences encoding amino acid sequences derived from New World alphavirus VEEV nonstructural proteins nsP1, nsP2, nsP3 and nsP4; a sub-genomic promoter that is operably linked to and regulates translation of the RNA sequence encoding the protein; a 5' cap and a 3' poly-A tail; positive sense, single-stranded RNA; a DLP from Sindbis virus upstream of the non-structural protein 1 (nsP1); a 2A ribosome skipping element; and a nsp1 nucleotide repeat downstream of the 5'-UTR and upstream of the DLP.

In some embodiments, the self-replicating RNA molecules may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size.

Any of the above-disclosed self-replicating RNA molecules can further include a coding sequence for an autoprotease peptide (e.g., autocatalytic self-cleaving peptide), where the coding sequence for the autoprotease is optionally operably linked upstream to the second nucleic acid sequence.

Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. As used herein the term "autoprotease" refers to a "self-cleaving" peptide that possesses autoproteolytic activity and is capable of cleaving itself from a larger polypeptide moiety. First identified in the foot-and-mouth disease virus (FMDV), a member of the picornavirus group, several autoproteases have been subsequently identified such as, for example, "2A like" peptides from equine rhinitis A virus (E2A), porcine teschovirus-1 (P2A) and Thosea asigna virus (T2A), and their activities in proteolytic cleavage have been shown in various ex vitro and in vivo eukaryotic systems. As such, the concept of autoproteases is available to one of skill in the art as many naturally occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoprotease peptides suitable for the compositions and methods of the present disclosure include the peptide sequences from porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

In some embodiments, the coding sequence for the autoprotease peptide is operably linked downstream of the DLP motif and upstream to the first and second polynucleotides.

In some embodiments, the autoprotease peptide comprises, or consists of, a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the autoprotease peptide includes a peptide sequence of porcine teschovirus-1 2A (P2A).

In some embodiments, the autoprotease peptide is porcine teschovirus-1 2A (P2A).

The incorporation of the P2A peptide in the modified viral RNA replicons of the present disclosure allows release of protein encoded by GOI (e.g. ovarian neoantigen polypeptides of the disclosure) from the capsid-GOI fusion.

In some embodiments disclosed herein, the porcine teschovirus-1 2A (P2A) peptide sequence is engineered in-frame immediately after the DLP sequence and in-frame immediately upstream of all GOI.

Any of the above-disclosed self-replicating RNA molecules can further include a coding sequence downstream Loop (DLP) motif.

Some viruses have sequences capable of forming one or more stem-loop structures which regulate, for example increase, capsid gene expression. Viral capsid enhancer as used herein refers to a regulatory element comprising sequences capable of forming such stem-loop structures. In some examples, the stem-loop structures are formed by sequences within the coding sequence of a capsid protein and named Downstream Loop (DLP) sequence. As disclosed herein, these stem-loop structures or variants thereof can be used to regulate, for example increase, expression level of genes of interest. For example, these stem-loop structures or variants thereof can be used in a recombinant vector (e.g., in a heterologous viral genome) for enhancing transcription and/or translation of coding sequence operably linked downstream thereto.

Alphavirus replication in host cells is known to induce the double-stranded RNA-dependent protein kinase (PKR). PKR phosphorylates the eukaryotic translation initiation factor 2α (eIF2α). Phosphorylation of eIF2α blocks translation initiation of mRNA and in doing so keeps viruses from a completing a productive replication cycle. Members of the Alphavirus genus can resist the activation of antiviral RNA-activated protein kinase (PKR) by means of the dowsntream loop (DLP) present within the viral 26S transcripts, which allows an eIF2-independent translation initiation of these mRNAs. The DLP structure can stall a ribosome on the wild type AUG and this supports translation of the subgenomic mRNA without the requirement for functional eIF2α. The DLP structure was first characterized in Sindbis virus (SINV) 26S mRNA and also detected in Semliki Forest virus (SFV). Similar DLP structures have been reported to be present in at least 14 other members of the Alphavirus genus including New World (for example, MAYV, UNAV, EEEV (NA), EEEV (SA), AURAV) and Old World (SV, SFV, BEBV, RRV, SAG, GETV, MIDV, CHIKV, and ONNV) members. The DLP is located downstream from the AUG in SINV 26S mRNA and in other members of the Alphavirus genus.

In some embodiments, the nucleic acid molecules of the disclosure can include a coding sequence for a gene of interest (GOI) operably linked to DLP motif(s) and/or the coding sequence for the DLP motifs.

In some embodiments, the DLP of the self-replicating RNA molecule is derived from Sindbis virus.

In some embodiments, the downstream loop (DLP) comprises at least one RNA-stem-loop.

In some instances, DLP activity depends on the distance between the DLP motif and the initiation codon AUG (AUGi). The AUG-DLP spacing in Alphavirus 26S mRNAs is tuned to the topology of the ES6S region of the ribosomal 18S rRNA in a way that allows the placement of the AUGi in the P site of the 40S subunit stalled by the DLP, allowing the incorporation of Met-tRNA without the participation of eIF2. In the case of Sindbis virus, the DLP motif is found in the first ~150 nt of the Sindbis subgenomic RNA. The hairpin is located downstream of the Sindbis capsid AUG initiation codon (AUG at nt 50 of the Sindbis subgenomic RNA) and results in stalling a ribosome such that the correct capsid gene AUG is used to initiate translation.

Without being bound by any particular theory, it is believed that placing the DLP motif upstream of a coding sequence for any GOI typically results in a fusion-protein of N-terminal capsid amino acids that are encoded in the hairpin region to the GOI encoded protein because initiation occurs on the capsid AUG not the GOI AUG.

In some embodiments, the self-replicating RNA molecule comprises a downstream loop placed upstream of the non-structural protein 1 (nsP1).

In some embodiments, the downstream loop is placed upstream of the non-structural protein 1 (nsP1) and is joined to the nsP1 by a porcine teschovirus-1 2A (P2A) ribosome skipping element.

The DLP-containing self-replicating RNA of the disclosure can also be useful in conferring a resistance to the innate immune system in a subject. Unmodified RNA replicons are sensitive to the initial innate immune system state of cells they are introduced into. If the cells/individuals are in a highly active innate immune system state, the RNA replicon performance (e.g., replication and expression of a GOI) can be negatively impacted. By engineering a DLP to control initiation of protein translation, particularly of non-structural proteins, the impact of the pre-existing activation state of the innate immune system to influence efficient RNA replicon replication is removed or lessened. The result is more uniform and/or enhanced expression of a GOI that can impact vaccine efficacy or therapeutic impact of a treatment.

The DLP motif of the self-replicating RNA of the disclosure can confer efficient mRNA translation in cellular environments where cellular mRNA translation is inhibited. When a DLP is linked with translation of a replicon vector's non-structural protein genes the replicase and transcriptase proteins are capable of initiating functional replication in PKR activated cellular environments. When a DLP is linked with translation of subgenomic mRNAs robust GOI expression is possible even when cellular mRNA is restricted due to innate immune activation.

Accordingly, engineering self-replicating RNA that contain DLP structures to help drive translation of both non-structural protein genes and subgenomic mRNAs provides a powerful way to overcome innate immune activation.

Examples of a self-replicating RNA vector comprising a DLP motif are described in US Patent Application Publication US2018/0171340 and the International Patent Application Publication WO2018106615, the content of which is incorporated herein by reference in its entirety.

Any of the above-disclosed self-replicating RNA molecules can further comprise nonstructural genes nsP1, nsP2, nsP3 and/or nsP4.

Alphavirus genomes encode non-structural proteins nsP1, nsP2, nsP3, and nsP4, which are produced as a single polyprotein precursor, sometimes designated P1234 (or nsP1-4 or nsP1234), and which is cleaved into the mature proteins through proteolytic. nsP1 can be about 60 kDa in size and may have methyltransferase activity and be involved in the viral capping reaction. nsP2 has a size of about 90 kDa and may have helicase and protease activity while nsP3 is about 60 kDa and contains three domains: a macrodomain, a central (or alphavirus unique) domain, and a hypervariable domain (HVD). nsP4 is about 70 kDa in size and contains the core RNA-dependent RNA polymerase (RdRp) catalytic domain. After infection the alphavirus genomic RNA is translated to yield a P1234 polyprotein, which is cleaved into the individual proteins.

Alphavirus genomes also encode three structural proteins: the core nucleocapsid protein C, and the envelope proteins P62, and E1 that associate as a heterodimer. Structural proteins are under the control of a subgenomic promoter and can be replaced by gene of interests (GIO).

In some embodiments, the self-replicating RNA molecule does not encode functional viral structural proteins.

In some embodiments of the present disclosure, the self-replicating RNA can lack (or not contain) the sequence(s) of at least one (or all) of the structural viral proteins (e.g. nucleocapsid protein C, and envelope proteins P62, 6K, and E1). In these embodiments, the sequences encoding one or more structural genes can be substituted with one or more sequences such as, for example, a coding sequence for at least one protein or peptide (or other gene of interest (GOI)) e.g. the ovarian cancer neoantigen polypeptides of the disclosure.

In some embodiments, the self-replicating RNA lack sequences encoding alphavirus structural proteins; or do not encode alphavirus (or, optionally, any other) structural proteins. In some embodiments, the self-replicating RNA molecules are further devoided of a part or the entire coding region for one or more viral structural proteins. For example, the alphavirus expression system may be devoid of a portion of or the entire coding sequence for one or more of the viral capsid protein C, E1 glycoprotein, E2 glycoprotein, E3 protein and 6K protein.

In some embodiments, the self-replicating RNA molecule does not contain coding sequences for at least one of the structural viral proteins. In these instances, the sequences encoding structural genes can be substituted with one or more sequences such as, for example, a coding sequence for a ovarian neoantigen polynucleotides of the disclosure.

The disclosure also provides a self-replicating RNA molecule comprising nonstructural genes nsP1, nsP2, nsP3 and nsP4, and wherein the self-replicating RNA molecule does not encode a functional viral structural protein.

In some embodiments, the self-replicating RNA molecule can include one or more nonstructural viral proteins. In certain embodiments, the one or more nonstructural viral proteins are derived from the same virus. In other embodiments, the one or more nonstructural proteins are derived from different viruses.

In some embodiments, the disclosure provides a self-replicating RNA molecule comprising the coding sequence for at least one, at least two, at least three, or at least four nonstructural viral proteins (e.g. nsP1, nsP2, nsP3, nsP4). The nsP1, nsP2, nsP3, and nsP4 proteins encoded by the replicon are functional or biologically active proteins.

In some embodiments, the self-replicating RNA molecule includes the coding sequence for a portion of the at least one nonstructural viral protein. For example, the self-replicating RNA molecules can include about 10%, 20%, 30%, 40%, 50%, 60%, 70%, 80%, 90%, 95%, 100%, or a range between any two of these values, of the encoding sequence for the at least one nonstructural viral protein. In some embodiments, the self-replicating RNA molecule can include the coding sequence for a substantial portion of the at least one non-structural viral protein. As used herein, a "substantial portion" of a nucleic acid sequence encoding a nonstructural viral protein comprises enough of the nucleic acid sequence encoding the nonstructural viral protein to afford putative identification of that protein, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993).

In some embodiments, the self-replicating RNA molecule can include the entire coding sequence for the at least one nonstructural protein. In some embodiments, the self-replicating RNA molecule comprises substantially all the coding sequence for the native viral nonstructural proteins.

In some embodiments, the self-replicating RNA molecule comprises nsP1, nsP2, nsP3 and nsP4 sequences derived from the Venezuelan equine encephalitis virus (VEEV) and a DLP motif derived from the Sindbis virus (SIN).

In some embodiments, the self-replicating RNA molecules also have an RNA sub-sequence encoding an amino acid sequence derived from an alphavirus nsP3 macro domain, and an RNA sub-sequence encoding an amino acid sequence derived from an alphavirus nsP3 central domain. In various embodiments the macro and central domain(s) can both be derived from a New World wild type alphavirus nsP3 or can both be derived from an Old World wild type alphavirus nsP3 protein. In other embodiments, the macro domain can be derived from a New World wild type alphavirus macro domain and the central domain can be derived from an Old World wild type alphavirus central domain, or vice versa. The various domains can be of any sequence described herein. The self-replicating RNA molecules can also have an RNA sub-sequence encoding an amino acid sequence derived entirely from an Old World alphavirus nsP3 hypervariable domain; or can have an amino acid sequence having a portion derived from a New World alphavirus nsP3 hypervariable domain, and a portion derived from an Old World alphavirus nsP3 hypervariable domain. i.e. the hyper variable domain (HVD) can be a hybrid or chimeric New World/Old World sequence.

In some embodiments, the self-replicating RNA molecules can have an RNA sequence encoding amino acid sequences derived from a wild type New World alphavirus nsP1, nsP2, nsP3 and nsP4 protein sequences.

In some embodiments, the self-replicating RNA molecule contains non VEEV nonstructural proteins nsP1, nsP2, nsP3 and nsP4.

The accumulated experimental evidence has demonstrated that replication/amplification of VEEV and other alphavirus genomes and their defective interfering (DI) RNAs is determined by three promoter elements: (i) the conserved 3'-terminal sequence element (3' CSER) and the following poly(A) tail; (ii) the 5' UTR, which functions as a key promoter element for both negative- and positive-strand RNA synthesis; and (iii) the 51-nt conserved sequence element (51-nt CSE), which is located in the nsP1-coding sequence and functions as an enhancer of alphavirus genome replication (Kim et al., PNAS, 2014, 111: 10708-10713).

The 5' and 3' untranslated regions can be operably linked to any of the other sequences encoded by the replicon. The UTRs can be operably linked to a promoter and/or sequence encoding a protein or peptide by providing sequences and spacing necessary for recognition and transcription of the other encoded sequences.

Any of the above-disclosed self-replicating RNA molecules can further include an unmodified 5' untranslated region (5'UTR).

In some embodiment, a self-replicating RNA molecule comprises a modified 5' untranslated region (5'-UTR). For example, the modified 5'-UTR can comprise one or more nucleotide substitutions at position 1, 2, 4, or a combination thereof. Preferably, the modified 5'-UTR comprises a nucleotide substitution at position 2, more preferably, the modified 5'-UTR has a U→G substitution at position 2. Examples of such self-replicating RNA molecules are described in US Patent Application Publication US2018/0104359 and the International Patent Application Publication WO2018075235, the content of which is incorporated herein by reference in its entirety.

In some embodiments, the UTRs can be wild type New World or Old World alphavirus UTR sequences, or a sequence derived from any of them. The 5' UTR can be of any suitable length, such as about 60 nt or 50-70 nt or 40-80 nt. In some embodiments the 5' UTR can also have conserved primary or secondary structures (e.g. one or more stem-loop(s)) and can participate in the replication of alphavirus or of replicon RNA. The 3' UTR can be up to several hundred nucleotides, for example it can be 50-900 or 100-900 or 50-800 or 100-700 or 200 nt-700 nt. The '3 UTR also can have secondary structures, e.g. a step loop, and can be followed by a polyadenylate tract or poly-A tail.

In some embodiments, the self-replicating RNA molecules can have a 3' poly-A tail. It can also include a poly-A polymerase recognition sequence (e.g. AAUAAA) near its 3' end.

In those instances where the self-replicating RNA molecule is to be packaged into a recombinant alphavirus particle, it can contain one or more sequences, so-called packaging signals, which serve to initiate interactions with alphavirus structural proteins that lead to particle formation. In some embodiments, the alphavirus particles comprise RNA derived from one or more alphaviruses; and structural proteins wherein at least one of said structural proteins is derived from two or more alphaviruses.

In some embodiments, the self-replicating RNA molecule comprises a VEEV derived vector wherein the structural viral proteins (e.g. nucleocapsid protein C, and envelope proteins P62, 6K, and E1) are removed and replaced by the coding sequence of the ovarian neoantigen polynucleotides of the disclosure.

Previous studies have demonstrated that during VEEV and Sindbis virus infections only a small portion of viral nonstructural proteins (nsPs) is colocalized with dsRNA replication intermediates. Thus, it appears that a large fraction of nsPs are not involved in RNA replication (Gorchakov R, et al. (2008) A new role for ns polyprotein cleavage in Sindbis virus replication. J Virol 82(13):6218-6231). This has provided an opportunity to exploit the under used ns proteins for amplification of the subgenomic RNAs encoding proteins of interest, which is normally transcribed from the subgenomic promoter and is not further amplified.

In some embodiments, a fragment of the nsP1 of the self-replicating RNA molecule of the disclosure is duplicated downstream of the 5'-UTR and upstream of the DLP. In some embodiments the first 193 nucleotides of nsP1 are duplicated downstream of the 5' UTR and upstream of the DLP Other Viral Vectors and Recombinant Viruses The viral vector comprising the polynucleotide of the disclosure may be derived from other viral vectors including vectors derived from human adeno-associated viruses, such as AAV-2 (adeno-associated virus type 2). An attractive feature of AAV vectors is that they do not express any viral genes. The only viral DNA sequences included in the AAV vectors are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{11}$ particles or copies of DNA in contrast to naked DNA doses of 50 µg or about $10^{15}$ copies. AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay).

Retroviral vectors may also be used. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (Int. Pat. Publ. No. WO1995/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323).

The polynucleotides of the disclosure may be inserted downstream of the encapsidation sequence, such as in opposite direction relative to the retroviral genome. Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. Packaging cell line, such as the PA317 cells (ATCC CRL 9078) or 293EI6 (WO97/35996) containing an amphotropic envelope protein may therefore be used to allow infection of human and other species' target cells. The retroviral particles are recovered from the culture supernatant and may optionally be further purified according to standard techniques (e.g. chromatography, ultracentrifugation).

Regulatory Elements

The polynucleotide or the heterologous polynucleotide of the disclosure may be operably linked to one or more regulatory elements in the vector. The regulatory elements may comprise promoters, enhancers, polyadenylation signals, repressors and the like. As used herein, the term "operably linked" is to be taken in its broadest reasonable context and refers to a linkage of polynucleotide elements in a functional relationship. A polynucleotide is "operably linked" when it is placed into a functional relationship with another polynucleotide. For instance, a promoter is operably linked to a coding sequence if it affects the transcription of the coding sequence.

Some of the commonly used enhancer and promoter sequences in expression vectors and viral vectors are, for example, human cytomegalovirus (hCMV), vaccinia P7.5 early/late promoter, CAG, SV40, mouse CMV (mCMV), EF-1 and hPGK promoters. Due to its high potency and moderate size of ca. 0.8 kB, the hCMV promoter is one of the most commonly used of these promoters. The hPGK promoter is characterized by a small size (ca. 0.4 kB), but it is less potent than the hCMV promoter. On the other hand, the CAG promoter consisting of a cytomegalovirus early enhancer element, promoter, first exon and intron of chicken beta-actin gene, and splice acceptor of the rabbit beta-globin gene, can direct very potent gene expression that is comparable to the hCMV promoter, but its large size makes it less suitable in viral vectors where space constraints can be a significant concern, e.g., in adenoviral vectors (AdV), adeno-associated viral vectors (AAV) or lentiviral vectors (LVs).

Additional promoters that may be used are Aotine Herpesvirus 1 major immediate early promoter (AoHV-1 promoter) described in Int. Pat. Publ. No. WO2018/146205. The promoter may be operably coupled to a repressor operator sequence, to which a repressor protein can bind in order to repress expression of the promoter in the presence of the repressor protein. In certain embodiments, the repressor operator sequence is a TetO sequence or a CuO sequence (see e.g. U.S. Pat. No. 9,790,256).

In certain cases, it may be desirable to express at least two separate polypeptides from the same vector. In this case each polynucleotide may be operably linked to the same or different promoter and/or enhancer sequences, or well-known bicistronic expression systems for example by utilizing internal ribosome entry site (IRES) from encephalomyocarditis virus may be used. Alternatively, bidirectional synthetic promoters may be used, such as a hCMV-rhCMV promoter and other promoters described in Int. Pat. Publ. No. WO2017/220499. Polyadenylation signals may be derived from SV40 or bovine growth hormone (BGH).

The self-replicating RNA vectors comprising the polynucleotide encoding the polypeptide of the disclosure can further comprise any regulatory elements to establish conventional function(s) of the vector, including but not limited to replication and expression of the polypeptide of the disclosure encoded by the polynucleotide sequence of the vector. Regulatory elements include, but are not limited to, a promoter, an enhancer, a polyadenylation signal, translation stop codon, a ribosome binding element, a transcription terminator, selection markers, origin of replication, etc. A vector can comprise one or more expression cassettes. An "expression cassette" is part of a vector that directs the cellular machinery to make RNA and protein. An expression cassette typically comprises three components: a promoter sequence, an open reading frame, and a 3'-untranslated region (UTR) optionally comprising a polyadenylation signal. An open reading frame (ORF) is a reading frame that contains a coding sequence of a protein of interest (e.g., the polypeptides of the disclosure) from a start codon to a stop codon. Regulatory elements of the expression cassette can be operably linked to a polynucleotide sequence encoding the polypeptides of interest. Any components suitable for use in an expression cassette described herein can be used in any combination and in any order to prepare vectors of the application.

The vector can comprise a promoter sequence, preferably within an expression cassette, to control expression of the polypeptides of the disclosure.

In a self-replicating RNA, the vector can further comprise additional polynucleotide sequences that stabilize the expressed transcript, enhance nuclear export of the RNA transcript, and/or improve transcriptional-translational coupling. Examples of such sequences include polyadenylation signals and enhancer sequences. A polyadenylation signal is typically located downstream of the coding sequence for a protein of interest (e.g., the polypeptides of the disclosure) within an expression cassette of the vector. Enhancer sequences are regulatory DNA sequences that, when bound by transcription factors, enhance the transcription of an associated gene. An enhancer sequence is preferably located upstream of the polynucleotide sequence encoding the polypeptides of the disclosure, but downstream of a promoter sequence within an expression cassette of the vector.

Any enhancer sequence known to those skilled in the art in view of the present disclosure can be used.

Any of the components or sequences of the self-replicating RNA vector of the disclosure can be functionally or operably linked to any other of the components or sequences.

A promoter or UTR operably linked to a coding sequence is capable of effecting the transcription and expression of the coding sequence when the proper enzymes are present. The promoter need not be contiguous with the coding sequence, so long as it functions to direct the expression thereof. Thus, an operable linkage between an RNA sequence encoding a protein or peptide and a regulatory sequence (for example, a promoter or UTR) is a functional link that allows for expression of the polynucleotide of interest. Operably linked can also refer to sequences such as the sequences encoding the RdRp (e.g. nsP4), nsP1-4, the UTRs, promoters, and other sequences encoding in the RNA replicon, are linked so that they enable transcription and translation of the polypeptide and/or replication of the replicon. The UTRs can be operably linked by providing sequences and spacing necessary for recognition and translation by a ribosome of other encoded sequences.

A molecule is functional or biologically active if it performs at least 50% of the same activity as its natural (or wild type), corresponding molecule, but a functional molecule can also perform at least 60% or at least 70% or at least 90% or at least 95% or 100% of the same activity as its natural (or wild type) corresponding molecule. The self-replicating RNA molecules can also encode an amino acid sequence derived from or based on a wild type alphavirus amino acid sequence, meaning that they have at least 60% or at least 65% or at least 68% or at least 70% or at least 80% or at least 70% or at least 80% or at least 90% or at least 95% or at least 97% or at least 98% or at least 99% or 100% or 80-99% or 90-100% or 95-99% or 95-100% or 97-99% or 98-99% sequence identity with an amino acid sequence (which can be a corresponding sequence) encoded by a wild type RNA alphavirus genome, which can be a New World or Old World alphavirus genome. Sequences derived from other sequences can be up to 5% or up to 10% or up to 20% or up to 30% longer or shorter than the original sequence. In any of the embodiments the sequence identity can be at least 95% or at least 97% or at least 98% or at least 99% or 100% for any nucleotide sequence encoding (or amino acid sequence having) a G3BP or FXR binding site thereon. These sequences can also be up to 5% or up to 10% or up to 20% or up to 30% longer or shorter than the original sequence.

Cells of the Disclosure

The disclosure also provides a cell comprising or transduced with one or more vectors of the disclosure or one or more recombinant viruses of the disclosure.

Suitable cells include prokaryotic and eukaryotic cells, e.g., mammalian cells, yeast, fungi and bacteria (such as *E. coli*), such as Hek 293, CHO, PER.C6 or chicken embryonic fibroblast (CEF) cells. The cell can be used in vitro, such as for research or for production of the polypeptides or viruses, or the cell can be used in vivo. In some embodiments, the cell is a muscle cell. In some embodiments, the cell is an antigen presenting cell (APC). Suitable antigen presenting cells include dendritic cells, B lymphocytes, monocytes and macrophages.

The cells that are transfected with the polynucleotides or vectors of the disclosure may typically be obtained through cell culture repositories such as ATCC. APCs may be obtained from the peripheral blood using leukopheresis and "FICOLL/HYPAQUE" density gradient centrifugation (stepwise centrifugation through Ficoll and discontinuous Percoll density gradients). APCs may be isolated, cultured and engineered using known methods. For example, immature and mature dendritic cells may be generated from peripheral blood mononuclear cells (PBMCs) using known methods. In an exemplary method, isolated PBMCs are pre-treated to deplete T- and B-cells by means of an immunomagnetic technique. Lymphocyte-depleted PBMC are then cultured for in RPMI medium 9 e.g., about 7 days), supplemented with human plasma (preferably autologous plasma) and GM-CSF/IL-4, to generate dendritic cells. Dendritic cells are nonadherent when compared to their monocyte progenitors. Thus, on approximately day 7, non-adherent cells are harvested for further processing. The dendritic cells derived from PBMC in the presence of GM-CSF and IL-4 are immature, in that they can lose the nonadherence property and revert back to macrophage cell fate if the cytokine stimuli are removed from the culture. The dendritic cells in an immature state are effective in processing native protein antigens for the MHC class II restricted pathway (Romani, et al., J. Exp. Med. 169: 1169, 1989). Further maturation of cultured dendritic cells is accomplished by culturing for 3 days in a macrophage-conditioned medium (CM), which contains the necessary maturation factors. Mature dendritic cells are less able to capture new proteins for presentation but are much better at stimulating resting T cells (both CD4 and CD8) to grow and differentiate. Mature dendritic cells can be identified by their change in morphology, such as the formation of more motile cytoplasmic processes; by their nonadherence; by the presence of at least one of the following markers: CD83, CD68, HLA-DR or CD86; or by the loss of Fc receptors such as CD115 (reviewed in Steinman, Annu. Rev. Immunol. 9: 271, 1991). Mature dendritic cells can be collected and analyzed using typical cytofluorography and cell sorting techniques and devices, such as FACScan and FACStar. Primary antibodies used for flow cytometry are those specific to cell surface antigens of mature dendritic cells and are commercially available. Secondary antibodies can be biotinylated Igs followed by FITC- or PE-conjugated streptavidin. The vectors and recombinant viruses of the disclosure can be introduced into cells including APCs using the methods known in the art, including, but not limited to, transfection, electroporation, fusion, microinjection, viral-based delivery, or cell-based delivery.

Vaccines and Pharmaceutical Compositions

The disclosure also provides compositions comprising any of the polynucleotides, any of the polypeptides, and any of the vectors disclosed herein. In some embodiments, the compositions may comprise a vector comprising any of the nucleotides disclosed herein, wherein the vector is selected from Ad26, GAd20, MVA, or a self-replicating RNA molecule. In some embodiments, the compositions may comprise a recombinant virus or a self-replicating RNA molecule expressing any of the polypeptides or neoantigens disclosed herein. In some embodiments, the recombinant virus may be Ad26 virus, GAd20 virus or MVA virus.

Any of the compositions described above may comprise or may be formulated into a pharmaceutical composition comprising the composition and a pharmaceutically acceptable excipient.

The polypeptides or the heterologous polypeptides or fragments thereof, or the polynucleotides encoding them may be delivered into the subject utilizing any known delivery vehicle suitable for administering to the subject. It is expected that the polypeptides, the heterologous polypeptides or fragments thereof will be immunogenic in the subject regardless of the delivery vehicle used. The polynucleotide may be DNA or RNA, or derivatives thereof. RNA may be in the form of oligonucleotide RNA, tRNA (transfer RNA), snRNA (small nuclear RNA), rRNA (ribosomal RNA), mRNA (messenger RNA), antisense RNA, siRNA (small interfering RNA), self-replicating RNA, ribozymes, chimeric sequences, or derivatives of these groups.

The disclosure also provides a vaccine comprising the polynucleotide of the disclosure.

In some embodiments, the polynucleotide is DNA.

In some embodiments, the polynucleotides is RNA.

In some embodiments, RNA is mRNA.

The disclosure also provides a vaccine comprising the vector of the disclosure.

The disclosure also provides a vaccine comprising the rAd26 of the disclosure.

The disclosure also provides a vaccine comprising the rMVA of the disclosure.

The disclosure also provides a vaccine comprising the rGAd of the disclosure.

The disclosure also provides a vaccine comprising the rGAd20 of the disclosure.

The disclosure also provides a vaccine comprising the ChAd20 of the disclosure.

The disclosure also provides a vaccine comprising the self-replicating RNA molecule of the disclosure.

The disclosure also provides a vaccine comprising the cell of the disclosure.

The preparation of vaccine compositions is well known. Vaccines may comprise or may be formulated into a pharmaceutical composition comprising the vaccine and a pharmaceutically acceptable excipient.

"Pharmaceutically acceptable" refers to the excipient that at the dosages and concentrations employed, will not cause unwanted or harmful effects in the subjects to which they are administered and include carrier, buffers, stabilizers or other materials well known to those skilled in the art. The precise nature of the carrier or other material may depend on the route of administration, e.g., intramuscular, subcutaneous, oral, intravenous, cutaneous, intramucosal (e.g., gut), intranasal or intraperitoneal routes. Liquid carriers such as water, petroleum, animal or vegetable oils, mineral oil or synthetic oil may be included. Physiological saline solution, dextrose or other saccharide solution or glycols such as ethylene glycol, propylene glycol or polyethylene glycol may be included. Exemplary viral formulation are the Adenovirus World Standard (Hoganson et al, 2002): 20 mM Tris pH 8, 25 mM NaCl, 2.5% glycerol; or 20 mM Tris, 2 mM $MgCl_2$, 25 mM NaCl, sucrose 10% w/v, polysorbate-80 0.02% w/v; or 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Many other buffers can be used, and examples of suitable formulations for the storage and for pharmaceutical administration of purified pharmaceutical preparations are known.

Adjuvants

The pharmaceutical composition may comprise one or more adjuvants. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine). Suitable adjuvants include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59. Other adjuvants that may be used include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-1, IL-2, IL-4, IL-6, IL-8, IL-10, IL-12 or TLR agonists, and particulate adjuvants (e g immuno-stimulatory complexes (ISCOMS).

"Adjuvant" and "immune stimulant" are used interchangeably herein and are defined as one or more substances that cause stimulation of the immune system. In this context, an adjuvant is used to enhance an immune response to the vaccines or viral vectors described herein.

A pharmaceutical composition according to the disclosure may in certain embodiments be the vaccine of the disclosure.

Similarly, the polynucleotides, the heterologous polynucleotides, the polypeptides and the heterologous polypeptides of the disclosure may be formulated into pharmaceutical compositions comprising the polynucleotides, the heterologous polynucleotides, the polypeptides and the heterologous polypeptides and the pharmaceutically acceptable excipients.

In some embodiments, the pharmaceutical compositions are devoid of adjuvants.

Nanoparticles

In some embodiments, the compositions may comprise nanoparticles. Any of the polynucleotides of the disclosure may be attached to or in contact with nanoparticles for delivery to a subject. Delivery of any of the polynucleotides or polypeptides of the disclosure using nanoparticles may eliminate the need to include a virus or an adjuvant in the vaccine composition. The nanoparticles may contain immune danger signals that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells.

The nanoparticles are typically from about 1 nm to about 100 nm in diameter, such as about 20 nm to about 40 nm. Nanoparticles with a mean diameter of 20 to 40 nm may facilitate uptake of the nanoparticle to the cytosol (see. e.g. WO2019/135086). Exemplary nanoparticles are polymeric nanoparticles, inorganic nanoparticles, liposomes, lipid nanoparticles (LNP), an immune stimulating complex (ISCOM), a virus-like particle (VLP), or a self-assembling protein.

The nanoparticles may be calcium phosphate nanoparticles, silicon nanoparticles or gold nanoparticles. The polymeric nanoparticles may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene or one or more natural polymers such as a polysaccharide, for example pullulan, alginate, inulin, and chitosan. The use of a polymeric nanoparticles may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may also form hydrogel nanoparticles, hydrophilic three-dimensional polymer networks with favorable properties including flexible mesh size, large surface area for multivalent conjugation, high water content, and high loading capacity for antigens. Polymers such as Poly (L-lactic acid) (PLA), PLGA, PEG, and polysaccharides are suitable for forming hydrogel nanoparticles. Inorganic nanoparticles typically have a rigid structure and comprise a shell in which an antigen is encapsulated or a core to which the antigen may be covalently attached. The core may comprise one or more atoms such as gold (Au), silver (Ag), copper (Cu) atoms, Au/Ag, Au/Cu, Au/Ag/Cu, Au/Pt, Au/Pd or Au/Ag/Cu/Pd or calcium phosphate (CaP).

In some embodiments, the nanoparticles may be liposomes. Liposomes are typically formed from biodegradable, non-toxic phospholipids and comprise a self-assembling phospholipid bilayer shell with an aqueous core. Liposomes may be an unilamellar vesicle comprising a single phospholipid bilayer, or a multilamellar vesicle that comprises several concentric phospholipid shells separated by layers of water. As a consequence, liposomes may be tailored to incorporate either hydrophilic molecules into the aqueous core or hydrophobic molecules within the phospholipid bilayers. Liposomes may encapsulate polynucleotides or the polypeptides or fragments thereof of the disclosure within the core for delivery. Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. The liposomes may comprise a targeting molecule for targeting liposome complexes to a particular cell type. Targeting molecule may comprise a binding partner (e.g., a ligand or receptor) for a biomolecule (e.g., a receptor or ligand) on the surface of a blood vessel or a cell found in a target tissue. Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028). Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

In some embodiments, the nanoparticles can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powder like form. This film is covered with an aqueous solution of the polypeptide or polynucleotide and allowed to hydrate, typically over a 15 to 60 minute period with agitation.

The size distribution of the resulting multilamellar vesicles can be shifted toward smaller sizes by hydrating the lipids under more vigorous agitation conditions or by adding solubilizing detergents such as deoxycholate. The hydration medium may comprise the nucleic acid at a concentration which is desired in the interior volume of the liposomes in the final liposome suspension. Suitable lipids that may be used to form multilamellar vesicles include DOTMA, DOGS or Transfectain™, DNERIE or DORIE, DC-CHOL, DOTAP™, Lipofectamine™ and glycerolipid compounds.

In some embodiments, the nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*).

In some embodiments, the nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

Encapsulated Self-Replicating RNA Molecules

The self-replicating RNA molecules and/or compositions comprising the same can also be formulated as a nanoparticle using a combination of polymers, lipids, and/or other biodegradable agents, such as, but not limited to, calcium phosphate, polymers. Components can be combined in a core-shell, hybrid, and/or layer-by-layer architecture, to allow for fine-tuning of the nanoparticle so that delivery of the molecules and/or compositions of the disclosure can be enhanced.

The disclosed self-replicating RNA molecules and/or compositions comprising the self-replicating RNA molecules encoding any of the polypeptides of the disclosure can be encapsulated using one or more liposomes, lipoplexes, and/or lipid nanoparticles. Liposomes are artificially prepared vesicles which can primarily be composed of a lipid bilayer and can be used as a delivery vehicle for the administration of polynucleotides and self-replicating RNA molecules. Liposomes can be of different sizes such as, but not limited to, a multilamellar vesicle (MLV) which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but is not limited to, opsonins or ligands in order to improve the attachment of liposomes to unhealthy tissue or to activate events such as, but not limited to, endocytosis. Liposomes can contain a low or a high pH in order to improve the delivery of the polynucleotides and self-replicating RNA molecules disclosed herein.

The formation of liposomes can depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In some embodiments, the self-replicating RNA molecule is encapsulated in, bound to or adsorbed on a liposome, a lipoplex, a lipid nanoparticle, or combinations thereof, preferably the self-replicating RNA molecule is encapsulated in a lipid nanoparticle.

In some embodiments, the self-replicating RNA molecule encoding the any of the polypeptides of the disclosure can be fully encapsulated within the lipid portion of the particle, thereby protecting the RNA from nuclease degradation. "Fully encapsulated" means that the RNA is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In some embodiments, the self-replicating RNA molecules and/or compositions of the disclosure comprising the same can be formulated in a lipid vesicle which can have crosslinks between functionalized lipid bilayers. In some embodiments, the self-replicating RNA molecules and/or compositions of the disclosure can be formulated in a lipid-polycation complex. The formation of the lipid-polycation complex can be accomplished by methods known in the art. As a non-limiting example, the polycation can include a cationic peptide or a polypeptide such as, but not limited to, polylysine, polyornithine and/or polyarginine and the cationic peptides. In some embodiments, the self-replicating RNA molecules and/or compositions disclosed herein can be formulated in a lipid-polycation complex which can further include a neutral lipid such as, but not limited to, cholesterol or dioleoyl phosphatidylethanolamine (DOPE). The lipid nanoparticle formulation can be influenced by, but not limited to, the selection of the cationic lipid component, the degree of cationic lipid saturation, the nature of the PEGylation, ratio of all components and biophysical parameters such as size.

In some embodiments, the self-replicating RNA molecule disclosed herein is encapsulated in a lipid nanoparticle (LNP). Lipid nanoparticles typically comprise four different lipids—an ionizable lipid, a neutral helper lipid, cholesterol, and a diffusible polyethylene glycol (PEG) lipid. LNPs are similar to liposomes but have slightly different function and composition. LNPs are designed toward encapsulating polynucleotides, such as DNA, mRNA, siRNA and sRNA. Traditional liposomes contain an aqueous core surrounded by one or more lipid bilayers. LNPs may assume a micelle-like structure, encapsulating polynucleotides in a non-aqueous core. LNPs typically contain a cationic lipid, a non-cationic lipid, and a lipid that prevents aggregation of the particle (e.g., a PEG-lipid conjugate). LNPs are useful for systemic applications, as they exhibit extended circulation lifetimes following intravenous (i.e.) injection and accumulate at distal sites (e.g., sites physically separated from the administration site). The LNPs may have a mean diameter of about 50 nm to about 150 nm, such as about 60 nm to about 130 nm, or about 70 nm to about 110 nm, or about 70 nm to about 90 nm, and are substantially nontoxic. Preparation of polynucleotide loaded LNPs are disclosed in, e.g., U.S. Pat. Nos. 5,976,567; 5,981,501; 6,534,484; 6,586,410; 6,815,432; and PCT Publication No. WO 96/40964. Polynucleotide containing LNPs are described for example in WO2019/191780.

In some embodiments, the lipid nanoparticles comprise a cationic lipid (e.g., one or more cationic lipids or salts thereof described herein), a phospholipid, and a conjugated lipid that inhibits aggregation of the particles (e.g., one or more PEG-lipid conjugates). The lipid particles can also include cholesterol. The lipid particles may encapsulate at least 1, 2, 3, 4, 5, 6, 7, 8, 9, 10, or more self-replicating RNA molecules that encode for one or more polypeptides.

In some embodiments, the LNP formulations comprising a polycationic composition can be used for the delivery of the self-replicating RNA molecules described herein in vivo and/or ex vitro. The disclosure further provides a LNP formulations comprising a cationic lipid.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the pKa of the cationic lipid and is substantially neutral at a pH above the pKa. The cationic lipids may also be termed titratable cationic lipids. In some embodiments, the cationic lipids comprise: a protonatable tertiary amine (e.g., pH-titratable) head group; C18 alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, γ-DLen-C2K-DMA, DLin-M-C2-DMA (also known as MC2), DLin-M-C3-DMA (also known as MC3) and (DLin-MP-DMA)(also known as 1-B1 1).

The disclosure also provides an encapsulated self-replicating RNA molecule, wherein the cationic lipid comprises a protonatable tertiary amine. In some embodiments, the cationic lipid is di((Z)-non-2-en-1-yl) 8,8'-((((2-(dimethylamino)ethyl)thio)carbonyl)azanediyl) dioctanoate.

In some embodiments, the cationic lipid compounds are relatively non-cytotoxic. The cationic lipid compounds may be biocompatible and biodegradable. The cationic lipid may have a pKa in the range of approximately 5.5 to approximately 7.5, more preferably between approximately 6.0 and approximately 7.0.

The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the self-replicating RNA molecule to be delivered, they can be synthesized from commercially available starting materials; and/or they are pH responsive and can be engineered with a desired pKa.

Lipid nanoparticle formulations can be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and can be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain.

In some embodiments, the self-replicating RNA molecule can be packaged or encapsulated in cationic molecules, such as, polyamidoamine, dendritic polylysine, polyethylene irinine or polypropylene h-nine, polylysine, chitosan, DNA-gelatin coarcervates or DEAE dextran, dendrimers, or polyethylenimine (PEI).

In some embodiments, the lipid particles may comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g, HO-PEG-S, HO-PEG-S-NHS, HO-PEG-NH2).

The PEG moiety of the PEG-lipid conjugates described herein may comprise an average molecular weight ranging from 550 daltons to 10,000 daltons. Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof. In some embodiments, the PEG conjugated lipid is a DMG-PEG-2000.

The self-replicating RNA molecules can also be formulated in a particle comprising non-cationic lipids. Suitable non-cationic lipids include, for example, neutral uncharged, zwitterionic, or anionic lipids capable of producing a stable complex. Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoylo-leoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), phosphatidylethanolamine phosphatidylethanolamine phosphatidylethanolamine phosphatidylethanolamine, phosphatidylethanolamine, phosphatidylethanolaminedipalmitoyl-dimyristoyl-distearoyl-monomethyl-dimethyl-dielaidoyl-stearoyloleoyl-hosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5a-cholestanol, 5a-coprostanol, cholesteryl-(2'-hydroxy)-ethyl ether, cholesteryl-(4'-hydroxy)-butyl ether, and 6-ketocholestanol; non-polar analogues such as 5a-cholestane, cholestenone, 5a-cholestanone, 5a-cholestanone, and cholesteryl decanoate; and mixtures thereof. In preferred embodiments, the cholesterol derivative is a polar analogue such as cholesteryl-(4'-hydroxy)-butyl ether. In some embodiments, the phospholipid is DSPC. In some embodiments, the non-cationic lipid present in lipid particles comprises or consists of a mixture of one or more phospholipids and cholesterol or a derivative thereof. In some embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, LNPs may comprise 30-70% cationic lipid compound, 0-60% cholesterol, 0-30% phospholipid, and 1-10% polyethylene glycol (PEG).

In some embodiments, the cationic lipid, zwitterion lipid, cholesterol and conjugated lipid are combined in a molar ratio of 50:7:40:3, respectively in the lipid nanoparticle In some embodiments, the LNP formulations described herein can additionally comprise a permeability enhancer molecule.

In some embodiments, the nanoparticle formulations can be a carbohydrate nanoparticle comprising a carbohydrate carrier and self-replicating RNA molecule. As a non-limiting example, the carbohydrate carrier can include, but is not limited to, an anhydride-modified phytoglycogen or glycogen-type material, phtoglycogen octenyl succinate, phytoglycogen beta-dextrin, and anhydride-modified phytoglycogen beta-dextrin.

Kits

The disclosure also provides a kit comprising one or more compositions, one or more polynucleotides, one or more polypeptides or one or more vectors of the disclosure. The disclosure also provides a kit comprising one or more recombinant viruses of the disclosure. The kits may be used to facilitate performing the methods described herein. In some embodiments, the kit further comprises reagents to facilitate entry of the vaccines of the disclosure into a cell, such as lipid-based formulations or viral packaging materials.

In some embodiments, the kit comprises one or more Ad26 vectors comprising any of the polynucleotides of the disclosure. In some embodiments, the kit comprises one or more MVA vectors comprising any of the polynucleotides of the disclosure. In some embodiments, the kit comprises one or more GAd20 vectors comprising any of the polynucleotides of the disclosure. In some embodiments, the kit comprises one or more self-replicating RNA molecules comprising any of the polynucleotides of the disclosure.

In some embodiments, the kit comprises an Ad26 vector of the disclosure and a MVA vector of the disclosure. In some embodiments, the kit comprises a GAd20 vector of the disclosure and a MVA vector of the disclosure. In some embodiments, the kit comprises an Ad26 vector of the disclosure and a Gad20 vector of the disclosure. In some embodiments, the kit comprises a self-replicating RNA molecule of the disclosure and a Gad20 vector of the disclosure. In some embodiments, the kit comprises a self-replicating RNA molecule of the disclosure and a MVA vector of the disclosure. In some embodiments, the kit comprises a self-replicating RNA molecule of the disclosure and an Ad26 vector of the disclosure. In some embodiments, the kit comprises one or more polynucleotides of the disclosure. In some embodiments, the kit comprises one or more polypeptides of the disclosure. In some embodiment, the kit comprises one or more cells of the disclosure.

In some embodiments, the kit comprises:
a first vaccine comprising a recombinant virus derived from Ad26, GAd20, or MVA, or a self-replicating RNA molecule comprising a heterologous polynucleotide encoding a heterologous polypeptide, wherein the heterologous polypeptide comprises two or more polypeptides selected from the group consisting SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof; and a second vaccine comprising a recombinant virus derived from Ad26, Gad20 or MVA or a self-replicating RNA molecule comprising a heterologous polynucleotide encoding a heterologous polypeptide, wherein the heterologous polypeptide comprises two or more polypeptides selected from the group consisting SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, and fragments thereof.

In some embodiments, the kit comprises:

a first vaccine comprising a recombinant virus derived from Ad26, GAd20, or MVA or a self-replicating RNA molecule comprising a heterologous polynucleotide encoding a heterologous polypeptide, wherein the heterologous polypeptide comprises two or more polypeptides selected from the group consisting SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and fragments thereof; and a second vaccine comprising a recombinant virus derived from Ad26, Gad20 or MVA or a self-replicating RNA molecule comprising a heterologous polynucleotide encoding a heterologous polypeptide, wherein the heterologous polypeptide comprises two or more polypeptides selected from the group consisting SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and fragments thereof.

Other Molecules

Ovarian Cancer Neoantigen/HLA Complexes

The disclosure also provides a protein complex comprising an ovarian cancer neoantigen and HLA. The disclosure also provides a protein complex comprising a fragment of the ovarian cancer neoantigen and HLA. The disclosure also provides a protein complex comprising a variant of the ovarian cancer neoantigen and HLA. The disclosure also provides a protein complex comprising a variant of a fragment of the ovarian cancer neoantigen and HLA.

In some embodiments, the ovarian cancer neoantigen comprises the polypeptide sequence selected from the group of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403 and 405, and fragments thereof.

In some embodiments, HLA is class I HLA. In some embodiments, HLA is class II HLA. In some embodiments, HLA is HLA-A. In some embodiments, HLA is HLA-B. In some embodiments, HLA is HLA-C. In some embodiments, HLA is HLA-DP. In some embodiments, HLA is HLA-DQ. In some embodiments, HLA is HLA-DR. In some embodiments, HLA is HLA-A*01:01, A*02:01, A*03:01, A*24:02, B*07:02 or B*08:01. In some embodiments, the protein complex is conjugated to a detection agent or a cytotoxic agent.

The complex of the ovarian cancer neoantigen and HLA may be used to for example isolate cognate T cells in vitro or in vivo. The complex of the ovarian cancer neoantigen and HLA may also be conjugated to a detectable label and used as a detection agent to detect, visualize or isolate cognate TCR or T cells expressing the cognate TCR. The complex of the ovarian cancer neoantigen and HLA may also be conjugated to a cytotoxic agent and used to deplete or reduce the number of cells expressing the cognate TCR. The complex may be in its native configuration or alternatively the ovarian cancer neoantigen and/or the HLA may be engineered.

Engineering concepts include covalent coupling of the peptide to the HLA, for example by using covalent linkers that may be cleavable. The ovarian cancer neoantigen and HLA complex may be a monomer or a multimer. The ovarian cancer neoantigen and HLA complex may be coupled to a toxin or a detection agent. Various engineering concepts include expressing the complex as a covalent ovarian cancer neoantigen-β2-α2-α1-β1 chain or ovarian cancer neoantigen-β chain, e.g. as a soluble complex. Linkers which are at least 15 amino acids long may be used between the ovarian cancer neoantigen and the HLA. Alternatively, the complex may be expressed as covalently coupled ovarian cancer neoantigen-single chain β1-α1. The ovarian cancer neoantigen/HLA complex may also be expressed as a full length HLAαβ chains to which the ovarian cancer neoantigen is covalently coupled to the N-terminus of the α chain or alternatively the ovarian cancer neoantigen is associated with the αβ chain via non-covalent interactions. Various expression formats are disclosed in U.S. Pat. Nos. 5,976,551, 5,734,023, 5,820,866, 7,141, 656B2, 6,270,772B1 and 7,074,905B2. Additionally. the HLA may be expressed as a single chain construct which is mutated at al chain or stabilized via disulfide bonds via α2 and β2 domains as described in U.S. Pat. Nos. 8,377,447B2 and 8,828,379B2. The ovarian cancer neoantigen or fragment thereof may be coupled to the HLA via light sensitive or periodate sensitive cleavable linkers as described in U.S. Pat. No. 9,079,941B2. The ovarian cancer neoantigen/HLA complexes may be engineered into multimeric format. Multimeric formats may be generated by incorporating a reactive side chain to the C-terminus of the HLA α or β chain to facilitate cross-linking of two or more ovarian cancer neoantigen/HLA complexes, as described in U.S. Pat. No. 7,074,904B2. Alternatively, a biotinylation recognition sequence BirA may be incorporated to the C-terminus of the HLA α or β chain which is subsequently biotinylated and the multimer is formed by binding to avidin/streptavidin as described in US563536. Multimeric ovarian cancer neoantigen/HLA complexes may further be generated utilizing Fc fusions, coupling the ovarian cancer neoantigen/HLA complexes in dextran carriers, oligomerizing the via coiled-coil domains, utilizing additional biotinylation peptides or conjugating the ovarian cancer neoantigen/HLA complexes onto nanoparticles or chelate carrier as is described in U.S. Pat. Nos. 6,197,302B1, 6,268,411B1, US20150329617A1, EP1670823B1, EP1882700B1, EP2061807B1, US20120093934A1, US20130289253A1, US20170095544A1, US20170003288A1 and WO2017015064A1.

The disclosure also provides protein complex comprising human leucocyte antigen (HLA) and a polypeptide of the disclosure comprising the amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, or a fragment thereof.

In some embodiments, HLA may comprise class I or class II.

In some embodiments, HLA may comprise HLA-A, HLA-B or HLA-C.

In some embodiments, HLA may comprise HLA-DP, HLA-DQ or HLA-DR.

In some embodiments, HLA may comprise class I alleles HLA-A*01:01, A*02:01, A*03:01, A*24:02, B*07:02 or B*08:01.

Proteinaceous Molecules

The disclosure also provides an isolated proteinaceous molecule that specifically binds the polypeptide of the disclosure or the complex of the HLA and the polypeptide.

In some embodiments, the proteinaceous molecule is an antibody, an alternative scaffold, a chimeric antigen receptor (CAR) or a T cell receptor (TCR).

In some embodiments, the proteinaceous molecule is an antigen binding fragment of an antibody.

In some embodiments, the proteinaceous molecule is a multispecific molecule. In some embodiments, the proteinaceous molecule is a bispecific molecule. In some embodiments, the proteinaceous molecule is a trispecific molecule. In some embodiments, the multispecific molecule binds two or more distinct ovarian neoantigens. In some embodiments, the multispecific molecule binds an ovarian neoantigen and a T cell receptor (TCR) complex. In some embodiments, the multispecific molecule binds two or more distinct ovarian neoantigens and a T cell receptor (TCR) complex.

In some embodiments, the proteinaceous molecule is an antibody.

In some embodiments, the proteinaceous molecule is a multispecific antibody. In some embodiments, the proteinaceous molecule is a bispecific antibody. In some embodiments, the proteinaceous molecule is a trispecific antibody. In some embodiments, the proteinaceous molecule is a T cell redirecting molecule.

In instances where the ovarian neoantigen of the disclosure is part of an extracellular domain of a protein, the ovarian neoantigen may be used as a tumor associated antigen for recruiting T cells to tumors or targeting CAR-T and other cellular therapies to tumor utilizing antigen binding domains that selectively bind the ovarian neoantigen on tumor cells.

In instances in which the ovarian neoantigen is part of an intracellular domain, antigen binding domains having the ability to be delivered into intracellular compartments conjugated to cytotoxic agent or a therapeutic agent may be used as therapeutics. Alternatively, cells engineered to express cognate TCR which bind the ovarian neoantigen/HLA complex may be used as therapeutics.

In some embodiments, the proteinaceous molecule is an alternative scaffold.

In some embodiments, the proteinaceous molecule is a chimeric antigen receptor (CAR).

In some embodiments, the proteinaceous molecule is a T cell receptor (TCR).

Binding of the proteinaceous molecule to the ovarian neoantigen or the ovarian neoantigen/HLA complex of the disclosure may be determined experimentally using any suitable method. Such methods may utilize ProteOn XPR36, Biacore 3000 or KinExA instrumentation, ELISA or competitive binding assays known to those skilled in the art. The measured binding may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. "Insubstantial" refers to binding that is 100-fold less when compared to the measured binding of the proteinaceous molecule to the ovarian neoantigen of the disclosure. The proteinaceous molecule of the disclosure may further be characterized for their activity and function using know methods and those described herein, such as ability of the proteinaceous molecules to kill cells expressing the ovarian neoantigens or ovarian neoantigen/HLA complexes.

Antibodies and Antigen Binding Domains

Antibodies and antigen binding domains that specifically bind the ovarian neoantigens or the ovarian neoantigen/HLA complexes may be generated using known methods. Such antibodies may include immunoglobulin molecules of any type (e.g., IgG, IgE, IgM, IgD, IgA and IgY), class (e.g., IgG1, IgG2, IgG3, IgG4, IgA1, and IgA2) or subclass.

For example, the hybridoma method of Kohler and Milstein, Nature 256:495, 1975 may be used to generate monoclonal antibodies. In the hybridoma method, a mouse or other host animal, such as a hamster, rat or monkey, is immunized with one or more ovarian neoantigens, or/ovarian neoantigen/HLA complexes followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding and affinity for the ovarian neoantigen of the disclosure.

Various host animals may be used to produce the antibodies. For example, Balb/c mice, rats or chickens may be used to generate antibodies containing the VH/VL pair, and llama and alpaca may be used to generated heavy chain only (VHH) antibodies using standard immunization protocols. The antibodies made in non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) and superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or any combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rats carrying human immunoglobulin (Ig) loci in their genome may be used to generate human antibodies against the ovarian neoantigens of the ovarian neoantigen/HLA complexes, and are described in for example U.S. Pat. No. 6,150,584, Int. Patent Publ. No. WO99/45962, Int. Patent Publ. Nos. WO2002/066630, WO2002/43478, WO2002/043478 and WO1990/04036, Lonberg et al (1994) *Nature* 368:856-9; Green et al (1994) *Nature Genet.* 7:13-21; Green & Jakobovits (1998) *Exp. Med.* 188:483-95; Lonberg and Huszar (1995) *Int Rev Immunol* 13:65-93; Bruggemann et al., (1991) *Eur J Immunol* 21:1323-1326; Fishwild et al., (1996) *Nat Biotechnol* 14:845-851; Mendez et al., (1997) *Nat Genet* 15:146-156; Green (1999) *J Immunol Methods* 231:11-23; Yang et al., (1999) *Cancer Res* 59:1236-1243; Brüggemann and Taussig (1997) *Curr Opin Biotechnol* 8:455-458. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www.trianni_com) and Ablexis (http://_www-_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), domain antibodies or unpaired or paired antibody variable regions (Knappik et al., (2000) *J Mol Biol* 296:57-86; Krebs et al., (2001) *J Immunol Meth* 254:67-84; Vaughan et al., (1996) *Nature Biotechnology* 14:309-314; Sheets et al., (1998) *PITAS* (USA) 95:6157-6162; Hoogenboom and Winter (1991) *J Mol Biol* 227:381; Marks et al., (1991) *J Mol Biol* 222:581). The antibodies of the disclosure may be isolated for example from phage display library expressing antibody heavy and light chain variable regions as heterologous polypeptides with bacteriophage pIX coat protein as described in Shi et al., (2010) *J Mol Biol* 397:385-96, and Int. Patent Publ. No. WO09/085462). The libraries may be screened for phage binding to the ovarian neoantigen or the ovarian neoantigen/HLA complex and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580,717, 5,969,108, 6,172,197, 5,885,793; 6,521,404; 6,544,731; 6,555,313; 6,582,915 and 6,593,081. The antibodies may further be tested for their binding to the HLA/neoantigen complex or to the neoantigen alone.

Preparation of immunogenic antigens and monoclonal antibody production may be performed using any suitable technique, such as recombinant protein production or by chemical synthesis of peptides. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Antigen binding domains that specifically bind the ovarian neoantigen or ovarian neoantigen/HLA complexes may also be derived from the antibodies described herein. Antigen binding domains include single chain antibodies, Fab fragments, Fv fragments, single-chain Fv fragments (scFv), VHH domains, VH, VL, alternative scaffolds (e.g. non-antibody antigen binding domains), a divalent antibody fragment such as an (Fab)2'-fragment, F(ab') fragments, disulfide-linked Fvs (sdFv), intrabodies, minibodies, diabodies, triabodies and decabodies.

Bispecific and multispecific antibodies that specifically bind the ovarian neoantigen or ovarian neoantigen/HLA complexes and a second antigen may be generated using known methods. The second antigen may be a T cell receptor complex (TCR complex). The second antigen may be CD3 within the TCR complex. The bispecific and multispecific antibodies that specifically bind the ovarian neoantigen or ovarian neoantigen/HLA complexes of the disclosure and the second antigen may be engineered into any multivalent format using any known antigen binding domains format that specifically bind the ovarian neoantigens or ovarian neoantigen/HLA complexes and the second antigen. The antigen binding domain that specifically bind the ovarian neoantigen or ovarian neoantigen/HLA complex may be conjugated to one or more Fc domains or fragment thereof, or optionally to other scaffolds such as half-life extending moieties including albumin, PEG or transferrin.

Multispecific antibodies that specifically bind two or more ovarian neoantigens may provide a benefit in terms of improved specificity in targeting tumor cells expressing the ovarian neoantigens.

The antigen binding domains that specifically bind the ovarian neoantigen or ovarian neoantigen/HLA complexes may be engineered into full length multispecific antibodies which are generated using Fab arm exchange, in which substitutions are introduced into two monospecific bivalent antibodies within the Ig constant region CH3 domain which promote Fab arm exchange in vitro. In the methods, two monospecific bivalent antibodies are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing.

Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

CH3 mutations that may be used include technologies such as Knob-in-Hole mutations (Genentech), electrostatically-matched mutations (Chugai, Amgen, NovoNordisk, Oncomed), the Strand Exchange Engineered Domain body (SEEDbody) (EMD Serono), Duobody® mutations (Genmab), and other asymmetric mutations (e.g. Zymeworks).

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promote heavy chain heterodimerization are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849 (Zymeworks).

SEEDbody mutations involve substituting select IgG residues with IgA residues to promote heavy chai heterodimerization as described in US20070287170.

Other exemplary mutations that may be used are R409D_K370E/D399K_E357K, S354C_T366W/Y349C_T366S_L368A_Y407V, Y349C_T366W/S354C_T366S_L368A_Y407V, T366K/L351D, L351K/Y349E, L351K/Y349D, L351K/L368E, L351Y_Y407A/T366A_K409F, L351Y_Y407A/T366V_K409F, K392D/D399K, K392D/E356K, K253E_D282K_K322D/D239K_E240K_K292D, K392D_K409D/D356K_D399K as described in WO2007/147901, WO 2011/143545, WO2013157954, WO2013096291 and US2018/0118849.

Duobody® mutations (Genmab) are disclosed for example in U.S. Pat. No. 9,150,663 and US2014/0303356 and include mutations F405L/K409R, wild-type/F405L_R409K, T350I_K370T_F405L/K409R, K370W/K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/K409AGRH and Y407LWQ/K409AGRH.

Additional bispecific or multispecific structures into which the antigen binding domains that specifically bind the ovarian neoantigen or ovarian neoantigen/HLA complexes can be incorporated include Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)₂-Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, Receptor-Logics), Human Serum Albumin ScFv Fusion (Merrimack) and COMBODY (Epigen Biotech), dual targeting nanobodies (Ablynx), dual targeting heavy chain only domain antibodies.

Alternative Scaffolds

Alternative scaffolds (also referred to as antibody mimetics) that specifically bind the ovarian neoantigen or ovarian neoantigen/HLA complexes may be generated using various scaffolds known in the art and described herein. Alternative scaffolds may be monobodies, designed to incorporate the fibronectin type III domain (Fn3) of fibronectin or tenascin as a protein scaffold (U.S. Pat. Nos. 6,673,901; 6,348,584) or synthetic FN3 domains such as tencon as described in U.S. Pat. Publ. No. 2010/0216708 and U.S. Pat. Pub. No. 2010/0255056. Additional alternative scaffolds comprise Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer. Alternative scaffolds are single chain polypeptidic frameworks that contains a highly structured core associated with variable domains of high conformational tolerance allowing insertions, deletions, or other substitutions within the variable domains. Libraries introducing diversity to one or more variable domains, and in some instances to the structured core, may be generated using known protocols and the resulting libraries may be screened for binding to the neoantigen of the disclosure, and the identified binders may be further characterized for their specificity using known methods. Alternative scaffold may be derived from Protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain, or thioredoxin (Skerra, A., "Alternative Non-Antibody Scaffolds for Molecular Recognition," *Curr. Opin. Biotechnol.* 18:295-304 (2005); Hosse et al., "A New Generation of Protein Display Scaffolds for Molecular Recognition," *Protein Sci.* 15:14-27 (2006); Nicaise et al., "Affinity Transfer by CDR Grafting on a Nonimmunoglobulin Scaffold," *Protein Sci.* 13:1882-1891 (2004); Nygren and Uhlen, "Scaffolds for Engineering Novel Binding Sites in Proteins," *Curr. Opin. Struc. Biol.* 7:463-469 (1997).

Chimeric Antigen Receptors (CAR)

CARs may be generated that bind the ovarian neoantigens or the ovarian neoantigen/HLA complex by incorporating an antigen binding domain that specifically binds the ovarian neoantigens or the ovarian neoantigen/HLA complex to the extracellular domain of the CAR. CARs are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

The CAR typically comprises an extracellular domain that binds the antigen (e.g. the ovarian neoantigen or the ovarian neoantigen/HLA complex), an optional linker, a transmembrane domain, and a cytosolic domain comprising a costimulatory domain and/or a signaling domain.

The extracellular domain of the CAR may contain any polypeptide that specifically binds the desired antigen (e.g. ovarian neoantigen). The extracellular domain may comprise a scFv, a portion of an antibody or an alternative scaffold. The CARs may also be engineered to bind two or more desired antigens that may be arranged in tandem and separated by linker sequences. For example, one or more domain antibodies, scFvs, llama VHH antibodies or other VH only antibody fragments may be organized in tandem via a linker to provide bispecificity or multispecificity to the CAR.

The transmembrane domain of the CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI la, CD18), ICOS (CD278), 4-1 BB (CD137), 4-1 BBL, GITR, CD40, BAFFR, HVEM (LIGHTR), SLAMF7, NKp80 (KLRFI), CD160, CD1 9, IL2R beta, IL2R gamma, IL7R a, ITGA1, VLA1, CD49a, ITGA4, IA4, CD49D, ITGA6, VLA-6, CD49f, ITGAD, CDI Id, ITGAE, CD103, ITGAL, CDI la, LFA-1, ITGAM, CDI lb, ITGAX, CDI lc, ITGB1, CD29, ITGB2, CD1 8, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMFI), CD152 (CTLA4), CD223 (LAG3), CD270 (HVEM), CD278 (ICOS), DAP10, LAT, NKD2C SLP76, TRIM, BTLA, GITR, CD226, HVEM, and ZAP70.

The intracellular signaling domain of the CAR may be derived from the signaling domains of for example CD3ζ, CD3ε, CD22, CD79a, CD66d, CD39 DAP10, DAP12, Fc epsilon receptor I gamma chain (FCER1G), FcR β, CD3δ, CD3γ, CD5, CD226, or CD79B. "Intracellular signaling domain" refers to the part of the CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker of the CAR positioned between the extracellular domain and the transmembrane domain may be a polypeptide of about 2 to 100 amino acids in length. The linker may include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof.

The linker may also be derived from a hinge region or portion of the hinge region of any immunoglobulin. Non-limiting examples of linkers include a part of human CD8α chain, partial extracellular domain of CD28, FcγRIIIa receptor, IgG, IgM, IgA, IgD, IgE, an Ig hinge, or functional fragment thereof.

Exemplary CARs that may be used are for example CAR that contains an extracellular domain that binds the ovarian neoantigen of the disclosure, CD8 transmembrane domain and CD3ζ signaling domain. Other exemplary CARs contain an extracellular domain that binds the ovarian neoantigen of the disclosure, CD8 or CD28 transmembrane domain, CD28, 41BB or OX40 costimulatory domain and CD3ζ signaling domain.

The CARs are generated by standard molecular biology techniques. The extracellular domain that binds the desired antigen may be derived from antibodies or their antigen binding fragments generated using the technologies described herein.

T Cell Receptor (TCR)

TCRs may be generated that bind the ovarian neoantigen/HLA complexes. The TCRs may be identified based on T cell binding to the ovarian neoantigen/HLA complex, isolating the T cell and sequencing the TCR expressed in the T cells. The identified TCRs may be identified from αβ T cells or γδ T cells. The identified TCRs may be further engineered to improve their affinity, stability, solubility or the like.

TCRs may be affinity matured utilizing the same technologies utilized to affinity mature immunoglobulins. TCRs may be expressed as soluble TCRs which have been cysteine stabilized, they can be stabilized by engineering mutations onto α/β interaction surface, for example G192R on α chain and R208G on β chain. TCRs may also be stabilized by engineering cysteine residues which form disulfide bonds into TCR constant domain, by introducing mutations into the hydrophobic core, such as at positions 11, 13, 19, 21, 53, 76, 89, 91 or 94 of α chain, utilizing domain swaps including swaps between α and β chain V domains, transmembrane domains or constant domains as described in U.S. Pat. Nos. 7,329,731, 7,871,817B2, 7,569,664, 9,133,264, 9,624,292, US20120252742A1, US2016/0130319, EP3215164A1, EP3286210A1, WO2017091905A1 or U.S. Pat. No. 9,884,075.

Cells Expressing the CARs or the TCRs of the Disclosure

Cells expressing the CARs or the TCRs that specifically bind the ovarian neoantigens of the disclosure of the ovarian neoantigen/HLA complexes of the disclosure are within the scope of the disclosure. The disclosure also provides isolated cells comprising the CAR of the disclosure or the TCR of the disclosure. In some embodiments, the isolated cells are transduced with the CAR or the TCR of the disclosure, resulting in constitutive expression of the CAR or the TCR of the disclosure on the surface of the cell. The cells expressing the CAR or the TCR of the disclosure may further be engineered to express one or more co-stimulatory molecules. Exemplary co-stimulatory molecules are CD28, ICOS, LIGHT, GITR, 4-1BB and OX40. The cells expressing the CAR or the TCR of the disclosure may further be engineered to produce one or more cytokines or chemokines or proinflammatory mediators, such as TNFα, IFNγ, IL-2, IL-3, IL-6, IL-7, IL-11, IL-12, IL-15, IL-17 or IL-21. The cells may have their endogenous TCR locus and/or HLA locus inactivated using known gene editing technologies. In some embodiment, the cell comprising the CAR or the TCR of the disclosure is a T cell, a natural killer (NK) cell, a cytotoxic T lymphocyte (CTL), a regulatory T cell (Treg), a human embryonic stem cell, a lymphoid progenitor cell, a T cell-precursor cell, or a pluripotent stem cell or induced pluripotent stem cell (iPSC) from which lymphoid cells may be differentiated.

In some embodiments, the isolated cell comprising the CAR or the TCR of the disclosure is a T cell. The T cell may be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from any source, including to bone marrow, blood, lymph node, thymus, or other tissues or fluids. T cells may also be enriched for or purified. The T cell may be a human T cell. The T cell may be a T cell isolated from a human. The T cell can be any type of T cell and may be of any developmental stage, including, $CD4^+CD8^+$ double positive T cells, $CD8^+$ T cells (e.g., cytotoxic T cells), $CD4^+$ helper T cells, e.g., Th1 and Th2 cells, peripheral blood mononuclear cells (PBMCs), peripheral blood leukocytes (PBLs), tumor infiltrating cells, memory T cells, naïve T cells, and the like.

The T cell may be a $CD8^+$ T cell or a $CD4^+$ T cell. The T cell may be an αβ T cell or a γδ T cell.

In some embodiments, the isolated cell comprising the CAR of the disclosure or the TCR of the disclosure is a NK cell.

In some embodiments, the isolated cell comprising the CAR of the disclosure or the TCR of the disclosure is an αβ T cell.

In some embodiments, the isolated cell comprising the CAR of the disclosure or the TCR of the disclosure is a γδ T cell.

In some embodiments, the isolated cell comprising the CAR of the disclosure or the TCR of the disclosure is a CTL.

In some embodiments, the isolated cell comprising the CAR of the disclosure or the TCR of the disclosure is a human embryonic stem cell.

In some embodiments, the isolated cell comprising the CAR of the disclosure or the TCR of the disclosure is a lymphoid progenitor cell.

In some embodiments, the isolated cell comprising the CAR of the disclosure or the TCR of the disclosure is a pluripotent stem cell.

In some embodiments, the isolated cell comprising the CAR of the disclosure or the TCR of the disclosure is an induced pluripotent stem cell (iPSC).

The cells of the disclosure may be generated by introducing a lentiviral vector comprising a desired CAR or TCR into the cells using known methods. The cells of the disclosure are able to replicate in vivo resulting in long-term persistence that can lead to sustained tumor control.

Conjugates with Cytotoxic Agents, Drugs, Detectable Labels, and the Like

The polypeptides, the heterologous polypeptide and the proteinaceous molecules binding them may be conjugated to a cytotoxic agent, therapeutics, detectable labels and the like. These molecules are referred herein to immunoconjugates. The immunoconjugates comprising the ovarian neoantigens may be used to detect, deliver payload or kill cells expressing a HLA molecule that binds the ovarian neoantigen. The immunoconjugates comprising the antibodies, antigen binding fragments or alternative scaffolds which specifically bind the ovarian neoantigen or the ovarian neoantigen/HLA complex may be used to detect, deliver payload or kill cells that express the ovarian neoantigen on their surface in the context or a larger protein or in complex with HLA, or detect intracellular ovarian neoantigens after lysis of the cells.

In some embodiments, the immunoconjugate comprises a detectable label.

In some embodiments, the immunoconjugate comprises a cytotoxic agent.

In some embodiments, the immunoconjugate comprises a therapeutic.

Detectable label includes compositions that can be visualized via spectroscopic, photochemical, biochemical, immunochemical, or chemical means. Detectable labels may also include cytotoxic agents, cytotoxic agents may include detectable labels.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field.

Exemplary radioactive isotopes may be γ-emitting, Auger-emitting, β-emitting, an alpha-emitting or positron-emitting radioactive isotope. Exemplary radioactive isotopes include $^{3}$H, $^{11}$C, $^{13}$C, $^{15}$N $^{18}$F, $^{19}$F, $^{55}$Co, $^{57}$Co, $^{60}$Co, $^{61}$Cu, $^{62}$Cu, $^{64}$Cu, $^{67}$Cu, $^{68}$Ga, $^{72}$As, $^{75}$Br, $^{86}$Y, $^{89}$Zr, $^{90}$Sr, $^{94m}$Tc, $^{99m}$Tc, $^{115}$In, $^{123}$I, $^{124}$I, $^{125}$I, $^{131}$I, $^{211}$At, $^{212}$Bi, $^{213}$Bi, $^{223}$Ra, $^{226}$Ra, $^{225}$Ac and $^{227}$Ac.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e. iodine) to 83 (i.e. bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^{+}$, $Ca^{2+}$, $Cr^{2+}$, $Cr^{3+}$, $Cr^{6+}$, $Co^{2+}$, $Co^{3+}$, $Cu^{+}$, $Cu^{2+}$, $Cu^{3+}$, $Ga^{3+}$, $Gd^{3+}$, $Au^{+}$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^{+}$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyanate (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The immunoconjugates comprising a detectable label may be used as an imaging agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}$Bi, $^{131}$I, $^{131}$In, $^{90}$Y, and $^{186}$Re.

In some embodiments, the cytotoxic agent is dolastatins or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the antibody of the invention through the N (amino) terminus or the C (carboxyl) terminus of the peptidic drug moiety (WO02/088172), or via any cysteine engineered into the antibody.

The immunoconjugates may be made using known methods.

In some embodiments, the detectable label is complexed with a chelating agent.

The detectable label, cytotoxic agent or therapeutic may be linked directly, or indirectly via a linker, to the polypeptides, the heterologous polypeptides or the proteinaceous molecules that bind the polypeptides or the heterologous polypeptides. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

Methods of Treatment, Uses and Administration of any of the Compositions Herein

Provided herein are methods for treating a subject with the compositions disclosed herein. The methods provided herein comprise administering a composition comprising any of the polynucleotides, polypeptides, vectors, and recombinant viruses, of the disclosure. The composition comprising polynucleotides, polypeptides, vectors, recombinant viruses, and administration regimens of the disclosure may be used to treat, prevent or reduce the risk of a clinical condition.

In some embodiments, the clinical condition is ovarian cancer.

"Ovarian cancer" is meant to include all types of cancerous growths within the ovary or oncogenic processes, metastatic tissues or malignantly transformed cells, tissues, or organs, irrespective of histopathology type or stage of invasiveness.

In some embodiments, the ovarian cancer is an adenocarcinoma.

In some embodiments, the ovarian cancer is a metastatic ovarian cancer. In some embodiments, the ovarian cancer has metastasized to pelvis, fallopian tubes, bladder, rectum, uterus, lining of the abdomen, abdomen, lymph nodes, liver, lungs, spleen, skin, brain, or bone, or any combination thereof.

In some embodiments, the ovarian cancer is an epithelial ovarian cancer, germ cell ovarian cancer, stromal cell ovarian cancer or small cell carcinoma, or a combination thereof.

In some embodiments, the ovarian cancer is stage 1 ovarian cancer. In some embodiments, the ovarian cancer is stage 2 ovarian cancer. In some embodiments, the ovarian cancer is stage 3 ovarian cancer. In some embodiments, the ovarian cancer is stage 4 ovarian cancer.

In some embodiments, the ovarian cancer is an epithelial ovarian cancer.

In some embodiments, the ovarian cancer is a relapsed or a refractory ovarian cancer.

In some embodiments, the ovarian cancer is a platinum-resistant ovarian cancer.

In some embodiments, the ovarian cancer is sensitive to chemotherapy.

In some embodiments, the ovarian cancer is insensitive to chemotherapy.

In some embodiments, the subject is treatment naïve.

In some embodiments, the subject has received surgery.

In some embodiments, the subject has an elevated level of the cancer antigen 125 (CA 125). CA 125 is elevated in a subject when the level is typically about ≥35 U/mL. CA 125 levels may also be compared to post-surgery levels.

Provided herein, are methods for treating, preventing or reducing the risk of ovarian cancer in a subject comprising administering the various compositions of the disclosure that can be used to introduce the ovarian cancer neoantigens of the disclosure into the subject, e.g. the polynucleotides, the heterologous polynucleotides, the polypeptides, the heterologous polypeptides, the vectors, the recombinant viruses and vaccines of the disclosure. Additionally, the proteinaceous molecules that bind the ovarian cancer neoantigens of the disclosure can be used in the methods of the disclosure.

The disclosure also provides methods for inducing an immune response in a subject comprising administering the various compositions of the disclosure that can be used to introduce the ovarian cancer neoantigens of the disclosure into the subject, e.g. the polynucleotides, the heterologous polynucleotides, the polypeptides, the heterologous polypeptides, the vectors, the recombinant viruses and vaccines of the disclosure.

In some embodiments, the ovarian cancer neoantigens identified herein are present at a frequency of at least about 1% or more, about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 16% or more about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 35% or more, about 40% or more, about 45% or more, about 50% or more, about 55% or more, about 60% or more, about 65% or more or about 70% or more in a population of subjects having the ovarian cancer.

In some embodiments, the method of treating, preventing, reducing a risk of onset or delaying the onset of ovarian cancer in a subject comprises administering to the subject in need thereof any of the compositions disclosed herein, and wherein the administration comprises one or more administrations of the composition. In some embodiments, the ovarian cancer is selected from epithelial ovarian cancer, germ cell ovarian cancer, stromal cell ovarian cancer, small cell ovarian cancer, relapsed or refractory ovarian cancer, platinum-resistant ovarian cancer, stage 1 ovarian cancer, stage 2 ovarian cancer, stage 3 ovarian cancer, and stage 4 ovarian cancer, In some embodiments, the method of inducing an immune response comprises administering to the subject in need thereof any of the compositions disclosed herein, and wherein the administration comprises one or more administrations of the composition.

In any of the methods disclosed herein, the composition that is administered to a subject may comprise a recombinant virus selected from adenovirus, alphavirus, poxvirus, adeno-associated virus, retrovirus, or may comprise a self-replicating RNA, or a combination thereof.

In some embodiments, the recombinant virus comprises the ovarian cancer neoantigens of the disclosure, e.g. the polynucleotides, the heterologous polynucleotides, the polypeptides, the heterologous polypeptides and the vectors, of the disclosure.

In some embodiments, the virus or recombinant virus is selected from Ad26, MVA, GAd20, and combinations thereof.

In some embodiments, the composition comprises the rAd26 of the disclosure.

In some embodiments, the composition comprises the rMVA of the disclosure.

In some embodiments, the composition comprises the rGAd of the disclosure.

In some embodiments, the composition comprises the rGAd20 of the disclosure.

In some embodiments, the composition comprises the rCh20 of the disclosure.

In some embodiments, the composition comprises the self-replicating RNA of the disclosure.

Second Administration

In some embodiments, the methods disclosed herein comprise one or more administrations of the compositions provided in the disclosure. For example, the method comprises a first administration followed by a second administration, with a time period between the two administrations.

In some embodiments, the first administration and the second administration may comprise the same or different compositions. For example, the first administration may comprise a composition comprising a recombinant virus selected from Ad26, GAd20, or MVA or a self-replicating RNA molecule comprising a polynucleotide encoding for any of the polypeptide of the disclosure, or combination thereof. In some embodiments, the second administration may comprise a composition comprising a recombinant virus selected from Ad26, GAd20, or MVA or a self-replicating RNA molecule comprising a polynucleotide encoding for any of the polypeptides of the disclosure, or combination thereof.

In some embodiments, the first administration and the second administration are administered once in a lifetime of the subject. In some embodiments, first administration and the second administration are administered two or more times in the lifetime of the subject. In some embodiments, the time period between the first administration and the second administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks. In some embodiments, the time period between the first administration and the second administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the first administration and the second administration is about 2 weeks.

In some embodiments, the time period between the first administration and the second administration is about 4 weeks.

In some embodiments, the first administration and the second administration constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

The following example is provided to further describe some of the embodiments disclosed herein. The examples are intended to illustrate, not to limit, the disclosed embodiments. In some embodiments, the first administration and second administration can comprise any combination of recombinant virus or self-replicating RNA molecule provided in Table 1 comprising a polynucleotide encoding one or more polypeptides of the disclosure, or any combination thereof.

TABLE 1

Recombinant Virus and self-replicating RNA molecule composition in first and second administration

| First administration | Second administration |
| --- | --- |
| Ad26 | MVA |
| Ad26 | GAd20 |
| Ad26 | Self-replicating RNA molecule |
| Ad26 | Ad26 |
| MVA | Ad26 |
| MVA | GAd20 |
| MVA | Self-replicating RNA molecule |
| MVA | MVA |
| GAd20 | Ad26 |
| GAd20 | MVA |
| GAd20 | Self-replicating RNA molecule |
| GAd20 | GAd20 |
| Self-replicating RNA molecule | Ad26 |
| Self-replicating RNA molecule | MVA |
| Self-replicating RNA molecule | GAd20 |
| Self-replicating RNA molecule | Self-replicating RNA molecule |

In some embodiments, the first administration and second administration can comprise a polynucleotide encoding for any polypeptide of the disclosure or combination thereof. In some embodiments, the first administration and second administration can comprise a polynucleotide encoding for any polypeptide selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and combinations thereof. In some embodiments, the first administration and second administration can comprise a polynucleotide encoding two or more tandem repeats of any polypeptides of the disclosure.

In some embodiments, the first and the second administration may comprise a distinct recombinant virus.

In some embodiments, the first and the second administration comprise a recombinant virus comprising a polynucleotide encoding for a polypeptide of distinct amino acid sequence.

In some embodiments, a method of inducing an immune response or a method of treating, preventing, reducing a risk of onset or delaying the onset of ovarian cancer in a subject comprises a treatment cycle, wherein each cycle comprises:
  a first administration comprising a first composition comprising a recombinant virus or self-replicating RNA molecule comprising a polynucleotide encoding one or more polypeptides of the disclosure or combination thereof, wherein the virus or recombinant virus is selected from Ad26, MVA, GAd20; and
  a second administration comprising a second composition comprising a recombinant virus, or a self-replicating RNA molecule comprising a polynucleotide encoding for any polypeptide of the disclosure, or combination thereof, wherein the recombinant virus is selected from Ad26, MVA, GAd20.

Third Administration

In some embodiments, any of the methods disclosed herein may further comprise a third administration. For example, the method may comprise a first administration, a second administration, followed by a third administration, with a time period between each administration.

In some embodiments, the first administration, second administration, and third administration may comprise the same or different compositions. For example, the first administration may comprise a composition comprising a recombinant virus selected from Ad26, GAd20, or MVA or a self-replicating RNA molecule comprising a polynucleotide encoding for any of the polypeptides of the composition or combination thereof. In some embodiments, the second administration may comprise a recombinant virus selected from Ad26, GAd20, or MVA or a self-replicating RNA molecule comprising a polynucleotide encoding for any of the polypeptides of the composition or combination thereof. In some embodiments, the third administration may comprise a composition comprising a recombinant virus selected from Ad26, GAd20, or MVA or a self-replicating RNA molecule comprising a polynucleotide encoding for any of the polypeptides of the composition or combination thereof.

In some embodiments, the first administration, second administration and third administration comprise a composition comprising a recombinant virus selected from Ad26, GAd20, or MVA or a self-replicating RNA molecule comprising a polynucleotide encoding one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and combinations thereof.

In some embodiments, the first, the second or the third administration comprise a polynucleotide encoding two or more tandem repeats of any polypeptides of the disclosure.

In some embodiments, the first, the second or the third administration may comprise a distinct recombinant virus.

In some embodiments, the first, the second or the third administration may comprise a recombinant virus comprising a polynucleotide encoding for a polypeptide of distinct amino acid sequence.

For example, the first administration may comprise a polynucleotide encoding one or more polypeptides selected from the group consisting of SEQ ID NOs 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and combinations thereof. In some embodiments, the second administration may comprise a polynucleotide encoding one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and combination thereof. In some embodiments, the third administration may comprise a polynucleotide encoding one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and combinations thereof.

In some embodiments, the first administration, the second administration, and the third administration are administered once in a lifetime of the subject. In some embodiments, the first, second, and third administration are administered two or more times in the lifetime of the subject. In some embodiments, the time period between the second administration and the third administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the second administration and the third administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the second administration and the third administration is about 6 weeks.

In some embodiments, the time period between the second administration and the third administration is about 8 weeks.

In some embodiments, the first administration, second administration, and third administration together constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

The following examples are provided to further describe some of the embodiments disclosed herein. The first, second, and third administrations used in the methods disclosed herein can comprise any combination of the epitopes and compositions provided in Table 2.

TABLE 2

Recombinant Virus and self-replicating RNA molecule composition in first, second and third administration

| First administration | Second administration | Third administration |
|---|---|---|
| Ad26 | Ad26 | Ad26 |
| Ad26 | Ad26 | MVA |
| Ad26 | Ad26 | GAd20 |
| Ad26 | Ad26 | Self-replicating RNA molecule |
| Ad26 | MVA | Ad26 |

TABLE 2-continued

Recombinant Virus and self-replicating RNA molecule composition in first, second and third administration

| First administration | Second administration | Third administration |
|---|---|---|
| Ad26 | MVA | MVA |
| Ad26 | MVA | GAd20 |
| Ad26 | MVA | Self-replicating RNA molecule |
| Ad26 | GAd20 | Ad26 |
| Ad26 | GAd20 | MVA |
| Ad26 | GAd20 | GAd20 |
| Ad26 | GAd20 | Self-replicating RNA molecule |
| Ad26 | Self-replicating RNA molecule | Ad26 |
| Ad26 | Self-replicating RNA molecule | MVA |
| Ad26 | Self-replicating RNA molecule | GAd20 |
| Ad26 | Self-replicating RNA molecule | Self-replicating RNA molecule |
| MVA | Ad26 | Ad26 |
| MVA | Ad26 | MVA |
| MVA | Ad26 | GAd20 |
| MVA | Ad26 | Self-replicating RNA molecule |
| MVA | MVA | Ad26 |
| MVA | MVA | MVA |
| MVA | MVA | GAd20 |
| MVA | MVA | Self-replicating RNA molecule |
| MVA | GAd20 | Ad26 |
| MVA | GAd20 | MVA |
| MVA | GAd20 | GAd20 |
| MVA | GAd20 | Self-replicating RNA molecule |
| MVA | Self-replicating RNA molecule | Ad26 |
| MVA | Self-replicating RNA molecule | MVA |
| MVA | Self-replicating RNA molecule | GAd20 |
| MVA | Self-replicating RNA molecule | Self-replicating RNA molecule |
| GAd20 | Ad26 | Ad26 |
| GAd20 | Ad26 | MVA |
| GAd20 | Ad26 | GAd20 |
| GAd20 | Ad26 | Self-replicating RNA molecule |
| GAd20 | MVA | Ad26 |
| GAd20 | MVA | MVA |
| GAd20 | MVA | GAd20 |
| GAd20 | MVA | Self-replicating RNA molecule |
| GAd20 | GAd20 | Ad26 |
| GAd20 | GAd20 | MVA |
| GAd20 | GAd20 | GAd20 |
| GAd20 | GAd20 | Self-replicating RNA molecule |
| GAd20 | Self-replicating RNA molecule | Ad26 |
| GAd20 | Self-replicating RNA molecule | MVA |
| GAd20 | Self-replicating RNA molecule | GAd20 |
| GAd20 | Self-replicating RNA molecule | Self-replicating RNA molecule |
| Self-replicating RNA molecule | Ad26 | Ad26 |
| Self-replicating RNA molecule | Ad26 | MVA |
| Self-replicating RNA molecule | Ad26 | GAd20 |
| Self-replicating RNA molecule | Ad26 | Self-replicating RNA molecule |
| Self-replicating RNA molecule | MVA | Ad26 |
| Self-replicating RNA molecule | MVA | MVA |
| Self-replicating RNA molecule | MVA | GAd20 |
| Self-replicating RNA molecule | MVA | Self-replicating RNA molecule |
| Self-replicating RNA molecule | GAd20 | Ad26 |
| Self-replicating RNA molecule | GAd20 | MVA |
| Self-replicating RNA molecule | GAd20 | GAd20 |
| Self-replicating RNA molecule | GAd20 | Self-replicating RNA molecule |
| Self-replicating RNA molecule | Self-replicating RNA molecule | Ad26 |
| Self-replicating RNA molecule | Self-replicating RNA molecule | MVA |
| Self-replicating RNA molecule | Self-replicating RNA molecule | GAd20 |
| Self-replicating RNA molecule | Self-replicating RNA molecule | Self-replicating RNA molecule |

In some embodiments, a method of inducing an immune response or a method of treating, preventing, reducing a risk of onset or delaying the onset of ovarian cancer in a subject comprises a treatment cycle, wherein each cycle comprises:
  a first administration comprising a first composition comprising a recombinant virus or self-replicating RNA molecule comprising a polynucleotide encoding one or more polypeptides of the disclosure, wherein the recombinant virus is selected from Ad26, MVA, GAd2O; and
  a second administration comprising a second composition comprising a recombinant virus or self-replicating RNA molecule comprising a polynucleotide encoding one or more polypeptides of the disclosure, wherein the recombinant virus is selected from Ad26, MVA, GAd20; and
  a third administration comprising a third composition comprising a recombinant virus or self-replicating RNA molecule comprising a polynucleotide encoding one or more polypeptides of the disclosure, wherein the recombinant virus is selected from Ad26, MVA, GAd20.

Fourth Administration

In some embodiments, any of the methods disclosed herein may further comprise a fourth administration. For example, the method may comprise a first administration, a second administration, a third administration, and a fourth administration, with a time period between each administration. In some embodiments, the first administration, second administration, third administration, and fourth administration may comprise the same or different compositions. For example, the fourth administration may comprise a composition comprising a recombinant virus selected from Ad26, GAd20, or MVA or a self-replicating RNA molecule encoding one or more polypeptides of the disclosure.

In some embodiment the first administration, the second administration, the third administration, and the fourth administration comprise a composition comprising a recombinant virus selected from Ad26, GAd20, or MVA or a self-replicating RNA molecule encoding one or more polypeptides selected from the group consisting of SEQ ID NO 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, and combinations thereof.

In some embodiments, the first, the second, the third, or the fourth administration comprise a polynucleotide encoding two or more tandem repeats of any polypeptides of the disclosure.

In some embodiments, the first, the second, the third, or the fourth administration may comprise a distinct recombinant virus.

In some embodiments, the first, the second, the third or the fourth administration may comprise a recombinant virus comprising a polynucleotide encoding for a polypeptide of distinct amino acid sequence.

In some embodiments, the first administration, the second administration, the third administration, and the fourth administration are administered once in a lifetime of the subject. In some embodiments, the first, second, third, and the fourth administration are administered two or more times in the lifetime of the subject.

In some embodiments, the time period between the third administration and the fourth administration is about 1 week to about 2 weeks, about 1 week to about 4 weeks, about 1 week to about 6 weeks, about 1 week to about 8 weeks, about 1 week to about 12 weeks, about 1 week to about 20 weeks, about 1 week to about 24 weeks, or about 1 week to about 52 weeks.

In some embodiments, the time period between the third administration and the fourth administration is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In some embodiments, the time period between the third administration and the fourth administration is about 4 weeks.

In some embodiments, the time period between the third administration and the fourth administration is about 8 weeks.

In some embodiments, the first administration, second administration, third administration, and the fourth administration together constitute a cycle, and the treatment regime may include two or more cycles, each cycle being spaced apart by about 1 month, about 2 months, about 3 months, about 4 months, about 5 months, about 6 months, about 7 months, about 8 months, about 9 months, about 10 months, about 11 months, or about 12 months.

In some embodiments, a method of inducing an immune response or a method of treating, preventing, reducing a risk of onset or delaying the onset of ovarian cancer in a subject comprises a treatment cycle, wherein each cycle comprises:
a first administration comprising a first composition comprising a recombinant virus, or self-replicating RNA molecule comprising a polynucleotide encoding one or more polypeptides of the disclosure, wherein the recombinant virus is selected from Ad26, MVA, GAd20; and
a second administration comprising a second composition comprising a recombinant virus, or self-replicating RNA molecule comprising a polynucleotide encoding one or more polypeptides of the disclosure, wherein the recombinant virus is selected from Ad26, MVA, GAd20; and
a third administration comprising a third composition comprising a recombinant virus, or self-replicating RNA molecule comprising a polynucleotide encoding one or more polypeptides of the disclosure, wherein the recombinant virus is selected from Ad26, MVA, GAd20, or a self-replicating RNA molecule; and
a fourth administration comprising a fourth composition comprising a recombinant virus, or self-replicating RNA molecule comprising a polynucleotide encoding one or more polypeptides of the disclosure, wherein the recombinant virus is selected from Ad26, MVA, GAd20.

Maintenance Administration

In some embodiments, the method further comprises administering to the subject a composition at regular intervals during the treatment cycles, and may continue even after the treatment cycles have ended. For example, the composition may be administered to a subject every month during the treatment regimen, and may continue for additional 6 months. In some embodiments, the composition may be administered between two treatment cycles. In some embodiments, the composition may be any of the compositions disclosed herein, such as a composition comprising a vector selected from Ad26 vector, GAd20 vector, MVA vector or self-replicating RNA molecule encoding the epitope sequences Dose and Route of Administration The compositions of the disclosure may be administered to a subject by a variety of routes such as subcutaneous, topical, oral and intramuscular. Administration of the compositions may be accomplished orally or parenterally. Methods of parenteral delivery include topical, intra-arterial (directly to the tissue), intramuscular, intradermal, subcutaneous, intramedullary, intrathecal, intraventricular, intravenous, intraperitoneal, or intranasal administration. The present disclosure also has the objective of providing suitable topical, oral, systemic and parenteral formulations for use in the methods of prophylaxis and treatment.

In some embodiments, intramuscular administration of the vaccine composition can be achieved by using a needle. An alternative is the use of a needleless injection device to administer the composition (using, e.g., Biojector™) or a freeze-dried powder containing the vaccine.

For intravenous, cutaneous or subcutaneous injection, or injection at the site of affliction, the vaccine composition may be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation may also be employed.

Typically, administration will have a prophylactic aim to generate an immune response against the ovarian neoantigens before development of symptoms of ovarian cancer.

The compositions of the disclosure are administered to a subject, giving rise to an immune response in the subject. The amount of the vaccine or composition able to induce a detectable immune response is defined to be an "immunologically effective dose." The compositions of the disclosure may induce a humoral as well as a cell-mediated immune response. In a typical embodiment the immune response is a protective immune response.

In some embodiments, the methods of treating, preventing, reducing a risk of onset or delaying the onset of ovarian cancer in a subject, comprise administering to the subject a therapeutically effective amount of one or more vaccines of the disclosure.

In some embodiments, the methods of treating, preventing, reducing a risk of onset or delaying the onset of ovarian cancer in a subject, comprise administering to the subject a therapeutically effective amount of one or more compositions of the disclosure.

In some embodiments, the method of creating an immune response in a subject, comprise administering to the subject an immunologically therapeutically effective amount of one or more compositions of the disclosure.

In some embodiments, the method of treating, preventing, reducing a risk of onset or delaying the onset of ovarian cancer in a subject, comprises administering to the subject a therapeutically effective amount of a vaccine or composition comprising a polynucleotide encoding one or more polypeptide of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375 or fragments thereof, thereby treating, preventing, reducing a risk of onset or delaying the onset of the ovarian cancer in the subject, wherein the administration comprises one or more administrations of the composition.

In any of the methods disclosed herein, the composition that is administered to a subject may comprise a recombinant virus selected from adenovirus, alphavirus, poxvirus, adeno-associated virus, retrovirus, or may comprise a self-replicating RNA, or a combination thereof.

In some embodiments, the subject is suspected to have or is suspected to develop ovarian cancer.

The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners.

In some embodiments, the compositions comprising recombinant adenovirus is administered at a dose from about $1 \times 10^4$ IFU (Infectious Unit) to about $1 \times 10^{12}$ IFU per dose, about $1 \times 10^4$ IFU to about $1 \times 10^{11}$ IFU per dose, about $1 \times 10^4$ IFU to about $1 \times 10^{10}$ IFU per dose, about $1 \times 10^4$ IFU to about $1 \times 10^9$ IFU per dose, about $1 \times 10^4$ IFU to about $1 \times 10^8$ IFU per dose, or about $1 \times 10^4$ IFU to about $1 \times 10^6$ IFU per dose.

In some embodiments, the compositions comprising recombinant adenovirus is administered at a dose from about $1 \times 10^6$ VP (viral particles) to about $1 \times 10^{14}$ VP per dose, about $1 \times 10^6$ VP to about $1 \times 10^{12}$ VP per dose, about $1 \times 10^6$ VP to about $1 \times 10^{10}$ VP per dose, about $1 \times 10^6$ VP to about $1 \times 10^8$ VP per dose, or about $1 \times 10^6$ VP to about $1 \times 10^7$ VP per dose.

In some embodiments, a composition comprising recombinant Ad26 virus is administered at about $1 \times 10^{10}$ IFU per dose. In some embodiments, a composition comprising recombinant Ad26 virus is administered at about $1 \times 10^{11}$ IFU per dose. In some embodiments, a composition comprising recombinant Ad26 virus is administered at about $1 \times 10^{10}$ VP per dose. In some embodiments, a composition comprising recombinant Ad26 virus is administered at about $1 \times 10^{11}$ VP per dose.

In some embodiments, a composition comprising recombinant GAd20 virus is administered at about $1 \times 10^8$ IFU per dose. In some embodiments, a composition comprising recombinant GAd20 virus is administered at about $1 \times 10^{10}$ IFU per dose. In some embodiments, a composition comprising recombinant GAd20 virus is administered at about $1 \times 10^{10}$ VP per dose.

In some embodiments, a composition comprising recombinant GAd20 virus is administered at about $1 \times 10^{11}$ VP per dose.

In some embodiments, the compositions comprising recombinant poxvirus is administered at dose from about $1 \times 10^4$ IFU (Infectious Unit) to about $1 \times 10^{12}$ IFU per dose, about $1 \times 10^4$ IFU to about $1 \times 10^{11}$ IFU per dose, about $1 \times 10^4$ IFU to about $1 \times 10^{10}$ IFU per dose, about $1 \times 10^4$ IFU to about $1 \times 10^9$ IFU per dose, about $1 \times 10^4$ IFU to about $1 \times 10^8$ IFU per dose, or about $1 \times 10^4$ IFU to about $1 \times 10^6$ IFU per dose.

In some embodiments, a composition comprising recombinant MVA virus is administered from about $1 \times 10^8$ IFU per dose. In some embodiments, a composition comprising recombinant MVA virus is administered from about $1 \times 10^{10}$ IFU per dose.

In some embodiments, the compositions comprising self-replicating RNA molecule is administered at a dose from about 1 microgram to about 100 microgram, about 1 microgram to about 90 micrograms, about 1 microgram to about 80 microgram, about 1 microgram to about 70 micrograms, about 1 microgram to about 60 micrograms, about 1 microgram to about 50 micrograms, about 1 microgram to about 40 micrograms, about 1 microgram to about 30 micrograms, about 1 microgram to about 20 micrograms, about 1 microgram to about 10 micrograms, or about 1 microgram to about 5 micrograms of the self-replicating RNA molecule.

In one exemplary regimen, the composition comprising the adenovirus is administered (e.g., intramuscularly) in a volume ranging between about 100 µL to about 10 ml containing concentrations of about $10^4$ to $10^{12}$ virus particles/ml. The adenovirus vector may be administered in a volume ranging between 0.25 and 1.0 ml, such as in a volume of 0.5 ml.

The adenovirus may be administered in an amount of about $10^9$ to about $10^{12}$ viral particles (vp) to a human subject during one administration, more typically in an amount of about $10^{10}$ to about $10^{12}$ vp.

In one exemplary regimen, the composition comprising the rMVA virus of the disclosure is administered (e.g., intramuscularly) in a volume ranging between about 100 µl to about 10 ml of saline solution containing a dose of about $1 \times 10^7$ $TCID_{50}$ to $1 \times 10^9$ $TCID_{50}$ (50% Tissue Culture Infective Dose) or Inf.U. (Infectious Unit). The rMVA virus may be administered in a volume ranging between 0.25 and 1.0 ml. Compositions may be administered two or more times, weeks or months after the first administration of the first composition, for example, about 1 or 2 weeks or 3 weeks, or 4 weeks, or 6 weeks, or 8 weeks, or 12 weeks, or 16 weeks, or 20 weeks, or 24 weeks, or 28 weeks, or 32 weeks or one to two years after administration of the first composition. Additional administrations of the compositions may be administered 6 weeks to 5 years after the boosting step (b), such as 6, 7, 8, 9, 10, 11, 12, 13, 14, 15, 16, 17, 18, 19, 20, 21, 22, 23, 24 or 25 weeks, or 7, 8, 9, 10, 11 or 12 months, or 2, 3, 4 or 5 years, after the initial boosting inoculation. Optionally, the further administration step (c) can be repeated one or more times as needed.

Combination Therapies

The vaccines and compositions of the disclosure may be used in combination with at least one additional cancer therapeutic agent for treating ovarian cancer.

The additional cancer therapeutic agent may be a surgery, radiation therapy, chemotherapy, hormone therapy, targeted therapy, a checkpoint inhibitor, an antibiotic, an immunostimulating agent, or cellular therapy, or any combination thereof.

Surgery may include total abdominal hysterectomy, bilateral salpingo-oophorectomy, omentectomy, visualization of all peritoneal surfaces, and random peritoneal biopsies plus peritoneal washing, or a combination thereof.

Exemplary chemotherapeutic agents include, but are not limited to, platinum agents (e.g., carboplatin, cisplatin, oxaliplatin), alkylating agents; nitrosoureas; antimetabolites; antitumor antibiotics; plant alkyloids; taxanes (e.g., paclitaxel, docetaxel); hormonal agents, busulfan, chlorambucil, cyclophosphamide, dacarbazine, ifosfamide, mechlorethamine hydrochloride, melphalan, procarbazine, thiotepa, uracil mustard, 5-fluorouracil, 6-mercaptopurine, capecitabine, cytosine arabinoside, floxuridine, fludarabine, gemcitabine, methotrexate, thioguanine, dactinomycin, daunorubicin, doxorubicin, idarubicin, mitomycin-C, and mitoxantrone, vinblastine, vincristine, vindesine, vinorelbine, albumin bound paclitaxel (nab-paclitaxel, Abraxane®), altretamine (Hexalen®), etoposide (VP-16), irinotecan (CPT-11, Camptosar®), liposomal doxorubicin (Doxil®), pemetrexed (Alimta®), and topotecan, or a combination thereof. Exemplary hormone therapies include luteinizing-hormone-releasing hormone (LHRH) agonists, tamoxifen and aromatase inhibitors FEMARA® (letrozole), ARIMIDEX® (anastrozole), and AROMASIN® (exemestane).

In some embodiments, the chemotherapeutic agents include a platinum agent and a taxane.

In some embodiments, the chemotherapeutic agents include carboplatin and paclitaxel.

In some embodiments, the chemotherapeutic agents include cisplatin and paclitaxel.

In some embodiments, the chemotherapy includes an intravenous (IV) chemotherapy and/or intraperitoneal (IP) chemotherapy.

In some embodiments, the chemotherapy includes a dose-dense chemotherapy. As a non-limiting example, the chemotherapy may include weekly IV dose-dense paclitaxel (e.g., 80 mg/m$^2$) in combination with IV carboplatin every 3 weeks.

Radiation therapy may be administered using various methods, including external-beam therapy, internal radiation therapy, implant radiation, stereotactic radiosurgery, systemic radiation therapy, radiotherapy and permanent or temporary interstitial brachytherapy. External-beam therapy involves three-dimensional, conformal radiation therapy where the field of radiation is designed, local radiation (e.g., radiation directed to a preselected target or organ), or focused radiation. Focused radiation may be selected from stereotactic radiosurgery, fractionated stereotactic radiosurgery or intensity-modulated radiation therapy. Focused radiation may have particle beam (proton), cobalt-60 (photon) linear accelerator (x-ray) as a radiation source (see e.g. WO 2012/177624). "Brachytherapy," refers to radiation therapy delivered by a spatially confined radioactive material inserted into the body at or near a tumor or other proliferative tissue disease site, and includes exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner include both solids and liquids. The radiation source can be a radionuclide, such as I-125, I-131, Yb-169, Ir-192 as a solid source, I-125 as a solid source, or other radionuclides that emit photons, beta particles, gamma radiation, or other therapeutic rays.

The radioactive material may also be a fluid made from any solution of radionuclide(s), e.g., a solution of I-125 or I-131, or a radioactive fluid can be produced using a slurry of a suitable fluid containing small particles of solid radionuclides, such as Au-198, Y-90. The radionuclide(s) may be embodied in a gel or radioactive micro spheres. The radioactive fluid may be introduced to the peritoneum.

Targeted therapies include, but are not limited to, monoclonal antibody therapies such as Bevacizumab (AVASTIN®), pembrolizumab, catumaxomab, cetuximab; tyrosine-kinase inhibitors such as sunitinib, sorafenib, pazopanib, cediranib, cabozantinib, erlotinib, gefitinib and nintedanib (BIBF 1120); poly(ADP-ribose) polymerase (PARP) inhibitors such as olaparib (Lynparza), rucaparib (Rubraca), and niraparib (Zejula); and other angiongenesis inhibitors such as aflibercept and trebananib (AMG 386).

Additional cancer therapeutic agents may also include genetic therapies such as BRCA1-targeted microRNAs.

Exemplary checkpoint inhibitors are antagonists of PD-1, PD-L1, PD-L2, VISTA, BTNL2, B7-H3, B7-H4, HVEM, HHLA2, CTLA-4, LAG-3, TIM-3, BTLA, CD160, CEACAM-1, LAIR1, TGFβ, IL-10, Siglec family protein, KIR, CD96, TIGIT, NKG2A, CD112, CD47, SIRPA or CD244. "Antagonist" refers to a molecule that, when bound to a cellular protein, suppresses at least one reaction or activity that is induced by a natural ligand of the protein. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. Antagonist may be an antibody, a soluble ligand, a small molecule, a DNA or RNA such as siRNA. Exemplary antagonists of checkpoint inhibitors are described in U.S. Pat. Publ. No. 2017/0121409.

In some embodiments, one or more vaccines or compositions of the disclosure is administered in combination with a CTLA-4 antibody, a CTLA4 ligand, a PD-1 axis inhibitor, a PD-L1 axis inhibitor, a TLR agonist, a CD40 agonist, an OX40 agonist, hydroxyurea, ruxolitinib, fedratinib, a 41BB agonist, aa CD28 agonist, a STING agonist, a RIG-I agonist, TCR-T therapy, CAR-T therapy, FLT3 ligand, aluminum sulfate, BTK inhibitor, CD38 antibody, CDK inhibitor, CD33 antibody, CD37 antibody, CD25 antibody, GM-CSF inhibitor, IL-2, IL-15, IL-7, CD3 redirection molecules, pomalimib, IFNγ, IFNα, TNFα, VEGF antibody, CD70 antibody, CD27 antibody, BCMA antibody or GPRC5D antibody, or any combination thereof.

In some embodiments, the checkpoint inhibitor is ipilimumab, cetrelimab, pembrolizumab, nivolumab, sintilimab, cemiplimab, toripalimab, camrelizumab, tislelizumab, dostralimab, spartalizumab, prolgolimab, AK-105, HLX-10, balstilimab, MEDI-0680, HX-008, GLS-010, BI-754091, genolimzumab, AK-104, MGA-012, F-520, 609A, LY-3434172, AMG-404, SL-279252, SCT-I10A, RO-7121661, ICTCAR-014, MEDI-5752, CS-1003, XmAb-23104, Sym-021, LZM-009, hAB21, BAT-1306, MGD-019, JTX-4014, budigalimab, XmAb-20717, AK-103, MGD-013, IBI-318, sasanlimab, CC-90006, avelumab, atezolizumab, durvalumab, CS-1001, bintrafusp alpha, envafolimab, CX-072, GEN-1046, GS-4224, KL-A167, BGB-A333, SHR-1316, CBT-502, IL-103, KN-046, ZKAB-001, CA-170, TG_1501, LP-002, INCB-86550, ADG-104, SHR-1701, BCD-135, IMC-001, MSB-2311, FPT-155, FAZ-053, HLX-20, iodapolimab, FS-118, BMS-986189, AK-106, MCLA-145, IBI-318 or CK-301, or any combination thereof.

In some embodiments, one or more vaccines or compositions of the disclosure are administered in combination with ipilimumab, cetrelimab, pembrolizumab, nivolumab, sintilimab. cemiplimab, toripalimab, camrelizumab, tislelizumab, dostralimab, spartalizumab, prolgolimab, balstilimab, budigalimab, sasanlimab, avelumab, atezolizumab, durvalumab, envafolimab or iodapolimab, or any combination thereof.

In some embodiments, the second therapeutic agent may be administered in combination with a first composition of the first administration or a second composition of the second administration or a third composition of the third administration, or a fourth composition of the fourth administration.

In some embodiments, the anti-CTLA-4 antibody is combined with any of the first, or the second, or the third, or the fourth administration of the composition of the disclosure. In some embodiments, the anti-PD-1 or anti-PD-L1 antibody is combined with any of the first, or the second, or the third, or the fourth administration of the composition of the disclosure.

In some embodiments, the checkpoint inhibitors are administered at as dose of about 0.5 to about 5 mg/kg, about 5 to about 10 mg/kg, about 10 to about 15 mg/kg, about 15 to about 20 mg/kg, about 20 to about 25 mg/kg, about 20 to about 50 mg/kg, about 25 to about 50 mg/kg, about 50 to about 75 mg/kg, about 50 to about 100 mg/kg, about 75 to about 100 mg/kg, about 100 to about 125 mg/kg, about 125 to about 150 mg/kg, about 150 to about 175 mg/kg, about 175 to about 200 mg/kg, about 200 to about 225 mg/kg, about 225 to about 250 mg/kg, or about 250 to about 300 mg/kg.

EXAMPLES

The following examples are provided to further describe some of the embodiments disclosed herein. The examples are intended to illustrate, not to limit, the disclosed embodiments.

Example 1: Identification of Neoantigens by Bioinformatics

A computational framework was developed to analyze various cancer RNA-seq datasets by bioinformatics means to identify common cancer neoantigens resulting from gene fusion events that resulted in generation of novel peptide sequences, intron retention, alternatively spliced variants, aberrant expression of developmentally silenced genes or point mutations.

The datasets queried were:

The Genotype-Tissue Expression (GTEx) Consortium. This dataset encompasses 6137 RNA-seq datasets from 49 normal tissues and was used to annotate RNA features in normal tissues and assess frequency of potential ovarian cancer neoantigen candidates in normal tissue.

Immune cell-type specific RNA-seq dataset. This internal study comprised of 110 RNA-seq datasets obtained from 20 immune cell-types (1 cells, B cells, NK cells and Myeloid cell-types) derived from five healthy donors.

TCGA Ovarian Cancer. This study comprised of 330 RNA-seq datasets obtained from treatment naïve patients with localized ovarian cancer.

Internal Ovarian Cancer study. This study comprised of 43 RNA-seq datasets obtained from patients with localized ovarian cancer.

Quality control (QC) of raw data was conducted prior to analysis. Sequencing reads were first trimmed to remove Illumina's adapter sequences and reads mapping to human tRNA and rRNA were removed from downstream analysis. Reads were also trimmed of low-quality base calls (<10 Phred quality score; indicating a base with a 1 in 10 probability of being incorrect) at either ends. Trimmed reads with less than 25 base pairs (bp) were removed from the datasets. Additionally, following QC steps were considered to remove poor quality reads: remove reads having maximal base quality score less than 15, remove reads with average base quality score less than 10, remove reads having polyATCG rate >80%, remove RNA sequences in which one of the two reads failed.

Reads were later mapped to Human Genome Build 38 using ArrayStudio ((https_//www_omicsoft_com/array-studio/) platform. NCBF's Refseq gene model (release date Jun. 6, 2017) was used to map reads to known exonic regions of human genome.

Identification of Gene Fusion Events

FusionMap algorithm was used to identify gene fusion events in the cancer datasets described above. See Ge H et al., Bioinformatics. 2011; 27(14):1922-8., which is incorporated herein by reference in its entirety for all purposes. FusionMap detected fusion junctions based on reads that contained the fusion position in the middle region of the sequencing reads. This was followed by searching possible fusion junction positions from the consensus of seed reads. FusionMap build the reference index based on the pseudo fusion library and aligned unmapped potential fusion reads to this pseudo reference. Reads mapped during this step were considered as rescue reads.

Figure 2:
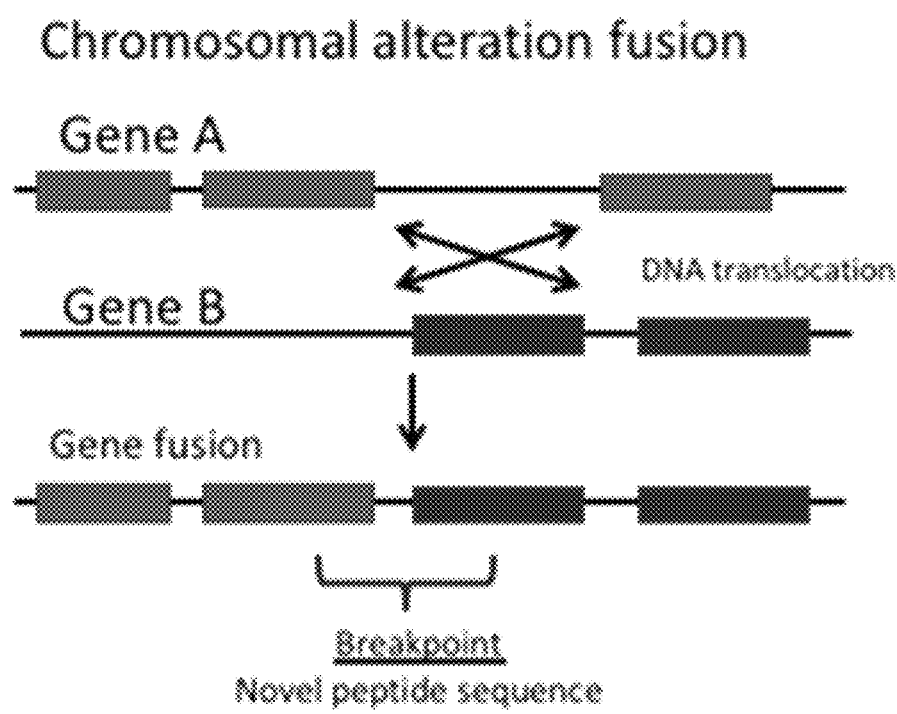
FIG. 2 shows a cartoon of gene fusions resulting from chromosomal alteration, such as DNA translocations.

This algorithm identified both chimeric read-through fusions as shown in FIG. 1 and gene fusion events resulting from chromosomal translocations as shown in FIG. 2. A gene fusion event was called in a RNA-seq dataset when following criteria were met: at least two seed reads with different mapping position in the genome, at least four seed and rescued reads supporting the fusion junction and at least one junction spanning read pair. Gene fusion events coming from gene pairs that shared high sequence similarity (orthologs and protein families) were ignored from downstream analysis.

Shared neoantigens originating from gene fusion events were identified using following criteria: the incidence of gene fusion event in a disease cohort should be greater than 5% (10% for internal ovarian cancer dataset), the occurrence of the gene fusion event were to be less than 1% in the entire GTEx dataset using a lenient criteria (at least 2 seed reads and one junction spanning read) and the occurrence of the gene fusion event were to be <=2 RNA-seq datasets derived from normal immune cell-types. The open reading frame from Gene A (FIGS. 1 and 2) was used to obtain protein sequence originating from the identified novel junction.

Identification of Splice Variants

Figure 3:
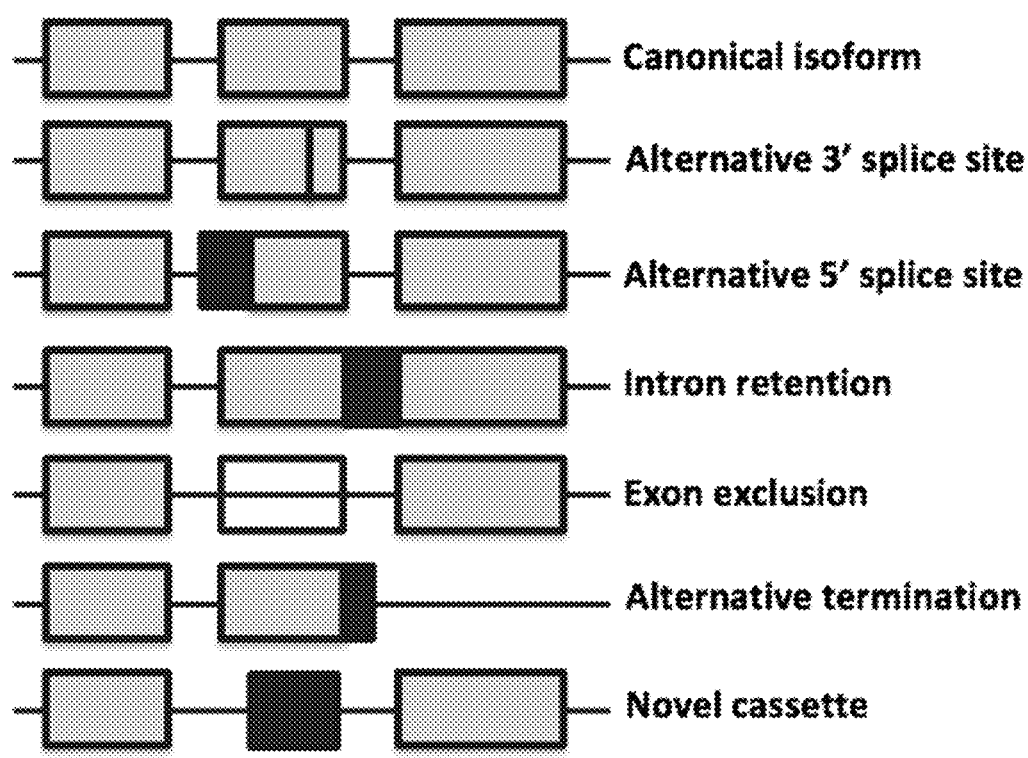
FIG. 3 shows a cartoon of splice variants with alternative 5' or 3' splice sites, retained introns, excluded exons or alternative terminations or insertions.
Figure 4:
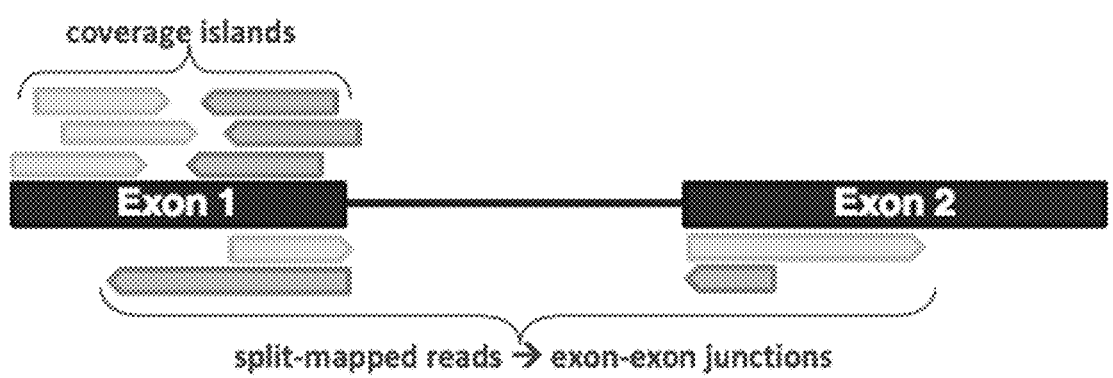
FIG. 4 shows the cartoon for approach of identification of splice variants.

A custom bioinformatics process was developed to analyze paired-end RNA-seq data to identify potential neoantigens arising from alternative splicing events. Utilizing the developed process, splice variants with alternative 5' or 3' splice sites, retained introns, excluded exons, alternative terminations or insertion(s) of novel cassettes as shown in FIG. 3 were identified. The process identified splice variants that were not present in the NCBI's RefSeq gene model through two main functionalities: 1) Identification of novel junctions based on sequencing reads with alignment gaps >5 base pair and ≥15 base pair aligned on each side of the gap, henceforth referred to as split-mapped reads. For each RNA-seq dataset, novel junctions were called if they were supported by at least 5 split-mapped reads and one mate pair of junction-spanning reads 2) Identification of islands of aligned reads, henceforth referred to as coverage islands. FIG. 4 shows the cartoon of the approach.

In order to assess the signal to noise ratio in each sample, where genomic DNA and pre-mRNA are potential contributors to noise, two parameters were computed from a set of 200 highly expressed housekeeping genes:

1. Intron depth of coverage (IDC): $90^{th}$ percentile depth of coverage for all housekeeping intronic bases. If the coverage of a particular region fell below this value, the first base where this occurred was defined as a coverage island boundary.
2. Intron/exon coverage ratio (IECR): $90^{th}$ percentile of the ratio between median intron coverage and median coverage of the nearest upstream exon of all housekeeping gene introns Following criteria was used to classify the various splice variants:

Alternative 3'/5' Splice Site Identification:
  Novel splice site boundary was defined by split-mapped reads
  Intronic region resulting from using the splice site (if applicable) exceeded IECR and entire region exceeded IDC Novel Cassette Identification:
  Two novel splice sites in an intronic region defined by split-mapped reads
  Region between the two splice sites exceeded IECR and entire region exceeded IDC Intron Retention Identification:
  Intronic region exceeded IECR and entire region exceeded IDC
  At least 5 reads spanned both intron-exon boundaries, with at least 15 bp aligned on each side of the boundaries Alternative Termination Identification:
  3' boundary defined as the edge of a coverage island that did not fall within 60 bp of the 3' end of a canonical exon
  Any intronic regions between 5' end of a canonical exon and the 3' boundary exceeded IECR and entire region exceeded IDC Exon Exclusion Identification:
  Novel junction defined by split-mapped reads where one or more canonical exons were skipped Shared neoantigens originating from aberrant splicing events were identified using following criteria: the incidence of a splicing event in a disease cohort were to be greater than 5% (10% for internal ovarian cancer dataset), the occurrence of the splicing event were to be less than 1% in the entire GTEx dataset using a lenient criteria (at least 2 split-mapped reads) and the splicing event were to be present in ≤2 RNA-seq datasets derived from normal immune cell-types. For exon exclusion, novel cassette, and alternative 3'/5' splice sites, events were to have a median split-mapped read counts per million mapped reads (CPM) ≥0.05 and a median percent spliced-in (PSI) ≥0.1, calculated using the formula below:

$$PSI = \frac{\text{inclusion reads}}{\text{inclusion} + \text{exclusion reads}}$$

Events with median value of 0.05≥PSI≥0.1 were selected if the aberrantly spliced gene was found to be 2-fold upregulated in disease cohort versus healthy tissue differential gene expression analysis. For alternative termination and retained introns, events were to have a median number of split-mapped CPM ≥0.1 and a median PSI >0.5. Neoantigens originating from genes MUC16 and NR2F2 were included regardless of median split-mapped CPM and PSI values.

Isoform Prediction and Translation:

In order to assemble isoforms containing the alternatively spliced neoantigens, canonical exons neighboring the novel spliced features were identified using the split-mapped reads. The most highly expressed isoform that could potentially contain the predicted neoepitope was chosen for translation into the corresponding protein by choice of the appropriate open reading frame. The neoantigen portion of the protein sequence was extracted and concatenated with an additional 8 amino acid residues upstream of the first altered amino acid. This protein sequence was then used for subsequent validation studies.

Identification of DNA Mutation and Frameshift Based Neoantigens

Datasets generated by The Cancer Genome Atlas (TCGA) consortium containing exome sequencing data from patients with Ovarian Cancer were examined. See Berger A. C. et. al. Cancer Cell 2018; 33(4) 690-705, which is incorporated herein by reference in its entirety for all purposes. Mutation calls published by the consortia that generated this dataset were downloaded, and gene mutations that were present in >10% of the patient population or in genes known to be critical drivers of cancer were identified. For each single point mutation chosen, a 17 mer peptide with the mutated amino acid at its center was identified for further validation studies.

Table 3 shows gene origin and amino acid sequence of identified neoantigens that arose from gene fusion (FUS) events. In Table 3, bolded letters indicate canonical amino acids from gene 1. Italic letters indicate canonical amino acids from gene 2 for in-frame gene fusion events. Unbolded letters indicate novel amino acid sequences generated from out-of-frame gene fusion events. Table 4 shows their corresponding polynucleotide sequences. Table 5 lists long-form names for the genes fused to form each gene fusion.

TABLE 3

| Neopeptide ID | Fusion Gene | Amino Acid Sequence | SEQ ID NO: |
|---|---|---|---|
| FUS1 | TSTD1->F11R | MAGGVLRRLLCREPDRDGDKGASREETVV PLHIGDPVVLPGIGQCYSALF | 1 |
| FUS2 | VAX2->ATP6V1B1 | QLNLSETQFAQYAEIV | 3 |
| FUS3 | PTH2R->LOC101927960 | APILAAIGIGRLLCMDKIPATASLTP | 5 |
| FUS4 | HIGD1A->CCDC13 | VVGAMTVGQDGSR | 7 |
| FUS5 | MACC1->LOC101927668 | NTGDVAVEIAS | 9 |
| FUS6 | PKHD1L1->EBAG9 | STLNITLSFDSHHGHHPVSVI | 11 |
| FUS7 | SLC25A16->DNA2 | LPEFEKCLFQKKVVA | 13 |
| FUS8 | TYSND1->AIFM2 | AAEQAGCMQCLI | 15 |
| FUS9 | TBCEL->TECTA | PQEEVPFRMNYSSFLR | 17 |
| FUS10 | SCNN1A->TNFRSF1A | RGGRGAQENSLD | 19 |
| FUS11 | AJUBA->HAUS4 | HFECYHCEIRIPRKSNGIRGFLLTWRRDGN TSTSVQQTTSSL | 21 |
| FUS12 | CFAP161->IL16 | EYEGFPVPGLMKWQLSPVQWPPVSQGPET RKGRKAASLPL | 23 |
| FUS13 | MFGE8->HAPLN3 | YGNDQWLQMRKWRHRE | 25 |
| FUS14 | GCSH->C16orf46 | VNKSCYEDAQEKEDKVGEGSVSHSVLSSN TVEM | 27 |
| FUS15 | NXN->GLOD4 | LLFFVAGEVLRHEEFE | 29 |
| FUS16 | NDUFA11->FUT5 | GGLTLGARNTLTHGSPGPSQATVAVAPLS GRAAVSAAGGCVFLLLPACVPRRCHWIP | 31 |
| FUS17 | C20orf204->TCEA2 | RASCGAQKACDVNQLTSS | 33 |
| FUS18 | FOXRED2->TXN2 | GYLRMQGLMAQRLLLR | 35 |
| FUS19 | STX6->KIAA1614-AS1 | AKVSHMTSVLEAVAFDQAWDQEVRPALR HQPKDPLNLPSPPANKGTSRC | 37 |
| FUS20 | CMTM8->CMTM7 | FLIVAEIVTLLIAFI | 39 |
| FUS21 | TWF2->TLR9 | FHLEIAKKPLLPLWEGTSSVKHPSL | 41 |
| FUS22 | C8orf82->LRRC24 | KNFITCFKGGHASAAEPRKGR | 43 |
| FUS23 | ARID3C->DCTN3 | TYEEQFKQVADGLVKV | 45 |
| FUS24 | TSPAN14->LOC102723703 | FIAISLLQNPQRT | 47 |
| FUS25 | CLCF1->POLD4 | LRSLAGTYGRSPSPATRRKRSWSC | 49 |
| FUS26 | HEPHL1->PANX1 | TCQVSDHLATEYVFS | 51 |

TABLE 3-continued

| Neopeptide ID | Fusion Gene | Amino Acid Sequence | SEQ ID NO: |
|---|---|---|---|
| FUS27 | C17orf99->SYNGR2 | ALTVVPPGLRLDRVLLHLW | 53 |
| FUS28 | JUND->KIAA1683 | CQLLPQHQPRAVLLHIAWMKG | 55 |
| FUS29 | DMPK->SIX5 | LQERMELLACGAERGAGGWGGGGGGG GDRRGGGGSAPALADFAGGRG | 57 |

TABLE 4

| Neopeptide ID | Polynucleotide sequence | SEQ ID NO: |
|---|---|---|
| FUS1 | ATGGCTGGAGGAGTCCTTCGGCGGCTGTTGTGTCGGGAG CCTGATCGCGATGGGACAAAGGCGCAAGTCGAGAGGAA ACTGTTGTGCCTCTTCATATTGGCGATCCTGTTGTGCTC CCTGGCATTGGGCAGTGTTACAGTGCACTCTTC | 2 |
| FUS2 | CAGCTGAACCTCTCCGAGACCCAGTTTGCCCAGTATGCG GAGATCGTC | 4 |
| FUS3 | GCACCGATCTTAGCAGCTATTGGGATTGGGAGGCTGCTG TGTATGGATAAGATACCTGCTACAGCCAGCTTGACACCA | 6 |
| FUS4 | GTTGTAGGAGCAATGACTGTTGGGCAGGATGGCAGCAGA | 8 |
| FUS5 | AACACTGGAGATGTTGCTGTTGAGATCGCTTCT | 10 |
| FUS6 | TCAACTTTGAATATAACTTTAAGTTTTGATTCCCACCAT GGCCATCACCCAGTTTCGGTTATT | 12 |
| FUS7 | CTGCCGGAATTTGAAAAGTGCCTATTTCAGAAGAAAGTG GTAGCT | 14 |
| FUS8 | GCGGCCGAGCAGGCGGGCTGCATGCAGTGCCTGATT | 16 |
| FUS9 | CCACAGGAAGAAGTGCCATTCAGGATGAATTATTCATCA TTCCTTAGA | 18 |
| FUS10 | CGAGGGGCAGGGGTGCTCAGGAGAATTCTCTGGAC | 20 |
| FUS11 | CACTTTGAGTGCTACCACTGTGAGATTAGAATCCCAAGA AAATCAAATGGCATCCGGGGATTTCTGCTCACCTGGAGA AGGGATGGAAATACTTCAACAAGTGTGCAGCAAACAACT TCCTCCTTG | 22 |
| FUS12 | GAATATGAAGGCTTCCCCGTCCCGGGACTCATGAAGTGG CAGCTAAGCCCTGTCCAGTGGCCACCCGTCAGCCAAGGG CCAGAGACCAGGAAAGGAAGAAAGGCAGCTTCACTTCCT CTT | 24 |
| FUS13 | TACGGTAACGATCAGTGGCTGCAGATGAGGAAATGGAGG CACAGAGAG | 26 |
| FUS14 | GTAAACAAATCTTGTTATGAAGATGCACAGGAAAAGAA GATAAAGTAGGAGAGGGATCAGTTTCACATTCAGTCCTA AGCAGCAACACGGTTGAGATG | 28 |
| FUS15 | CTTCTGTTCTTCGTAGCCGGGGAGGTTCTGCGGCATGAG GAATTTGAA | 30 |
| FUS16 | GGAGGCCTGACTCTGGGAGCACGCAATACTCTGACCCAT GGATCCCCTGGGCCCAAGCCACAGTGGCTGTGGCG CCGCTGTCTGGCCGGGCTGCTGTTTCAGCTGCTGGTGGC TGTGTGTTTCTTCTCCTACCTGCGTGTGTCCCGAGACGA TGCCACTGGATCCCC | 32 |
| FUS17 | CGGGCCTCCTGTGGCGCCCAGAAGGCATGTGATGTGAAT CAGCTGACATCATCT | 34 |
| FUS18 | GGGTACCTGAGGATGCAGGGACTCATGGCTCAGCGACTT CTTCTGAGG | 36 |
| FUS19 | GCAAAAGTATCTCATATGACCAGTGTGTTGGAGGCTGTA GCCTTTGACCAGGCATGGGACCAGGAGGTGAGGCCGGCT CTCAGGCATCAACCAAAGGATCCACTGAATCTCCCTTCT CCCCCTGCCAACAAAGGTACAAGTAGATGT | 38 |
| FUS20 | TTCCTCATCGTGGCCGAGATCGTCACCCTGCTGATTGCC TTCATC | 40 |
| FUS21 | TTCCATCTGGAGATCGCCAAGAAACCGCTGCTGCCCCTG TGGGAAGGGACCTCGAGTGTGAAGCATCCTTCCCTG | 42 |
| FUS22 | AAGAATTTCATCACCTGCTTCAAAGGAGGGCACGCGTCT GCGGCTGAACCGCGGAAGGGCCGG | 44 |
| FUS23 | ACCTACGAGGAACAATTCAAGCAGGTGGCTGACGGCCTG GTCAAGGTG | 46 |
| FUS24 | TTCATCGCCATCTCGCTGTTGCAGAACCCCCAGAGGACA | 48 |
| FUS25 | CTCCGCAGCTTGGCTGGGACCTATGGGAGGAGCCCCAGC CCCGCGACGAGGAGGAAGCGGAGCTGGAGCTGC | 50 |
| FUS26 | ACCTGCCAGGTCAGCGACCACCTGGCCACGGAGTACGTG TTCTCG | 52 |
| FUS27 | GCCCTCACAGTGGTGCCCCCAGGTCTTCGCCTTGATCGT GTTCTCCTGCATCTATGG | 54 |
| FUS28 | TGCCAGCTGCTGCCCCAGCACCAGCCCAGGGCAGTGTTG CTGCATATTGCATGGATGAAAGGC | 56 |
| FUS29 | TTGCAGGAGCGGATGGAGTTGCTTGCCTGCGGAGCCGAG CGCGGGGCCGGCGGCTGGGGGGAGGCGGTGGCGGCGGC GGCGGCGACCGAAGAGGAGGAGGAGGAAGCGCGCCAGCT CTTGCAGACTTTGCAGGCGGCCGAGGG | 58 |

TABLE 5

| Neopeptide ID | Full Name of Fusion Gene 1 | Full Name of Fusion Gene 2 |
|---|---|---|
| FUS1 | thiosulfate sulfurtransferase like domain containing 1 | F11 receptor |
| FUS2 | ventral anterior homeobox 2 | ATPase H+ transporting V1 subunit B1 |
| FUS3 | parathyroid hormone 2 receptor | uncharacterized LOC101927960 |
| FUS4 | HIGI hypoxia inducible domain family member 1A | coiled-coil domain containing 13 |
| FUS5 | MET transcriptional regulator MACC1 | uncharacterized LOC101927668 |
| FUS6 | PKHD1 like 1 | estrogen receptor binding site associated antigen 9 |
| FUS7 | solute carrier family 25 member 16 | DNA replication helicase/nuclease 2 |
| FUS8 | trypsin domain containing 1 | apoptosis inducing factor mitochondria associated 2 |
| FUS9 | tubulin folding cofactor E like | tectorin alpha |
| FUS10 | sodium channel epithelial 1 subunit alpha | TNF receptor superfamily member 1A |
| FUS11 | ajuba LIM protein | HAUS augmin like complex subunit 4 |
| FUS12 | cilia and flagella associated protein 161 | interleukin 16 |
| FUS13 | milk fat globule EGF and factor V/VIII domain containing | hyaluronan and proteoglycan link protein 3 |
| FUS14 | glycine cleavage system protein H | chromosome 16 open reading frame 46 |
| FUS15 | nucleoredoxin | glyoxalase domain containing 4 |
| FUS16 | NADH:ubiquinone oxidoreductase subunit A11 | fucosyltransferase 5 |
| FUS17 | chromosome 20 open reading frame 204 | transcription elongation factor A2 |
| FUS18 | FAD dependent oxidoreductase domain containing 2 | thioredoxin 2 |
| FUS19 | syntaxin 6 | KIAA1614 antisense RNA 1 |
| FUS20 | CKLF like MARVEL transmembrane domain containing 8 | CKLF like MARVEL transmembrane domain containing 7 |
| FUS21 | twinfilin actin binding protein 2 | toll like receptor 9 |
| FUS22 | chromosome 8 open reading frame 82 | leucine rich repeat containing 24 |
| FUS23 | AT-rich interaction domain 3C | dynactin subunit 3 |
| FUS24 | tetraspanin 14 | LOC102723703 |
| FUS25 | cardiotrophin like cytokine factor 1 | DNA polymerase delta 4, accessory subunit |
| FUS26 | hephaestin like 1 | pannexin 1 |
| FUS27 | chromosome 17 open reading frame 99 | synaptogyrin 2 |
| FUS28 | JunD proto-oncogene, AP-1 transcription factor subunit | KIAA1683 |
| FUS29 | DM1 protein kinase | SIX homeobox 5 |

Table 6 shows gene origin and amino acid sequences of identified neoantigens that arose from alternative splicing (AS) events. Bolded letters represent sequences from the wild-type protein while regular letters represent mutant sequences resulted from alternative splicing events. Table 7 shows their corresponding polynucleotide sequences. Table 8 shows long-form names for each gene and the genomic coordinates of the alternative splicing events.

TABLE 6

| Neoepitope ID | Gene | Amino acid sequence | SEQ ID NO: |
|---|---|---|---|
| AS1 | ADAMTS14 | LRLRPNRRRASSAQTAPTSSLSLWSGASRRRRP AGGHMWCTAGRPSSRSGQNLTGTCTMKPLAW ETFPTCWAWWGTSWATQSGSGGMPSQAATAS RCCWWWTTRWFASMARSMCRTMSSPS | 59 |
| AS2 | DEAF1 | CSTFCQRKVGLTYTRLSAPASSLATKTPGWPSL PLCSWCHT | 61 |
| AS3 | ETV4 | QTDFAYDSGKRLGWGRVACDQVFS | 63 |
| AS4 | MUC16 | PSLSTRLTSKDPQPLQSHYWGLIGNDPFLRSKK RVN | 65 |
| AS5 | PLAG1 | VIPGDLSEAHGYSFS | 67 |

TABLE 6-continued

| Neoepitope ID | Gene | Amino acid sequence | SEQ ID NO: |
|---|---|---|---|
| AS6 | RGL3 | AEGPGGSQVRRGFGGWRGAGSDQLRAELESR AQAARCSGRKEGRGSEATR | 69 |
| AS7 | SAMD10 | FGERRDVDGERGWIGERGFLGRGSQGPRGTGA GRDPAGFERRWLGVFGGCLGSTGSRSLCPALGG SQPQALGVSAPLAWGEGVSSRGACVQAGTTLG SPFPAHGENPPPLLQWGRKGAEVTSRLGAPAPF PSGILTLGREGPDRQTAGRTELPPGVQAGNGRS LLGRGRCRAG | 71 |
| AS8 | SCGB1D1 | RVLITKTLVISVSFMCPGFWSAAQCEVRSACLL LCEGHRWWGTCLTGHRLRRSPGTTGEK | 73 |
| AS9 | TRAPPC12 | KVKTVCSKVGGAVILPCHGENMPSTPSPQDMP VLFPARPAPCTIAASAFRRLGDPVCVAW | 75 |
| AS10 | DENND6A | KDLPVYLKDPAYFYGY | 77 |
| AS11 | DNMT3A | SLKDECDTVKGWRLCNGRITGAEKKAKVI | 79 |
| AS12 | IQGAP3 | AMAKKQRPDTAFWVQH | 81 |
| AS13 | SEC31B | MTLGSKSQPPEDIKAL | 83 |
| AS14 | FOXH1 | SRRLKLAQGRLRGLERLHSPQPFLQPMLPQGA QGPCKAPGQGQLLGGRREPDPS | 85 |
| AS15 | IMPG2 | QATPSSILCFRLACLWLLRKGLLDLTW | 87 |
| AS16 | LHX1 | YCKNDFFRSLPCHLL | 89 |
| AS17 | KRT8 | WSQDLQEGFSAPSRISAWFGPP | 91 |
| AS18 | LZTS3 | QSEAAVAQDKKQLQEE | 93 |
| AS19 | PLEKHG4B | QHLQQEACVTSAGKQS | 95 |
| AS20 | STRA6 | RAFPRELKKGQRMSSQ | 97 |
| AS21 | ZNF334 | MKMKKFQDLTVNFTQ | 99 |
| AS22 | ATP11A | PTATERVQRGVKHKAPVQAAQSSDGPLLKDLL RRPRRS | 101 |
| AS23 | CELSR1 | ALMEVSVSGQRG | 103 |
| AS24 | CLDN16 | VNADDSLEAGLQLQASSDPLASAS | 105 |
| AS25 | ERI2 | MATKRLARKGTLASSFARRVH | 107 |
| AS26 | FRMD4A | GSLLSSGSGARRHCILLPGGFLRLLKMRNTLSIV SQGMISPFSAF | 109 |
| AS27 | GTSE1 | FKIPKFSIVLSSNSAFRCDPLSSRPRCFGGSLEAP | 111 |
| AS28 | HYDIN | EEDREKYRWMAPFVPGQVWTWEYFL | 113 |
| AS29 | IL17RC | LKQDVRSGGPGARQLRGGLLRQAAPPGRRTRP FPHRARLHTALPTARLPGGPAAASRPAFRAAPR ESGASVPGPSASPG | 115 |
| AS30 | LOC102723360 | THSAEEIGQEYFLRPRTPDMRWGKS | 117 |
| AS31 | MECR | GDPAKVVEIPRLL | 119 |
| AS32 | MUC16 | RSWISTTSTPMTSMFSPRPLVSVSPTPSATGRNL ASSSHETSAAIQWLINCCVV | 121 |
| AS33 | RGS12 | TRSLDDLEKLDTLCCKLSVHVT | 123 |
| AS34 | SDHAF4 | ATAWRAARIRAPGPGSSRKGFVAVYSLSFKNG KSAEVSQRQISIT | 125 |

TABLE 6-continued

| Neoepitope ID | Gene | Amino acid sequence | SEQ ID NO: |
|---|---|---|---|
| AS35 | SPATA17 | KQYQLTVQMESHSLPQAGVQWHDFVSPQPLPP GFKRFSCLSFLSSWDYRLQPPHLANFFVFLVETG FHHVGQAGLKLLTSDDLPASASQSAGITGVSHH ARPNFFFSLLLS | 127 |
| AS36 | STK32C | IGKGSFGKFLEDATHMV | 129 |
| AS37 | TRIQK | KKTAIGIKTHHGC | 131 |
| AS38 | TSEN2 | YLQLSLEECTQKCLFCL | 133 |
| AS39 | WISP3 | LLLAGLAQVMAPKPPFAMFEQRHAFLYIFIAEP KAQPGTVRETVSLHASSRRRLNFPLLFAKCAKS PWKNEF | 135 |
| AS40 | XPOT | ADSDFRQRSLTLLPSLEWNGTILAHSNLQLPGS RDSPASAGIRVARIRSTHHHA | 137 |
| AS41 | ZNF726 | EMVDEPPGHRSTGSQGRRIFLSTEQNEKSPMST SFYTDTATIRFLNLFPTCPPFLFHKTAIVIMARSQ | 139 |
| AS42 | ZNF736 | EAVAKHPGVQPYYILHRSEIIQYLSVSVMFHSA | 141 |
| AS43 | ZNF98 | HEMVTEPPGLQ | 143 |
| AS44 | FGFR3 | VLTVTSTDQEYLDLSAP | 145 |
| AS45 | BICD1 | KRLTVAPPGKHFFLGCM | 147 |
| AS46 | COX7A1 | TMTLCLGGERRARLGCGGGGAGPRVRGGWFL GRTDQDLGWGLAFRKGVEY | 149 |
| AS47 | DNMT3B | RKLESRKYGISFLSFDCALFSMHFLLISLHIKWS LEKNQIS | 151 |
| AS48 | EHD3 | EKQRISRGKQPA | 153 |
| AS49 | MACROD2 | DVEMKEDSGIKFILLLLGGR | 155 |
| AS50 | MAK | SIVKNMPTVSSQS | 157 |
| AS51 | MAP3K13 | CVEERGYEVGASPFSSHHCSLFCSLGFKSLGPL QFSFNNKIQQWPCISLFSHCYKELPETG | 159 |
| AS52 | NR2F2 | LKVGMRREGIGLSFLLPSSWVPGSWVRLASLL WVRTRSPKLFSSYCSGKGFYTRSEFCIGTQTPNP HALAD | 161 |
| AS53 | RBP5 | LEGEMLYLVNGVGAGCLGEGPPAIRHPLVQTR | 163 |
| AS54 | SYCE2 | RNSLKTKVTDSTQREGGFLMQKGRE | 165 |
| AS55 | SYNPO2L | ELQDSFYAGTTLPYL | 167 |
| AS56 | TESMIN | DQNNYLQSGTKLINKKNYVIYVSW | 169 |
| AS57 | TRPM2 | LASLEEQVGPRSGPPSGGATAGPGGRLCHVVA PRRRALRSDGEEEAGTLGQPFPAGRGTLCVLQK TPPKGFCD | 171 |
| AS58 | ADAMTS14 | AAAGSRTPGGPHPHRQHRLLH | 173 |
| AS59 | DNMT3B | KAMYHALERTRLEDAQLTTQPPLTTAPHPSASR QIAITTAKTEGMKIRAENKWLQMLPTTRAAWK MAVCLVAGKTPCPSTLSLRGGSVRHAGIASLSC FTCMMTMAISLTALCAARAESCCFAATRAAAG VSVWSAWRCWWAQAQRPRPSFRSPGAVTCVS RSAVMASCGAGRTGTCACRPSSPVTRGLNMKP PSCTLPFPQPEGGPFESCHCLMASRQAT | 175 |
| AS60 | HMCN2 | LASGVPPPGLPWGPGPHLG | 177 |
| AS61 | IGF2BP3 | IPPHLQWESTRQTEWISVREFHLESSLYP | 179 |
| AS62 | IMPG2 | PGHGAICREEV | 181 |

TABLE 6-continued

| Neoepitope ID | Gene | Amino acid sequence | SEQ ID NO: |
|---|---|---|---|
| AS63 | IMPG2 | LEEEFISEWRRCLLCSYLQW | 183 |
| AS64 | IQGAP3 | QTQEETDRDRGSWSCAVA | 185 |
| AS65 | LCN10 | SHALNWNKIGRMFRASRV | 187 |
| AS66 | MMP10 | DSNKDLAQDCELYTRFAKRCC | 189 |
| AS67 | PARD6B | GTMEVKSKKKQTTVPLVQTR | 191 |
| AS68 | PKHD1L1 | LLFPYNQLDLHLHRPSGSRKNEIHWDKCFSSED | 193 |
| AS69 | PTH2R | GFILIGWGAGNLVLETSSGFIKHRS | 195 |
| AS70 | RUFY4 | HFVRSQDKGMVWTPEPSALPRTPRRHPGLSLCSQWGGLRVGPPAARPGWSLAHVLRVTLLQFHPNPGKETQKKQRCPKEDPSRIWRA | 197 |
| AS71 | SLC6A2 | NIEDVATEDGRHGGCHHGPGR | 199 |
| AS72 | SMC1B | RRHGEVQGLLEREKTARGNPSG | 201 |
| AS73 | TLK2 | SLSDKEVEGKALLGDIKLVITLSDE | 203 |
| AS74 | TRPM5 | VLRKTAHRSTTARCSCPPWLTCWPRVAAPGALSTVAREASWWLLTTEVV | 205 |
| AS75 | TSPAN10 | MHRKLQARSPSLCTGHPPQAA | 207 |
| AS76 | CENPI | LLDLQAKMIYFKNSEN | 209 |
| AS77 | EP400 | SISLTDDEAELPLLDL | 211 |
| AS78 | ETV4 | SLPPLDSEAQVPDSDE | 213 |
| AS79 | FBN3 | APSCGVSRAICDRGCH | 215 |
| AS80 | FBN3 | APSCGVSRDYRTGPCF | 217 |
| AS81 | FBN3 | LSPGGACVDIDECDRQ | 219 |
| AS82 | IMPG2 | MPGHGAICSGSSRQPD | 221 |
| AS83 | NUF2 | VQKLKNARSLNLEDQI | 223 |
| AS84 | PAEP | NPKKFKINSRVLVEDD | 225 |
| AS85 | PKD1L1 | RKPRNWLERARWLRGI | 227 |
| AS86 | RASEF | DEAKFIPRAQDKAAMQ | 229 |
| AS87 | SFI1 | LQAQQQVQVSAQRATP | 231 |
| AS88 | UPK3B | CLRPSLSLASRGFQNP | 233 |
| AS89 | ZNF727 | NYGNLFSLAGSLHFTA | 235 |
| AS90 | ACIN1 | VEDEEKKEPDGAQRHLVDIGGSHQTSHAEKFLFLLCPPVV | 237 |
| AS91 | ACIN1 | VEDEEKKEAGTHFIHLTGTTVSAGVPEEMPATTLRREVF | 239 |
| AS92 | ACIN1 | VEDEEKKEGLISST | 241 |
| AS93 | ACIN1 | VEDEEKKEGSMLVAPTSPPSLEAGTHFIHLTGTTVSAGVPEEMPATTLRREVF | 243 |
| AS94 | AFDN | SMMEGVIQLSFKAIVCLLSCLDLLSLFRVVRHLS | 245 |
| AS95 | DMXL2 | TKKRKQSELQQP | 247 |
| AS96 | ESR1 | AFFKRSIQELPTLC | 249 |
| AS97 | ETV4 | FQETWLAEDAAAGALSPCTIPTPPQPPLLSLPTSSGTRQ | 251 |

TABLE 6-continued

| Neoepitope ID | Gene | Amino acid sequence | SEQ ID NO: |
|---|---|---|---|
| AS98 | FAM110C | SQEQSRTRAIFTFILDTKKKEIPVEAHRKLLEQSCVSYLQRCRKNKPGTSSFLFLSSLTILRSYATRSTF | 253 |
| AS99 | FAM221A | RLDDSGIGNFITSLLNFISKFFCSFMGA | 255 |
| AS100 | FRYL | NANSRLPEACEK | 257 |
| AS101 | GAD1 | DGDGIFSPELS | 259 |
| AS102 | GRHL2 | MSQESDKNGLSSRSWMNTWILPEVL | 261 |
| AS103 | GTF2IRD1 | LDLAGNARPCRSQSPTSSDQTPSVPSLGSPELPDGEEGGSPDGSPQESEQVRQGQHV | 263 |
| AS104 | METTL24 | PRGRPRRKVDVLPQ | 265 |
| AS105 | MPRIP | PSPSTPNHSQQAICHPGRRP | 267 |
| AS106 | MPRIP | SPSTPNHRPSGSATEKPSRWREGGWSVELGPGALAGRRWPVCLATSGGGPR | 269 |
| AS107 | MUC16 | SGCRLTLLSLSPVSSLGCPVPMP | 271 |
| AS108 | NADSYN1 | SQFSLDDVGFLARGQARVWPSRLQALLST | 273 |
| AS109 | NPIPB3 | CPCEYLRKIQVDGRMATWM | 275 |
| AS110 | NPIPB5 | PCEYLRKVEFVPEPHKIITSMIKRSRLQKKQFGRM | 277 |
| AS111 | PCNX3 | WLLRTWERADSGL | 279 |
| AS112 | PIGG | PDLGHWLTRAVWGNSATS | 281 |
| AS113 | PLPP4 | TIKLIVGRTSALGQY | 283 |
| AS114 | PTPN4 | FIQLRKELNFTSTPDA | 285 |
| AS115 | RGL2 | EEEEEEEPLRLHRGPEAAGVGLSGPQWGRPGVTSSPNPSSHSLVLCPATTGPCVRLG | 287 |
| AS116 | RGL3 | FQVLPGDRETGFHHVGQTGLEFLTSSDPPTSASQSAGITGTRHRARPVCSNFYCRLPCLYGEGENIRRLPRLMIREGMRWCKFSSEKSSRFPVTAE | 289 |
| AS117 | RNF207 | CDLECSEQRQGFAMLASS | 291 |
| AS118 | SAMD12 | NLQLLTQGYSGIWRYP | 293 |
| AS119 | SMAD6 | HFSRLCGPVSHLSAHLAHLR | 295 |
| AS120 | STRA6 | KHHLWALEAAWLSGRSPLSEPQLPLQPSGNSSSV | 297 |
| AS121 | TENM4 | TEHENTETGAPLHCSSCFINPY | 299 |
| AS122 | TMEM221 | CGISVYLAGRTRWLTPVIPALWETEAGRSRGQEIETILANKHCPSMPCYFSRSRQAQQLLPSSARAPWFWWLC | 301 |
| AS123 | VWA2 | KLCSRQRPDCQPVDSRHGPILSIQHLISALHTGDG | 303 |
| AS124 | HUWE1 | EEMETDMDDVAMESSPGSSISMEHRLDVELRASGSSSSTNISSGPSPGPSPGPGTGPGPGPGPGPGPGPGPGPGPGPGPGPGPRPGVQCIPQR | 305 |
| AS125 | LRRC75B | RDLQCPKKTQTPQAQSRLESERKKNTLTWLVPTPWDRQWSTAPSRGLVWPPPPVDYELWKSS | 307 |
| AS126 | SRGAP3 | HQYIVVQDIHTETQHSALGAQPADSIPPFLQHTLQHLACPSLELPGNEQARREKRRRDDAFSDSL | 309 |
| AS127 | TET1 | IDPSSPLHTYYERITKGRNPERRYMKPERISPGHEAMEKNLEDNL | 311 |

TABLE 6-continued

| Neoepitope ID | Gene | Amino acid sequence | SEQ ID NO: |
|---|---|---|---|
| AS128 | ATP2A1 | VGNKMFVKVRNRNVPQPPLLPTPSHLSLPWKESGGL | 313 |
| AS129 | AVPR1B | WDKNAPDEGKWGLCGGSEVGETEREDGGLGQGYNASQGQAGDKLVGQ | 315 |
| AS130 | CRYGB | MGKVSPGYRMLSLGPNAVASVGANHSMLPHLPFFRSPSTRTGPSRAAATNAPLTAPTYNPISAAATPSGWRAAAG | 317 |
| AS131 | EBF3 | YGMPHNNQVGGGRLPSPILPPMPEPVGSRRGSSVGFLDISMLFQRLHRSLM | 319 |
| AS132 | GMNC | MVSEELALASPLANLGL | 321 |
| AS133 | HRAS | CDPAAPRAVSLPGRQGSEGGEGRGLGSRPAVLGRHSSGEGGGPWGELP | 323 |
| AS134 | HSF4 | ARLRELRQCGGGRGKRGQGWGVRDETITGRPAVLGSPFLSPALAPPSRLMGDLWDGQSAGWSPGSPASPFCGGW | 325 |
| AS135 | KCND2 | LHCLEKTTVRRQHDCLPLLSDSNSICFCAYLMLPSVISLSALLENMLKNKQTKTPQYLKLL | 327 |
| AS136 | LY6G6F | RVRGAPGRGESLPPRGKKRAHGWEAKG | 329 |
| AS137 | LY6G6F | LCGTPQAAGKGQEVRDSLAICKVGEGLLLFLLGAWRRHLTQEDRITPTNLLLPLTLGKTQRQRGSRLCSFLYKIRRMSKCFQKSRNE | 331 |
| AS138 | LY6G6F | YDVLVLKGEWGHADQGLLWPRKSR | 333 |
| AS139 | MUC16 | RSSVPTTSSEYSTDVPMAPILQQT | 335 |
| AS140 | MUC16 | PSSLPGPTGKYQSMVFGAWLMSVNISVYTLLEHG | 337 |
| AS141 | MUC16 | RSSGLTTSSEYSTHVHMPLILHQAEQELLLLINP | 339 |
| AS142 | MUC16 | WIPVPTSSSEYSTHVQMPLILHQVEQELAPPL | 341 |
| AS143 | MUC16 | RYWTPATSSEYSNL | 343 |
| AS144 | NDRG4 | PTTTTFLKVRLSSPALGQLP | 345 |
| AS145 | PIF1 | QAGAEPSTVRTGKKGHL | 347 |
| AS146 | PIP5K1A | KRPMASEVSFILIQWLLKP | 349 |
| AS147 | PLXNC1 | EFLTQESKVSLESRNKLIFGYFTSFQNLSTSLSFRNMKMNLMKKWP | 351 |
| AS148 | PROSER3 | LTPALRTLVSRGREEPGGSWRRGWV | 353 |
| AS149 | RAD9A | YLEPLEDGVRG | 355 |
| AS150 | RTEL1 | AGSPGEEQVQFQGLGMDTDPLSPEANPTPPIWPQAPPHTPL | 357 |
| AS151 | SMTNL1 | RAMTKKYEVGMGQSCVGGAGVQGGSKWCKPQRVGGWEGGQVQAIWLSLTEASSVPCLP | 359 |
| AS152 | SPDYE2 | HKDFNSQLGRRIPQRAPPILFFLKRGNFQ | 361 |
| AS153 | SPDYE5 | VSPEELEEVGGAWGGGGGEESGGLEAG | 363 |
| AS154 | SPDYE5 | KDLRVSDKVRLFSM | 365 |
| AS155 | TESMIN | DQNNYLQSGTKLINKKNYVIYVSW | 367 |
| AS156 | TRPM2 | PAKRHKQLSMPAPVPLLNVLATRVQRGWRWHGSSAQNPGRSAGVQVTQAAGLLLALSKWWGLSPEAPLGAGVRWALPATQDWPPPTGPPRWVRASGPTS | 369 |

TABLE 6-continued

| Neoepitope ID | Gene | Amino acid sequence | SEQ ID NO: |
|---|---|---|---|
| AS157 | ZIC4 | RNTLKESSKLKSSFEYWFAGFFSSSSSFFFLSRK FCFVFCLCWVESLGGVS | 371 |
| AS158 | ZNF629 | SPNDAHRGEGHKKGLRSRQDGGPGSGRGLDSG GHPGEGRETKPRVLKGAGGCRLPFFL | 373 |
| AS159 | DRD4 | LCAISVDRCAALPARAPAPPRPARRPHRGLCAV RRPLGAPRRFVAVAVP | 375 |
| AS160 | ZNF469 | KIVQQKNRRHRRLGRRAGRCGSLAAGRPRPGA EDRRLREYDFA | 377 |

TABLE 7

| Neoepitope ID | Polynucleotide sequence | SEQ ID NO: |
|---|---|---|
| AS1 | TTGCGCCTGCGGCCCAATCGGAGGCGGGCCTCATCCGCACA GACAGCACCGACTTCTTCATTGAGCCTCTGGAGCGGGGCCA GCAGGAGAAGGAGGCCAGCGGGAGGACACATGTGGTGTAC CGCCGGGAGGCCGTCCAGCAGGAGTGGGCAGAACCTGACG GGGACCTGCACAATGAAGCCTTTGGCCTGGGAGACCTTCCC AACCTGCTGGGCCTGGTGGGGGACCAGCTGGGCGACACAGA GCGGAAGCGGCGGCATGCCAAGCCAGGCAGCTACAGCATC GAGGTGCTGCTGGTGGTGGACGACTCGGTGGTTCGCTTCCA TGGCAAGGAGCATGTGCAGAACTATGTCCTCACCCTCA | 60 |
| AS2 | TGCTCCACCTTCTGCCAACGCAAGGTAGGTCTCACCTACACC AGGCTCAGTGCCCCCGCCTCCTCCCTCGCTACGAAGACCCCT GGGTGGCCCTCCCTCCCCTTGTGCTCCTGGTGCCACACC | 62 |
| AS3 | CAGACGGACTTCGCCTACGACTCAGGTAAGAGACTGGGGTG GGGCAGGGTGGCATGTGATCAAGTGTTCAGT | 64 |
| AS4 | CCTTCACTCTCAACACGGTTGACAAGTAAGGACCCACAGCC CCTACAATCCCATTATTGGGGGCTCATAGGAAATGACCCCTT CCTAAGAAGCAAAAAAAGAGTTAAC | 66 |
| AS5 | GTCATTCCTGGTGATTTGTCAGAAGCACATGGCTACTCATTC TCC | 68 |
| AS6 | GCGGAGGGCCCCGGGGGCAGCCAGGTGAGGAGGGGGTTTG GTGGGTGGCGCGGGGCCGGAAGCGACCAGTTGAGGGCGGA GCTGGAGAGCCGAGCACAGGCCGCCAGGTGCAGTGGGCGG AAGGAAGGGAGGGGCTCGGAGGCGACCAGA | 70 |
| AS7 | TTCGGGGAGCGCCGGGATGTGGACGGTGAGCGGGGCTGGAT TGGGGAGCGGGGATTTCTCGGGCGGGGGTCTCAGGGACCCA GAGGCACGGGGCGGGGCGGGACCCGGGCTTCGAGCG GCGGTGGCTGGGGGTATTCGGCGGATGTCTCGGCTCAACGG GGTCCCGTAGCCTTTGTCCTGCTTTAGGGGGCAGCCAGCCTC AGGCCTTGGGGGTCAGCGCGCCCTTGGCTTGGGGTGAGGGG GTGTCAAGCCGGGGCGCCTGTGTCCAGGCTGGCACTACGCT CGGGTCACCTTTTCCTGCGCACGGGGAAAACCCTCCCCCGCT TTTGCAGTGGGGCCGAAAGGGGGCCGAGGTCACATCCCGCC TCGGTGCCCCCGCCCCATTTCCTTCTGGAATCCTGACGTTGG GGCGGGAGGGACCGGACCGACAGACCGCGGGACGGACGGA ACTCCCTCCGGGAGTGCAGGCAGGAAATGGGCGGAGCCTGC TTGGCCGGGGCAGGTGCCGTGCGGGC | 72 |
| AS8 | AGAGTGCTAATTACAAAAACATTGGTAATTTCTGTCTCTTTC ATGTGTCCAGGCTTCTGGTCAGCGGCACAGTGTGAAGTGAG GTCAGCTTGCTTGCTGCTCTGTGAGGGACACAGGTGGTGGG GCACCTGCCTTACTGGTCACCGCTTGAGAAGGTCACCTGGG ACCACAGGGGAAAAA | 74 |
| AS9 | AAGGTGAAGACTGTCTGCAGCAAGGTAGGTGGCGCTGTCAT TCTTCCCTGCCACGGGGAGAACATGCCCTCCACGCCCTCCCC ACAGGACATGCCCGTGCTGTTCCCTGCCCGTCCTGCCCCATG CACCATCGCTGCTTCTGCCTTCAGAAGGCTAGGTGACCCGGT TTGTGTGGCCTGG | 76 |
| AS10 | AAAGATTTACCAGTTTACTTAAAGGATCCTGCTTATTTTTAT GGATAT | 78 |

TABLE 7-continued

| Neoepitope ID | Polynucleotide sequence | SEQ ID NO: |
|---|---|---|
| AS11 | AGCCTGAAAGACGAGTGTGATACGGTGAAAGGATGGAGGCTGTGCAATGGGAGAATAACTGGGGCTGAGAAGAAAGCCAAGGTCATT | 80 |
| AS12 | GCCATGGCAAAGAAACAGCGTCCAGACACAGCTTTCTGGGTTCAACAT | 82 |
| AS13 | ATGACCCTGGGATCCAAGTCACAGCCTCCAGAGGACATCAAGGCACTG | 84 |
| AS14 | TCCCGCAGACTGAAGCTGGCCCAGGGAAGACTACGAGGGCTGGAAAGACTCCATTCGCCACAACCTTTCCTCCAACCGATGCTTCCGCAAGGTGCCCAAGGACCCTGCAAAGCCCCAGGCCAAGGGCAACTTCTGGGCGGTCGACGTGAGCCTGATCCCAGC | 86 |
| AS15 | CAGGCAACGCCGTCATCTATTCTGTGCTTCAGACTGGCTTGCCTGTGGCTTCTGAGGAAAGGACTTCTGGATCTCACTTGG | 88 |
| AS16 | TACTGCAAGAACGACTTCTTCCGGTCACTGCCTTGCCACCTTCTT | 90 |
| AS17 | TGGAGCCAGGACCTGCAGGAAGGCTTCTCCGCTCCTTCTAGGATCTCCGCCTGGTTCGGCCCGCCT | 92 |
| AS18 | CAGAGCGAGGCGGCTGTGGCCCAGGACAAGAAGCAGCTGCAGGAGGAG | 94 |
| AS19 | CAGCACCTGCAGCAGGAAGCCTGTGTCACGTCGGCGGGAAGCAGTCA | 96 |
| AS20 | CGGGCTTTTCCCAGAGAGCTAAAAAAGGGCCAGAGAATGTCGTCCCAG | 98 |
| AS21 | ATGAAAATGAAAAAATTTCAGGACCTGACTGTGAACTTCACCCAA | 100 |
| AS22 | CCAACAGCAACAGAGAGAGTCCAGAGGGGTGTGAAGCACAAGGCTCCAGTCCAGGCCGCACAGAGCAGCGATGGGCCCCCTCCTGAAGGACCTCCTACGGCGGCCAAGGCGCAGT | 102 |
| AS23 | GCGCTCATGGAGGTGTCTGTGTCTGGGCAACGTGGC | 104 |
| AS24 | GTGAATGCTGATGACTCTCTGGAGGCTGGTCTCCAACTCCAGGCCTCAAGTGATCCTCTTGCCTCGGCCTCC | 106 |
| AS25 | ATGGCGACCAAGCGGCTCGCGCGAAAGGGTACACTCGCCAGCAGTTTTGCCAGGAGAGTACAC | 108 |
| AS26 | GGCAGCCTGCTGTCTTCAGGATCTGGTGCCAGGAGACACTGCATTCTACTCCCAGGTGGGTTTCTCCGGCTTTTAAAAATGCGGAATACTCTCTCCATCGTGTCGCAGGGCATGATTTCTCCATTCAGTGCCTTT | 110 |
| AS27 | TTTAAAATTCCTAAGTTTTCTATTGTTCTTTCCTCCAACAGTGCTTTTCAGGTGTGACCCGCTGTCTTCTCGCCCACGTTGTTTTGGGGGGTCACTGGAGGCTCCC | 112 |
| AS28 | GAAGAGGACAGAGAAAAATATAGGTGGATGGCTCCATTTGTTCCAGGCCAAGTGTGGACATGGGAGTATTTCCTC | 114 |
| AS29 | TTGAAACAGGACGTCCGCTCGGGGGGGCCGGGCGCCCGGCAGCTACGTGGGGGCCTGCTTCGACAGGCTGCTCCACCCGGACGCCGTACCCGCCCTTTTCCGCACCGTGCCCGTCTTCACACTGCCCTCCCAACTGCCAGACTTCCTGGGGGCCCTGCAGCAGCCTCGCGCCCCGCGTTCCGGGCGGCTCCAAGAGAGGAGCGGAGCAAGTGTCCCGGGCCCTTCAGCCAGCCCTGGA | 116 |
| AS30 | ACTCATTCTGCTGAGGAAATAGGGCAAGAATATTTTCTAAGACCCCGAACTCCAGATATGCGATGGGGCAAATCC | 118 |
| AS31 | GGGGATCCAGCCAAGGTCGTCGAGATCCCGAGGCTTTTG | 120 |
| AS32 | CGGTCCTGGATCTCCACCACCAGCACTCCGATGACCTCCATGTTCTCTCCAAGGCCTCTCGTATCTGTGAGCCCCACCCCCAGCGCTACAGGTAGGAATCTGGCTTCCAGCTCCCATGAAACGTCGGCTGCCATTCAGTGGCTGATTAATTGCTGTGTGGTC | 122 |

TABLE 7-continued

| Neoepitope ID | Polynucleotide sequence | SEQ ID NO: |
|---|---|---|
| AS33 | ACTCGCTCCCTTGATGATCTTGAGAAATTGGACACCTTGTGCTGTAAGCTGTCCGTCCATGTTACA | 124 |
| AS34 | GCCACGGCGTGGAGAGCGGCAAGAATCCGCGCTCCTGGTCCAGGCTCCAGCAGAAAAGGATTTGTGGCAGTTTACAGTTTATCTTTTAAAAATGGGAAAAGTGCAGAAGTGAGCCAAAGGCAAATAAGTATAACG | 126 |
| AS35 | AAGCAATATCAACTAACTGTGCAGATGGAGTCTCACTCTCTTCCCCAGGCTGGAGTGCAATGGCACGATTTCGTCTCACCGCAACCTCTGCCTCCTGGGTTCAAGCGATTCTCCTGCCTTAGCTTTCTGAGTAGCTGGGATTACAGGCTCCAGCCACCACACCTGGCTAATTTTTTTGTGTTTTTAGTAGAGACAGGGTTTCACCATGTTGGCCAAGCTGGTCTCAAACTCCTGACCTCAGATGATCTGCCTGCCTCGGCCTCCCAAAGTGCTGGGATTACAGGTGTGAGCCACCACGCCCGGCCAAACTTTTTTTTTTCCCTTCTCCTGTCT | 128 |
| AS36 | ATTGGGAAGGGCAGCTTTGGCAAGTTTTTAGAAGATGCAACTCACATGGTA | 130 |
| AS37 | AAGAAAACAGCAATAGGCATAAAGACTCACCACGGATGT | 132 |
| AS38 | TATTTGCAACTCAGCCTAGAAGAGTGCACACAGAAATGTCTTTTCTGCCTT | 134 |
| AS39 | CTTCTGCTTGCTGGCCTGGCACAGGTAATGGCACCGAAGCCTCCTTTCGCTATGTTTGAACAGCGCCACGCTTTCCTATATATTTTTATAGCAGAGCCTAAGGCACAGCCTGGCACAGTGCGGGAAACAGTGTCTCTCCATGCCAGCTCCAGGCGGAGGCTCAACTTTCCATTGCTGTTTGCAAAATGTGCAAAGAGCCCCTGGAAAAACGAATTT | 136 |
| AS40 | GCTGATTCAGACTTTAGACAAAGGAGTCTCACTCTGTTGCCCAGCCTGGAGTGGAATGGCACCATCTTGGCTCACAGCAACCTCCAACTCCCGGGTTCAAGAGATTCTCCTGCCTCAGCTGGGATTAGAGTAGCTAGGATTAGAAGCACACACCACCACGCC | 138 |
| AS41 | GAGATGGTGGATGAACCCCCAGGTCACAGATCAACAGGATCCCAAGGCAGAAGAATTTTTCTTAGTACAGAACAAAATGAAAAGTCTCCCATGTCTACCTCTTTCTACACAGACACGGCAACCATCCGATTTCTCAATCTTTTCCCCACCTGTCCCCCCTTTCTATTCCACAAAACCGCCATTGTCATCATGGCCCGTTCTCAA | 140 |
| AS42 | GAGGCAGTAGCCAAACACCCAGGAGTCCAACCTTATTATATTCTCCATAGAAGTGAGATCATACAGTATTTGTCTGTTTCTGTGATGTTTCACTCGGCA | 142 |
| AS43 | CATGAGATGGTAACTGAACCCCCAGGTTTACAG | 144 |
| AS44 | GTCCTTACCGTGACGTCCACCGACCAGGAGTACCTGGACCTGTCGGCGCCT | 146 |
| AS45 | AAAAGGTTAACCGTGGCTCCACCAGGTAAACATTTTTTCCTTGGGTGCATG | 148 |
| AS46 | ACAATGACGCTGTGTCTGGGCGGTGAGCGCAGGGCCCGTCTGGGCTGCGGGGAGGCGGGGCTGGACCCAGAGTAAGAGGTGGCTGGTTTCTGGGCAGGACTGACCAGGATCTGGGTTGGGGGTTGGCGTTTAGGAAGGGGGTCGAGTAC | 150 |
| AS47 | AGGAAATTAGAATCAAGGAAATACGGTATTTCCTTCCTGTCTTTTGACTGTGCCCTGTTTTCTATGCACTTTCTTCTGATTTCTTTGCATATAAAATGGTCACTGGAAAAGAATCAAATTTCT | 152 |
| AS48 | GAGAAGCAGAGGATCAGCCGGGGTAAGCAACCTGCC | 154 |
| AS49 | GATGTTGAAATGAAAGAAGATTCAGGTATTAAATTCATACTTTTATTATTAGGGGGTAGG | 156 |
| AS50 | AGCATCGTCAAAAACATGCCAACTGTGAGTAGCCAGTCA | 158 |
| AS51 | TGTGTGGAGGAACGTGGCTATGAGGTGGGGGCTTCTCCCTTCTCCTCCCATCACTGTTCCCTTTTTTGCTCTTTGGGGTTCAAGTCTCTAGGGCCTTTACAATTTTCATTTAATAATAAGATACAACAGTGGCCTTGTATTAGTCTGTTTTCACACTGCTATAAAGAACTACCTGAGACTGGG | 160 |

TABLE 7-continued

| Neoepitope ID | Polynucleotide sequence | SEQ ID NO: |
|---|---|---|
| AS52 | CTCAAAGTGGGCATGAGACGGGAAGGTATCGGCCTCTCATTTCTCCTTCCCTCGTCCTGGGTCCCGGGGTCCTGGGTACGTTTGGCTAGCCTGCTCTGGGTAAGGACAAGAAGCCCCAAGCTCTTCTCTTCGTATTGCAGCGGAAAAGGGTTTTATACTAGAAGCGAGTTCTGCATTGGAACCCAGACCCCAAATCCGCATGCTTTGGCCGAC | 162 |
| AS53 | CTGGAGGGAGAGATGCTGTATCTGGTAAATGGGGTGGGGGCTGGGTGTCTGGGAGAAGGGCCTCCAGCTATAAGGCATCCCCTTGTCCAAACCAGA | 164 |
| AS54 | AGGAACAGCCTGAAGACCAAGGTGACAGACTCCACCCAGCGAGAGGGGGGATTCCTTATGCAAAAGGGGAGGGAA | 166 |
| AS55 | GAGCTCCAAGACTCGTTCTATGCAGGTACTACCCTCCCATATCTA | 168 |
| AS56 | GATCAAAATAATTATCTACAGTCAGGTACAAAGTTAATTAATAAAAAAAACTATGTCATATATGTAAGTTGG | 170 |
| AS57 | TTGGCCTCCCTGGAGGAGCAGGTGGGTCCGAGGTCGGGGCCTCCGTCAGGAGGTGCCACTGCTGGGCCTGGTGGGCGGCTCTGCCATGTGGTGGCACCAAGAAGGAGGGCTCTGAGGAGTGATGGTGAGGAGGAGGCCGGAACGTTGGGGCAGCCATTCCCAGCTGGAAGAGGCACCCTGTGTGTCCTCCAGAAAACCCCGCCCAAGGGTTTCTGTGAC | 172 |
| AS58 | GCCGCCGCGGGCAGCCGGACCCCAGGCGGGCCTCATCCGCACAGACAGCACCGACTTCTTCAT | 174 |
| AS59 | AAAGCCATGTACCATGCTCTGGAGAGAACAAGACTCGAAGACGCACAGCTGACGACTCAGCCACCTCTGACTACTGCCCCGCACCCAAGCGCCTCAAGACAAATTGCTATAACAACGGCAAAGACCGAGGGGATGAAGATCAGAGCCGAGAACAAATGGCTTCAGATGTTGCCAACAACAAGAGCAGCCTGGAAGATGGCTGTTTGTCTTGTGGCAGGAAAAACCCCGTGTCCTTCCACCCTCTCTTTGAGGGGGGGCTCTGTCAGACATGCCGGGATCGCTTCCTTGAGCTGTTTTACATGTATGATGACGATGGCTATCAGTCTTACTGCACTGTGTGCTGCGAGGGCCGAGAGCTGCTGCTTTGCAGCAACACGAGCTGCTGCCGGTGTTTCTGTGTGGAGTGCTGGAGGTGCTGGTGGGCACAGGCACAGCGGCCGAGGCCAAGCTTCAGGAGCCCTGGAGCTGTTACATGTGTCTCCCGCAGCGCTGTCATGGCGTCCTGCGGCGCCGGAAGGACTGGAACGTGCGCCTGCAGGCCTTCTTCACCAGTGACACGGGGCTTGAATATGAAGCCCCCAAGCTGTACCCTGCCATTCCCGCAGCCCGAAGGCGGCCCATTCGAGTCCTGTCATTGTTTGATGGCATCGCGACAGGCTACC | 176 |
| AS60 | CTGGCTTCGGGCGTGCCCCCTCCTGGTCTTCCCTGGGGCCGGGTCCTCACCTTGGC | 178 |
| AS61 | ATCCCGCCTCATTTACAGTGGGAGAGCACTAGACAAACTGAATGGATTTCAGTTAGAGAATTTCACCTTGAAAGTAGCCTATATCCC | 180 |
| AS62 | CCTGGGCACGGGGCCATTTGTAGGGAAGAGGTT | 182 |
| AS63 | CTTGAAGAAGAATTTATTTCAGAGTGGCGTAGATGTTACTATGCAGTTACCTTCAATGG | 184 |
| AS64 | CAGACCCAGGAAGAGACTGACCGTGACAGGGGATCCTGGAGCTGTGCTGTGGCT | 186 |
| AS65 | TCCCACGCCCTCAACTGGAACAAGATAGGCAGAATGTTTCGAGCTTCCAGAGTC | 188 |
| AS66 | GACTCCAACAAGGATCTTGCCCAGGATTGTGAATTATACACCAGATTTGCCAAGAGATGCTGT | 190 |
| AS67 | GGCACTATGGAGGTGAAGAGCAAGAAGAAGCAGACTACAGTGCCTTTGGTACAGACACGC | 192 |
| AS68 | TTATTGTTTCCTTATAATCAGCTGGACTTACACTTGCATAGACCTTCTGGATCTCGTAAGAACGAAATACACTGGGACAAATGTTTCTCTTCAGAGGAT | 194 |

TABLE 7-continued

| Neoepitope ID | Polynucleotide sequence | SEQ ID NO: |
|---|---|---|
| AS69 | GGCTTCATCTTGATAGGCTGGGGTGCTGGGAACTTAGTGCTGGAGACATCAAGTGGATTTATCAAGCACCGATCT | 196 |
| AS70 | CACTTTGTCCGTTCCCAGGACAAGGGAATGGTATGGACCCCGGAGCCCTCTGCTCTGCCCAGAACGCCAAGAAGACATCCTGGACTCTCTCTATGCTCTCAATGGGGTGGCCTTCGAGTTGGACCTCCAGCAGCCAGACCTGGATGGAGCCTGGCCCATGTTCTCAGAGTCACGCTGCTCCAGTTCCACCCAAACCCAGGGAAGGAGACCCAGAAAAAACAAAGATGCCCCAAAGAAGATCCCAGCCGCATATGGAGGGCC | 198 |
| AS71 | AACATTGAGGATGTGGCCACAGAAGATGGGAGGCATGGAGGCTGTCATCACGGGCCTGGCAGA | 200 |
| AS72 | AGGAGGCATGGAGAAGTTCAGGGATTGCTTGAAAGAGAAAAAACAGCAAGAGGAAACCCTAGTGGA | 202 |
| AS73 | TCCTTGAGTGATAAAGAAGTAGAGGGAAAGGCACTCCTAGGGGACATAAAATTAGTGATTACTTTGAGCGACGAG | 204 |
| AS74 | GTGCTGCGGAAAACCGCCCACAGATCAACTACTGCTCGGTGCTCGTGTCCTCCGTGGCTGACGTGCTGGCCCAGGGTGGCGGCCCCCGGAGCTCTCAGCACTGTGGCGAGGGAAGCCAGCTGGTGGCTGCTGACCACAGAGGTGGTT | 206 |
| AS75 | ATGCACAGGAAACTGCAGGCCAGAAGCCCCTCTCTGTGCACAGGCCACCCACCTCAGGCTGCC | 208 |
| AS76 | CTGCTTGATCTTCAGGCCAAAATGATATATTTTAAGAATTCAGAGAAT | 210 |
| AS77 | AGCATATCTTTGACTGATGACGAAGCTGAGCTGCCCCTCCTGGACCTG | 212 |
| AS78 | TCCCTGCCGCCCCTCGACTCTGAAGCTCAGGTACCAGACAGTGATGAG | 214 |
| AS79 | GCTCCCAGCTGCGGGGTGAGCCGAGCCATCTGTGACCGCGGCTGCCAC | 216 |
| AS80 | GCTCCCAGCTGCGGGGTGAGCCGAGATTACCGGACGGGACCCTGCTTT | 218 |
| AS81 | CTGTCGCCAGGGGGGCTTGTGTGGACATTGACGAGTGTGACCGGCAG | 220 |
| AS82 | ATGCCTGGGCACGGGGCCATTTGTAGTGGCTCCAGCAGGCAGCCTGAC | 222 |
| AS83 | GTCCAGAAGCTTAAAAATGCCAGAAGCCTGAACTTGGAGGACCAAATT | 224 |
| AS84 | AATCCAAAGAAGTTCAAGATCAACTCCAGAGTCCTGGTGGAGGACGAT | 226 |
| AS85 | CGAAAGCCAAGGAACTGGCTGGAGAGGGCTCGATGGCTCCGGGGAATC | 228 |
| AS86 | GACGAAGCCAAGTTCATTCCCAGAGCCCAGGACAAGGCAGCTATGCAG | 230 |
| AS87 | CTGCAGGCCCAGCAGCAGGTCCAGGTGTCAGCACAGCGGGCTACTCCT | 232 |
| AS88 | TGTCTCCGGCCCAGCCTGAGCCTGGCCTCCAGGGGCTTCCAGAACCCG | 234 |
| AS89 | AACTACGGAAACCTGTTCTCCTTGGCTGGCTCTTTGCATTTTACTGCA | 236 |
| AS90 | GTTGAAGATGAGGAGAAGAAAGAGCCTGATGGAGCCCAACGCCATCTAGTGGACATTGGTGGTTCTCACCAGACCAGCCATGCTGAGAAATTTTTGTTCCTCCTCTGCCCTCCAGTGGTC | 238 |
| AS91 | GTTGAAGATGAGGAGAAGAAAGAGGCAGGGACTCATTTCATCCACCTGACTGGAACCACTGTCTCAGCTGGAGTCCCTGAGGAGATGCCAGCCACAACTCTCCGAAGAGAAGTATTC | 240 |

TABLE 7-continued

| Neoepitope ID | Polynucleotide sequence | SEQ ID NO: |
|---|---|---|
| AS92 | GTTGAAGATGAGGAGAAGAAAGAGGGACTCATTTCATCCACC | 242 |
| AS93 | GTTGAAGATGAGGAGAAGAAAGAGGGCAGCATGTTGGTTGCTCCAACTTCTCCTCCATCCCTGGAGGCAGGGACTCATTTCATCCACCTGACTGGAACCACTGTCTCAGCTGGAGTCCCTGAGGAGATGCCAGCCACAACTCTCCGAAGAGAAGTATTC | 244 |
| AS94 | AGCATGATGGAGGGTGTCATCCAGTTGTCATTCAAAGCCATTGTCTGTCTTCTATCATGTTTGGACTTACTAAGCCTGTTTCGAGTTGTGAGACACCTATCA | 246 |
| AS95 | ACTAAGAAAAGAAAGCAGAGTGAGCTGCAGCAGCCA | 248 |
| AS96 | GCCTTCTTCAAGAGAAGTATTCAAGAACTTCCAACACTATGT | 250 |
| AS97 | TTCCAGGAGACGTGGCTCGCTGAAGATGCAGCTGCCGGGGCCCTGTCCCCTGCACCATCCCAACACCACCCCAGCCTCCTCTCCTGTCTCTTCCCACCAGCTCAGGTACCAGACAG | 252 |
| AS98 | AGCCAGGAGCAGAGCCGGACCCGAGCTATCTTCACATTTATCCTTGACACAAAGAAAAAAGAAATACCTGTAGAAGCGCATCGAAAGCTCCTGGAACAGAGTTGTGTCTCATATTTGCAAAGATGCAGAAAAAATAAACCCGGGACATCCAGCTTTCTTTTCCTTTCTTCTTTGACTATTCTGAGAAGCTATGCGACTAGGAGCACATTT | 254 |
| AS99 | CGGTTAGATGACAGTGGGATTGGTAATTTTATAACTAGCTTGTTAAATTTCATAAGTAAATTCTTCTGCAGTTTTATGGGTGCA | 256 |
| AS100 | AATGCTAACAGCCGGCTGCCTGAGGCCTGTGAGAAG | 258 |
| AS101 | GATGGTGATGGGATATTTTCTCCTGAGCTCTCC | 260 |
| AS102 | ATGTCACAAGAGTCGGACAAGAATGGTCTCAGCTCCCGCTCCTGGATGAATACTTGGATATTGCCAGAGGTTTTG | 262 |
| AS103 | CTTGACCTTGCTGGGAATGCTCGGCCCTGCAGGTCTCAGTCCCCCACAAGCAGTGATCAAACCCCCAGTGTGCCAAGCCTAGGATCCCCAGAGCTCCCAGATGGTGAAGAAGGGGGATCCCCAGATGGTTCACCCCAGGAGAGTGAGCAGGTCAGACAAGGGCAGCATGTC | 264 |
| AS104 | CCGCGCGGGCGCCCCCGCCGGAAGGTTGATGTGCTACCTCAA | 266 |
| AS105 | CCCAGCCCCAGCACCCCCAACCACAGCCAGCAGGCAATATGCCACCCTGGCCGACGTCCC | 268 |
| AS106 | AGCCCCAGCACCCCCAACCACAGGCCATCAGGATCAGCCACCGAGAAGCCTTCCAGGTGGAGAGAAGGCGGCTGGAGCGTAGAACTCGGGCCCGGAGCCCTGGCAGGGAGGAGGTGGCCCGTCTGTTTGGCAACGAGCGGAGGAGGTCCCAGG | 270 |
| AS107 | TCTGGCTGCAGACTGACTTTGCTCAGCTTGTCACCTGTCTCAAGTCTAGGCTGTCCTGTCCCCATGCCA | 272 |
| AS108 | TCCCAGTTTTCTCTGGATGACGTGGGGTTTCTTGCACGGGGGCAGGCAAGGGTGTGGCCGTCTCGACTCCAGGCCCTGCTTTCCACA | 274 |
| AS109 | TGCCCATGCGAGTACCTGAGGAAGATACAGGTTGATGGACGGATGGCTACATGGATG | 276 |
| AS110 | CCATGCGAGTACCTGAGGAAGGTGGAGTTTGTCCCAGAGCCGCACAAAATCATCACCAGCATGATTAAACGGAGTAGACTTCAGAAAAAGCAGTTTGGTCGGATG | 278 |
| AS111 | TGGCTCCTGCGCACCTGGGAGAGAGCTGACAGTGGCCTT | 280 |
| AS112 | CCTGACCTCGGCCACTGGCTCACCAGAGCCGTGTGGGGAATTCAGCCACCTCC | 282 |
| AS113 | ACTATTAAATTAATAGTGGGAAGGACCTCAGCTTTGGGTCAGTAT | 284 |

TABLE 7-continued

| Neoepitope ID | Polynucleotide sequence | SEQ ID NO: |
|---|---|---|
| AS114 | TTTATTCAACTTAGAAAAGAATTGAACTTTACCAGCACCCCAGATGCT | 286 |
| AS115 | GAAGAGGAGGAGGAAGAAGAAGAGCCCCTTCGACTCCACCGGGGCCCTGAGGCGGCTGGGGTGGGGCTGTCTGGGCCCCAGTGGGGGAGACCTGGGGTCACCAGCTCCCCCAACCCTTCCTCGCACTCGCTGGTACTATGCCCTGCCACCACAGGCCCCTGTGTCCGTCTGGGA | 288 |
| AS116 | TTTCAAGTCCTTCCTGGGGACCGGGAGACGGGGTTTCACCATGTTGGCCAGACTGGTCTCGAATTCCTGACCTCAAGTGATCCACCCACTTCGGCCTCCCAAAGCGCTGGGATTACAGGCACGAGGCATCGCGCCCGGCCAGTTTGCTCAAACTTTTACTGCAGGTTGCCTTGTCTCTATGGTGAGGGGAGAATATTAGGAGGTTGCCCAGGCTTATGATAAGGGAAGGCATGAGGTGGTGCAAGTTTTCAAGTGAGAAGTCGTCCAGGTTCCCAGTGACAGCAGAA | 290 |
| AS117 | TGTGACCTGGAGTGCAGCGAGCAGAGACAGGGTTTCGCCATGTTGGCCAGCTCC | 292 |
| AS118 | AATCTACAGTTACTCACACAAGGATATTCAGGAATATGGAGATATCCC | 294 |
| AS119 | CACTTCAGCCGGCTCTGCGGGCCCGTGTCCCACCTGAGTGCCCACCTTGCCCACCTGAGG | 296 |
| AS120 | AAGCACCATCTGTGGGCTCTGGAAGCAGCATGGCTGTCTGGGCGAAGCCCTCTCTCTGAGCCTCAGCTTCCTCTTCAGCCCAGTGGGAACAGTTCTTCTGTC | 298 |
| AS121 | ACCGAGCATGAAAACACTGAGACTGGTGCTCCCTTGCATTGTTCATCCTGCTTCATCAACCCCTAT | 300 |
| AS122 | TGTGGGATCTCCGTCTATTTAGCAGGCCGGACGCGGTGGCTCACGCCTGTAATCCCAGCACTTTGGGAGACCGAGGCGGGCAGATCACGAGGTCAGGAGATCGAGACCATCCTGGCTAACAAGCACTGTCCATCTATGCCTTGCTACTTTTCGAGATCGAGACAGGCGCAGCAGCTGCTTCCATCCTCGGCTCGGGCACCCTGGTTCTGGTGGCTGTGC | 302 |
| AS123 | AAGCTGTGCAGCCGGCAGCGGCCAGACTGTCAGCCTGTTGACAGCAGGCATGGGCCCATTTTGTCCATACAGCATCTAATTAGTGCCCTGCATACTGGGGATGGA | 304 |
| AS124 | GAGGAAATGGAAACTGATATGGATGATGTGGCTATGGAAAGCAGTCCAGGCTCATCCATCTCTATGGAGCACAGGCTGGATGTTGAATTAAGGGCATCAGGTTCCAGCAGCAGCACTAACATCTCTTCTGGCCCCAGCCCTGGTCCCAGTCCCGGCCCCGGCACCGGCCCTGGCCCCGGCCCCGGCCCCGGCCCCGGCCCTGGCCCCGGCCCCGGCCCCGGTCCTGGTCCCGGCCCTGGCCCCGGCCCTGGCCCCCGTCCTGGAGTCCAGTGTATTCCACAACGA | 306 |
| AS125 | CGGGACCTGCAGTGCCCCAAGAAGACCCAGACCCCGCAGGCGCAGTCTCGCTTGGAGAGTGAGAGGAAGAAGAACACGCTGACCTGGCTTGTTCCTACTCCCTGGGATTGGCGTCAGTGGAGCACGGCTCCCTCGAGGGGCCTGGTCTGGCCTCCTCCCCCTGTGGACTATGAGCTCTGGAAGTCCTCG | 308 |
| AS126 | CATCAGTACATAGTTGTACAGGACATTCACACAGAGACTCAGCACTCAGCCCTCGGTGCTCAGCCTGCGGACTCCATCCCCCCATTTCTCCAACACACCCTGCAGCATTTAGCTTGTCCTAGCCTGGAGCTGCCTGGGAATGAACAAGCTAGAAGAGAAAAAAGGAGGAGGGATGATGCCTTCTCCGACAGCCTG | 310 |
| AS127 | ATTGATCCAAGCTCTCCCTTACATACCTACTATGAAAGAATTACTAAAGGACGTAATCCAGAAAGAAGATATATGAAACGGAACGAATCAGTCCGGGACACGAGGCCATGGAAAAAAACCTTGAAGATAACTTA | 312 |
| AS128 | GTGGGCAACAAGATGTTTGTCAAGGTCAGAAATCGGAATGTGCCTCAGCCCCCTCTTCTTCCTACTCCTAGCCACCTGTCACTGCCCTGGAAGGAAAGTGGTGGTCTC | 314 |

TABLE 7-continued

| Neoepitope ID | Polynucleotide sequence | SEQ ID NO: |
|---|---|---|
| AS129 | TGGGACAAGAATGCCCCTGATGAAGGCAAGTGGGGTCTATGTGGGGGCAGTGAGGTGGGAGAGACAGAAAGAGAGGATGGGGGATTAGGTCAGGGTTACAATGCCTCCCAGGGCCAGGCAGGTGACAAACTAGTGGGGCAA | 316 |
| AS130 | ATGGGAAAGGTAAGTCCTGGGTACCGGATGCTCAGCCTTGGCCCTAATGCAGTGGCCTCAGTGGGGGCCAATCACTCCATGCTCCCACATCTTCCATTTTTCAGATCACCTTCTACGAGGACAGGGCCTTCCAGGGCCGCAGCTACGAATGCACCACTGACTGCCCCAACCTACAACCCTATTTCAGCCGCTGCAACTCCATCAGGGTGGAGAGCGGCTGCTGGA | 318 |
| AS131 | TACGGAATGCCTCACAACAACCAGGTAGGTGGAGGGCGGCTCCCCTCGCCCATCCTCCCCCCCATGCCAGAACCCGTGGGCAGCCGGCGTGGCTCCAGTGTGGGCTTTCTGGACATAAGCATGCTTTTCCAGCGACTCCACAGGAGTCTGATG | 320 |
| AS132 | ATGGTAAGTGAGGAACTGGCGTTAGCTAGTCCGCTGGCAAACTTGGGTCTC | 322 |
| AS133 | TGTGACCCAGCGGCCCCTCGCGCTGTAAGTCTCCCGGGACGGCAGGGCAGTGAGGGAGGCGAGGGCCGGGGTCTGGGCTCACGCCCTGCAGTCCTGGGCCGACACAGCTCCGGGGAAGGCGGAGGTCCTTGGGGAGAGCTGCCC | 324 |
| AS134 | GCGCGGCTGCGGGAGCTCAGGCAGTGCGGGGGGGCGGGGAAAGAGGGGACAGGGGTGGGGGGTTCGGGATGAGACCATAACTGGCCGGCCAGCAGTTCTGGGCAGCCCCTTCCTCTCTCCTGCCTTGGCGCCTCCATCTAGACTTATGGGCGATCTCTGGGATGGCCAGTCAGCGGGGTGGTCTCCTGGGTCCCCAGCCTCGCCATTCTGTGGGGGGTGG | 326 |
| AS135 | CTTCACTGCCTGGAAAAAACCACGGTAAGGAGACAGCATGACTGCCTTCCCTTGCTCTCTGACAGTAATTCCATTTGCTTTTGTGCATACTTAATGCTTCCGAGTGTGATTTCACTGTCTGCATTACTGGAAAACATGCTAAAAAACAAACAAACCAAAACCCCACAATATTTGAAATTACTT | 328 |
| AS136 | AGGGTCCGTGGGGCTCCAGGCAGAGGTGAGTCCCTCCCTCCCCGGGGAAAGAAGAGGGCACATGGGTGGGAGGCAAAGGGC | 330 |
| AS137 | CTATGTGGAACTCCCCAGGCTGCAGGTAAGGGGCAAGAGGTACGGGATTCCTTAGCTATTTGCAAGGTTGGGGAGGGACTACTGCTCTTTCTCCTAGGAGCCTGGCGAAGGCATCTGACTCAAGAAGATAGAATTACCCCAACCAACCTCCTCCTGCCTCTGACACTAGGGAAGACCCAGAGGCAACGAGGGTCCAGGTTATGCAGTTTCCTTTATAAAATAAGAAGAATGAGTAAATGCTTCCAGAAAAGTAGAAATGAG | 332 |
| AS138 | TACGACGTCTTGGTGCTCAAAGGTGAGTGGGGGCATGCAGACCAGGGGCTACTGTGGCCCAGGAAGTCCAGG | 334 |
| AS139 | CGGAGCTCTGTGCCCACCACCAGCAGTGAGTATTCTACTGATGTTCCCATGGCCCCAATCTTACAACAAACT | 336 |
| AS140 | CCATCATCCCTCCCTGGCCCCACAGGTAAATACCAGTCAATGGTATTTGGAGCATGGTTGATGAGTGTAAACATCTCTGTTTATACTCTGTTAGAGCATGGT | 338 |
| AS141 | CGGAGCTCTGGGCTCACCACCAGCAGTGAGTATTCAACTCATGTCCACATGCCCCTGATTCTACACCAAGCGGAACAGGAGCTACTCCTCCTCATAAACCCA | 340 |
| AS142 | TGGATCCCTGTGCCCACCAGCAGCAGTGAGTATTCAACTCATGTCCAGATGCCCCTGATCCTACATCAAGTGGAGCAAGAGCTGGCCCCTCCTCTT | 342 |
| AS143 | CGGTACTGGACCCCTGCCACCAGCAGTGAGTATTCAAACCTG | 344 |
| AS144 | CCGACCACTACGACCTTCCTGAAGGTGAGGCTTTCTTCCCCAGCCCTGGGCCAGCTTCCC | 346 |
| AS145 | CAGGCTGGGGCCGAGCCTAGCACAGTGAGGACGGGAAAGAAGGGACACCTT | 348 |

TABLE 7-continued

| Neoepitope ID | Polynucleotide sequence | SEQ ID NO: |
|---|---|---|
| AS146 | AAGAGACCCATGGCATCTGAGGTGAGTTTCATACTGATACA ATGGTTACTAAAACCT | 350 |
| AS147 | GAATTTTTAACTCAGGAATCTAAGGTATCATTAGAAAGCAG AAATAAGCTTATATTTGGTTACTTTACGTCATTTCAGAATCT CTCAACAAGTCTTTCTTTTAGAAACATGAAAATGAATTTAAT GAAGAAGTGGCCT | 352 |
| AS148 | CTGACCCCTGCCCTCCGCACGTTGGTGAGCCGAGGGAGGGA GGAGCCTGGGGGGAGCTGGAGGAGGGGCTGGGTC | 354 |
| AS149 | TACCTGGAACCCTTGGAGGACGGGGTGAGGGGC | 356 |
| AS150 | GCGGGGAGCCCTGGCGAGGAGCAGGTACAGTTCCAGGGCCT TGGGATGGACACAGACCCTCTGTCTCCTGAGGCCAACCCGA CCCCGCCCATCTGGCCTCAGGCACCTCCCCACACACCCCTG | 358 |
| AS151 | CGAGCCATGACAAAAAAATACGAGGTGGGCATGGGGCAGA GCTGCGTGGGTGGGGCAGGGGTCCAGGGAGGGTCCAAGTG GTGCAAACCCCAAAGGGTGGGAGGGTGGGAAGGGGGCCAA GTCCAGGCCATCTGGCTGAGCCTCACTGAGGCCTCCTCTGTG CCCTGCCTGCCA | 360 |
| AS152 | CACAAGGACTTCAACAGTCAGCTTGGTAGGAGGATACCCCA GAGAGCACCTCCAATCCTGTTCTTTCTAAAAAGAGGAAACT TCCAA | 362 |
| AS153 | GTTTCCCCGGAGGAGTTGGAGGAGGTAGGTGGGGCCTGGGG AGGTGGAGGAGGTGGGGAGGAATCGGGTGGGCTGGAGGCT GGA | 364 |
| AS154 | AAAGATCTGAGGGTGTCGGACAAGGTAAGGTTGTTCTCCAT G | 366 |
| AS155 | GATCAAAATAATTATCTACAGTCAGGTACAAAGTTAATTAA TAAAAAAAACTATGTCATATATGTAAGTTGG | 368 |
| AS156 | CCGGCCAAGAGGCACAAGCAGCTCAGTATGCCAGCCCCAGT GCCTCTCCTGAATGTCCTGGCCACCCGGGTGCAGAGGGGT GGAGATGGCATGGCAGCTCTGCCCAGAACCCTGGACGCTCA GCAGGCGTGCAGGTCACTCAGGCTGCTGGCCTTCTGCTGGC CTTGAGCAAGTGGTGGGGGCTGAGCCCAGAGGCCCCCTTGG GGGCAGGTGTGCGATGGGCTCTTCCTGCCACTCAGGACTGG CCCCCTCCCACGGGGCCCCCCCGGTGGGTCAGGGCTTCAGG GCCCACCTCC | 370 |
| AS157 | CGAAACACTCTTAAAGAGTCAAGTAAGTTAAAATCCTCCTT TGAATATTGGTTTGCTGGTTTCTTTTCTTCTTCTTCTTCTTTTT TTTTTTAAGTAGGAAGTTTTGTTTTGTCTTTTGTTTATGTTG GGTTGAGAGTTTGGGGGGAGTTTCT | 372 |
| AS158 | AGCCCCAACGATGCTCACAGAGGTGAGGGGCACAAGAAGG GGCTGCGGTCCCGGCAAGACGGTGGTCCCGGCTCAGGGAGG GGCCTGGACTCTGGGGGACACCCGGGGGAGGGAAGAGAGA CCAAACCCCGTGTTCTGAAAGGGGCTGGGGGCTGTAGACTC CCTTTCTTTCTG | 374 |
| AS159 | CTGTGCGCCATCAGCGTGGACAGGTGCGCCGCCCTCCCCGC CCGCGCCCCGGCGCCCCGCGCCCCGCCCGCCGCCCTCACC GCGGCCTGTGCGCTGTCCGGCGCCCCCTCGGCGCTCCCCGC AGGTTCGTGGCCGTGGCCGTGCCG | 376 |
| AS160 | AAGATCGTGCAGCAGAAGAACAGGCGCCACCGGCGGCTGG GGCGGCGGGCGGGCAGGTGCGGCTCCCTGGCGGCGGGGAG GCCCCGGCCCGGAGCTGAGGACCGCAGGCTCCGCGAGTACG ACTTCGCC | 378 |

TABLE 8

| Neopeptide ID | Full gene name | AS genomic coordinate |
|---|---|---|
| AS1 | ADAM metallopeptidase with thrombospondin type 1 motif 14 | ADAMTS14.70674850 |

TABLE 8-continued

| Neopeptide ID | Full gene name | AS genomic coordinate |
|---|---|---|
| AS2 | DEAF1, transcription factor | DEAF1.646327 |
| AS3 | ETS variant 4 | ETV4.43530666 |
| AS4 | mucin 16, cell surface associated | MUC16.8943848 |
| AS5 | PLAG1 zinc finger | PLAG1.56168237 |
| AS6 | ral guanine nucleotide dissociation stimulator like 3 | RGL3.11418507 |
| AS7 | sterile alpha motif domain containing 10 | SAMD10.63978245 |
| AS8 | secretoglobin family 1D member 1 | SCGB1D1.62192392 |
| AS9 | trafficking protein particle complex 12 | TRAPPC12.3457229 |
| AS10 | DENN domain containing 6A | DENND6A.57666126 |
| AS11 | DNA methyltransferase 3 alpha | DNMT3A.25249618 |
| AS12 | IQ motif containing GTPase activating protein 3 | IQGAP3.156548584 |
| AS13 | SEC31 homolog B, COPII coat complex component | SEC31B.100509010 |
| AS14 | forkhead box H1 | FOXH1.144475223 |
| AS15 | interphotoreceptor matrix proteoglycan 2 | IMPG2.101245867 |
| AS16 | LIM homeobox 1 | LHX1.36939937 |
| AS17 | keratin 8 | KRT8.52905045 |
| AS18 | leucine zipper tumor suppressor family member 3 | LZTS3.3165625 |
| AS19 | pleckstrin homology and RhoGEF domain containing G4B | PLEKHG4B.139606 |
| AS20 | stimulated by retinoic acid 6 | STRA6.74202279 |
| AS21 | zinc finger protein 334 | ZNF334.46504722 |
| AS22 | ATPase phospholipid transporting 11A | ATP11A.112880546 |
| AS23 | cadherin EGF LAG seven-pass G-type receptor 1 | CELSR1.46530500 |
| AS24 | claudin 16 | CLDN16.190390998 |
| AS25 | ERI1 exoribonuclease family member 2 | ERI2.20805945 |
| AS26 | FERM domain containing 4A | FRMD4A.13693517 |
| AS27 | G2 and S-phase expressed 1 | GTSE1.46316511 |
| AS28 | HYDIN, axonemal central pair apparatus protein | HYDIN.71133283 |
| AS29 | interleukin 17 receptor C | IL17RC.9933297 |
| AS30 | uncharacterized LOC102723360 | LOC102723360.6232833 |
| AS31 | mitochondrial trans-2-enoyl-CoA reductase | MECR.29226315 |
| AS32 | mucin 16, cell surface associated | MUC16.8932514 |
| AS33 | regulator of G-protein signaling 12 | RGS12.3373937 |
| AS34 | succinate dehydrogenase complex assembly factor 4 | SDHAF4.70567416 |
| AS35 | spermatogenesis associated 17 | SPATA17.217652253 |
| AS36 | serine/threonine kinase 32C | STK32C.132236107 |
| AS37 | triple QxxK/R motif containing | TRIQK.92886667 |
| AS38 | tRNA splicing endonuclease subunit 2 | TSEN2.12506708 |
| AS39 | WNT1 inducible signaling pathway protein 3 | WISP3.112054623 |
| AS40 | exportin for tRNA | XPOT.64412049 |
| AS41 | zinc finger protein 726 | ZNF726.23936779 |
| AS42 | zinc finger protein 736 | ZNF736.64338551 |
| AS43 | zinc finger protein 98 | ZNF98.22402564 |
| AS44 | fibroblast growth factor receptor 3 | FGFR3.1807113 |
| AS45 | BICD cargo adaptor 1 | BICD1.32338786-GKHFFLGCM* |
| AS46 | cytochrome c oxidase subunit 7A1 | COX7A1.36151546-LAFRKGVEY* |
| AS47 | DNA methyltransferase 3 beta | DNMT3B.32793536-WSLEKNQIS* |
| AS48 | EH domain containing 3 | EHD3.31249371-RISRGKQPA* |
| AS49 | MACRO domain containing 2 | MACROD2.15885764-FILLLLGGR* |
| AS50 | male germ cell associated kinase | MAK.10796309-NMPTVSSQS* |
| AS51 | mitogen-activated protein kinase kinase kinase 13 | MAP3K13.185480232-SQNSVPKIF* |
| AS52 | nuclear receptor subfamily 2 group F member 2 | NR2F2.96330882-TPNPHALAD* |
| AS53 | retinol binding protein 5 | RBP5.7124730-IRHPLVQTR* |
| AS54 | synaptonemal complex central element protein 2 | SYCE2.12904666-GFLMQKGRE* |
| AS55 | synaptopodin 2 like | SYNPO2L.73651039-YAGTTLPYL* |
| AS56 | testis expressed metallothionein like protein | TESMIN.68745111-KNYVIYVSW* |
| AS57 | transient receptor potential cation channel subfamily M member 2 | TRPM2.44423645-KTPPKGFCD* |
| AS58 | ADAM metallopeptidase with thrombospondin type 1 motif 14 | ADAMTS14.70672884-70702312 |
| AS59 | DNA methyltransferase 3 beta | DNMT3B.32791708-32795409 |

TABLE 8-continued

| Neopeptide ID | Full gene name | AS genomic coordinate |
|---|---|---|
| AS60 | hemicentin 2 | HMCN2.130359414-130362867 |
| AS61 | insulin like growth factor 2 mRNA binding protein 3 | IGF2BP3.23351586-23418776 |
| AS62 | interphotoreceptor matrix proteoglycan 2 | IMPG2.101226981-101232781 |
| AS63 | interphotoreceptor matrix proteoglycan 2 | IMPG2.101257773-101273581 |
| AS64 | IQ motif containing GTPase activating protein 3 | IQGAP3.156550351-156551974 |
| AS65 | lipocalin 10 | LCN10.136740048-136742787 |
| AS66 | matrix metallopeptidase 10 | MMP10.102779361-102780487 |
| AS67 | par-6 family cell polarity regulator beta | PARD6B.50731852-50749659 |
| AS68 | polycystic kidney and hepatic disease 1 | PKHD1L1.109412414-109419097 |
| AS69 | parathyroid hormone 2 receptor | PTH2R.208444887-208459895 |
| AS70 | RUN and FYVE domain containing 4 | RUFY4.218072499-218073243 |
| AS71 | solute carrier family 6 member 2 | SLC6A2.55695402-55697897 |
| AS72 | structural maintenance of chromosomes 1B | SMC1B.45393841-45396346 |
| AS73 | tousled like kinase 2 | TLK2.62520844-62523134 |
| AS74 | transient receptor potential cation channel subfamily M member 5 | TRPM5.2405593-2406661 |
| AS75 | tetraspanin 10 | TSPAN10.81637406-81644992 |
| AS76 | centromere protein I | CENPI.101120784-101127138 |
| AS77 | E1A binding protein p400 | EP400.131992230-132005077 |
| AS78 | ETS variant 4 | ETV4.43536479-43545274 |
| AS79 | fibrillin 3 | FBN3.8144972-8146127 |
| AS80 | fibrillin 3 | FBN3.8142137-8146127 |
| AS81 | fibrillin 3 | FBN3.8096080-8096881 |
| AS82 | interphotoreceptor matrix proteoglycan 2 | IMPG2.101229590-101232781 |
| AS83 | NUF2, NDC80 kinetochore complex component | NUF2.163343870-163347763 |
| AS84 | progestagen associated endometrial protein | PAEP.135562893-135565410 |
| AS85 | polycystin 1 like 1, transient receptor potential channel interacting | PKD1L1.47803344-47809473 |
| AS86 | RAS and EF-hand domain containing | RASEF.83022426-83062437 |
| AS87 | SFI1 centrin binding protein | SFI1.31613530-31616745 |
| AS88 | uroplakin 3B | UPK3B.76510737-76511657 |
| AS89 | zinc finger protein 727 | ZNF727.64069017-64077276 |
| AS90 | apoptotic chromatin condensation inducer 1 | ACIN1.23067314-23069111 |
| AS91 | apoptotic chromatin condensation inducer 1 | ACIN1.23067314-23068008 |
| AS92 | apoptotic chromatin condensation inducer 1 | ACIN1.23067314-23068004 |
| AS93 | apoptotic chromatin condensation inducer 1 | ACIN1.23067314-23068050 |
| AS94 | afadin, adherens junction formation factor | AFDN.167912626-167913423 |
| AS95 | Dmx like 2 | DMXL2.51459598-51460377 |
| AS96 | estrogen receptor 1 | ESR1.151863665-151865643 |
| AS97 | ETS variant 4 | ETV4.43542971-43543046 |
| AS98 | family with sequence similarity 110 member C | FAM110C.42118-42305 |
| AS99 | family with sequence similarity 221 member A | FAM221A.23694404-23694913 |
| AS100 | FRY like transcription coactivator | FRYL.48520524-48520572 |

TABLE 8-continued

| Neopeptide ID | Full gene name | AS genomic coordinate |
|---|---|---|
| AS101 | glutamate decarboxylase 1 | GAD1.170844997-170845050 |
| AS102 | grainyhead like transcription factor 2 | GRHL2.101493049-101493103 |
| AS103 | GTF2I repeat domain containing 1 | GTF2IRD1.74537778-74537904 |
| AS104 | methyltransferase like 24 | METTL24.110332440-110332565 |
| AS105 | myosin phosphatase Rho interacting protein | MPRIP.17138273-17138429 |
| AS106 | myosin phosphatase Rho interacting protein | MPRIP.17138311-17138429 |
| AS107 | mucin 16, cell surface associated | MUC16.8886022-8886090 |
| AS108 | NAD synthetase 1 | NADSYN1.71476544-71477438 |
| AS109 | nuclear pore complex interacting protein family member B3 | NPIPB3.21419635-21419772 |
| AS110 | nuclear pore complex interacting protein family member B5 | NPIPB5.22516126-22519269 |
| AS111 | pecanex homolog 3 | PCNX3.65635969-65636031 |
| AS112 | phosphatidylinositol glycan anchor biosynthesis class G | PIGG.525177-525837 |
| AS113 | phospholipid phosphatase 4 | PLPP4.120520655-120520746 |
| AS114 | protein tyrosine phosphatase, non-receptor type 4 | PTPN4.119916612-119916690 |
| AS115 | ral guanine nucleotide dissociation stimulator like 2 | RGL2.33297214-33297343 |
| AS116 | ral guanine nucleotide dissociation stimulator like 3 | RGL3.11394606-11394922 |
| AS117 | ring finger protein 207 | RNF207.6208504-6208609 |
| AS118 | sterile alpha motif domain containing 12 | SAMD12.118239715-118239975 |
| AS119 | SMAD family member 6 | SMAD6.66708361-66708738 |
| AS120 | stimulated by retinoic acid 6 | STRA6.74185311-74185843 |
| AS121 | teneurin transmembrane protein 4 | TENM4.78962143-78962353 |
| AS122 | transmembrane protein 221 | TMEM221.17440426-17440523 |
| AS123 | von Willebrand factor A domain containing 2 | VWA2.114288350-114288531 |
| AS124 | HECT, UBA and WWE domain containing 1, E3 ubiquitin protein ligase | HUWE1.53625786-53626028 |
| AS125 | leucine rich repeat containing 75B | LRRC75B.24588679-24588819 |
| AS126 | SLIT-ROBO Rho GTPase activating protein 3 | SRGAP3.8993284-8993427 |
| AS127 | tet methylcytosine dioxygenase 1 | TET1.68673401-68673487 |
| AS128 | ATPase sarcoplasmic/endoplasmic reticulum Ca2+ transporting 1 | ATP2A1.28898126-28898232 |
| AS129 | arginine vasopressin receptor 1B | AVPR1B.206110524-206115950 |
| AS130 | crystallin gamma B | CRYGB.208146017-208146111 |
| AS131 | early B-cell factor 3 | EBF3.129842294-129843136 |
| AS132 | geminin coiled-coil domain containing | GMNC.190860859-190862612 |
| AS133 | HRas proto-oncogene, GTPase | HRAS.532756-533276 |
| AS134 | heat shock transcription factor 4 | HSF4.67166071-67166319 |
| AS135 | potassium voltage-gated channel subfamily D member 2 | KCND2.120742603-120745779 |
| AS136 | lymphocyte antigen 6 complex, locus G6F | LY6G6F.31710182-31710351 |
| AS137 | lymphocyte antigen 6 complex, locus G6F | LY6G6F.31706959-31707457 |
| AS138 | lymphocyte antigen 6 complex, locus G6F | LY6G6F.31707788-31707870 |
| AS139 | mucin 16, cell surface associated | MUC16.8894259-8894517 |

TABLE 8-continued

| Neopeptide ID | Full gene name | AS genomic coordinate |
|---|---|---|
| AS140 | mucin 16, cell surface associated | MUC16.8893015-8894192 |
| AS141 | mucin 16, cell surface associated | MUC16.8896877-8897132 |
| AS142 | mucin 16, cell surface associated | MUC16.8906047-8906304 |
| AS143 | mucin 16, cell surface associated | MUC16.8927461-8927703 |
| AS144 | NDRG family member 4 | NDRG4.58509010-58509153 |
| AS145 | PIF1 5'-to-3' DNA helicase | PIF1.64822611-64823777 |
| AS146 | phosphatidylinositol-4-phosphate 5-kinase type 1 alpha | PIP5K1A.151224280-151224370 |
| AS147 | plexin C1 | PLXNC1.94303897-94303976 |
| AS148 | proline and serine rich 3 | PROSER3.35766956-35767803 |
| AS149 | RAD9 checkpoint clamp component A | RAD9A.67392232-67392653 |
| AS150 | regulator of telomere elongation helicase 1 | RTEL1.63690948-63691741 |
| AS151 | smoothelin like 1 | SMTNL1.57546348-57546500 |
| AS152 | speedy/RINGO cell cycle regulator family member E2 | SPDYE2.102554578-102555899 |
| AS153 | speedy/RINGO cell cycle regulator family member E5 | SPDYE5.75501756-75501877 |
| AS154 | speedy/RINGO cell cycle regulator family member E5 | SPDYE5.75497997-75499230 |
| AS155 | testis expressed metallothionein like protein | TESMIN.68742395-68744990 |
| AS156 | transient receptor potential cation channel subfamily M member 2 | TRPM2.44418109-44418422 |
| AS157 | Zic family member 4 | ZIC4.147396470-147402727 |
| AS158 | zinc finger protein 629 | ZNF629.30784274-30784409 |
| AS159 | dopamine receptor D4 | DRD4.639546-639647 |
| AS160 | zinc finger protein 469 | ZNF469.88430650-88430733 |

Table 9 shows gene origin, full gene name, mutation and amino acid sequence of identified neoantigens that arose from point mutations events (M). Point mutations are indicated with bolded letters. Table 10 shows their corresponding polynucleotide sequences. Point mutations are indicated with bolded letters and the codons for the mutated residues are underlined.

TABLE 9

| Neoepitope ID | Gene | Full Gene Name | Mutation | Amino Acid Sequence | SEQ ID NO |
|---|---|---|---|---|---|
| M1 | TP53 | Tumor Protein p53 | R248Q | SSCMGGMNQRPILTIIT | 379 |
| M2 | TP53 | Tumor Protein p53 | R248W | SSCMGGMNWRPILTIIT | 381 |
| M3 | TP53 | Tumor Protein p53 | R273C | LGRNSFEVCVCACPGRD | 383 |
| M4 | TP53 | Tumor Protein p53 | R273H | LGRNSFEVHVCACPGRD | 385 |
| M5 | TP53 | Tumor Protein p53 | R273L | LGRNSFEVLVCACPGRD | 387 |
| M6 | TP53 | Tumor Protein p53 | R175H | QHMTEVVRHCPHHERCS | 389 |

TABLE 9-continued

| Neoepitope ID | Full Gene Gene Name | Mutation | Amino Acid Sequence | SEQ ID NO |
| --- | --- | --- | --- | --- |
| M7 | TP53 Tumor Protein p53 | I195T | GLAPPQHLTRVEGNLRV | 391 |
| M8 | TP53 Tumor Protein p53 | Y163C | TRVRAMAICKQSQHMTE | 393 |
| M9 | TP53 Tumor Protein p53 | Y220C | FRHSVVVPCEPPEVGSD | 395 |
| M10 | TP53 Tumor Protein p53 | C176Y | HMTEVVRRYPHHERCSD | 397 |
| M11 | TP53 Tumor Protein p53 | C176F | HMTEVVRRFPHHERCSD | 399 |
| M12 | TP53 Tumor Protein p53 | S241F | HYNYMCNSFCMGGMNRR | 401 |
| M13 | TP53 Tumor Protein p53 | G245D | MCNSSCMGDMNRRPILT | 403 |
| M14 | TP53 Tumor Protein p53 | G266R | EDSSGNLLRRNSFEVRV | 405 |

TABLE 10

| Neoepitope ID | Polynucleotide sequence | SEQ ID NO: |
| --- | --- | --- |
| M1 | AGTTCCTGCATGGGCGGCATGAACCAGAGGCCCATCCTCACCATCATCACA | 380 |
| M2 | AGTTCCTGCATGGGCGGCATGAACTGGAGGCCCATCCTCACCATCATCACA | 382 |
| M3 | CTGGGACGGAACAGCTTTGAGGTGTGTGTTTGTGCCTGTCCTGGGAGAGAC | 384 |
| M4 | CTGGGACGGAACAGCTTTGAGGTGCATGTTTGTGCCTGTCCTGGGAGAGAC | 386 |
| M5 | CTGGGACGGAACAGCTTTGAGGTGCTTGTTTGTGCCTGTCCTGGGAGAGAC | 388 |
| M6 | CAGCACATGACGGAGGTTGTGAGGCACTGCCCCCACCATGAGCGCTGCTCA | 390 |
| M7 | GGTCTGGCCCCTCCTCAGCATCTTACCCGAGTGGAAGGAAATTTGCGTGTG | 392 |
| M8 | ACCCGCGTCCGCGCCATGGCCATCTGCAAGCAGTCACAGCACATGACGGAG | 394 |
| M9 | TTTCGACATAGTGTGGTGGTGCCCTGTGAGCCGCCTGAGGTTGGCTCTGAC | 396 |
| M10 | CACATGACGGAGGTTGTGAGGCGCTACCCCCACCATGAGCGCTGCTCAGATAGCGAT | 398 |
| M11 | CACATGACGGAGGTTGTGAGGCGCTTCCCCCACCATGAGCGCTGCTCAGATAGCGAT | 400 |
| M12 | CACTACAACTACATGTGTAACAGTTTCTGCATGGGCGGCATGAACCGGAGG | 402 |
| M13 | ATGTGTAACAGTTCCTGCATGGGCGACATGAACCGGAGGCCCATCCTCACC | 404 |
| M14 | GAAGACTCCAGTGGTAATCTACTGAGACGGAACAGCTTTGAGGTGCGTGTT | 406 |

Example 2: Quantitative PCR Analysis of Ovarian Cancer Neoantigens in Tumor and Normal Tissues Ovarian Cancer (OV) neoantigen candidates were tested for their expression in following samples:
  80 primary tumor resections from ovarian cancer patients
  Sorted immune cells derived from 3 healthy donors (B-cells, Plasma Cells, T-cells, PBMCs and monocytes) and
  17 healthy donor derived tissues (liver, kidney, pancreas, mammary gland, colon, stomach, skeletal muscle, lung, ovary, placenta, small intestine, spinal cord, uterus, spleen, brain, heart and bladder)

Quantitative PCR primers were designed to span the breakpoint junction sequences using the Primer Express software (version 3.0.1). Primers with Tm of 60° C., GC content between 30-80% and low likelihood of forming stable secondary structures were selected for expression analysis.

RNA from these samples was isolated using Qiagen RNA isolation kit (#430098094) as per manufacturer's protocol. Complementary DNA libraries were prepared using oligo dT primers provided in the high-capacity cDNA reverse transcription kit (Invitrogen-part #11904018) from 200 ng of total RNA. Next, 3-10 ng of cDNA was pre-amplified for 10 PCR cycles in 15 µl of pre-amplification mix using TaqMan preamplification kit (ThermoFisher Scientific, #4384267). For each sample, input cDNA was estimated to keep the Ct values of endogenous controls (RPL19, RPL13A, GAPDH, GUSB, PGK1) in the range of 13-15 Ct values. Among the tested control genes, RPL19 showed the most consistent expression among the healthy tissues. Finally, the pre-amplified cDNA was diluted 5 folds and loaded onto Fluidigm Biomark™ HD for 40 cycles of PCR amplification.

Figure 5A:
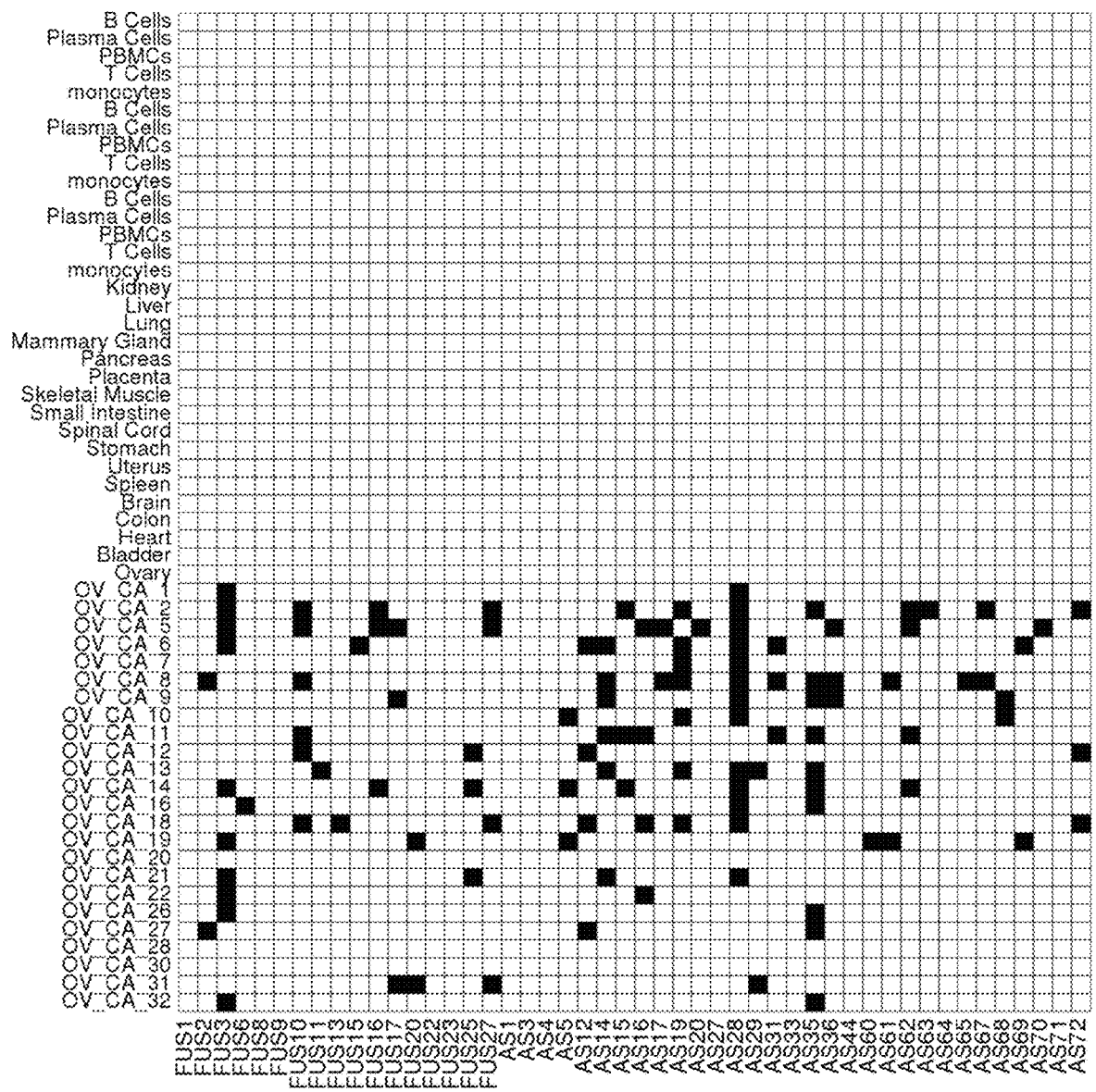
FIG. 5A, FIG. 5B, FIG. 5C and FIG. 5D show the heat maps representing tumor restricted expression of Ovarian Cancer neoantigen candidates. These antigens do not have detectable expression in either healthy tissues or immune cells derived from healthy donors. Immune cell types (first 15 rows) were derived from three healthy donors (donor ID: D001003103, D001000682 and D001004622). Ovarian cancer samples are labeled with "OV_CA" prefix. The raw Ct values were normalized against the expression of an endogenous control gene, RPL19. The black cells represent high expression ($\Delta$Ct below 15) in each sample.
Figure 5B:
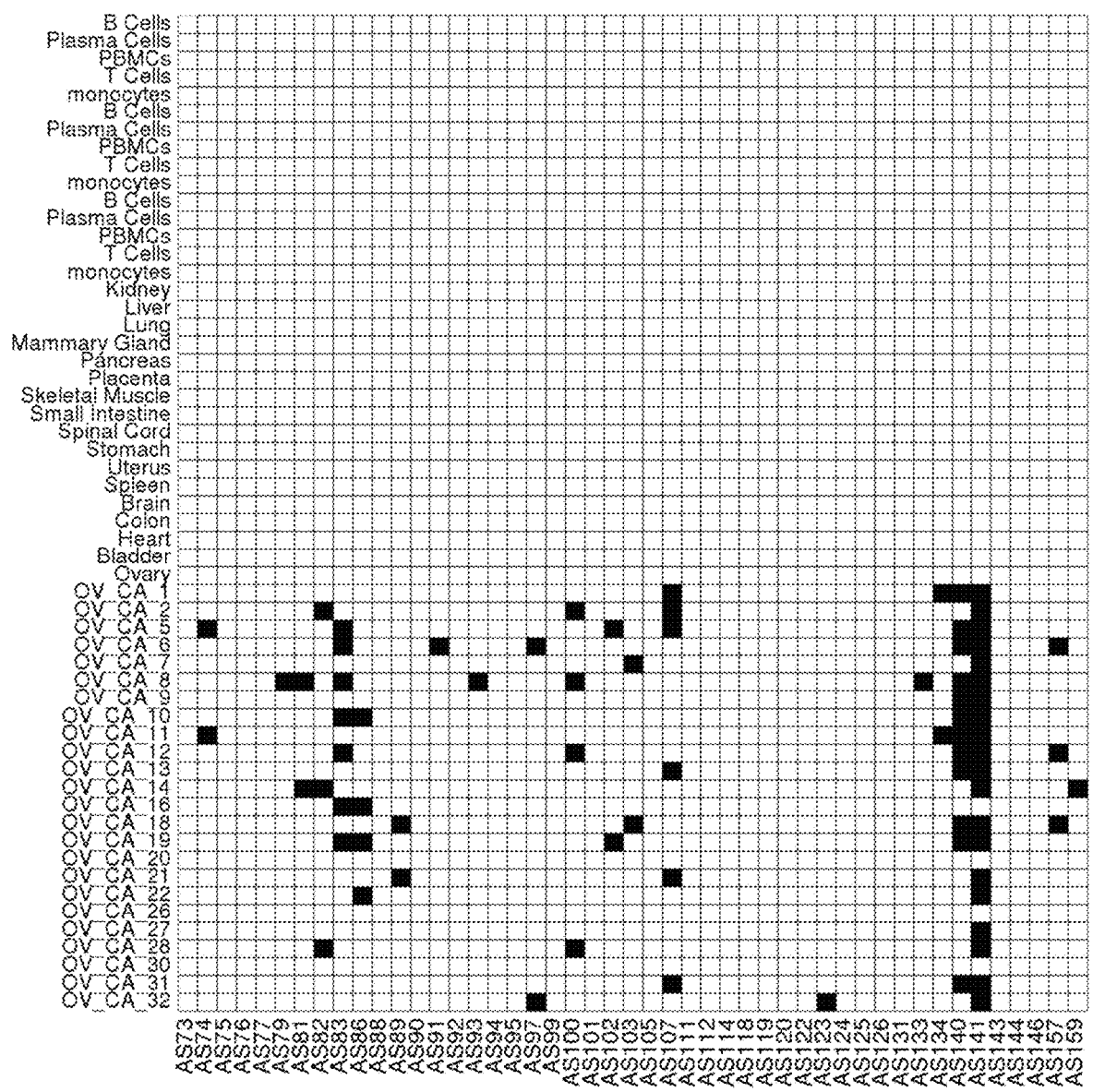
Figure 5C:
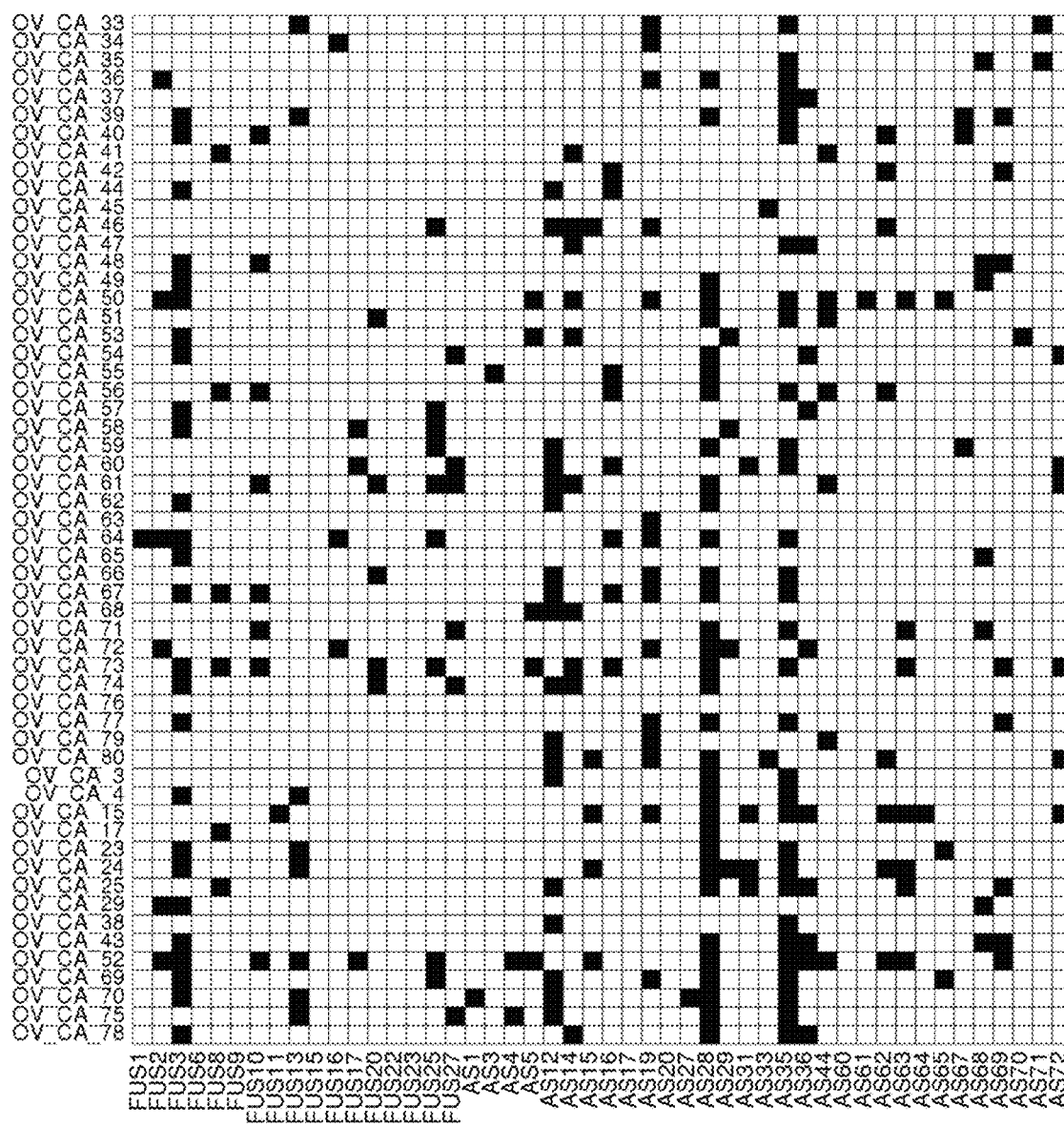
Figure 5D:
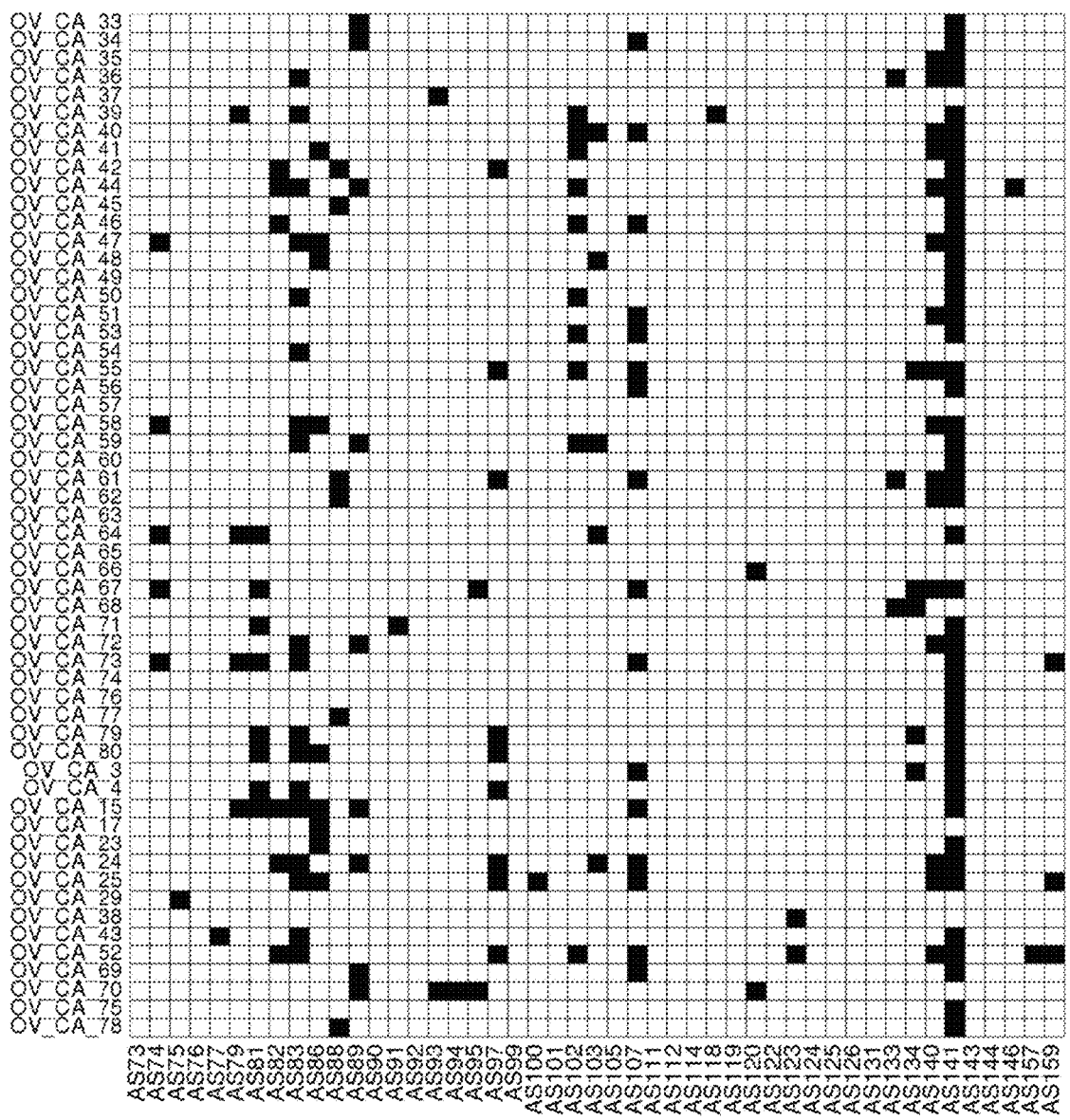
Figure 6A:
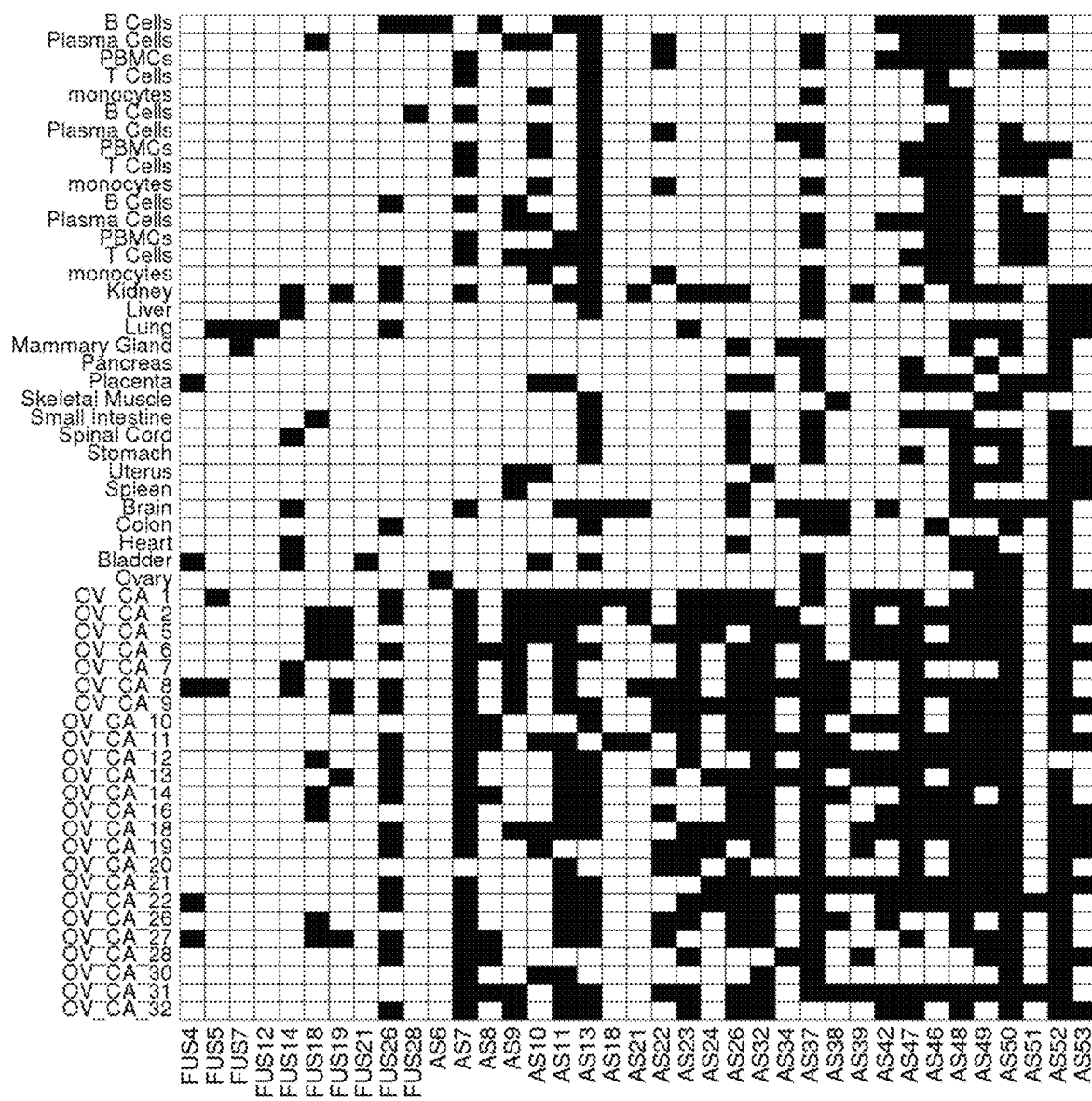
FIG. 6A, FIG. 6B, FIG. 6C and FIG. 6D show the heat maps representing Ovarian Cancer neoantigen candidates with expression in both control (tissues and immune cells derived from healthy donors) and tumor samples. Immune cell types (first 15 rows) were derived from three healthy donors (donor ID: D001003103, D001000682 and D001004622). Ovarian cancer samples are labeled with "OV_CA" prefix. The raw Ct values were normalized against the expression of an endogenous control gene, RPL19. The black cells represent high expression ($\Delta$Ct below 15) in each sample.
Figure 6B:
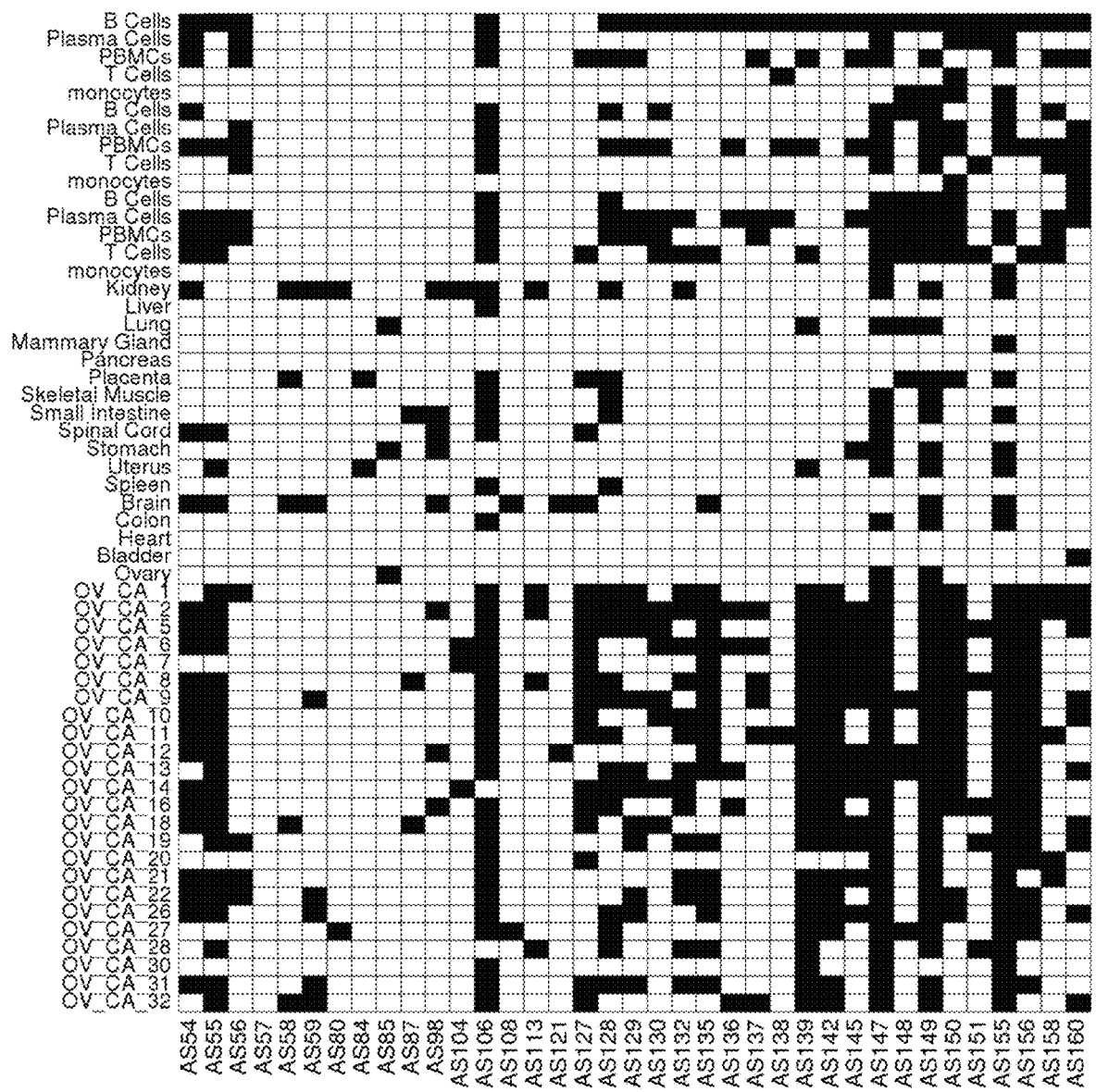
Figure 6C:
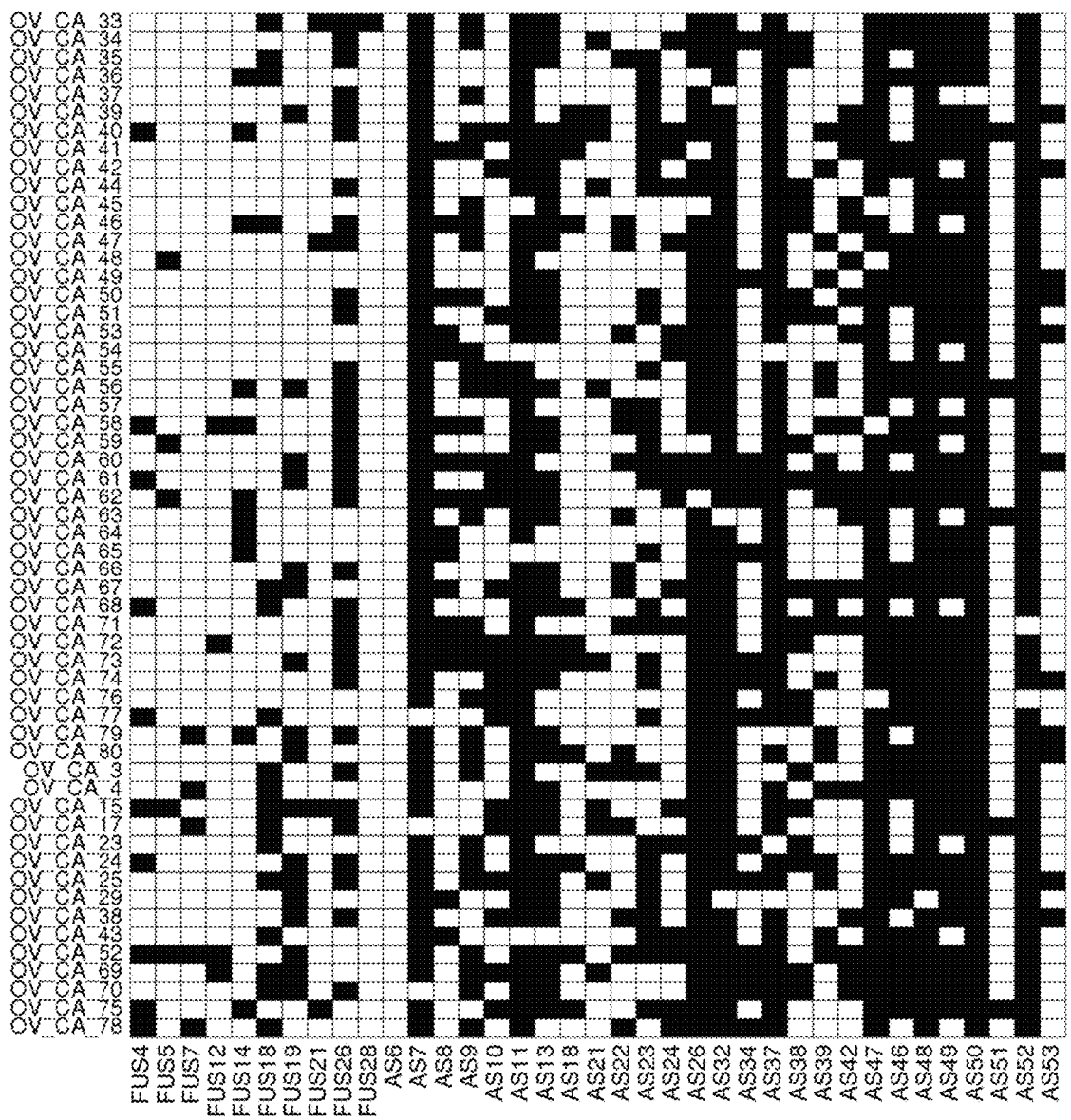
Figure 6D:
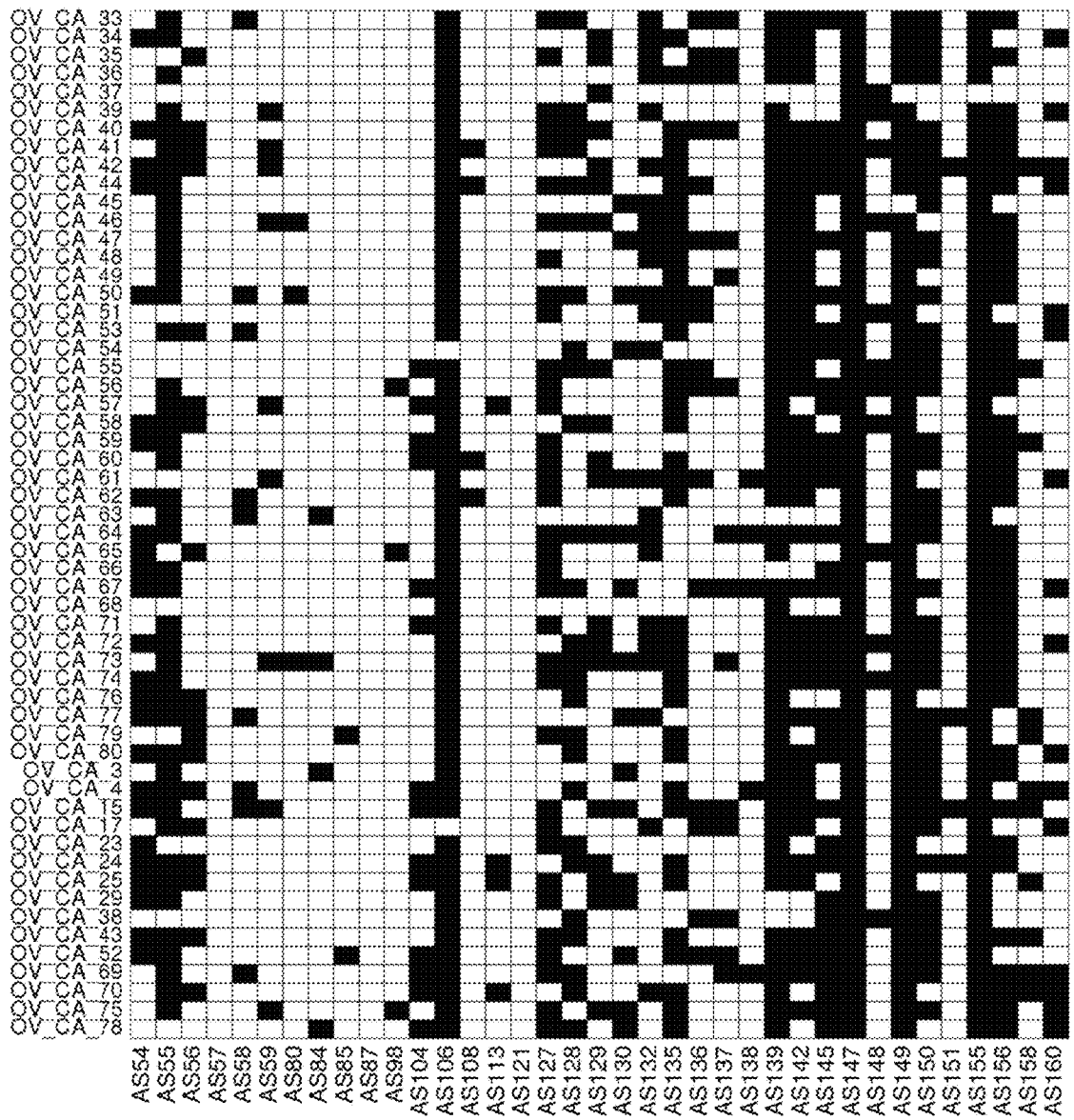

The expression of the neoantigen candidates (Ct values) was normalized against an endogenous control, RPL19. A cutoff value of ΔCt<15 (fold change of ~32,000) was used to determine the expression of neoantigen candidates in a biological sample. The results of the expression profile for all the tumor restricted neoantigen candidates are shown in FIG. 5A, FIG. 5B, FIG. 5D and FIG. 5D. Antigens with expression in both control and tumor samples are shown in FIG. 6A, FIG. 6B, FIG. 6C and FIG. 6D.

Example 3: In Vitro Immunogenicity Assessment of Neoantigens

The immunogenicity of neoantigens was assessed using the exogenous autologous normal donor restimulation assay. Peptides were synthesized by GenScript with purity >80%. The lyophilized peptides were solubilized in 100% DMSO.

CD1c+ Dendritic Cells (CD1c+DC) isolated from human healthy PBMCs were thawed using media (IMDM (Gibco) supplemented with glutamine, HEPES, 5% human serum (Sigma), and 1× Pen-Strep). DC cells were resuspended in media supplemented with IL-4 (Peprotech, 20 ng/mL) and GM-CSF (Gibco, 20 ng/mL), plated in 6 well microplates, and rested overnight at 37° C. and 5% CO2 incubator. The following day, DC cells were counted and plated in a 96 well round bottom microplate at a concentration of 30,000 viable cells per well. Lyophilized neoantigen peptide pools (15-mer peptides with 8-mer overlapping peptide sequences) were solubilized in 100% DMSO with a stock concentration of 20 mg/mL Neoantigen peptides pools were added to DCs for a final concentration of 10 µg/mL and rested for 2 hours at 37° C. and 5% CO2 incubator. CEF Peptide Pool "Plus" (Cellular Technologies, Ltd.) was utilized as a positive control (each viral peptide at a final concentration of 4 ug/ml) and DMSO at the same final concentration (0.05%) as the experimental peptides was utilized as a negative control. After 2 hours, DC cells were irradiated with 50 gray of ionizing radiation. Autologous CD3+ Pan-T cells isolated from human normal PBMCs were thawed using media. Following irradiation, autologous Pan-T cells were added to the irradiated DCs at 300,000 viable cells per well. Human IL-15 (Peprotech) was added to all wells at final concentration of 10 ng/ml. Plates were incubated at 37° C. and 5% CO2 incubator for a total of 12 days. Media was refreshed every 2-3 days with IL-15 (R&D System, 10 ng/mL final concentration) and IL-2 (R&D systems, 10 IU/mL final concentration).

On Day 11, cells were re-stimulated with identical experimental peptide pools or controls, at same concentration as peptide stimulation on Day 1. Protein Inhibitor Cocktail (eBioscience) was added to every well and plate was incubated overnight for 14-16 hours at 37° C. and 5% CO2 incubator. On Day 12, cells were stained for surface and intracellular flow cytometry analysis. The cells were washed with PBS and stained with Live/Dead Fixable Aqua Dead Cell stain (Thermo-Fisher). Following the live/dead stain, cells were blocked using Biotin-Fre Fc Receptor Blocker (Accurate Chemical & Scientific Corp). Extracellular cellular flow panel (1 L/antibody per well in 50 µL) consisted of CD3 PerCP-Cy5.5 (Biolegend), CD4 BV421 (Biolegend), and CD8 APC-Cy7 (Biolegend). After extracellular staining, cells were fixed and permeabilized using Foxp3/Transcription Factor Staining Buffer Set (eBioscience) and stained for intracellular proteins (1:50 dilution) using TNFα FITC (R&D Systems) and IFNγ BV785 (Biolegend). Cells were washed and resuspended in stain buffer, analyzed, and recorded in a BD Celesta flow cytometer.

Flow cytometry analysis was conducted on FlowJo v10.6 software. Cells were gated on live, singlet, CD3+, CD4+ and CD8+ T cells. The CD8+ and CD4+ T cells were analyzed for TNFα and IFNγ expression.

Immunogenicity responses were considered as positive for a peptide pool if the following criteria was met:
  Frequency of double positive TNFα/IFNγ CD8+ and/or TNFα/IFNγ CD4+ T cells upon stimulation with an experimental peptide pool was greater than or equal to 3-fold over the DMSO control
  Frequency of double positive TNFα/IFNγ CD8+ and/or double positive TNFα/IFNγ CD4+ T cells was at least 0.01%

Figure 7A:
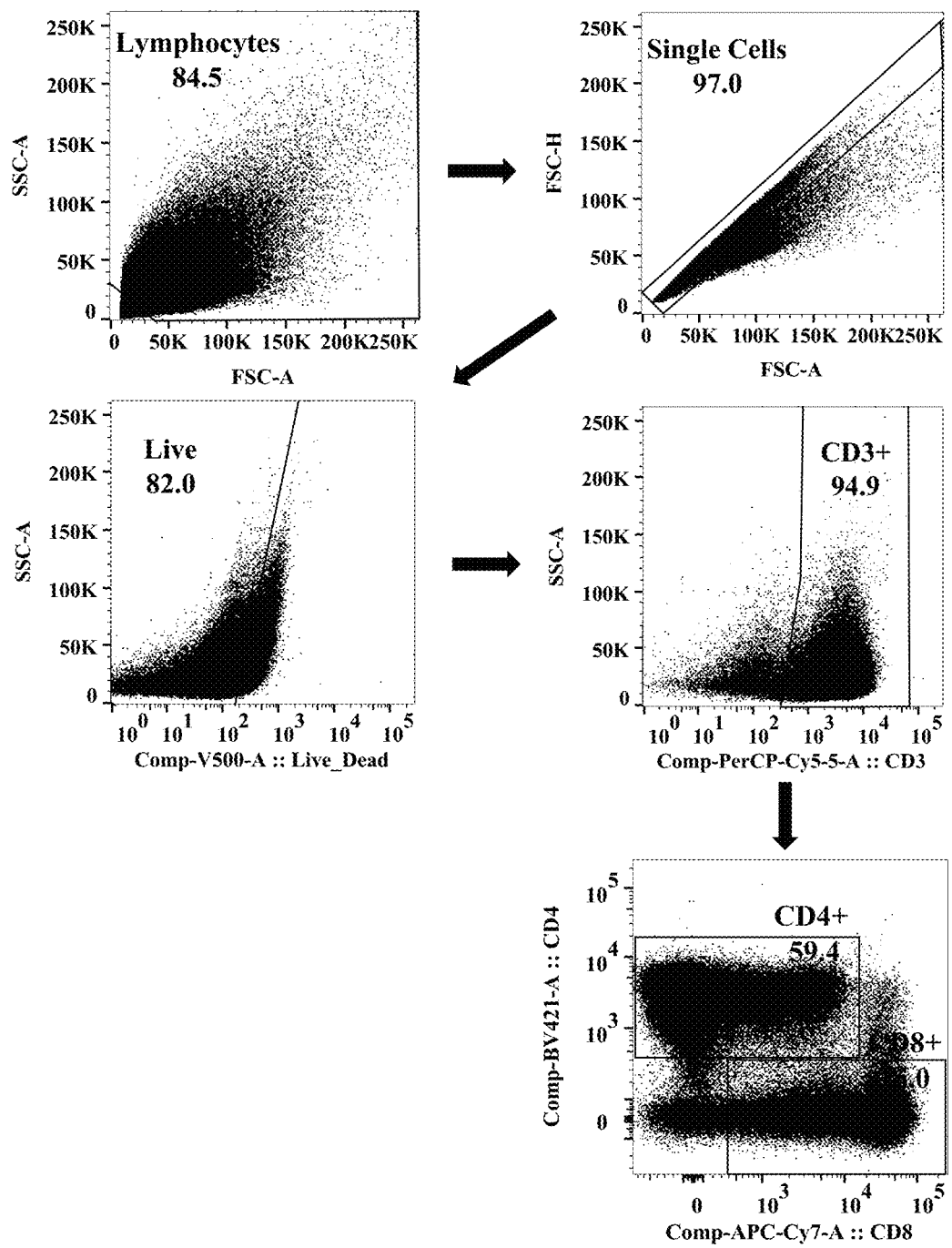
FIG. 7A and FIG. 7B show a representative dot plots depicting positive immunogenic responses of neoantigens by using exogenous autologous healthy donor restimulation assay. Immunogenicity responses were measured by estimating IFN$\gamma$ TNF$\alpha$ double positive cells in the CD4+ and/or CD8+ T-cell populations. A response is considered positive if IFN$\gamma$ TNF$\alpha$ double positive fraction was greater than or equal to three-fold over unstimulated cells (DMSO negative control) with a minimum frequency >=0.01%.
Figure 7B:
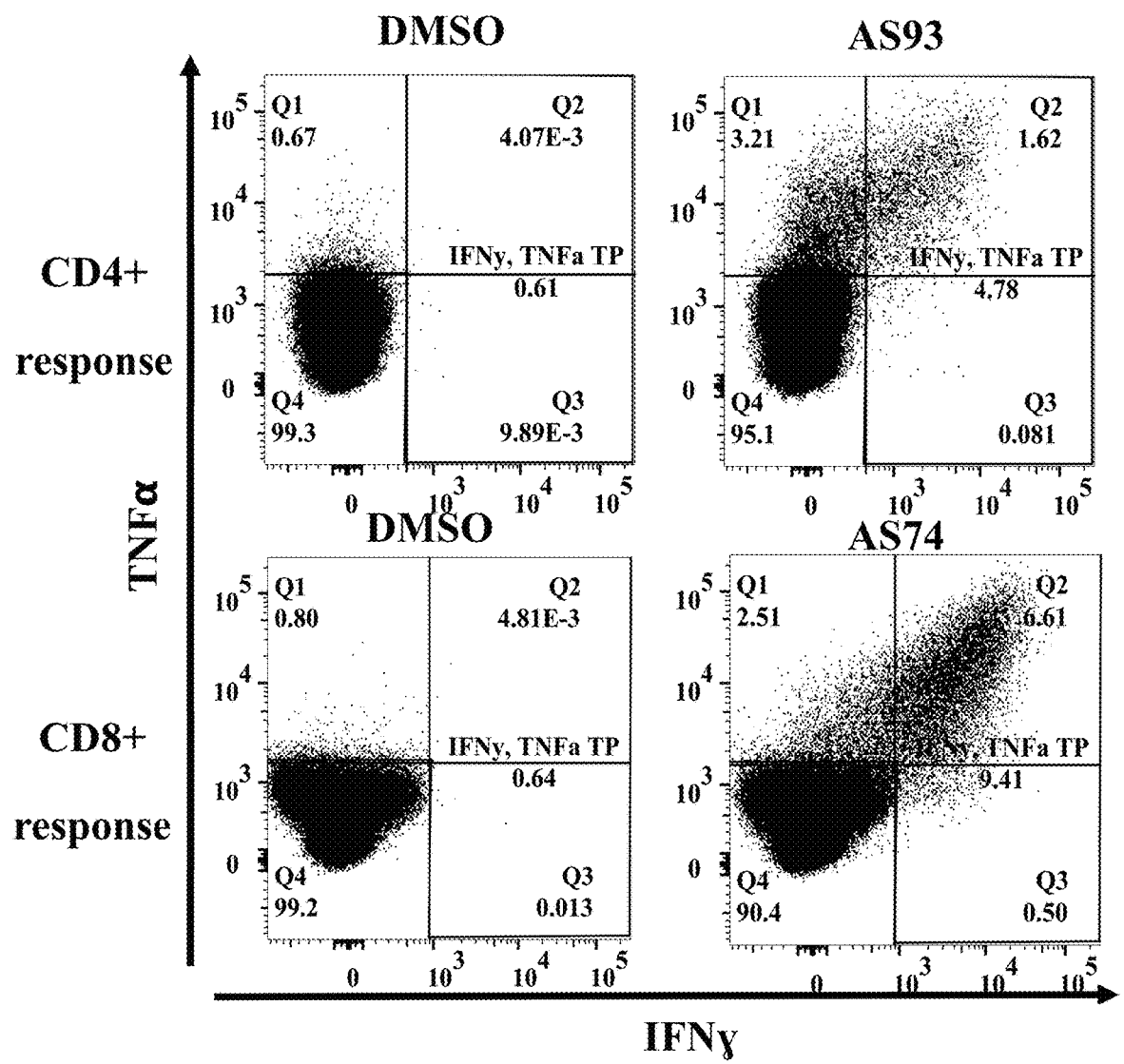
Figure 8:
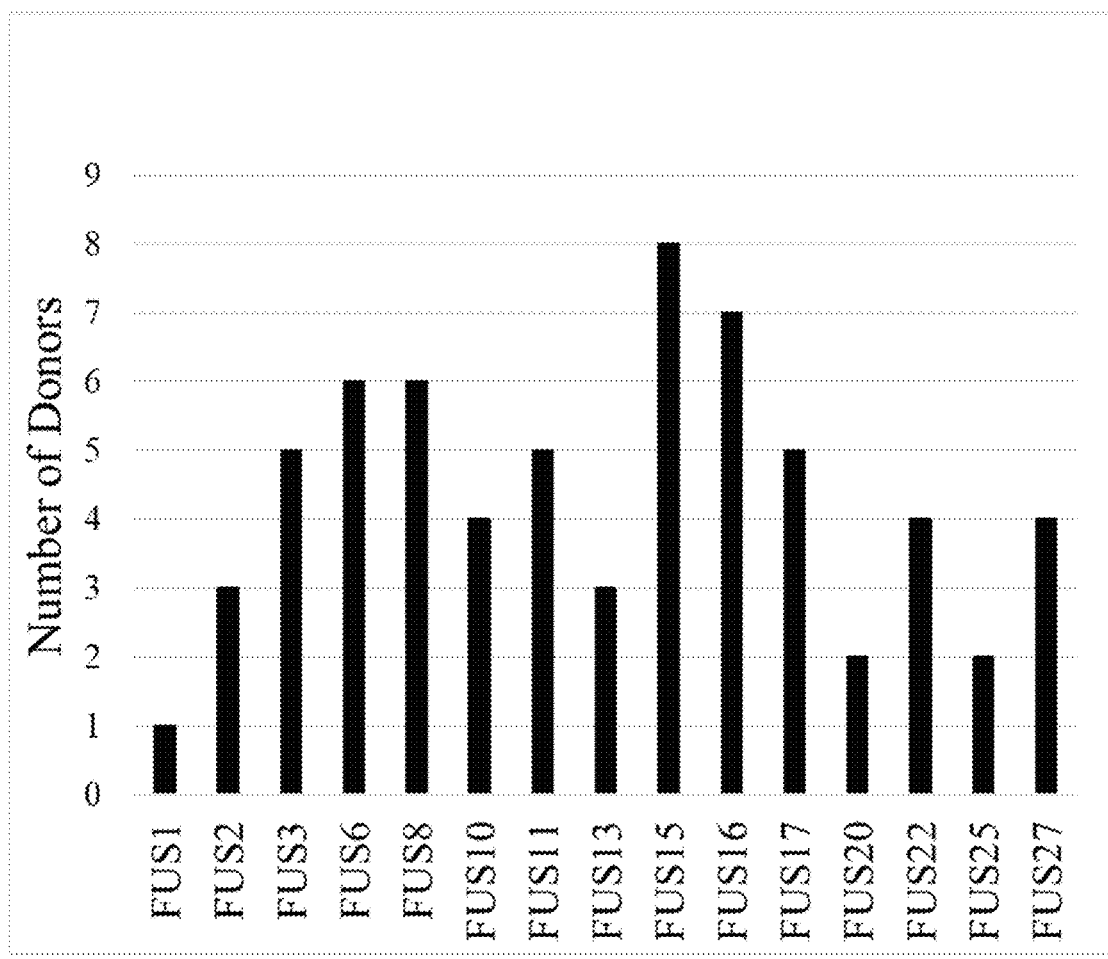
FIG. 8 shows the number of donors with positive immunogenicity responses (CD8+ and/or CD4+ T-cell) for gene fusion associated neoantigens.
Figure 9A:
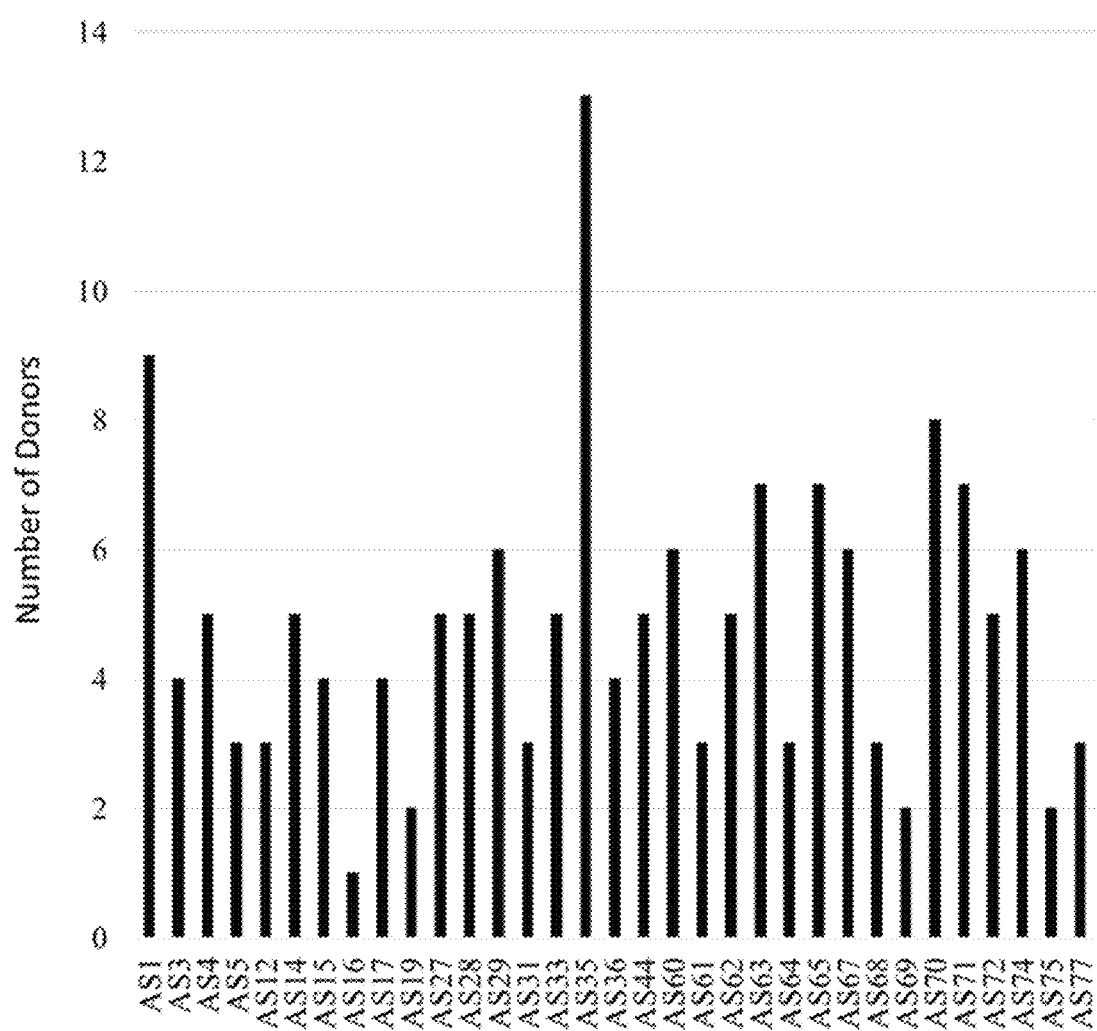
FIG. 9A and FIG. 9B show the number of donors with positive immunogenicity responses (CD8+ and/or CD4+ T cells) for alternative splicing associated neoantigens.
Figure 9B:
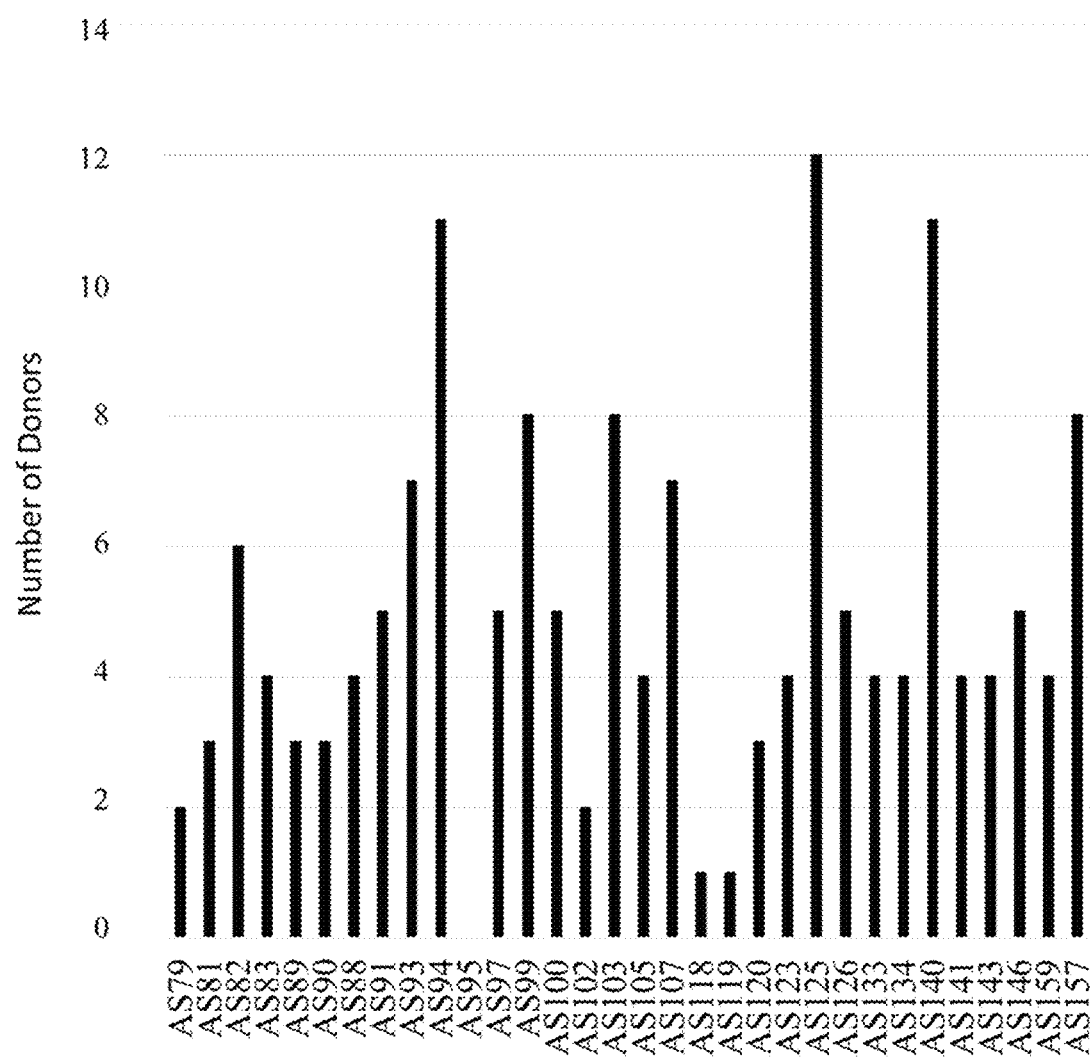

The immunogenicity of neoantigens was first investigated in 9-16 healthy donors. The non-reactive neoantigens were further tested on a new cohort of 7 healthy donors. The immunogenicity data for the neoantigens is summarized in Table 11. FIG. 7A, and FIG. 7B display a representative dot plot showing the gating strategy and the immunogenic responses achieved for few neoantigens. Interestingly, majority of the neoantigens showed immunogenic responses in multiple donors (FIG. 8, FIG. 9A and FIG. 9B).

TABLE 11

Immunogenicity data summarization of all tumor specific neoantigens. For each neoantigen, the maximum CD8+ and CD4+ T-cell responses (TNFα and IFNγ) are reported. The responses reported are donor independent.

| Neo-peptide/ Neo-epitope ID | SEQ ID | Gene ID | Neoantigen Sequence | Fold change (CD8+) vs. DMSO | Frequency (TNFα + IFNγ + CD8 Tcells) | Fold change (CD4+) vs. DMSO | Frequency (TNFα + IFNγ + CD4 T cells) | Immunogenic (yes/no) |
|---|---|---|---|---|---|---|---|---|
| FUS1 | 1 | TSTD1-> F11R | MAGGVLRRLLCREPDRDGDKGASREETVVPLHIGDPVVLPGIGQCYSALF | 2.79 | 0.06 | 5.43 | 0.011 | yes |
| FUS2 | 3 | VAX2-> ATP6V1B1 | QLNLSETQFAQYAEIV | 593.75 | 2.28 | 21.76 | 0.026 | yes |
| FUS3 | 5 | PTH2R-> LOC101927960 | APILAAIGIGRLLCMDKIPATASLTP | 158.8 | 0.74 | 5.02 | 0.025 | yes |
| FUS6 | 11 | PKHDIL1-> EBAG9 | STLNITLSFDSHHGHHPVSVI | 4.47 | 0.096 | 26.51 | 0.11 | yes |
| FUS8 | 15 | TYSND1-> AIFM2 | AAEQAGCMQCLI | 6.27 | 0.12 | 5.93 | 0.029 | yes |
| FUS10 | 19 | SCNN1A-> TNFRSF1A | RGGRGAQENSLD | 896.55 | 19.5 | 20.13 | 0.072 | yes |
| FUS11 | 21 | AJUBA-> HAUS4 | HFECYHCEIRIPRKSNGIRGFLLTWRRDGNTSTSVQQTTSSL | 3.3 | 0.071 | 39.13 | 0.14 | yes |
| FUS13 | 25 | MFGE8-> HAPLN3 | YGNDQWLQMRKWRHRE | 5.12 | 0.11 | 3.35 | 0.12 | yes |
| FUS15 | 29 | NXN-> GLOD4 | LLFFVAGEVLRHEEFE | 8.84 | 0.19 | 16.21 | 0.08 | yes |
| FUS16 | 31 | NDUFA11-> FUT5 | GGLTLGARNTLTHGSPGPSQATVAVAPLSGRAAVSAAGGCVFLLLPACVPRRCHWIP | 261.6 | 5.69 | 12.58 | 0.045 | yes |
| FUS17 | 33 | C20orf204-> TCEA2 | RASCGAQKACDVNQLTSS | 13.53 | 0.23 | 6.91 | 0.045 | Yes |
| FUS20 | 39 | CMTM8-> CMTM7 | FLIVAEIVTLLIAFI | 28.23 | 0.54 | 2.36 | 0.019 | Yes |
| FUS22 | 43 | C8orf82-> LRRC24 | KNFITCFKGGHASAAEPRKGR | 8.05 | 0.087 | 8.67 | 0.31 | Yes |
| FUS25 | 49 | CLCF1-> POLD4 | LRSLAGTYGRSPSPATRRKRSWSC | 2.79 | 0.048 | 16.49 | 0.059 | Yes |
| FUS27 | 53 | C17orf99-> SYNGR2 | ALTVVPPGLRLDRVLLHLW | 19.77 | 0.43 | 10.37 | 0.021 | Yes |
| AS1 | 59 | ADAMTS14 | LRLRPNRRRASSAQTAPTSSLSLWSGASRRRPAGGHMWCTAGRPSSRSGQ | 29.8 | 0.57 | 16.77 | 0.15 | Yes |

TABLE 11-continued

Immunogenicity data summarization of all tumor specific neoantigens.
For each neoantigen, the maximum CD8+ and CD4+ T-cell responses (TNFα
and IFNγ) are reported. The responses reported are donor independent.

| Neo-peptide/ Neo-epitope ID | SEQ ID | Gene ID | Neoantigen Sequence | Fold change (CD8+) vs. DMSO | Frequency (TNFα + IFNγ + CD8 Tcells) | Fold change (CD4+) vs. DMSO | Frequency (TNFα + IFNγ + CD4 T cells) | Immunogenic (yes/no) |
|---|---|---|---|---|---|---|---|---|
| | | | NLTGTCTM | | | | | |
| | | | KPLAWETFP | | | | | |
| | | | TCWAWWG | | | | | |
| | | | TSWATQSG | | | | | |
| | | | SGGMPSQA | | | | | |
| | | | ATASRCCW | | | | | |
| | | | WWTTRWF | | | | | |
| | | | ASMARSMC | | | | | |
| | | | RTMSSPS | | | | | |
| AS3 | 63 | ETV4 | QTDFAYDS GKRLGWGR VACDQVFS | 133.13 | 0.43 | 7.31 | 0.1 | Yes |
| AS4 | 65 | MUC16 | PSLSTRLTS KDPQPLQS HYWGLIGN DPFLRSKKR VN | 7.55 | 0.068 | 11.53 | 0.093 | Yes |
| AS5 | 67 | PLAG1 | VIPGDLSEA HGYSFS | 2.41 | 0.017 | 17.14 | 0.18 | Yes |
| AS12 | 81 | IQGAP3 | AMAKKQRP DTAFWVQH | 6.05 | 0.13 | 8.4 | 0.017 | Yes |
| AS14 | 85 | FOXH1 | SRRLKLAQ GRLRGLERL HSPQPFLQP MLPQGAQG PCKAPGQG QLLGGRREP DPS | 257.47 | 5.6 | 59.26 | 0.12 | Yes |
| AS15 | 87 | IMPG2 | QATPSSILC FRLACLWL LRKGLLDLT W | 48.05 | 0.08 | 11.36 | 0.023 | Yes |
| AS16 | 89 | LHX1 | YCKNDFFR SLPCHLL | 2.88 | 0.062 | 5.43 | 0.011 | Yes |
| AS17 | 91 | KRT8 | WSQDLQEG FSAPSRISA WFGPP | 169.53 | 0.79 | 29.97 | 0.41 | Yes |
| AS19 | 95 | PLEKHG4B | QHLQQEAC VTSAGKQS | 182.29 | 0.7 | 5.69 | 0.06 | Yes |
| AS27 | 111 | GTSE1 | FKIPKFSIVL SSNSAFRCD PLSSRPRCF GGSLEAP | 108.36 | 0.35 | 31.11 | 0.063 | Yes |
| AS28 | 113 | HYDIN | EEDREKYR WMAPFVPG QVWTWEYF L | 8.82 | 0.15 | 12.43 | 0.17 | Yes |
| AS29 | 115 | IL17RC | LKQDVRSG GPGARQLR GGLLRQAA PPGRRTRPF PHRARLHT ALPTARLPG GPAAASRP AFRAAPRES GASVPGPSA SPG | 25.75 | 0.36 | 10.73 | 0.12 | Yes |

TABLE 11-continued

Immunogenicity data summarization of all tumor specific neoantigens.
For each neoantigen, the maximum CD8+ and CD4+ T-cell responses (TNFα
and IFNγ) are reported. The responses reported are donor independent.

| Neo-peptide/ Neo-epitope ID | SEQ ID | Gene ID | Neoantigen Sequence | Fold change (CD8+) vs. DMSO | Frequency (TNFα + IFNγ + CD8 Tcells) | Fold change (CD4+) vs. DMSO | Frequency (TNFα + IFNγ + CD4 T cells) | Immunogenic (yes/no) |
|---|---|---|---|---|---|---|---|---|
| AS31 | 119 | MECR | GDPAKVVEIPRLL | 4.54 | 0.045 | 6.91 | 0.016 | Yes |
| AS33 | 123 | RGS12 | TRSLDDLEKLDTLCCKLSVHVT | 6958.6 | 43.7 | 32.24 | 0.28 | Yes |
| AS35 | 127 | SPATA17 | KQYQLTVQMESHSLPQAGVQWHDFVSPQPLPPGFKRFSCLSFLSSWDYRLQPPHLANFFVFLVETGFHHVGQAGLKLLTSDDLPASASQSAGITGVSHHARPNFFFSLLLS | 162.59 | 8.78 | 89.66 | 0.14 | Yes |
| AS36 | 129 | STK32C | IGKGSFGKFLEDATHMV | 7.44 | 0.45 | 3.36 | 0.04 | Yes |
| AS44 | 145 | FGFR3 | VLTVTSTDQEYLDLSAP | 85.94 | 0.33 | 13.45 | 0.067 | Yes |
| AS60 | 177 | HMCN2 | LASGVPPPGLPWGPGPHLG | 265.02 | 1.9 | 4.3 | 0.019 | Yes |
| AS61 | 179 | IGF2BP3 | IPPHLQWESTRQTEWISVREFHLESSLYP | 4.86 | 0.13 | 4.26 | 0.038 | Yes |
| AS62 | 181 | IMPG2 | PGHGAICREEV | 28.06 | 0.055 | 14.25 | 0.063 | Yes |
| AS63 | 183 | IMPG2 | LEEEFISEWRRCLLCSYLQW | 185.74 | 0.5 | 13.54 | 0.15 | Yes |
| AS64 | 185 | IQGAP3 | QTQEETDRDRGSWSCAVA | 33.44 | 0.21 | 5.43 | 0.024 | Yes |
| AS65 | 187 | LCN10 | SHALNWNKIGRMFRASRV | 82.3 | 2.2 | 73.69 | 0.64 | Yes |
| AS67 | 191 | PARD6B | GTMEVKSKKKQTTVPLVQTR | 6.36 | 0.17 | 3.15 | 0.028 | Yes |
| AS68 | 193 | PKHD1L1 | LLFPYNQLDLHLHRPSGSRKNEIHWDKCFSSED | 17.52 | 0.11 | 5.43 | 0.024 | Yes |
| AS69 | 195 | PTH2R | GFILIGWGAGNLVLETSSGFIKHRS | 260.42 | 1 | 9.21 | 0.011 | Yes |
| AS70 | 197 | RUFY4 | HFVRSQDKGMVWTPEPSALPRTPRRHPGLSLCSQWGGLRVGPPAARPGWS | 69.96 | 1.87 | 279.88 | 0.28 | Yes |

TABLE 11-continued

Immunogenicity data summarization of all tumor specific neoantigens.
For each neoantigen, the maximum CD8+ and CD4+ T-cell responses (TNFα
and IFNγ) are reported. The responses reported are donor independent.

| Neo-peptide/ Neo-epitope ID | SEQ ID | Gene ID | Neoantigen Sequence | Fold change (CD8+) vs. DMSO | Frequency (TNFα + IFNγ + CD8 Tcells) | Fold change (CD4+) vs. DMSO | Frequency (TNFα + IFNγ + CD4 T cells) | Immunogenic (yes/no) |
|---|---|---|---|---|---|---|---|---|
| | | | LAHVLRVT LLQFHPNPG KETQKKQR CPKEDPSRI WRA | | | | | |
| AS71 | 199 | SLC6A2 | NIEDVATED GRHGGCHH GPGR | 11.78 | 0.074 | 10.95 | 0.038 | Yes |
| AS72 | 201 | SMC1B | RRHGEVQG LLEREKTAR GNPSG | 8.6 | 0.23 | 4.15 | 0.036 | Yes |
| AS74 | 205 | TRPM5 | VLRKTAHR STTARCSCP PWLTCWPR VAAPGALS TVAREASW WLLTTEVV | 1018.49 | 6.6 | 17.23 | 0.064 | Yes |
| AS75 | 207 | TSPAN10 | MHRKLQAR SPSLCTGHP PQAA | 2.64 | 0.16 | 3.46 | 0.014 | Yes |
| AS77 | 211 | EP400 | SISLTDDEA ELPLLDL | 6.59 | 0.12 | 20.73 | 0.18 | Yes |
| AS79 | 215 | FBN3 | APSCGVSR AICDRGCH | 2.88 | 0.076 | 5.85 | 0.12 | Yes |
| AS81 | 219 | FBN3 | LSPGGACV DIDECDRQ | 10.83 | 0.1 | 3.22 | 0.028 | Yes |
| AS82 | 221 | IMPG2 | MPGHGAIC SGSSRQPD | 13.55 | 0.82 | 5.88 | 0.026 | Yes |
| AS83 | 223 | NUF2 | VQKLKNAR SLNLEDQI | 10.83 | 0.14 | 71.14 | 0.061 | Yes |
| AS89 | 235 | ZNF727 | NYGNLFSL AGSLHFTA | 142.04 | 0.26 | 7.02 | 0.061 | Yes |
| AS90 | 237 | ACIN1 | VEDEEKKEP DGAQRHLV DIGGSHOTS HAEKFLFLL CPPVV | 28.95 | 0.1 | 4.93 | 0.044 | Yes |
| AS88 | 233 | UPK3B | CLRPSLSLA SRGFQNP | 3.13 | 0.063 | 15.85 | 0.062 | Yes |
| AS91 | 239 | ACIN1 | VEDEEKKE AGTHFIHLT GTTVSAGV PEEMPATTL RREVF | 46.44 | 0.21 | 36.02 | 0.23 | Yes |
| AS93 | 243 | ACIN1 | VEDEEKKE GSMLVAPT SPPSLEAGT HFIHLTGTT VSAGVPEE MPATTLRR EVF | 459.18 | 0.9 | 253.72 | 1.62 | Yes |
| AS94 | 245 | AFDN | SMMEGVIQ LSFKAIVCL LSCLDLLSL FRVVRHLS | 1080.99 | 9.61 | 62.76 | 0.098 | Yes |

TABLE 11-continued

Immunogenicity data summarization of all tumor specific neoantigens.
For each neoantigen, the maximum CD8+ and CD4+ T-cell responses (TNFα
and IFNγ) are reported. The responses reported are donor independent.

| Neo-peptide/ Neo-epitope ID | SEQ ID | Gene ID | Neoantigen Sequence | Fold change (CD8+) vs. DMSO | Frequency (TNFα + IFNγ + CD8 Tcells) | Fold change (CD4+) vs. DMSO | Frequency (TNFα + IFNγ + CD4 T cells) | Immunogenic (yes/no) |
|---|---|---|---|---|---|---|---|---|
| AS95 | 247 | DMXL2 | TKKRKQSELQQP | 2.54 | 0.03 | 2.91 | 0.026 | No |
| AS97 | 251 | ETV4 | FQETWLAEDAAAGALSPCTIPTPPQPPLLSLPTSSGTRQ | 433.66 | 1.34 | 6.12 | 0.15 | Yes |
| AS99 | 255 | FAM221A | RLDDSGIGNFITSLLNFISKFFCSFMGA | 160.85 | 1.43 | 4 | 0.077 | Yes |
| AS100 | 257 | FRYL | NANSRLPEACEK | 63.36 | 0.099 | 6.02 | 0.039 | Yes |
| AS102 | 261 | GRHL2 | MSQESDKNGLSSRSWMNTWILPEVL | 5.65 | 0.096 | 4.47 | 0.029 | Yes |
| AS103 | 263 | GTF2IRD1 | LDLAGNARPCRSQSPTSSDQTPSVPSLGSPELPDGEEGGSPDGSPQESEQVRQGQHV | 48.82 | 0.83 | 6.62 | 0.086 | Yes |
| AS105 | 267 | MPRIP | PSPSTPNHSQQAICHPGRRP | 1.76 | 0.02 | 14.72 | 0.14 | Yes |
| AS107 | 271 | MUC16 | SGCRLTLLSLSPVSSLGCPVPMP | 2351.27 | 16.6 | 14.89 | 0.062 | Yes |
| AS118 | 293 | SAMD12 | NLQLLTQGYSGIWRYP | 2.42 | 0.038 | 5.25 | 0.034 | Yes |
| AS119 | 295 | SMAD6 | HFSRLCGPVSHLSAHLAHLR | 1.32 | 0.037 | 4.17 | 0.027 | Yes |
| AS120 | 297 | STRA6 | KHHLWALEAAWLSGRSPLSEPQLPLQPSGNSSSV | 6.24 | 0.067 | 2.01 | 0.013 | Yes |
| AS123 | 303 | VWA2 | KLCSRQRPDCQPVDSRHGPILSIQHLISALHTGDG | 115.04 | 1.09 | 3.7 | 0.024 | yes |
| AS125 | 307 | LRRC75B | RDLQCPKKTQTPQAQSRLESERKKNTLTWLVPTPWDWRQWSTAPSRGLVWPPPPVDYELWKSS | 143.98 | 1.28 | 10.84 | 0.047 | Yes |
| AS126 | 309 | SRGAP3 | HQYIVVQDIHTETQHSALGAQPADSIPPFLQHTLQH | 14.89 | 0.16 | 12.03 | 0.078 | Yes |

TABLE 11-continued

Immunogenicity data summarization of all tumor specific neoantigens.
For each neoantigen, the maximum CD8+ and CD4+ T-cell responses (TNFα
and IFNγ) are reported. The responses reported are donor independent.

| Neo-peptide/ Neo-epitope ID | SEQ ID | Gene ID | Neoantigen Sequence | Fold change (CD8+) vs. DMSO | Frequency (TNFα + IFNγ + CD8 Tcells) | Fold change (CD4+) vs. DMSO | Frequency (TNFα + IFNγ + CD4 T cells) | Immunogenic (yes/no) |
|---|---|---|---|---|---|---|---|---|
| | | | LACPSLELP GNEQARRE KRRRDDAF SDSL | | | | | |
| AS133 | 323 | HRAS | CDPAAPRA VSLPGRQGS EGGEGRGL GSRPAVLG RHSSGEGG GPWGELP | 171.88 | 0.84 | 54.15 | 0.16 | Yes |
| AS134 | 325 | HSF4 | ARLRELRQ CGGGRGKR GQGWGVR DETITGRPA VLGSPFLSP ALAPPSRL MGDLWDG QSAGWSPG SPASPFCGG W | 66.2 | 0.62 | 6.63 | 0.043 | Yes |
| AS140 | 337 | MUC16 | PSSLPGPTG KYQSMVFG AWLMSVNI SVYTLLEHG | 115.04 | 0.22 | 79.1 | 0.14 | Yes |
| AS141 | 339 | MUC16 | RSSGLTTSS EYSTHVHM PLILHQAEQ ELLLLINP | 3.82 | 0.041 | 6.94 | 0.045 | Yes |
| AS143 | 343 | MUC16 | RYWTPATS SEYSNL | 12.1 | 0.13 | 3.6 | 0.033 | Yes |
| AS146 | 349 | PIP5K1A | KRPMASEV SFILIQWLL KP | 24.2 | 0.26 | 8.88 | 0.037 | Yes |
| AS157 | 371 | ZIC4 | RNTLKESSK LKSSFEYWF AGFFSSSSS FFFLSRKFC FVFCLCWV ESLGGVS | 51.78 | 0.16 | 5.53 | 0.083 | Yes |
| AS159 | 375 | DRD4 | LCAISVDRC AALPARAP APPRPARRP HRGLCAVR RPLGAPRRF VAVAVP | 39.04 | 0.12 | 12.5 | 0.081 | Yes |
| AS86 | 229 | RASEF | DEAKFIPRA QDKAAMQ | N/A | N/A | N/A | N/A | N/A |
| AS144 | 345 | NDRG4 | PTTTTFLKV RLSSPALGQ LP | N/A | N/A | N/A | N/A | N/A |
| AS20 | 97 | STRA6 | RAFPRELKK GQRMSSQ | N/A | N/A | N/A | N/A | N/A |
| FUS9 | 17 | TBCEL-> TECTA | PQEEVPFR MNYSSFLR | N/A | N/A | N/A | N/A | N/A |
| AS76 | 209 | CENPI | LLDLQAKM IYFKNSEN | N/A | N/A | N/A | N/A | N/A |

TABLE 11-continued

Immunogenicity data summarization of all tumor specific neoantigens.
For each neoantigen, the maximum CD8+ and CD4+ T-cell responses (TNFα
and IFNγ) are reported. The responses reported are donor independent.

| Neo-peptide/ Neo-epitope ID | SEQ ID | Gene ID | Neoantigen Sequence | Fold change (CD8+) vs. DMSO | Frequency (TNFα + IFNγ + CD8 Tcells) | Fold change (CD4+) vs. DMSO | Frequency (TNFα + IFNγ + CD4 T cells) | Immunogenic (yes/no) |
|---|---|---|---|---|---|---|---|---|
| AS92 | 241 | ACIN1 | VEDEEKKEGLISST | N/A | N/A | N/A | N/A | N/A |
| AS101 | 259 | GAD1 | DGDGIFSPELS | N/A | N/A | N/A | N/A | N/A |
| AS112 | 281 | PIGG | PDLGHWLTRAVWGNSATS | N/A | N/A | N/A | N/A | N/A |
| AS114 | 285 | PTPN4 | FIQLRKELNFTSTPDA | N/A | N/A | N/A | N/A | N/A |
| FUS23 | 45 | ARID3C->DCTN3 | TYEEQFKQVADGLVKV | N/A | N/A | N/A | N/A | N/A |
| AS73 | 203 | TLK2 | SLSDKEVEGKALLGDIKLVITLSDE | N/A | N/A | N/A | N/A | N/A |
| AS122 | 301 | TMEM221 | CGISVYLAGRTRWLTPVIPALWETEAGRSRGOEIETILANKHCPSMPCYFSRSRQAQQLLPSSARAPWFWWLC | N/A | N/A | N/A | N/A | N/A |
| AS124 | 305 | HUWE1 | EEMETDMDDVAMESSPGSSISMEHRLDVELRASGSSSSTNISSGPSPGPSPGPGTGPGPGPGPGPGPGPGPGPGPGPGPGPGPGPRPGVQCIPQR | N/A | N/A | N/A | N/A | N/A |
| AS131 | 319 | EBF3 | YGMPHNNQVGGGRLPSPILPPMPEPVGSRRGSSVGFLDISMLFQRLHRSLM | N/A | N/A | N/A | N/A | N/A |
| AS111 | 279 | PCNX3 | WLLRTWERADSGL | N/A | N/A | N/A | N/A | N/A |

Example 4: HLA Binding Predictions

Amino acid sequences of neoantigens identified using the various approaches as described in Example 1 are split into all possible unique, contiguous 9 mer amino acid fragments and HLA binding predictions to six common HLA alleles (HLA-A*01:01, HLA-A*02:01, HLA-A*03:01, HLA-A*24:02, HLA-B*07:02, HLA-B*08:01) are performed for each of these 9 mers using netMHCpan4.0. Several 9 mer fragments are selected for further analysis based on ranking by likelihood of binding to one or more of the tested HLA alleles and their prevalence in ovarian cancer patients.

Example 5: In Vitro Binding of Neoantigens to Class I MHC

Binding of selected neoantigens of fragments thereof to HLA-A*01:01, HLA-A*02:01, HLA-A*03:01, HLA-A*24:02, HLA-B*07:02 and HLA-B*08:01 or any other HLA is evaluated using known methods.

9 mer peptides which are identified by bioinformatics analysis are analyzed for their binding propensities to 6 common HLA class I alleles (HLA-A*01:01, A*02:01, A*03:01, A*24:02, B*07:02, B*08:01). The principle of the method is briefly described below and consists of two parts, one involving exchange of peptide with a positive control induced by Ultraviolet (UV) radiation, and the second is an enzyme immunoassay to detect stable HLA-peptide and empty HLA complexes.

HLA-bound peptides are critical for the stability of the HLA complex. A conditional HLA class I complex is stabilized by an UV-labile peptide utilizing a different peptide (Pos) for each HLA (Pos: HLA-A*01:01: CTELKLSDY (SEQ ID NO: 407), HLA-A*02:01: NLVPMVATV (SEQ ID NO: 408), HLA-A*03:01: LIYRRRLMK (SEQ ID NO: 409), HLA-A*24:02: LYSACFWWL (SEQ ID NO: 410), HLA-B*07:02: NPKASLLSL (SEQ ID NO: 411), HLA-B*08:01: ELRSRYWAI (SEQ ID NO: 412)), which could be cleaved by UV irradiation when bound to the HLA molecule. Upon cleavage, the resulting peptide fragments dissociate from the HLA class I complex since their length is insufficient to bind stably to HLA. Under the conditions in which peptide cleavage is performed (neutral pH, on melting ice), the peptide-free HLA complex remains stable. Thus, when cleavage is performed in the presence of another HLA class I peptide of choice, this reaction results in net exchange of the cleaved UV-labile peptide Pos with the chosen peptide (Rodenko, B et al. (2006) Nature Protocols 1: 1120-32, Toebes, M et al. (2006) Nat Med 12: 246-51, Bakker, A H et al. (2008) Proc Natl Acad Sci USA 105: 3825-30).

The exchange efficiency between the peptide of interest and Pos is analyzed using an HLA class I ELISA. The combined technologies allow the identification of ligands for an HLA molecule of interest which are potentially immunogenic.

Exchange control peptide Pos is a high affinity binder to the relevant HLA class I allele while exchange control peptide Neg is a non-binder. UV control represents UV-irradiation of conditional HLA class I complex in the absence of a rescue peptide. Binding of exchange control peptide Neg (HLA-A*01:01: NPKASLLSL (SEQ ID NO: 413), HLA-A*02-01: IVTDFSVIK (SEQ ID NO: 414), HLA-A*03:01: NPKASLLSL (SEQ ID NO: 415), HLA-A*24:02: NLVPMVATV (SEQ ID NO: 416), HLA-B*07: 02: LIYRRRLMK (SEQ ID NO: 417), HLA-B*08:01: NLVPMVATV (SEQ ID NO: 418)) and all experimental peptides are evaluated relative to that of exchange control peptide Pos. The absorption of the latter peptide is set at 100%. This procedure results in a range of different exchange percentages that reflects the affinities of the different experimental peptides for the HLA allele used.

HLA class I ELISA is an enzyme immunoassay based on the detection of beta2-microglobulin (B2M) of (peptide-stabilized) HLA class I complexes. To this end streptavidin is bound onto polystyrene microtiter wells. After washing and blocking, HLA complex present in exchange reaction mixtures or ELISA controls is captured by the streptavidin on the microtiter plate via its biotinylated heavy chain. Non-bound material is removed by washing. Subsequently, horseradish peroxidase (HRP)-conjugated antibody to human B2M is added. The HRP-conjugated antibody binds only to an intact HLA complex present in the microtiter well because unsuccessful peptide exchange results in disintegration of the original UV-sensitive HLA complex upon UV illumination. In the latter case B2M is removed during the washing step. After removal of non-bound HRP conjugate by washing, a substrate solution is added to the wells. A colored product forms in proportion to the amount of intact HLA complex present in the samples. After the reaction is terminated by the addition of a stop solution, absorbance is measured in a microtiter plate reader. The absorbance is normalized to the absorbance of an exchange control peptide (represents 100%). Suboptimal HLA binding of peptides with a moderate to low affinity for HLA class I molecules can also be detected by this ELISA technique (Rodenko, B et al. (2006) Nature Protocols 1: 1120-32).

HLA allele that is tested has a corresponding positive control (Pos) and a negative control (Neg) peptide against which the peptide of interest is exchanged. An exchange rate of 100% with Pos means that the peptide of interest has the same binding affinity to the HLA allele as the positive control peptide. Peptides with an exchange rate of at least 10% with the corresponding Pos peptide for at least one of the 6 HLA alleles are considered for further evaluation. Higher percentages correspond to stronger binding to the HLA allele.

Embodiments

The following list of embodiments is intended to complement, rather than displace or supersede, the previous descriptions.

Embodiment 1. A polypeptide comprising at least one or more peptides sequences selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, or 405, or fragments thereof.

Embodiment 2. A polypeptide comprising at least one or more peptides sequences selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 3. A polypeptide comprising two or more tandem repeats of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 4. The polypeptide of any of one of embodiments 1-3, wherein the polypeptide sequences are connected to each other in any order.

Embodiment 5. The polypeptide of embodiment 2, wherein the polypeptide is selected from:
an amino acid sequence of SEQ ID NO: 1 or having at least 90% sequence identity to SEQ ID NO: 1;

an amino acid sequence of SEQ ID NO: 3 or having at least 90% sequence identity to SEQ ID NO: 3;
an amino acid sequence of SEQ ID NO: 5 or having at least 90% sequence identity to SEQ ID NO: 5;
an amino acid sequence of SEQ ID NO: 11 or having at least 90% sequence identity to SEQ ID NO: 11;
an amino acid sequence of SEQ ID NO: 15 or having at least 90% sequence identity to SEQ ID NO: 15;
an amino acid sequence of SEQ ID NO: 17 or having at least 90% sequence identity to SEQ ID NO: 17;
an amino acid sequence of SEQ ID NO: 19 or having at least 90% sequence identity to SEQ ID NO: 19;
an amino acid sequence of SEQ ID NO: 21 or having at least 90% sequence identity to SEQ ID NO: 21;
an amino acid sequence of SEQ ID NO: 25 or having at least 90% sequence identity to SEQ ID NO: 25;
an amino acid sequence of SEQ ID NO: 29 or having at least 90% sequence identity to SEQ ID NO: 29;
an amino acid sequence of SEQ ID NO: 31 or having at least 90% sequence identity to SEQ ID NO: 31;
an amino acid sequence of SEQ ID NO: 33 or having at least 90% sequence identity to SEQ ID NO: 33;
an amino acid sequence of SEQ ID NO: 39 or having at least 90% sequence identity to SEQ ID NO: 39;
an amino acid sequence of SEQ ID NO: 43 or having at least 90% sequence identity to SEQ ID NO: 43;
an amino acid sequence of SEQ ID NO: 45 or having at least 90% sequence identity to SEQ ID NO: 45;
an amino acid sequence of SEQ ID NO: 49 or having at least 90% sequence identity to SEQ ID NO: 49;
an amino acid sequence of SEQ ID NO: 53 or having at least 90% sequence identity to SEQ ID NO: 53;
an amino acid sequence of SEQ ID NO: 59 or having at least 90% sequence identity to SEQ ID NO: 59;
an amino acid sequence of SEQ ID NO: 63 or having at least 90% sequence identity to SEQ ID NO: 63;
an amino acid sequence of SEQ ID NO: 65 or having at least 90% sequence identity to SEQ ID NO: 65;
an amino acid sequence of SEQ ID NO: 67 or having at least 90% sequence identity to SEQ ID NO: 67;
an amino acid sequence of SEQ ID NO: 81 or having at least 90% sequence identity to SEQ ID NO: 81;
an amino acid sequence of SEQ ID NO: 85 or having at least 90% sequence identity to SEQ ID NO: 85;
an amino acid sequence of SEQ ID NO: 87 or having at least 90% sequence identity to SEQ ID NO: 87;
an amino acid sequence of SEQ ID NO: 89 or having at least 90% sequence identity to SEQ ID NO: 89;
an amino acid sequence of SEQ ID NO: 91 or having at least 90% sequence identity to SEQ ID NO: 91;
an amino acid sequence of SEQ ID NO: 95 or having at least 90% sequence identity to SEQ ID NO: 95;
an amino acid sequence of SEQ ID NO: 97 or having at least 90% sequence identity to SEQ ID NO: 97;
an amino acid sequence of SEQ ID NO: 111 or having at least 90% sequence identity to SEQ ID NO: 111;
an amino acid sequence of SEQ ID NO: 113 or having at least 90% sequence identity to SEQ ID NO: 113;
an amino acid sequence of SEQ ID NO: 115 or having at least 90% sequence identity to SEQ ID NO: 115;
an amino acid sequence of SEQ ID NO: 119 or having at least 90% sequence identity to SEQ ID NO: 119;
an amino acid sequence of SEQ ID NO: 123 or having at least 90% sequence identity to SEQ ID NO: 123;
an amino acid sequence of SEQ ID NO: 127 or having at least 90% sequence identity to SEQ ID NO: 127;
an amino acid sequence of SEQ ID NO: 129 or having at least 90% sequence identity to SEQ ID NO: 129;
an amino acid sequence of SEQ ID NO: 145 or having at least 90% sequence identity to SEQ ID NO: 145;
an amino acid sequence of SEQ ID NO: 177 or having at least 90% sequence identity to SEQ ID NO: 177;
an amino acid sequence of SEQ ID NO: 179 or having at least 90% sequence identity to SEQ ID NO: 179;
an amino acid sequence of SEQ ID NO: 181 or having at least 90% sequence identity to SEQ ID NO: 181;
an amino acid sequence of SEQ ID NO: 185 or having at least 90% sequence identity to SEQ ID NO: 185;
an amino acid sequence of SEQ ID NO: 187 or having at least 90% sequence identity to SEQ ID NO: 187;
an amino acid sequence of SEQ ID NO: 191 or having at least 90% sequence identity to SEQ ID NO: 191;
an amino acid sequence of SEQ ID NO: 193 or having at least 90% sequence identity to SEQ ID NO: 193;
an amino acid sequence of SEQ ID NO: 195 or having at least 90% sequence identity to SEQ ID NO: 195;
an amino acid sequence of SEQ ID NO: 197 or having at least 90% sequence identity to SEQ ID NO: 197;
an amino acid sequence of SEQ ID NO: 199 or having at least 90% sequence identity to SEQ ID NO: 199;
an amino acid sequence of SEQ ID NO: 201 or having at least 90% sequence identity to SEQ ID NO: 201;
an amino acid sequence of SEQ ID NO: 203 or having at least 90% sequence identity to SEQ ID NO: 203;
an amino acid sequence of SEQ ID NO: 205 or having at least 90% sequence identity to SEQ ID NO: 205;
an amino acid sequence of SEQ ID NO: 207 or having at least 90% sequence identity to SEQ ID NO: 207;
an amino acid sequence of SEQ ID NO: 209 or having at least 90% sequence identity to SEQ ID NO: 209;
an amino acid sequence of SEQ ID NO: 211 or having at least 90% sequence identity to SEQ ID NO: 211;
an amino acid sequence of SEQ ID NO: 215 or having at least 90% sequence identity to SEQ ID NO: 215;
an amino acid sequence of SEQ ID NO: 219 or having at least 90% sequence identity to SEQ ID NO: 219;
an amino acid sequence of SEQ ID NO: 221 or having at least 90% sequence identity to SEQ ID NO: 221;
an amino acid sequence of SEQ ID NO: 223 or having at least 90% sequence identity to SEQ ID NO: 223;
an amino acid sequence of SEQ ID NO: 235 or having at least 90% sequence identity to SEQ ID NO: 235;
an amino acid sequence of SEQ ID NO: 237 or having at least 90% sequence identity to SEQ ID NO: 237;
an amino acid sequence of SEQ ID NO: 239 or having at least 90% sequence identity to SEQ ID NO: 239;
an amino acid sequence of SEQ ID NO: 241 or having at least 90% sequence identity to SEQ ID NO: 241;
an amino acid sequence of SEQ ID NO: 243 or having at least 90% sequence identity to SEQ ID NO: 243;
an amino acid sequence of SEQ ID NO: 245 or having at least 90% sequence identity to SEQ ID NO: 245;
an amino acid sequence of SEQ ID NO: 247 or having at least 90% sequence identity to SEQ ID NO: 247;
an amino acid sequence of SEQ ID NO: 251 or having at least 90% sequence identity to SEQ ID NO: 251;
an amino acid sequence of SEQ ID NO: 255 or having at least 90% sequence identity to SEQ ID NO: 255;
an amino acid sequence of SEQ ID NO: 257 or having at least 90% sequence identity to SEQ ID NO: 257;
an amino acid sequence of SEQ ID NO: 259 or having at least 90% sequence identity to SEQ ID NO: 259;

an amino acid sequence of SEQ ID NO: 261 or having at least 90% sequence identity to SEQ ID NO: 261;
an amino acid sequence of SEQ ID NO: 263 or having at least 90% sequence identity to SEQ ID NO: 263;
an amino acid sequence of SEQ ID NO: 267 or having at least 90% sequence identity to SEQ ID NO: 267;
an amino acid sequence of SEQ ID NO: 271 or having at least 90% sequence identity to SEQ ID NO: 271;
an amino acid sequence of SEQ ID NO: 279 or having at least 90% sequence identity to SEQ ID NO: 279;
an amino acid sequence of SEQ ID NO: 281 or having at least 90% sequence identity to SEQ ID NO: 281;
an amino acid sequence of SEQ ID NO: 285 or having at least 90% sequence identity to SEQ ID NO: 285;
an amino acid sequence of SEQ ID NO: 293 or having at least 90% sequence identity to SEQ ID NO: 293;
an amino acid sequence of SEQ ID NO: 295 or having at least 90% sequence identity to SEQ ID NO: 295;
an amino acid sequence of SEQ ID NO: 297 or having at least 90% sequence identity to SEQ ID NO: 297;
an amino acid sequence of SEQ ID NO: 301 or having at least 90% sequence identity to SEQ ID NO: 301;
an amino acid sequence of SEQ ID NO: 305 or having at least 90% sequence identity to SEQ ID NO: 305;
an amino acid sequence of SEQ ID NO: 307 or having at least 90% sequence identity to SEQ ID NO: 307;
an amino acid sequence of SEQ ID NO: 309 or having at least 90% sequence identity to SEQ ID NO: 309;
an amino acid sequence of SEQ ID NO: 319 or having at least 90% sequence identity to SEQ ID NO: 319;
an amino acid sequence of SEQ ID NO: 323 or having at least 90% sequence identity to SEQ ID NO: 323;
an amino acid sequence of SEQ ID NO: 325 or having at least 90% sequence identity to SEQ ID NO: 325;
an amino acid sequence of SEQ ID NO: 337 or having at least 90% sequence identity to SEQ ID NO: 337;
an amino acid sequence of SEQ ID NO: 339 or having at least 90% sequence identity to SEQ ID NO: 339;
an amino acid sequence of SEQ ID NO: 343 or having at least 90% sequence identity to SEQ ID NO: 343;
an amino acid sequence of SEQ ID NO: 345 or having at least 90% sequence identity to SEQ ID NO: 345;
an amino acid sequence of SEQ ID NO: 349 or having at least 90% sequence identity to SEQ ID NO: 349;
an amino acid sequence of SEQ ID NO: 371 or having at least 90% sequence identity to SEQ ID NO: 371;
an amino acid sequence of SEQ ID NO: 375 or having at least 90% sequence identity to SEQ ID NO: 375;
and combinations thereof.

Embodiment 6. A polynucleotide encoding a polypeptide of any one of the embodiments 1-5.

Embodiment 7. The polynucleotide of embodiment 6, wherein the polynucleotide is selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, or 406, or fragments thereof.

Embodiments 8. A vector comprising a polynucleotide of embodiment 6 or embodiment 7.

Embodiments 9. The vector of embodiment 8, wherein the vector is selected from an adenovirus vector, an alphaviral vector, a poxvirus vector, an adeno-associated virus vector, a retrovirus vector, a self-replicating RNA molecule, and a combination thereof.

Embodiment 10. The vector of embodiment 9, wherein the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

Embodiment 11. The vector of embodiment 9, wherein the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Embodiment 12. The vector of embodiment 9, wherein the vector is the adenovirus vector comprising a polynucleotide encoding any one of the polypeptides of any one of embodiments 1-5.

Embodiment 13. The vector of embodiment 9, wherein the vector is the poxvirus vector comprising a polynucleotide encoding any one of the polypeptides of any one of embodiments 1-5.

Embodiment 14. The vector of embodiment 9, wherein the vector is the self-replicating RNA molecule comprising a polynucleotide encoding any one of the polypeptides of any one of embodiments 1-5.

Embodiment 15. A pharmaceutical composition comprising a polypeptide of any one of embodiments 1-5.

Embodiment 16. A pharmaceutical composition comprising a polynucleotide any one of embodiments 6 and 7.

Embodiment 17. A pharmaceutical composition comprising a vector of any one of embodiments 8-14.

Embodiment 18. The pharmaceutical composition of embodiment 17, wherein the vector is selected from an Ad26 vector, a MVA vector, a GAd20 vector, a self-replicating RNA molecule, and combinations thereof.

Embodiment 19. The pharmaceutical composition of embodiment 18, wherein the vector is an Ad26 vector comprising
a polynucleotide encoding one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, or
a polynucleotide encoding one or more polypeptides having at least 90% sequence identity to SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 20. The pharmaceutical composition of embodiment 18, wherein the vector is an GAd20 vector comprising
- a polynucleotide encoding one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, or
- a polynucleotide encoding one or more polypeptides having at least 90% sequence identity to SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 21. The pharmaceutical composition of embodiment 18, wherein the vector is an MVA vector comprising
- a polynucleotide encoding one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, or
- a polynucleotide encoding one or more polypeptides having at least 90% sequence identity to SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 22. The pharmaceutical composition of embodiment 18, wherein the vector is a self-replicating RNA molecule comprising
- a polynucleotide encoding one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, or
- a polynucleotide encoding one or more polypeptides having at least 90% sequence identity to SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 23. A method of inducing an immune response in a subject comprising administering to the subject in need thereof a pharmaceutical composition of any one of embodiments 15-22.

Embodiment 24. A method of inducing an immune response in a subject comprising administering to the subject in need thereof a composition comprising a recombinant virus and/or a composition comprising a self-replicating RNA molecule, wherein the recombinant virus or the self-replicating RNA molecule comprises a polynucleotide encoding at least one or more polypeptide selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 25. The method of embodiment 23 or 24, wherein the subject expresses or is suspected to express one or more polypeptides of claim 1.

Embodiment 26. A method of treating, preventing, reducing a risk of onset or delaying the onset of ovarian cancer in a subject comprising administering to the subject in need thereof a pharmaceutical composition of any one of embodiments 15-22.

Embodiment 27. A method of treating, preventing, reducing a risk of onset or delaying the onset of ovarian cancer in a subject comprising administering to the subject in need thereof a composition comprising a recombinant virus and/or a composition comprising a self-replicating RNA molecule, wherein the recombinant virus or the self-replicating RNA molecule comprises a polynucleotide encoding at least one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 28. A method of treating, preventing, reducing a risk of onset or delaying the onset of ovarian cancer in a subject comprising administering to the subject in need thereof a composition comprising a recombinant virus and/or a composition comprising a self-replicating RNA molecule, wherein the recombinant virus or the self-replicating RNA molecule comprises a polynucleotide encoding at least one or more polypeptides selected from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the administration comprises one or more administrations of the composition.

Embodiment 29. The method of any one of embodiments 23-28, wherein the virus or recombinant virus is selected from Ad26, MVA, GAd20, and combinations thereof.

Embodiment 30. The method of embodiment 29, wherein the recombinant virus is an Ad26 virus comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 31. The method of embodiment 29, wherein the recombinant virus is a GAd20 virus comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 32. The method of embodiment 29, wherein the recombinant virus is a MVA virus comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 33. The method of embodiment 29, wherein the self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof.

Embodiment 34. The method of any one of embodiments 23-33, comprising one or more treatment cycles, wherein each cycle comprises:
  a first administration comprising a first composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20; and
  a second administration comprising a second composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20.

Embodiment 35. The method of any one of embodiments 23-33, comprising one or more treatment cycles, wherein each cycle comprises:
  a first administration comprising a first composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20; and
  a second administration comprising a second composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20; and
  a third administration comprising a third composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20.

Embodiment 36. The method of any one of embodiments 23-33, comprising one or more treatment cycles, wherein each cycle comprises:

a first administration comprising a first composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20; and a second administration comprising a second composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20; and a third administration comprising a third composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20; and a fourth administration comprising a fourth composition comprising a recombinant virus or a self-replicating RNA molecule comprising a polynucleotide encoding one or more polypeptides from the group consisting of SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, or 375, or fragments thereof, and wherein the recombinant virus is selected from Ad26, MVA, or GAd20.

Embodiment 37. The method of embodiments 34-36, wherein the first, the second, the third or the fourth administration comprise a distinct recombinant virus.

Embodiment 38. The method of embodiments 34-37, wherein the first, the second, the third or the fourth administration comprise a recombinant virus comprising a polynucleotide encoding for a polypeptide of distinct amino acid sequence.

Embodiment 39. The method of any one of embodiments 26-38, further comprising administering a second therapeutic agent selected from a CTLA-4 antibody, a PD-1 antibody, a PD-L1 antibody, a TLR agonist, a CD40 agonist, an OX40 agonist, hydroxyurea, ruxolitinib, fedratinib, a 41BB agonist, a CD28 agonist, FLT3 ligand, aluminum sulfate, a BTK inhibitor, a JAK inhibitor, a CD38 antibody, a CDK inhibitor, a CD33 antibody, a CD37 antibody, a CD25 antibody, a GM-CSF inhibitor, IL-2, IL-15, IL-7, IFNγ, IFNα, TNFα, a VEGF antibody, a CD70 antibody, a CD27 antibody, a BCMA antibody, a GPRCSD antibody, and combinations thereof.

Embodiments 40. The method of embodiment 25-39, wherein the ovarian cancer is an epithelial ovarian cancer, germ cell ovarian cancer, stromal cell ovarian cancer or small cell carcinoma, or a combination thereof.

Embodiment 41. The method of embodiment 23-40, wherein the one or more polypeptides of claim 1 is present at a frequency of at least about 1% or more, about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 16% or more, about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 35% or more, about 40% or more, about 45% or more, about 50% or more, about 55% or more, about 60% or more, about 65% or more or about 70% or more in a population of subjects having the ovarian cancer.

We claim:

1. A polypeptide comprising two or more amino acid sequences selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, or fragments thereof, wherein the amino acid sequences are connected to each other in any order.

2. The polypeptide of claim 1, wherein the two or more amino acid sequences are selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, or fragments thereof.

3. The polypeptide of claim 1, wherein the two or more amino acid sequences are connected to each other without a linker.

4. The polypeptide of claim 1, wherein the polypeptide comprises one or more reverse peptide bonds, D-isomers of amino acids, chemical modifications, or any combination thereof.

5. A polynucleotide encoding two or more polypeptides selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, or fragments thereof, wherein the polypeptides are connected to each other in any order.

6. The polynucleotide of claim 5, comprising two or more sequences selected from SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, and 406, or fragments thereof.

7. The polynucleotide of claim 5, wherein the polynucleotide comprises DNA or RNA.

8. The polynucleotide of claim 7, wherein the RNA is mRNA.

9. A vector comprising a polynucleotide encoding two or more polypeptides selected from SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, and 405, or fragments thereof, wherein the polypeptides are connected to each other in any order.

10. The vector of claim 9, wherein the vector is selected from an adenovirus vector, a poxvirus vector, adeno-associated virus vector, a retrovirus vector, a self-replicating RNA molecule, and a combination thereof.

11. The vector of claim 10, wherein the adenovirus vector is derived from hAd5, hAd7, hAd11, hAd26, hAd34, hAd35, hAd48, hAd49, hAd50, GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, or PanAd3.

12. The vector of claim 10, wherein the poxvirus vector is derived from smallpox virus vector, vaccinia virus vector, cowpox virus vector, monkeypox virus vector, Copenhagen vaccinia virus (W) vector, New York Attenuated Vaccinia Virus (NYVAC) vector, or Modified Vaccinia Ankara (MVA) vector.

13. The vector of claim 10, wherein the vector is an adenovirus vector.

14. The vector of claim 10, wherein the vector is a poxvirus vector.

15. The vector of claim 10, wherein the vector is a self-replicating RNA molecule.

16. The vector of claim 11, wherein the adenovirus vector is derived from hAd26 and wherein the polynucleotide encodes two or more polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, or fragments thereof, wherein the polypeptides are connected to each other in any order.

17. The vector of claim 11, wherein the adenovirus vector is derived from GAd20 and wherein the polynucleotide encodes two or more polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, or fragments thereof, wherein the polypeptides are connected to each other in any order.

18. The vector of claim 12, wherein the poxvirus vector is derived from MVA and wherein the polynucleotide encodes two or more polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, or fragments thereof, wherein the polypeptides are connected to each other in any order.

19. The vector of claim 10, wherein the vector is a self-replicating RNA molecule and wherein the polynucleotide encodes two or more polypeptides selected from SEQ ID NOs: 1, 3, 5, 11, 15, 17, 19, 21, 25, 29, 31, 33, 39, 43, 45, 49, 53, 59, 63, 65, 67, 81, 85, 87, 89, 91, 95, 97, 111, 113, 115, 119, 123, 127, 129, 145, 177, 179, 181, 183, 185, 187, 191, 193, 195, 197, 199, 201, 203, 205, 207, 209, 211, 215, 219, 221, 223, 229, 233, 235, 237, 239, 241, 243, 245, 247, 251, 255, 257, 259, 261, 263, 267, 271, 279, 281, 285, 293, 295, 297, 301, 303, 305, 307, 309, 319, 323, 325, 337, 339, 343, 345, 349, 371, and 375, or fragments thereof, wherein the polypeptides are connected to each other in any order.

20. A pharmaceutical composition comprising the vector of claim 9.

21. The polynucleotide of claim 5, comprising two or more sequences selected from SEQ ID NOs: 2, 4, 6, 12, 16, 18, 20, 22, 26, 30, 32, 34, 40, 44, 46, 50, 54, 60, 64, 64, 68, 82, 86, 88, 90, 92, 96, 98, 112, 114, 116, 120, 124, 128, 130, 146, 178, 180, 182, 184, 186, 188, 192, 194, 196, 198, 200, 202, 204, 206, 208, 210, 212, 216, 220, 222, 224, 230, 234, 236, 238, 240, 242, 244, 246, 248, 252, 256, 258, 260, 262, 264, 268, 272, 280, 282, 286, 294, 296, 298, 302, 304, 306, 308, 310, 320, 324, 326, 338, 340, 344, 346, 350, 372, and 376, or fragments thereof.

* * * * *